(12) United States Patent
Erlander et al.

(10) Patent No.: US 10,538,816 B2
(45) Date of Patent: *Jan. 21, 2020

(54) IDENTIFICATION OF TUMORS

(71) Applicant: BIOTHERANOSTICS, INC., San Diego, CA (US)

(72) Inventors: Mark G. Erlander, Redwood City, CA (US); Xiao-Jun Ma, San Diego, CA (US)

(73) Assignee: Biotheranostics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/368,411

(22) Filed: Dec. 2, 2016

(65) Prior Publication Data
US 2017/0268064 A1    Sep. 21, 2017

Related U.S. Application Data

(63) Continuation of application No. 11/145,307, filed on Jun. 3, 2005, now abandoned.

(60) Provisional application No. 60/577,084, filed on Jun. 4, 2004.

(51) Int. Cl.
| | | |
|---|---|---|
| C12Q 1/68 | (2018.01) | |
| C12Q 1/6886 | (2018.01) | |
| G16B 25/00 | (2019.01) | |
| G06Q 50/22 | (2018.01) | |
| G16B 40/00 | (2019.01) | |
| C12Q 1/6837 | (2018.01) | |

(52) U.S. Cl.
CPC ........... *C12Q 1/6886* (2013.01); *G06Q 50/22* (2013.01); *G16B 25/00* (2019.02); *C12Q 1/6837* (2013.01); *C12Q 2600/112* (2013.01); *C12Q 2600/158* (2013.01); *G16B 40/00* (2019.02)

(58) Field of Classification Search
None
See application file for complete search history.

(56) References Cited

U.S. PATENT DOCUMENTS

| | | |
|---|---|---|
| 7,514,209 B2 | 4/2009 | Dai et al. |
| 2002/0110820 A1 | 8/2002 | Ramaswamy et al. |
| 2003/0017481 A1 | 1/2003 | Golub et al. |
| 2003/0138793 A1 | 7/2003 | Su et al. |
| 2003/0148295 A1 | 8/2003 | Wan et al. |
| 2003/0219767 A1 | 11/2003 | Ayers et al. |
| 2003/0224374 A1 | 12/2003 | Dai et al. |
| 2003/0225526 A1 | 12/2003 | Golub et al. |
| 2003/0225528 A1 | 12/2003 | Baker et al. |
| 2004/0002067 A1 | 1/2004 | Erlander et al. |
| 2004/0098367 A1 | 5/2004 | Tamayo et al. |
| 2004/0253606 A1 | 12/2004 | Aziz et al. |
| 2005/0003341 A1 | 1/2005 | Polansky |
| 2005/0208500 A1 | 9/2005 | Erlander et al. |
| 2005/0260572 A1 | 11/2005 | Kato et al. |
| 2005/0272061 A1 | 12/2005 | Petroziello et al. |
| 2006/0094035 A1 | 5/2006 | Erlander et al. |
| 2006/0265138 A1 | 11/2006 | Bowtell et al. |
| 2006/0292572 A1 | 12/2006 | Stuart et al. |
| 2007/0020655 A1 | 1/2007 | Erlander |
| 2009/0157326 A1 | 6/2009 | Dai et al. |
| 2010/0178653 A1 | 7/2010 | Aharonov et al. |
| 2010/0273172 A1 | 10/2010 | Rosenfeld et al. |
| 2010/0323903 A1 | 12/2010 | Rosenwald et al. |
| 2011/0077168 A1 | 3/2011 | Rosenwald et al. |
| 2011/0097756 A1 | 4/2011 | Hagmann et al. |

FOREIGN PATENT DOCUMENTS

| | | |
|---|---|---|
| WO | WO 2001/094629 A2 | 12/2001 |
| WO | 2002103320 A2 | 12/2002 |
| WO | WO 2002/103320 A2 | 12/2002 |
| WO | WO 2003/041562 A2 | 5/2003 |
| WO | WO 2005/059109 A2 | 6/2005 |
| WO | WO 2006/080597 A1 | 8/2006 |
| WO | WO 2007/137366 A1 | 12/2007 |
| WO | WO 2010/108638 A1 | 9/2010 |

OTHER PUBLICATIONS

DiRisi et al., "Use of a cDNA microarray to analyse gene expression patterns in human cancer" 14 Nature Genetics 457-460 (1996).*
"Affymetrix Genechip bHuman Genome U133 Array Set HG-U133A", GEO, XP002254749 Abstract (2003).
"Aftymetrix Genechip bHuman Genome U133 plus 2.0 Array", GEO, XP002343693 Abstract (2003).
Barden et al., "Classification of follicular thyroid tumors by molecular signature: results of gene profiling", Clin Cancer Res., 9(5):1792-1800 (2003).
Bhattacharjee et al., "Classification of human lung carcinomas by mRNA expression profiling reveals distinct adenocarcinoma subclasses", Proc Natl Acad Sci U S A., 98(24):13790-13705 (2001).
Bloom et al., "Multi-platform, multi-site, microarray-based human tumor classification", Am J Pathol., 164(1):9-16 (2004).
Feng et al., "Molecular biomarkers for cancer detection in blood and bodily fluids", Crit Rev Clin Lab Sci., 43(5-6):497-560 (2006).
Glinsky et al., "Classification of human breast cancer using gene expression profiling as a component of the survival predictor algorithm", Clin Cancer Res., 10(7):2272-2283 (2004).
Golub et al., "Molecular classification of cancer: class discovery and class prediction by gene expression monitoring", Science, 286(5439):531-537 (1999).
Kahh et al., "Classification and diagnostic prediction of cancers using gene expression profiling and artificial neural networks", Nat Med., 7(6):673-679 (2001).
Ma et al., "gene expression signatures associated with clinical outcome in breast cancer via laser capture microdissection", Breast Canser Research and Treatment, 82(1):S15 (2003).

(Continued)

*Primary Examiner* — Nancy J Leith
(74) *Attorney, Agent, or Firm* — Jones Day

(57) ABSTRACT

The invention provides methods for the use of gene expression measurements to classify or identify tumors in samples obtained from a subject in a clinical setting, such as in cases of formalin fixed, paraffin embedded (FFPE) samples.

20 Claims, 11 Drawing Sheets

Specification includes a Sequence Listing.

(56) References Cited

OTHER PUBLICATIONS

Martin et al., "Linking Gene Expression Patterns to Therapeutic Groups in Breast Cancer", Cancer Research, 60:2232-2238 (2000).
Nielsen et al., "Tissue Microarray Balidation of Epidermal Growth Factor Receptor and SALL2 in Synovial Sarcoma with Comparison to Tumors of Similar History", American Journal of Pathology, 163(4):1449-1456 (2003).
Okada et al., "Analysis of gene-expression profiles in testicular seminomas using a genome-wide cDNA microarray", Int J Oncol., 23(6):1615-1635 (2003).
Osoegawa et al., "A bacterial artificial chromosome library for sequencing the complete human genome", Genome Res., 11(3):483-496 (2001).
Perou et al., "Distinctive gene expression patterns in human mammary epithelial cells and breast cancers", Proc Natl Acad Sci U S A., 96(16):9212-9217 (1999).
Ramaswamy et al., "A molecular signature of metastasis in primary solid tumors", Nat Genet., 33(1):49-54 (2003).
Ramaswamy et al., "Multiclass cancer diagnosis using tumor gene expression signatures", Proc Natl Acad Sci U S A., 98(26):15149-15154 (2001).
Schena et al., "Quantitative monitoring of gene expression patterns with a complementary DNA microarray", Science 270(5235):467-470 (1995).
Sgroi et al., "In vivo gene expression profile analysis of human breast cancer progression", Cancer Res., 59(22):5656-5661 (1999).
Sgroi et al., "In Vivo Gene Expression Profiling of Human Breast Cancer", Laboratory Investigation, United States and Canadian Academy of Pathology, 82(1):51A (2002).
Srinivas et al., "Trends in Biornarker Research for Cancer Detection", Lancet Oncol., 2(11):698-704 (2001).
Su et al., "Molecular Classification of Human Carcinomas by Use of Gene Expression Signatures", Cancer Research, 61:7388-7393 (2001).
Takahashi et al., "Gene expression profiling of clear cell renal cell carcinoma: gene identification and prognostic classification", Proc Natl Acad Sci U S A., 98(17):9754-9759 (2001).
Tamayo et al., "Interpreting patterns of gene expression with self-organizing maps: methods and application to hematopoietic differentiation", Proc Natl Road Sci U S A., 96(6):2907-2912 (1999).
Tothill et al., "An expression-based site of origin diagnostic method designed for clinical application to cancer of unknown origin", Cancer Res., 65(10):4031-4040 (2005), together with Supplementary Information Parts 1-3, Supplementary Tables 1-7, available at Cancer Research Online (http://cancerres.aacrjournals.org/).
Van't Veer et al., "Gene expression clinical outcome of breast cancer", Nature, 415(6871):530-536 (2002).
Welford et al., "Detection of differentially expressed genes in primary tumor tissues using representational differences analysis coupled to microarray hybridization", Nucleic Acids Res., 26(12):3059-3065 (1998).
Yeung et al., "Multiclass classification of microarray data with repeated measuremets: application to cancer", Genome Biol., 4(12):R83-R8.319 (2003).

Brachtel et al., "Molecular classification of cancer with the 92-gene assay in cytology and limited tissue samples," Oncotarget, 7(19):27220-27231 (2016).
Bridgewater et al., "Gene expression profiling may improve diagnosis in patients with carcinoma of unknown primary," Br. J Cancer, 98(8):1425-1430 (2008).
Buckhaults et al., "Identifying tumor origin using a gene expression-based classification map," Cancer Res., 63(14):4144-4149 (2003).
CancerConnect.com (Pathology Tests, attached, available at http://news.cancerconnect.com/testingcenter/ Pathologytests, accessed Aug. 16, 2016).
Cole et al., "The genetics of cancer—a 3D model," Nat. Genet., 21:38-41 (1999).
Dash et al., "Distance Based Feature Selection for Clustering Microarray Data, in Database Systems for Advanced Applications," Eds. Tsuji, Jin, Higuchi, pp. 512-519 (2008).
Dennis et al., "Identification from public data of molecular markers of adenocarcinoma characteristic of the site of origin," Cancer Res., 62(21):5999-6005 (2002).
Derisi et al., "Use of a cDNA microarray to analyse gene expression patterns in human cancer," Nat. Genet., 14(4):457-460 (1996).
Epstein et al., "Microarray technology—enhanced versatility, persistent challenge," Curr. Opin. Biotechnol., 11(1):36-41 (2000).
Erlander et al., "Performance and clinical evaluation of the 92-gene real-time Pcr assay for tumor classification," J. Mol. Diagn., 13(5):493-503 (2011).
Giordano et al., "Organ-specific molecular classification of primary lung, colon, and ovarian adenocarcinomas using gene expression profiles," Am. J. Pathol., 159(4):1231-1238 (2001).
International Search Report and Written Opinion for PCT/US05/019736 dated Feb. 28, 2006 (14 pages).
Iwao et al., "Molecular classification of primary breast tumors possessing distinct prognostic properties," Hum. Mol. Genet., 11(2):199-206 (2002).
Kerr et al., "Multisite validation study to determine performance characteristics of a 92-gene molecular cancer classifier," Clin. Cancer Res., 18(14):3952-3960 (2012).
Lockart et al., "Genomics, gene expression and DNA arrays," Nature, 405:827-836 (2000).
Lopez-Encuentra et al., "Comparison between clinical and pathologic staging in 2,994 cases of lung cancer," Ann. Thorac. Surg., 79(3):974-979 (2005).
Ma et al., "Molecular classification of human cancers using a 92-gene real-time quantitative polymerase chain reaction assay," Arch. Pathol. Lab Med., 130(4):465-473 (2006).
Noonan et al., "Characterization of the homeodomain gene EMX2: sequence conservation, expression analysis, and a search for mutations in endometrial cancers," Genomics, 76(1-3):37-44 (2001).
Shedden et al., "Accurate molecular classification of human cancers based on gene expression using a simple classifier with a pathological tree-based framework," Am. J. Pathol., 163(5):1985-1995 (2003).
Winston, "Small Cell Lung Cancer," Medscape, accessed Feb. 17, 2015 http://emedicine.medscape.com/article/280104-overview.

\* cited by examiner

SEQUENCE LISTING

```
<160> NUMBER OF SEQ ID NOS: 268

<210> SEQ ID NO 1
<211> LENGTH: 2930
<212> TYPE: DNA
<213> ORGANISM: Homo sapiens

<400> SEQUENCE: 1
ggccactctg cagacagctc cagacaatca ggcactcgtc acacagagtc ttcctctcgt      60
ggacaggctg cgtcatccca tgaacaggca agatcaagtg caggagaaag acatggatcc     120
caccaccagc agtcagcaga cagctccaga cacgcaggca ttgggcacgg acaagcttca     180
tctgcagtca gagacagtgg acaccgaggg tacagaggta gtcaggccac tgacagtgag     240
ggacattcag aagactcaga cacacagtca gtgtcagcac agggacaagc tgggccccat     300
cagcagagcc accaagagtc cgcacgtggc cagtcagggg aaagctctgg acgttcaggg     360
tctttcctct accaggtgag cactcatgaa cagtctgagt ccacccatgg acagtctgtg     420
cccagcactg gaggaagaca aggatcccac catgatcagg cacaagacag ctccaggcac     480
```

```
tcagcatccc aagagggtca ggacaccatt cgtggacacc cggggccaag cagaggagga      540
agacagtggt cccaccacga gcaatcggta gataggtctg gacactcagg gtcccatcac      600
agccacacca catcccaggg aaggtctgat gcctcccgtg ggcagtcagg atccagaagt      660
gcaagcagac aaacacatga ccaggaacaa tcaggagacg gctctaggca ctcagggtcg      720
cgtcatcagg aagcttcctc ttgggccgac agctctagac actcacaggc agtccaggga      780
caatcagagg ggtccaggac aagcaggcgc cagggatcca gtgttagcca ggacagtgac      840
agtcagggac actcagaaga ctctgagagg cggtctgggt ctgcttccag aaaccatcgt      900
ggatctgctc aggagcagtc aagagatggc tccagacacc ccaggtccca tcacgaagac      960
agagccggtc acgggactc  tgcagagagc tccagacaat caggcactca tcatgcagag     1020
aattcctctg gtggacaggc tgcatcatcc catgaacagg caagatcaag tgcaggagag     1080
agacatggat cccactacca gcagtcagca gacagctcca gacactcagg cattgggcac     1140
ggacaagctt catctgcagt cagagacagt ggacaccgag ggtccagtgg tagtcaggcc     1200
agtgacaatg agggacattc agaagactca gacacacagt cagtgtcagc ccaccgacag     1260
gctgggcgcc atcacgagag ccaccaagag tccacgcgtg gccggtcacg aggaaggtct     1320
ggacgttcag ggtcttttcct ctaccaggtg agcactcatg aacagtctga gtctgcccat     1380
ggacgggctg ggcccagtac tggaggaaga caaggatccc gccacgagca ggcacgagac     1440
agctccaggc actcagcgtc ccaagagggt caggacacca ttcgtggaca cccggggtca     1500
aggagaggag gaagacaggg atcctaccac gagcaatcgg tagataggtc tggacactca     1560
gggtcccatc acagccacac cacatcccag ggaaggtctg atgcctccca tgggcagtca     1620
ggatccagaa gtgcaagcag agaaacacgt aatgaggaac agtcaggaga cggctccagg     1680
cactcagggt cgcgtcacca tgaagcttcc actcaggctg acagtctag  acactcacag     1740 tccggccagg gtgaatcagc ggggtccagg agaagcaggc gccagggatc cagtgttagc     1800
caggacagtg acagtgaggc atacccgaga gactctgaga ggcgatctga gtctgcttcc     1860
agaaaccatc atggatcttc tcgggagcag tcaagagatg gctccagaca ccccggatcc     1920
tctcaccgcg atacagccag tcatgtacag tcttcacctg tacagtcaga ctctagtacc     1980
gctaaggaac atggtcactt tagtagtctt tcacaagatt ctgcgtatca ctcaggaata     2040
cagtcacgtg gcagtcctca cagttctagt tcttatcatt atcaatctga gggcactgaa     2100
aggcaaaaag gtcaatcagg tttagttttgg agacatggca gctatggtag tgcagattat     2160
gattatggtg aatccggggtt tagacactct cagcacggaa gtgttagtta caattccaat     2220
cctgttcttt tcaaggaaag atctgatatc tgtaaagcaa gtgcgtttgg taaagatcat     2280
ccaaggtatt atgcaacgta tattaataag gacccaggtt tatgtggcca ttctagtgat     2340
atatcgaaac aactgggatt tagtcagtca cagagatact attactatga gtaagaaatt     2400
aatggcaaag gaattaatcc aagaatagaa gaatgaagca agttcacttt caatcaagaa     2460
acttcataat actttcaggg aagttatctt ttcctgtcaa tctgtttaaa atatgctata     2520
gtatttcatt agtttggtgg taacttattt ttattgtgta atgatcttta aacgctatat     2580
ttcagaaata ttaaatggaa gaaatcaata tcatggagag ctaactttag aaaactagct     2640
ggagtatttt aggagattct gggtcaagta atgttttatg ttttgaaag ttaagttttt     2700 agacactccc caaatttcta aattaatctt tttcagaaat atcgaaggag ccaaaaatat     2760 aaacagttc tgatatccaa agtggctata tcaacatcag gctagcaca tctttctcta     2820 ttatccttct attggaattc tagtattctg tattcaaaaa atcatcttgg acataattaa     2880
```

```
tattttagta agctgcatct aaattaaaaa taaactattc atcatataat        2930
```

<210> SEQ ID NO 2
<211> LENGTH: 1591
<212> TYPE: DNA
<213> ORGANISM: Homo sapiens

<400> SEQUENCE: 2

```
tagaatcggg ggtttcagct cactgctcct tttcttttttt ttctttctct ccccccgccca    60
ccccccaaa aataattgat ttgctttaca atcatccaca ctgtgttttg tggatcttta      120
attatatata acaatagtag tcattttaaa tatatattct gaaatctttg caaattttaa     180
cagaagagtc gaagctctgc gagacccaat atttgccaat aagaatggtt atgataatta     240
gcaccatgga gcctcaggtg tcaaatggtc cgacatccaa tacaagcaat ggaccctcca     300
gcaacaacag aaactgtcct tctcccatgc aaacaggggc aaccacagat gacagcaaaa     360
ccaacctcat cgtcaactat ttaccccaga atatgaccca agaagaattc aggagtctct     420
tcgggagcat tggtgaaata gaatcctgca acttgtgag agacaaaatt acaggacaga     480
gtttagggta tggatttgtt aactatattg atccaaagga tgcagagaaa gccatcaaca     540
cttttaaatgg actcagactc cagaccaaaa ccataaaggt ctcatatgcc cgtccgagct     600
ctgcctcaat cagggatgct aacctctatg ttagcggcct tcccaaaacc atgacccaga     660
aggaactgga gcaactttc tcgcaatacg gccgtatcat cacctcacga atcctggttg      720
atcaagtcac aggagtgtcc agaggggtgg gattcatccg ctttgataag aggattgagg     780
cagaagaagc catcaaaggg ctgaatggcc agaagcccag cggtgctacg gaaccgatta     840
ctgtgaagtt tgccaacaac cccagccaga agtccagcca ggccctgctc tcccagctct     900
accagtcccc taaccggcgc tacccaggtc cacttcacca ccaggctcag aggttcaggc     960
tggacaattt gcttaatatg gcctatggcg taaagagact gatgtctgga ccagtccccc    1020
cttctgcttg ttccccagg ttctccccaa ttaccattga tggaatgaca agccttgtgg     1080
gaatgaacat ccctggtcac acaggaactg ggtggtgcat cttttgtctac aacctgtccc    1140
ccgattccga tgagagtgtc ctctggcagc tctttgggccc cttttggagca gtgaacaacg  1200
taaaggtgat tcgtgacttc aacaccaaca agtgcaaggg attcggcttt gtcaccatga    1260
ccaactatga tgaggcggcc atggccatcg ccagcctcaa cgggtaccgc ctgggagaca   1320
gagtgttgca gtttcctttt aaaaccaaca agcccacaa gtcctgaatt tcccattctt     1380
acttactaaa atatatatag aaatatatac gaacaaaaca cacgcgcgca cacacacaca   1440
tacacgaaag agagagaaac aaactttttca aggcttatat tcaaccatgg actttataag   1500
ccagtgttgc ctaagtatta aaacattgga ttatcctgag gtgtaccagg aaaggatttt    1560
ataatgctta gaaaaaaaaa aaaaaaaaaa a                                   1591
```

<210> SEQ ID NO 3
<211> LENGTH: 2872
<212> TYPE: DNA
<213> ORGANISM: Homo sapiens

<400> SEQUENCE: 3

```
tccaggaatc gatagtgcat tcgtgcgcgc ggccgcccgt cgcttcgcac agggctggat      60
ggttgtattg gcagggtgg ctccaggatg ttaggaactg tgaagatgga agggcatgaa     120
accagcgact ggaacagcta ctacgcagac acgcaggagg cctactcctc ggtcccggtc   180
```

-continued

```
agcaacatga actcaggcct gggctccatg aactccatga cacctacat gaccatgaac    240 accatgacta cgagcggcaa catgaccccg gcgtccttca acatgtccta tgccaacccg    300
gccttagggg ccggcctgag tcccggcgca gtagccggca tgccgggggg ctcggcgggc    360
gccatgaaca gcatgactgc ggccggcgtg acggccatgg gtacggcgct gagcccgagc    420
ggcatgggcg ccatgggtgc gcagcaggcg gcctccatga tgaatggcct gggcccctac    480
gcggccgcca tgaacccgtg catgagcccc atggcgtacg cgccgtccaa cctgggccgc    540
agccgcgcgg gcggcggcgg cgacgccaag acgttcaagc gcagttaccc gcacgccaag    600
ccgccctact cgtacatctc gctcatcacc atggccatcc agcgggcgcc cagcaagatg    660
ctcacgctga gcgagatcta ccagtggatc atggacctct tccctatta ccggcagaac     720 cagcagcgct ggcagaactc catccgccac tcgctgtcct tcaatgactg cttcgtcaag    780
gtggcacgct ccccggacaa gccgggcaag ggctcctact ggacgctgca cccggactcc    840
ggcaacatgt tcgagaacgg ctgctacttg cgccgccaga gcgcttcaa gtgcgagaag     900 cagccggggg ccggcggcgg gggcgggagc ggaagcgggg gcagcggcgc caagggcggc    960
cctgagagcc gcaaggaccc ctctggcgcc tctaaccccca gcgccgactc gcccctccat   1020
cggggtgtgc acgggaagac cggccagcta gagggcgcgc cggccccggg cccggccgcc   1080
agcccccaga ctctggacca cagtggggcg acggcgacag ggggcgcctc ggagttgaag   1140
actccagcct cctcaactgc gcccccccata agctccgggc ccggggcgct ggcctctgtg   1200
cccgcctctc acccggcaca cggcttggca ccccacgagt cccagctgca cctgaaaggg   1260
gacccccact actccttcaa ccacccgttc tccatcaaca acctcatgtc ctcctcggag   1320
cagcagcata agctggactt caaggcatac gaacaggcac tgcaatactc gccttacggc   1380
tctacgttgc ccgccagcct gcctctaggc agcgcctcgg tgaccaccag gagccccatc   1440
gagccctcag ccctggagcc ggcgtactac caaggtgtgt attccagacc cgtcctaaac   1500
acttcctagc tcccgggact gggggggtttg tctggcatag ccatgctggt agcaagagag   1560
aaaaaatcaa cagcaaacaa aaccacacaa accaaaccgt caacagcata ataaaatcca   1620
acaactattt ttatttcatt tttcatgcac aaccttgccc ccagtgcaaa agactgttac   1680
tttattattg tattcaaaat tcattgtgta tattactaca aagacggccc caaaccaatt   1740
tttttcctgc gaagtttaat gatccacaag tgtatatatg aaattctcct ccttccttgc   1800 cccctctct ttcttccctc ttggcccctcc agacattcta gtttgtggag ggttatttaa    1860
aaaacaaaaa ggaagatggt caagtttgta aaatatttgt ttgtgctttt ccccctcct    1920 tacctgaccc cctacgagtt tacaggcttg tgcaatact cttaaccata agaattgaaa    1980
tggtgaagaa acaagtatac actagaggct cttaaaagta ttgaaaagac aatactgctg   2040
ttatatagca agacataaac agattataaa catcagagcc atttgcttct cagtttacat   2100
ttctgataca tgcagatagc agatgtcttt aaatgaaata catgtatatt gtgtatggac   2160
ttaattatgc acatgctcag atgtgtagac atcctccgta tatttacata acatatagag   2220
gtaatagata ggtgatatac gtgatacgtt ctcaagagtt gcttgaccga agttacaag    2280 gaccccaacc cctttgctct ctacccacag atggccctgg gaacaatcct caggaattgc   2340
cctcaagaac tcgcttcttt gctttgagag tgccatggtc atgtcattct gaggtacata   2400
acacataaat tagtttctat gagtgtatac catttaaaga ttttttcagt aaagggaata   2460
ttacatgttg ggaggaggag ataagttata gggagctgga tttcaaacgg tggtccaaga   2520
ttcaaaaatc ctattgatag tggccatttt aatcattgcc atcgtgtgct tgtttcatcc   2580
```

| | |
|---|---|
| agtgttatgc actttccaca gttggtgtta gtatagccag agggtttcat tattatttct | 2640 |
| ctttgctttc tcaatgttaa tttattgcat ggtttattct ttttctttac agctgaaatt | 2700 |
| gctttaaatg atggttaaaa ttacaaatta aattgggaat ttttatcaat gtgattgtaa | 2760 |
| ttaaaaatat tttgatttaa ataacaaaaa taataccaga ttttaagccg cggaaaatgt | 2820 |
| tcttgatcat ttgcagttaa ggactttaaa taaatcaaat gttaacaaaa aa | 2872 |

<210> SEQ ID NO 4
<211> LENGTH: 540
<212> TYPE: DNA
<213> ORGANISM: Homo sapiens

<400> SEQUENCE: 4

| | |
|---|---|
| tgttttcta gttcattttg tgtttccaac ttttcatgta aaattttaat tattttgaa | 60 |
| tgtgtggatg tgagactgag gtgccttttg gtactgaaat tcttttttcca tgtacctgaa | 120 |
| gtgttacttt tgtgatatag gaaatccttg tatatatact ttattggtcc ctaggcttcc | 180 |
| tattttgtta ccttgctttc tctatggcat ccaccatttt gattgttcta cttttatgat | 240 |
| atgttttcat aagtggttaa gcaagtattc tcgttacttt tgctcttaaa tccctattca | 300 |
| ttacagcaat gttggtggtc aaagaaaatg ataaacaact tgaatgttca atggtcctga | 360 |
| aatacataac aacattttag tacattgtaa agtagaatcc tctgttcata atgaacaaga | 420 |
| tgaaccaatg tggattagaa agaagtccga gatattaatt ccaaaatatc cagacattgt | 480 |
| taaagggaaa aaattgcaat aaaatatttg taacataaaa aaaaaaaaaa aaaaaaaaaa | 540 |

<210> SEQ ID NO 5
<211> LENGTH: 2508
<212> TYPE: DNA
<213> ORGANISM: Homo sapiens

<400> SEQUENCE: 5

| | |
|---|---|
| agctctcccc accaataaaa ggaccaggga ggatcagaga gagcagaagg atcctgagcc | 60 |
| tcgcactctg ccgcccgcac caccttccgc tgcctctcag actctgctca gcctcacacg | 120 |
| atgtcgtgcc gctcctacag gatcagctca ggatgcgggg tcaccaggaa cttcagctcc | 180 |
| tgctcagctg tggcccccaa aactggcaac cgctgctgca tcagcgccgc cccctaccga | 240 |
| ggggtgtcct gctaccgagg gctgacgggc ttcggcagcc gcagcctctg caacctgggc | 300 |
| tcctgcgggc cccggatagc tgtaggtggc ttccgagccg gctcctgcgg acgcagcttc | 360 |
| ggctaccgct ccgggggcgt gtgcggaccc agcccccat gcatcactac cgtgtcggtc | 420 |
| aacgagagcc tcctcacgcc cctcaacctg gagatcgacc ccaacgcaca gtgcgtgaag | 480 |
| caggaggaga aggagcagat caagtccctc aacagcaggt tcgcggcctt catcgacaag | 540 |
| gtgcgcttcc tggagcagca gaacaagctg ctggagacca gtggcagtt ctaccagaac | 600 |
| cagcgctgct gcgagagcaa cctggagcca ctgttcagtg gctacatcga gactctgcgg | 660 |
| cgggaggccg agtgcgtgga ggccgacagc gggaggctgg cctcagagct caaccatgtg | 720 |
| caggaggtgc tggagggcta caagaagaag tatgaagagg aggtggccct gagagccaca | 780 |
| gcagagaatg agtttgtcgt tctaaagaag gacgtggact gtgcctacct gcggaaatca | 840 |
| gacctggagg ccaatgtgga ggccctggtg gaggagtcta gcttcctgag gcgcctctat | 900 |
| gaagaggaga tccgcgttct ccaagcccac atctcagaca cctcggtcat agtcaagatg | 960 |
| gacaacagcc gagacctgaa catggactgc atcatcgctg agatcaaggc tcagtatgac | 1020 |

| | |
|---|---|
| gatgttgcca gccgcagccg ggccgaggct gagtcctggt accgtagcaa gtgtgaggag | 1080 |
| atgaaggcca cggtgatcag gcatggggag accctgcgcc gcaccaagga ggagatcaac | 1140 |
| gagctgaacc gcatgatcca gaggctgacg gccgagattg agaatgccaa gtgccagcgt | 1200 |
| gccaagctgg aggctgctgt ggctgaggca gagcagcagg gtgaggcggc cctcagcgat | 1260 |
| gcccgctgca agctggctga gctggagggc gccctgcaga aggccaagca ggacatggcc | 1320 |
| tgcctgctca aggagtacca ggaggtgatg aactccaagc tgggcctgga catcgagatc | 1380 |
| gccacctaca ggcgcctgct ggagggcgag gaacacaggc tgtgtgaagg tgtgggctct | 1440 |
| gtgaatgtct gtgtcagcag ctcccgtggt ggagtctcct gtgggggcct ctcctacagc | 1500 |
| accaccccag ggcgccagat cacttctggc ccctcagcca taggcggcag catcacggtg | 1560 |
| gtggcccctg actcctgtgc ccctgccag cctcgttcct ccagcttcag ctgcgggagt | 1620 |
| agccggtcgg tccgctttgc ctagtagagt catggagcca gggcttcctg ccaagcacct | 1680 |
| gcctgcctgc atcactgcac tgaatggcat gtgaatggaa aatgtgtgct tgcttccaga | 1740 |
| atcttctgga tgttcctaca gagggaaaga cctacagagg gaaagaccct cgggccgctc | 1800 |
| ccctgcgcct tttcatgcta gggagatgca tcctagttgt cctcctggca gctgttttca | 1860 |
| gaggcattcc cagcccttca cttaactcct acttagctcc aaaatacctg tatccaattt | 1920 |
| gtattattcc cccagctctc agggacaaga ccagtccccc agcgtggtgg tcagcacgga | 1980 |
| agctccacct tctgggtgga ggcgccatcc taaccatcca gccaggccac ccacaacccg | 2040 |
| agaatcaggg agaaagtccc tccccagcag ccccctcctc ctggctggga agaatggtcc | 2100 |
| cccagcaagc acttgcctgt tcattcccgt tcatgttttg cttctctctc agactgcctt | 2160 |
| cctgcttctg ggctaacctg ttccagccag gctcctcatg tgacctcgca gttgagaagc | 2220 |
| ccattatcgt ggggcatcct tttgcctaca gcccctggtt agggcacttt ggacaggtct | 2280 |
| tgctattcag tgaacctttg tacatttcaa agaagactcc atggctgctc cagatgcccc | 2340 |
| cttgctgggt gcaggtgggg actgtccaat gcagagctgg cggacagag agttaagcca | 2400 |
| cttcctgggt ctccttctta tgactgtcta tgggtgcatt gccttctggg ttgtctcgat | 2460 |
| ctgtgtttca ataaatgccg ctgcaatgca aaaaaaaaaa aaaaaaaa | 2508 |

<210> SEQ ID NO 6
<211> LENGTH: 1354
<212> TYPE: DNA
<213> ORGANISM: Homo sapiens
<220> FEATURE:
<221> NAME/KEY: misc_feature
<222> LOCATION: (57)..(57)
<223> OTHER INFORMATION: a or g or c or t/u

<400> SEQUENCE: 6

| | |
|---|---|
| caatcagtga aaattctata ttcctttggc atttttgtga catattcaat tcagttntat | 60 |
| gttccagcag agatcattat ccctgggatc acatccaaat ttcatactaa atggaagcaa | 120 |
| atctgtgaat ttgggataag atccttcttg gttagtatta cttgcgccgg agcaatgtct | 180 |
| tattcctcgt ttagacattg tgatttcctt cgttggagct gtgagcagca gcacattggc | 240 |
| cctaatcctg ccacctttgg ttgaaattct tacattttcg aaggaacatt ataatatatg | 300 |
| gatggtcctg aaaaatattt ctatagcatt cactggagtt gttggcttct tattaggtac | 360 |
| atatataact gttgaagaaa ttatttatcc tactcccaaa gttgtagctg gcactccaca | 420 |
| gagtcctttt ctaaatttga attcaacatg cttaacatct ggtttgaaat agtaaaagca | 480 |
| gaatcatgag tcttctattt ttgtcccatt tctgaaaatt atcaagataa ctagtaaaat | 540 |

```
acattgctat atacataaaa atggtaacaa actctgtttt ctttggcacg atattaatat    600
tttggaagta atcataactc tttaccagta gtggtaaacc tatgaaaaat ccttgctttt    660
aagtgttagc aatagttcaa aaaattaagt tctgaaaatt gaaaaaatta aaatgtaaaa    720
aaattaaaga ataaaaatac ttctattatt cttttatctc agtaagaaat accttaacca    780
agatatctct cttttatgct actcttttgc cactcacttg agaacagaat aggatttcaa    840
caataagaga ataaaataag aacatgtata acaaaaagct ctctccagat catccctgtg    900
aatgccaaag taaactttat gtacagtgta aaaaaaaaaa aatctcagtt atgtttttat    960
tagccaaatt ctaatgattg ctcctggaa gtatagaaaa ctcccattaa cataatataa    1020
gcatcagaaa attgcaaaca ctagaattaa ttttacactc taatggtagt tgatcttcat    1080
agtcaagagg cactgttcaa gatcatgact tagtgtttca atgaaatttg aaaagggact    1140
ttaaaactta tccagtgcaa ctcccttgtt tttcgtcaga ggaaaaggag gcctagaaag    1200
gttaagtaac ttggtcgaga ccactcagcc ttgagatcaa gaaaacctaa tcttctgact    1260
cccaggccag gatgttttat ttctcacatc atgtccaaga aaagaataa attatgttca    1320 gcttaaaaaa aaaaaaaaaa aaaaaaaaaa aaaa                                1354
```

<210> SEQ ID NO 7
<211> LENGTH: 2460
<212> TYPE: DNA
<213> ORGANISM: Homo sapiens

<400> SEQUENCE: 7

```
cggaggcggc gccgacgggg actgctgagg cgcgcagagg gtcggcggcg cccgggagcc     60
tgtcgctggc gcggtccggg cgggaggctc ggcggcgggc ggcagcatgt cggtggcggg    120
gctgaagaag cagttctaca aggcgagcca gctggtcagt gagaaggtcg aggggccga    180 ggggaccaag ctggatgatg acttcaaaga gatggagaag aaggtggatg tcaccagcaa    240
ggcggtgaca gaagtgctgg ccaggaccat cgagtacctg cagcccaacc cagcctcgcg    300
ggctaagctg accatgctca acacggtgtc caagatccgg ggccaggtga agaaccccgg    360
ctacccgcag tcggaggggc ttctgggcga gtgcatgatc cgccacggga aggagctggg    420
cggcgagtcc aactttggtg acgcattgct ggatgccggc gagtccatga agcgcctggc    480
agaggtgaag gactccctgg acatcgaggt caagcagaac ttcattgacc ccctccagaa    540
cctgtgcgag aaagacctga aggagatcca gcaccacctg aagaaactgg agggccgccg    600
cctggacttt gactacaaga agaagcggca gggcaagatc cccgatgagg agctacgcca    660
ggcgctggag aagttcgagg agtccaagga ggtggcagaa accagcatgc acaacctcct    720
ggagactgac atcgagcagg tgagtcagct ctcggccctg gtggatgcac agctggacta    780
ccaccggcag gccgtgcaga tcctggacga gctggcggag aagctcaagc gcaggatgcg    840
ggaagcttcc tcacgcccta gcgggagta taagccgaag ccccgggagc cctttgacct    900
tggagagcct gagcagtcca acgggggctt cccctgcacc acagccccca agatcgcagc    960
ttcatcgtct ttccgatctt ccgacaagcc catccggacc cctagccgga gcatgccgcc    1020 cctgaccag ccgagctgca aggcgctgta cgacttcgag cccgagaacg acggggagct    1080
gggcttccat gagggcgacg tcatcacgct gaccaaccag atcgatgaga actggtacga    1140
gggcatgctg gacggccagt cgggcttctt cccgctcagc tacgtggagg tgcttgtgcc    1200
cctgccgcag tgactcaccc gtgtccccgc cccgcccctc cgtccacact ggccggcacc    1260
```

```
cctgctggg tctcctgcat tccacggagc ccctgctgcc agggcggtgt ctgagcctgc    1320
cggcgccacc tgggcccggg cccttgaggt actccctgag caggaccca cacttgggtg     1380 gggggggctta tctgggtggg tggggatgcc tgtttacact agcgctgact cccaacggtg    1440
acggctccct tccccactcc atggcgccag cctcctcccc cgctcccaa cttctcgccc     1500 agctggccga ggcggggcaa cactaaggtg ctcttagaaa cactaatgtt cctctggggc    1560
agcccccacc tccgtcctga cccgacgggg gccggccca ctgcctaccc tcgagtcccg     1620
cagccttaac aggatgggat cgagggtccc catggggtgg ctcagagata ggaccctggt    1680
tttaaatccc tcccagcctg gtgctggtga tgggccctgg ccctactcca gggccaatgc    1740 accccgcct cacacacgca ctccttctcc tcaaggccag ggcagagggc ctcaccgcct     1800
cccgggcctg ctgtcagctt gcagcccggg gacagaggcc agctgggatc tgcctgagga    1860
cagagaacat ggtctcctgc agggccctgc ctcccaagcc ccgccctcag aaagccaagt    1920 acctttcag cttttaact gccccatcc caacccaggg aggcctgtgt cactctggca        1980
caagctgcca ccaccagcca cccacaccca cccagcaca cctcacacgg gaccacagcc     2040
gcgctgccga gggccaagca caaaggttcc agtgagcgca tgtcccagcc cctggtggcc    2100
aggctcccct tgctgagccg ctgccacttc acctgtggg aagtggcccc agccatctcc      2160
tctagaccaa ggcaggcagc cccgacatct gcttcctcta tcgcccaatg caaaatcgat    2220
gaaatgggga gttctctggg ccaggccaca ttcacattcc cctcccctg tggtccagtg      2280 aagcctccgg accccaggct ctgctctgcc ctgccctgca ccccctcgt cagaagtaca      2340 tgagggcgc agagatgagc acacagcttt gggcacggtc cagggcaaac tgaaatgtac    2400
gcctgaattt tgtaaacaga agtattaaat gtctctttct acaaaaaaa aaaaaaaaa      2460

<210> SEQ ID NO 8
<211> LENGTH: 1112
<212> TYPE: DNA
<213> ORGANISM: Homo sapiens

<400> SEQUENCE: 8
ggcacgaggg aggtgcagag ctgagaatga ggcgatttcg gaggatggag aaatagcccc       60
gagtcccgtg gaaaatgagg ccggcggact tgctgcagct ggtgctgctg ctcgacctgc     120
ccagggacct gggcggaatg gggtgttcgt ctccaccctg cgagtgccat caggaggagg    180
acttcagagt cacctgcaag gatattcaac gcatcccag cttaccgccc agtacgcaga     240
ctctgaagct tattgagact cacctgagaa ctattccaag tcatgcattt tctaatctgc      300
ccaatatttc cagaatctac gtatctatag atgtgactct gcagcagctg gaatcacact    360
ccttctacaa tttgagtaaa gtgactcaca tagaaattcg gaataccagg aacttaactt    420
acatagaccc tgatgccctc aaagagctcc ccctcctaaa gttccttggc attttcaaca    480
ctggacttaa aatgttccct gacctgacca agtttattc cactgatata ttctttatac      540
ttgaaattac agacaacccct acatgacgt caatccctgt gaatgctttt cagggactat    600
gcaatgaaac cttgacactg aagctgtaca acaatggctt tacttcagtc caaggatatg    660
ctttcaatgg gacaaagctg gatgctgttt acctaaacaa gaataaatac ctgacagtta    720
ttgacaaaga tgcatttgga ggagtataca gtggaccaag cttgctgctg cctcttggaa    780
gaaagtcctt gtcctttgag actcagaagg ccccaagctc cagtatgcca tcatgatgcc    840
tgctaaggca gccaccttgg tgtacatgct cacagaggct ctgttcatgg agcagctgct    900
gtttgaaaaa ttttgaaatg caagatccac aactagatgg aaggcactct agtctttgca    960
```

```
gaaaaaaatg tacctgaatg tacattgcac aatgcctggc acaaagaagg aagaatataa    1020
atgatagttc gactcgtctg tggaagaact tacaatcatg gggaagatg  gaataaaaac    1080 attttttaaa cagcaaaaaa aaaaaaaaaa aa                                  1112

<210> SEQ ID NO 9
<211> LENGTH: 478
<212> TYPE: DNA
<213> ORGANISM: Homo sapiens

<400> SEQUENCE: 9
ccccagcccc actcacccac cctccttccc accagcctgc tctccgcagg cccactgtct      60
ttgggtttaa tgacgtctct tctctgtgga acttcacgat tccttcccac ggtcaactcg     120
ggacctccca gcgaccactg cagcctgcgg acgaggccgg gacttggccg agcggatcct     180
aataagggga aaatggtaaa tgcaaacgtc ccgttacaat tttaccgcca gtgtgctgtc     240
gttccccctc ccctctccg agtcctcgtg ggacacggg ggggtctgta ggaagttggg       300 ccggggttggg ggttgctaga aggcgctggt gttttgctct gagttttaag agatcccttc    360
cttcctcttc ggtgaatgca ggttatttaa actttgggaa atgtactttt agtctgtcat     420
atcaaggcat gagtcactgt cttttttgt gtgaataaat ggtttctagt acaatgga        478

<210> SEQ ID NO 10
<211> LENGTH: 845
<212> TYPE: DNA
<213> ORGANISM: Homo sapiens

<400> SEQUENCE: 10
gcggccgccc gcacgtccgc gggtcccggc cgcgccgccg ccgcgcgccc ctgcccgaga      60
gagctctggc cccgctagcg gggccaggag ccgggcctcc caccgcagcg tccccgccg      120 cgccagtccc cgctagtggt agtatctcgt aatagcttct gtgtgtgagc taccgtggat     180
ctccttccct tctcttgggg gccggggggga aagaaaagga tttaagcaaa ggctccctcg    240
ccctgtgagg gcgagcggca aaggcccggc tgagccccc atgccctcc cctcccgtg        300 taaaaagcct ccttgtgcaa ttgtctttt tttcctttga acgtgcttct ttgtaatgac      360
caaggtaccg atttctgcta agttctccca acaacatgaa actgccatt cacgccgtaa     420 ttctttctgt ctcccttctc tctctctctc tcgctcgctc gctctcgctc tgctctctc     480 tcgctgcgtc tcatttccc ctcccaatcc tctctcccct ctgcaacccc ccagctcgct     540
ggctttctct ctggcttctc tcttttcctc ctccacccac ccccttggt ttgacaattt     600 tgtcttaagt gtttctcaaa agaggttact ttagttagca tgcgcgctgt gggcaattgt    660
tacaagtgtt cttaggttta ctgtgaagag aatgtattct gtatccgtga attgctttat    720 ggggggagg gagggctaat tatataattt gttgttcctc tatactttgt tctgttgtct     780
gcgcctgaaa agggcggaag agttacaata aagtttacaa gcgagaaccc gaaaaaaaaa    840
aaaaa                                                                845

<210> SEQ ID NO 11
<211> LENGTH: 1721
<212> TYPE: DNA
<213> ORGANISM: Homo sapiens

<400> SEQUENCE: 11
caccagcaca gcaaacccgc cgggatcaaa gtgtaccagt cggcagcatg gctacgaaat       60
```

| | |
|---|---|
| gtgggaattg tggacccggc tactccaccc ctctggaggc catgaaagga cccagggaag | 120 |
| agatcgtcta cctgccctgc atttaccgaa acacaggcac tgaggcccca gattatctgg | 180 |
| ccactgtgga tgttgacccc aagtctcccc agtattgcca ggtcatccac cggctgccca | 240 |
| tgcccaacct gaaggacgag ctgcatcact caggatggaa cacctgcagc agctgcttcg | 300 |
| gtgatagcac caagtcgcgc accaagctgg tgctgcccag tctcatctcc tctcgcatct | 360 |
| atgtggtgga cgtgggctct gagcccgggc cccaaagct gcacaaggtc attgagccca | 420 |
| aggacatcca tgccaagtgc gaactggcct ttctccacac cagccactgc ctggccagcg | 480 |
| gggaagtgat gatcagctcc ctgggagacg tcaagggcaa tggcaaaggg gttttgtgc | 540 |
| tgctggatgg ggagacgttc gaggtgaagg ggacatggga gagacctggg ggtgctgcac | 600 |
| cgttgggcta tgacttctgg taccagcctc gacacaatgt catgatcagc actgagtggg | 660 |
| cagctcccaa tgtcttacga gatggcttca accccgctga tgtggaggct ggactgtacg | 720 |
| ggagccactt atatgtatgg gactggcagc gccatgagat tgtgcagacc ctgtctctaa | 780 |
| aagatgggct tattcccttg gagatccgct tcctgcacaa cccagacgct gcccaaggct | 840 |
| tgtgggctg cgcactcagc tccaccatcc agcgcttcta caagaacgag ggaggtacat | 900 |
| ggtcagtgga aaggtgatc caggtgcccc ccaagaaagt gaagggctgg ctgctgcccg | 960 |
| aaatgccagg cctgatcacc gacatcctgc tctccctgga cgaccgcttc ctctacttca | 1020 |
| gcaactggct gcatggggac ctgaggcagt atgacatctc tgacccacag agaccccgcc | 1080 |
| tcacaggaca gctcttcctc ggaggcagca ttgttaaggg aggccctgtg caagtgctgg | 1140 |
| aggacgagga actaaagtcc cagccagagc ccctagtggt caagggaaaa cgggtggctg | 1200 |
| gaggccctca gatgatccag ctcagcctgg atgggaagcg cctctacatc accacgtcgc | 1260 |
| tgtacagtgc ctgggacaag cagttttacc ctgatctcat cagggaaggc tctgtgatgc | 1320 |
| tgcaggttga tgtagacaca gtaaaaggag ggctgaagtt gaaccccaac ttcctggtgg | 1380 |
| acttcgggaa ggagcccctt ggcccagccc ttgcccatga gctccgctac ctgggggcg | 1440 |
| attgtagctc tgacatctgg atttgaactc caccctcatc acccacactc cctatttggg | 1500 |
| gccctcactt ccttggggac ctggcttcat tctgctctct cttggcaccc gacccttggc | 1560 |
| agcatgtacc acacagccaa gctgagactg tggcaatgtg ttgagtcata tacatttact | 1620 |
| gaccactgtt gcttgttgct cactgtgctg cttttccatg agctcttgga ggcaccaaga | 1680 |
| aataaactcg taaccctgtc cttcaaaaaa aaaaaaaaa a | 1721 |

<210> SEQ ID NO 12
<211> LENGTH: 1061
<212> TYPE: DNA
<213> ORGANISM: Homo sapiens

<400> SEQUENCE: 12

| | |
|---|---|
| ccggagataa cttgagggct atagaggacc ggctaatact ggtcctgaat ttggcttcag | 60 |
| gcctcaccaa ccaagtggcc gtggccttgc cgtcttgccc gtcggccccc ggtgaggcct | 120 |
| ggaccctgg ggtcccggca ccaggcccg cttccgacc ctggcagaag cccaagatct | 180 |
| ggtcctcgc ggagactgcc acaagcccg acacccgcg ccggctcgcc tcccggcgcg | 240 |
| gggggtctc caccgggggg caacggtcgc gccttccgc cctgcagctc tctccgggcc | 300 |
| gccgccgccg ccgccgctca cagactggtc tcagcgccgc tggcaagtt ccgggcttgg | 360 |
| accaaccggc cgtttccagg cccaccgccc ggccccgcc cgcacccgct ctccctgctg | 420 |
| ggctctgccc ctccgcacct gctgggactt cccggagccg cgggccaccc ggctgccgcc | 480 |

```
gccgccttcg ctcggccagc ggagcccgaa ggcggaacag atcgctgtag tgccttggaa      540
gtggagaaaa agttactcaa gacagctttc catcccgtgc ccaggcggcc ccagaaccat      600
ctggacgccg ccctggtctt atcggctctc tcctcatcct agttctttaa aaaaaaacaa      660
aaaaacaaaa aaaactttt ttaatcgttg taataattgt ataaaaaaaa tcgctctgta       720
tagttacaac ttgtaagcat gtccgtgtat aaatacctaa aagcaaaact aaacaaagaa      780
agtaagaaaa agaaataaaa ccagtcctcc tcagccctcc ccaagtcgct tctgtggcac      840
cccgcattcg ctgtgaggtt tgtttgtccg gttgattttg ggggtggag tttcagtgag       900 aataaacgtg tctgcctttg tgtgtgtgta tatatacaga gaaatgtaca tatgtgtgaa      960
ccaaattgta cgagaaagta tctattttg gctaaataaa tgagctgctg ccactttgac      1020
tataaaaaaa aaaaaaaaaa aaaaaaaaaa aaaaaaaaa a                          1061

<210> SEQ ID NO 13
<211> LENGTH: 577
<212> TYPE: DNA
<213> ORGANISM: Homo sapiens

<400> SEQUENCE: 13
tatgagcacc ttcacatgga tccacttgag gaaagaaggt ggaccgaatt tgtaaacggt       60
gtgcagcaat atatcaat tcgttctgag ataatcgcca cttacgctct ctgtggtttt       120
gccaatatcg ggtccctagg aatcgtgatc ggcggactca catccatggc tccttccaga      180
aagcgtgata tcgcctcggg ggcagtgaga gctctgattg cggggaccgt ggcctgcttc      240
atgacagcct gcatcgcagg catactctcc agcactcctg tggacatcaa ctgccatcac      300
gttttagaga atgccttcaa ctccactttc cctggaaccc caaccaaggg tgatagcttg      360
ttgccaaagt ctgttgagca gccctgttgc ccagggtcct ggtgaagtca tcccaggagg      420 aaacccccagt ctgtattctt tgaagggctg ctgcacattg ttgaatccat cgaccttttag    480 ctgcaatggg atctctaata catttgagg tcagccactt ctccagtgga actctgaagt      540
acagatgctg aattttctgc tttggaaaga aaaaaa                                577

<210> SEQ ID NO 14
<211> LENGTH: 456
<212> TYPE: DNA
<213> ORGANISM: Homo sapiens

<400> SEQUENCE: 14
actcggcatg tgatgaacac ccatagttaa gaaaccatgg agcaagaaag cttgtggaaa       60
gtctctctcc ttcctcataa gacatgcaca ctaatacaca tacacaccaa aaaattacac      120
attttaaaac tgctaagctt ggatttaact gaatcatata tcttttatca tgttatccta      180
aaagtgagaa gacataacca agacatggaa ataaatgtga agctggagc cgaagagtca       240 aagagctaaa aaattaagtc tagaacattc tatgaggata gtataaataa aagaaatac       300 agtctagaca tgctgcaagg aaagaagatt ctaaagtccg tttatggagg caattccata      360
tcctttcttg aacgcacatt cagcttaccc cagagagcaa gtgaggcaat ctggcaaaag      420
attaataaag atgtaaaccc ctggaaaaaa aaaaaa                                456

<210> SEQ ID NO 15
<211> LENGTH: 3628
<212> TYPE: DNA
<213> ORGANISM: Homo sapiens
```

<400> SEQUENCE: 15

```
gaattcggca cgagatagtt ttcaggttaa gaaagccaga atctttgttc agccacactg      60
actgaacaga cttttagtgg ggttacctgg ctaacagcag cagcggcaac ggcagcagca     120
gcagcagcag cagcagcagc agcagcaggg ctcctgggat aactcaggca tagttcaaca     180
ctatgggtcc tcctctgaag ctcttcaaaa accagaaata ccaggaactg aagcaggaat     240
gcatcaaaga cagcagactt ttctgtgatc caacatttct gcctgagaat gattctcttt     300
tctacttccg actgcttcct ggaaaggtgg tgtggaaacg tccccaggac atctgtgatg     360
accccatct gattgtgggc aacattagca accaccagct gacccaaggg agactggggc      420
acaagccaat ggtttctgca ttttcctgtt tggctgttca ggagtctcat tggacaaaga     480
caattcccaa ccataaggaa caggaatggg accctcaaaa aacagaaaaa tacgctggga     540
tatttcactt tcgtttctgg cattttggag aatggactga agtggtgatt gatgacttgt     600
tgcccaccat taacggagat ctggtcttct ctttctccac ttccatgaat gagttttgga     660
atgctctgct ggaaaaagct tatgcaaagc tgctaggctg ttatgaggcc ctggatggtt     720
tgaccatcac tgatattatt gtggacttca cgggcacatt ggctgaaact gttgacatgc     780
agaaaggaag atacactgag cttgttgagg agaagtacag gctattcgga gaactgtaca     840
aaacatttac caaaggtggt ctgatctgct gttccattga gtctcccaat caggaggagc     900
aagaagttga aactgattgg ggtctgctga agggccatac ctataccatg actgatattc     960
gcaaaattcg tcttggagag agacttgtgg aagtcttcag tgctgagaag gtgtatatgg    1020
ttcgcctgag aaaccccttg ggaagacagg aatggagtgg ccctggagt gaaatttctg     1080
aagagtggca gcaactgact gcatcagatc gcaagaacct ggggcttgtt atgtctgatg    1140
atggagagtt ttggatgagc ttggaggact tttgccgcaa cttttcacaaa ctgaatgtct    1200
gccgcaatgt gaacaaccct atttttggcc gaaaggagct ggaatcggtg ttgggatgct    1260
ggactgtgga tgatgatccc ctgatgaacc gctcaggagg ctgctataac aaccgtgata    1320
ccttcctgca gaatccccag tacatcttca ctgtgcctga ggatgggcac aaggtcatta    1380
tgtcactgca gcagaaggac ctgcgcactt accgccgaat gggaagacct gacaattaca    1440
tcattggctt tgagctcttc aaggtggaga tgaaccgcaa attccgcctc caccacctct    1500
acatccagga gcgtgctggg acttccacct atattgacac ccgcacagtg tttctgagca    1560
agtacctgaa gaagggcaac tatgtgcttg tcccaaccat gttccagcat ggtcgcacca    1620
gcgagtttct cctgagaatc ttctctgaag tgcctgtcca gctcagggaa ctgactctgg    1680
acatgcccaa aatgtcctgc tggaacctgg ctcgtggcta cccgaaagta gttactcaga    1740
tcactgttca cagtgctgag gacctggaga agaagtatgc caatgaaact gtaaacccat    1800
atttggtcat caaatgtgga aaggaggaag tccgttctcc tgtccagaag aatacagttc    1860
atgccatttt tgacacccag gccattttct acagaaggac cactgacatt cctattatag    1920
tacaggtctg gaacagccga aaattctgtg atcagttctt ggggcaggtt actctggatg    1980
ctgaccccag cgactgccgt gatctgaagt ctctgtacct gcgtaagaag ggtggtccaa    2040
ctgccaaagt caagcaaggc cacatcagct tcaaggttat ttccagcgat gatctcactg    2100
agctctaaat ctgcaatccc agagaatcct gacaaagcgt gccaccctt tattttccgt     2160
caggtgccag gtcttagtta agattcacaa tcttagaaa gaatgagatt cacaataatt     2220
aactcttcct ctcttctgat aaattcccca tacctcccaa tccaagtagc atctgtagct    2280
acataaccta tatcctcca gcagctggac atggggagcg acagtcctat ctagacatca    2340
```

```
tacacatttg ccaagaaagg atctctgggg cttccggggg tgagattcaa gcaggacaat    2400
aacaagaggc tggacaccct acagatgtct ttgatgtttt cagttgtttg atatatctcc    2460
cctgtagggc atgttgagga aggaggaggg ctgatcaagg ccaagctggt ctagcctgac    2520
atcctagctc ctgactgaac actatagact tcccagcagc attttcaccc agcagccaga    2580
gccggcttta agtccccaac ccttacagac accactgcca ccaccaccaa ccacgaccac    2640
caccaccacc accactcacc accatcatca cctccggaaa gtgtagtcct gccctaaccc    2700
taaccccaag tcaccccca cagtaaattt taccttcatg ttgagaaagc ttcctggtgc     2760
ttaatcaaga gctggagttc aatgagtcct agacagtgag aggggcctga gcttcagctc    2820
aatggaagcc tgctgtgtgc tcacaagacg gaaaagtgga agaagctgca gtgggagaca    2880
aagcctcggt cccccaccca tccacacaca cctacactca cacacgcgca catgggcgcg    2940
caacggaact accatttcag gcagtcagtg ggcaagagga agataagta agtaccatac     3000 acaccttaaa agatgaggag aattcatcca gacatattac agccagtttg ggcccctga     3060 cttgcaatgt gaaacctctt cgcttgctgc taggtttaca aacaagccca ttgttcctgt    3120
gcctcctaat attcatttgt tactgaagga ccccatctgg ggacttgaga ctttggtccc    3180
agcccagacg cctcagactg gtctcaaagt caagcaaggc ttcacatcag ctgcaagtgt    3240
tagtttgcca gcgcatgatc tcactgagct tctacagaat ctgcaatccc agagtcaatc    3300
atgacgaaat gtacgtccca ccatcttaac ctatcaactt tctgcccctc cttcaaggcc    3360
cagtataaat gccacctcct ccatgaagcc ttccctaatt ccaccccaaa ccccaccttt    3420
caacaatatt tcaacgcttc tgcaatgatg aaaagaaac atagttgtag tacttagcct    3480
acctagacca gcaagcattc attttagct cgctcatttt ttaccatgtt ttccagtctg    3540
tttaacttct gcagtgcctt cactacactg ccttacataa accaaatcac aataaagttc    3600
atattcagta caattaaaaa aaaaaaaa                                       3628
```

<210> SEQ ID NO 16
<211> LENGTH: 1580
<212> TYPE: DNA
<213> ORGANISM: Homo sapiens

<400> SEQUENCE: 16

```
tatgcaagtg tttaacagat gcttcactat taaaatattt tccccccaag tctcaaatat      60
tgaagaatct ctaaccaggg acaccagtcc ctacgaagac cttgggcgat tttgaagtgc    120
gggcacctcg attccccgaa tctgtagtgt ggctggtatc ggtgttcccc tggtttaact    180
agcctgtttg aaggcacaga tcattcatgg ggaagtataa ccgaatccag tcctctccac    240
cgcctgggga tcttcacttt cgcagtctac gactgcctgt gactccagaa agacaaactg    300
cagattggcc aagatgggga aattgaggca gagaagccaa gacatgtgct aaaggtcatg    360
caggctatga atggagctgg aatgtgaacg caggccatat gaccccagag ccatgttct     420 tgaacccta gaaagacagc agcaacacac ctggtgcagc agctgcttag ttggagtggc    480
tgacaaggag agaatgattt ccaggaagag cggaacacat atggaaggcc ttagcttatc    540
tttagcgcct catacacccg ttctggactt cagaaaggcc agtgagtggg attaggcctc    600
agagatagga tgtcagtccc agtgagggat ggcctagagc attctttaat tctttccttt    660
gggtcacaca taagaaacaa ttttccagca ctgatgagtg ttattaacaa tgagatggga    720
tagaatttag ttttccctat ggctgtgctt caaaaataga aaagctgtct tttctctgga    780
```

```
atgattgaat gaagctctgg ggaggaaaag gtggattggc agatctctta aaggaagctt    840
ctccttctag gcactattct aaggcttaat attttaactc cctatattaa cctagttcaa    900
ctaaacagtg atctgagtaa ttttattttt attaaagctc agatcaaaat gccattaaca    960
ttgattgaga aaatcaaagg aatctttgat gtgagtggtt aaattgctga attatttcag   1020
tcccataccc tcacagcatg agtacctgat ctgatagact tctttggaat tccttttttg   1080
tttgagacag agtcttgctc tgtcgcccag gctggagtgc agcggtgtga tctcaaccat   1140
tgcaacctcc acctcccagg ttcaggtgat tctcatgcct cagcctcctg agtagctggg   1200
attacagatg tgcaccacca tgcccggcta attattttgt atctttagta gagatgaagt   1260
tttgccatgt gggccaggct gttctcaaac tactggcctc aagtgatctg cccgcctcgg   1320
cctcccagac tgctgggatt acaggcgtga ggcaccgtgc ctggctggga ttccataata   1380
aatccctctg tgtctatttc ttttttcaaa tataattttc ttcatttcca aacatcatct   1440
ttaagactcc aaggattttt ccaggcacag tggctcatac ctgtaatccc attgcttgga   1500
gaggccaagg tggaagttca tttgaggcca ggagttcgag accaggtggg caacatagtg   1560
aaaccttgtc tctacaacat                                               1580

<210> SEQ ID NO 17
<211> LENGTH: 809
<212> TYPE: DNA
<213> ORGANISM: Homo sapiens

<400> SEQUENCE: 17 tgttttatata actgtgttcg ttttgttgt tccgtcccgt cgtccttgta gactctcatc     60
ctcgtgtgtt ttggaccctc caggggtgac atcgggtctt gtgttcagct ctcctggact    120
gttattcctt gtccgcgtgt tcgtgttaga cattgtccac gatctgtatc atgcctatgt    180
ctcactttgg tctcttattt cagcgtgaac actatagttc caagtttgtt cggataattc    240
tgattccttgt caccagcgtg agatttcaac agaacttgtt tggaacaaat actcacttaa    300
aacttcagca gaagaaaaat tacttagtcc ttaggccaac caatttaact gcagtgtcat    360
gtttcacagg ccttcctaca tttagaaatc gtcacacagc tgtgataaga gtagattatt    420
ttactatgaa ataattctga atagatgaaa gcataaaatg tgagaaactg aatgtattat    480
tcaggaagaa tactgagtgc cttcattaa ctaaagttga atgtaaaagt caatttgcac    540
ttctttataa tcctctggtt tagaattata aattgttaaa accttgataa ttgtcattta    600
attatatttc aggtgtcctg aacaggtcac tagactctac attgggcagc ctttaaatat    660
gattctttgt aatgctaaat agcctttttt tctcttttta ctgcaactta atatttctat    720
ttagaacaca gaaaatgaaa atatttgaaa taagttgtac atttgatgac aaataaatca    780
ctattaaaat aaaaaaaaaa aaaaaaaaa                                      809

<210> SEQ ID NO 18
<211> LENGTH: 488
<212> TYPE: DNA
<213> ORGANISM: Homo sapiens
<220> FEATURE:
<221> NAME/KEY: misc_feature
<222> LOCATION: (95)..(95)
<223> OTHER INFORMATION: a or g or c or t/u

<400> SEQUENCE: 18
aggaacccct gtgggaaagg tttaaaccta aaacagtgcc cccctttggct cctcctccct     60
tggcggaatg ggttcctgga ccatgtgcat ttcantgggc catgggattt acatttcctt    120
```

```
gcatccccag gtggtttgat ccctgccagg gccccttcct tcctgctcat ggttttcagg    180
gggcctgatc atggaaagta aggggggttgg gccttcccectt ttggggg tga accctgactc    240 catcccccta ttgcccccct aaccaatcat gcaaactttt ccccccctgg ggtaattcac    300
cagttaaaaa aagcttttt taaatgtttt gttttggggg ggggcaggg cccccttttt    360 gttttttaa ggagttggtt ttggttttg gctgatgttt tgttttttaa catgccccca    420
gtttgtaagg ccaaaggtaa aaaaaaaaaa aaaaaaaaa aaaaaaaaa aaaaaaaaa    480 aaaaaaaa                                                              488
```

<210> SEQ ID NO 19
<211> LENGTH: 463
<212> TYPE: DNA
<213> ORGANISM: Homo sapiens

<400> SEQUENCE: 19

```
taagcttttaa aggctctgtg ttagggcata gtctagaaac atggggccca agggcaccgg     60
gaaaacttac aagggaaga gatggaactg ggagggttca agctaccagt tccatctctc    120
catgttttag agaattgggg cactaagtca gccaggtaag gtcaggtcag aggagggccc    180
ggatgaagca tgagatgcag agggacagtg cgtgaatgga gaccttgggt agcaccaacg    240
tgtagcggca gaggtggggt ggatgtggct gatgtcaggg agagaatggg gagcatgcac    300
agggctcagt cttatacata cattgaaaat cctttagcct ttcaaagatt attaaccaa    360 atcacctttc ttgcttactc cagatgcctc agcctctgat ataattgcta agtatctgcc    420
gtgttaaaaa taaacatttg agaatcaaaa aaaaaaaaaa aaa                    463
```

<210> SEQ ID NO 20
<211> LENGTH: 2148
<212> TYPE: DNA
<213> ORGANISM: Homo sapiens

<400> SEQUENCE: 20

```
gcttcagggt acagctcccc cgcagccaga agccgggcct gcagcgcctc agcaccgctc     60
cgggacaccc cacccgcttc ccaggcgtga cctgtcaaca gcaacttcgc ggtgtggtga    120
actctctgag gaaaaaccat tttgattatt actctcagac gtgcgtggca acaagtgact    180
gagacctaga atccaagcg ttggaggtcc tgaggcagc ctaagtcgct tcaaaatgga    240
acgaaggcgt tgtgggggtt ccattcagag ccgatacatc agcatgagtg tgtggacaag    300
cccacgagac cttgtggagc tggcagggca gagcctgctg aaggatgagg ccctggccat    360
tgccgccctg gagttgctgc ccagggagct cttcccgcca ctcttcatgg cagcctttga    420
cgggagacac agccagaccc tgaaggcaat ggtgcaggcc tggcccttca cctgcctccc    480
tctgggagtg ctgatgaagg acaacatct tcacctggag accttcaaag ctgtgcttga    540
tggacttgat gtgctccttg cccaggaggt tcgcccagg aggtggaaac ttcaagtgct    600
ggatttacgg aagaactctc atcaggactt ctggactgta tggtctggaa acagggccag    660
tctgtactca tttccagagc cagaagcagc tcagcccatg acaaagaagc gaaaagtaga    720
tggtttgagc acagaggcag agcagccctt cattccagta gaggtgctcg tagacctgtt    780
cctcaaggaa ggtgcctgtg atgaattgtt ctcctacctc attgagaaag tgaagcgaaa    840
gaaaaatgta ctacgcctgt gctgtaagaa gctgaagatt tttgcaatgc ccatgcagga    900
tatcaagatg atccctgaaaa tggtgcagct ggactctatt gaagatttgg aagtgacttg    960
```

```
tacctggaag ctacccacct tggcgaaatt ttctccttac ctgggccaga tgattaatct    1020
gcgtagactc ctcctctccc acatccatgc atcttcctac atttccccgg agaaggaaga    1080
gcagtatatc gcccagttca cctctcagtt cctcagtctg cagtgcctgc aggctctcta    1140
tgtggactct ttatttttcc ttagaggccg cctggatcag ttgctcaggc acgtgatgaa    1200 cccttggaa accctctcaa taactaactg ccggctttcg gaaggggatg tgatgcatct     1260
gtcccagagt cccagcgtca gtcagctaag tgtcctgagt ctaagtgggg tcatgctgac    1320
cgatgtaagt cccgagcccc tccaagctct gctggagaga gcctctgcca ccctccagga    1380 cctggtctt  tgatgagtgtg ggatcacgga tgatcagctc cttgccctcc tgccttccct    1440
gagccactgc tcccagctta aaccttaag cttctacggg aattccatct ccatatctgc     1500
cttgcagagt ctcctgcagc acctcatcgg gctgagcaat ctgacccacg tgctgtatcc    1560 tgtcccctg gagagttatg aggacatcca tggtaccctc cacctggaga ggcttgccta     1620
tctgcatgcc aggctcaggg agttgctgtg tgagttgggg cggccagca tggtctggct     1680 tagtgccaac ccctgtcctc actgtgggga cagaaccttc tatgacccgg agcccatcct    1740
gtgcccctgt ttcatgccta actagctggg tgcacatatc aaatgcttca ttctgcatac    1800
ttggacacta aagccaggat gtgcatgcat cttgaagcaa caaagcagcc acagtttcag    1860
acaaatgttc agtgtgagtg aggaaaaacat gttcagtgag gaaaaacat tcagacaaat    1920 gttcagtgag gaaaaaagg ggaagttggg gataggcaga tgttgacttg aggagttaat     1980
gtgatctttg gggagataca tcttatagag ttagaaatag aatctgaatt tctaaaggga    2040
gattctggct tgggaagtac atgtaggagt taatccctgt gtagactgtt gtaaagaaac    2100
tgttgaaaat aaagagaagc aatgtgaagc aaaaaaaaaa aaaaaaaa                 2148
```

<210> SEQ ID NO 21
<211> LENGTH: 707
<212> TYPE: DNA
<213> ORGANISM: Homo sapiens
<220> FEATURE:
<221> NAME/KEY: misc_feature
<222> LOCATION: (17)..(17)
<223> OTHER INFORMATION: a or g or c or t/u
<220> FEATURE:
<221> NAME/KEY: misc_feature
<222> LOCATION: (83)..(83)
<223> OTHER INFORMATION: a or g or c or t/u

<400> SEQUENCE: 21

```
aacacagccc taccaancaa tgatgaccag tggaaaacaa tgaagtcacc aaaccctgga     60
cagggctcat gctccaggac aanttgctgt ggcgtaaatg gtccatcaga ctggcaaaaa    120
tacacatctg ccttccggac tgagaataat gatgctgact atccctggcc tcgtcaatgc    180
tgtgttatga acaatcttaa agaacctctc aacctggagg cttgtaaact aggcgtgcct    240 ggttttatc acaatcaggg ctgctatgaa ctgatctctg gtccaatgaa ccgacacgcc     300
tggggggttg cctggtttgg atttgccatt ctctgctgga cttttgggt tctcctgggt     360 accatgttct actggagcag aattgaatat taagcataaa gtgttgccac catacctcct    420
tccccgagtg actctggatt tggtgctgga accagctctc tcctaatatt ccacgtttgt    480
gccccacact aacgtgtgtg tcttacattg ccaagtcaga tggtacggac ttcctttagg    540
atctcaggct tctgcagttc tcatgactcc tactttcat cctagtctag cattctgcaa     600
catttatata gactgttgaa aggagaattt gaaaatgca taataactac ttccatccct    660 gcttatttt aatttgggaa ataaatacatt tcgaaggaa aaaaaaa                    707
```

<210> SEQ ID NO 22
<211> LENGTH: 2832
<212> TYPE: DNA
<213> ORGANISM: Homo sapiens

<400> SEQUENCE: 22

```
ggcacgaggg cgaaattgag gtttcttggt attgcgcgtt tctcttcctt gctgactctc      60
cgaatggcca tggactcgtc gcttcaggcc cgcctgtttc ccggtctcgc tatcaagatc     120
caacgcagta atggtttaat tcacagtgcc aatgtaagga ctgtgaactt ggagaaatcc     180
tgtgtttcag tggaatgggc agaaggaggt gccacaaagg gcaaagagat tgattttgat     240
gatgtggctg caataaaccc agaactctta cagcttcttc ccttacatcc gaaggacaat     300
ctgcccttgc aggaaaatgt aacaatccag aaacaaaaac ggagatccgt caactccaaa     360
attcctgctc caaaagaaag tcttcgaagc cgctccactc gcatgtccac tgtctcagag     420
cttcgcatca cggctcagga gaatgacatg gaggtggagc tgcctgcagc tgcaaactcc     480
cgcaagcagt tttcagttcc tcctgccccc actaggcctt cctgccctgc agtggctgaa     540
ataccattga ggatggtcag cgaggagatg gaagagcaag tccattccat ccgaggcagc     600
tcttctgcaa accctgtgaa ctcagttcgg aggaaatcat gtcttgtgaa ggaagtggaa     660
aaaatgaaga caagcgaga agagaagaag gcccagaact ctgaaatgag aatgaagaga     720
gctcaggagt atgacagtag ttttccaaac tgggaatttg cccgaatgat taagaatttt     780
cgggctactt tggaatgtca tccacttact atgactgatc ctatcgaaga gcacagaata     840
tgtgtctgtg ttaggaaacg cccactgaat aagcaagaat tggccaagaa agaaattgat     900
gtgatttcca ttcctagcaa gtgtctcctc ttggtacatg aacccaagtt gaaagtggac     960
ttaacaaagt atctggagaa ccaagcattc tgctttgact ttgcatttga tgaaacagct    1020
tcgaatgaag ttgtctacag gttcacagca aggccactgg tacagacaat ctttgaaggt    1080
ggaaaagcaa cttgttttgc atatggccag acaggaagtg gcaagacaca tactatgggc    1140
ggagacctct ctgggaaagc ccagaatgca tccaaaggga tctatgccat ggcctcccgg    1200
gacgtcttcc tcctgaagaa tcaaccctgc taccggaagt tgggcctgga agtctatgtg    1260
acattcttcg agatctacaa tgggaagctg tttgacctgc tcaacaagaa ggccaagctg    1320
cgcgtgctga ggacggcaa gcaacaggtg caagtggtgg ggctgcagga gcatctggtt    1380
aactctgctg atgatgtcat caagatgatc gacatgggca gcgcctgcag aacctctggg    1440
cagacatttg ccaactccaa ttcctcccgc tcccacgcgt gcttccaaat tattcttcga    1500
gctaaaggga gaatgcatgg caagttctct ttggtagatc tggcagggaa tgagcgaggc    1560
gcggacactt ccagtgctga ccggcagacc cgcatggagg gcgcagaaat caacaagagt    1620
ctcttagccc tgaaggagtg catcagggcc ctgggacaga caaggctca caccccgttc    1680
cgtgagagca gctgacaca ggtgctgagg gactccttca ttggggagaa ctctaggact    1740
tgcatgattg ccacgatctc accaggcata agctcctgtg aatatacttt aaacaccctg    1800
agatatgcag acagggtcaa ggagctgagc ccccacagtg ggcccagtgg agagcagttg    1860
attcaaatgg aaacagaaga gatggaagcc tgctctaacg gggcgctgat tccaggcaat    1920
ttatccaagg aagaggagga actgtcttcc cagatgtcca gctttaacga agccatgact    1980
cagatcaggg agctggagga aaggctatg gaagagctca aggagatcat acagcaagga    2040
ccagactggc ttgagctctc tgagatgacc gagcagccag actatgacct ggagaccttt    2100
```

-continued

```
gtgaacaaag cggaatctgc tctggcccag caagccaagc atttctcagc cctgccagat    2160
gtcatcaagg ccttgcgcct ggccatgcag ctggaagagc aggctagcag acaaataagc    2220
agcaagaaac ggcccagtg acgactgcaa ataaaaatct gtttggtttg acacccagcc     2280
tcttccctgg ccctccccag agaactttgg gtacctggtg ggtctaggca gggtctgagc    2340
tgggacaggt tctggtaaat gccaagtatg ggggcatctg ggcccagggc agctggggag    2400
ggggtcagag tgacatggga cactcctttt ctgttcctca gttgtcgccc tcacgagagg    2460
aaggagctct tagttaccct tttgtgttgc ccttcttttcc atcaaggga atgttctcag    2520 catagagctt tctccgcagc atcctgcctg cgtggactgg ctgctaatgg agagctccct    2580
ggggttgtcc tggctctggg gagagagacg gagcctttag tacagctatc tgctggctct    2640
aaaccttcta cgcctttggg ccgagcactg aatgtcttgt actttaaaaa aatgtttctg    2700
agacctcttt ctactttact gtctccctag agatcctaga ggatccctac tgttttctgt    2760
tttatgtgtt tatacattgt atgtaacaat aaagagaaaa aataaaaaaa aaaaaaaaaa    2820
aaaaaaaaaa aa                                                        2832
```

<210> SEQ ID NO 23
<211> LENGTH: 670
<212> TYPE: DNA
<213> ORGANISM: Homo sapiens
<220> FEATURE:
<221> NAME/KEY: misc_feature
<222> LOCATION: (14)..(14)
<223> OTHER INFORMATION: a or g or c or t/u
<220> FEATURE:
<221> NAME/KEY: misc_feature
<222> LOCATION: (19)..(19)
<223> OTHER INFORMATION: a or g or c or t/u
<220> FEATURE:
<221> NAME/KEY: misc_feature
<222> LOCATION: (37)..(37)
<223> OTHER INFORMATION: a or g or c or t/u
<220> FEATURE:
<221> NAME/KEY: misc_feature
<222> LOCATION: (113)..(113)
<223> OTHER INFORMATION: a or g or c or t/u

<400> SEQUENCE: 23

```
atcggacttc ggtnaactnt ggcaaggatt ggacagncta ggtaggctaa atgtgtgctc      60
tgtccctgtt tgcttcaaca gaggagcaag cctcagctga gaaggagggc acntggaaca    120
cctagctcct cccgtgattc cccaaaccca taacattctt ccatagggct ggaaccagtg    180
ccccgtcctg acagggatga aaagtgaacc cctcaggtca ggagaggcca gagttgaggt    240
tctgccactt cctgtccctg gggagccact caagttacca gggctaccgg ctgaaataaa    300
tcttttccgg gtagggtcaa gggcagtgtg ttccaaggca actgatgtag gccagttgcg    360
tgactccagg tttgtcctgg tactcagtgg gtccaatcac ctggcattga tcacctggca    420
ttgatcagca cccaccccac ccctgaggct tgcccagccc caggccctc agatccctgc    480 tcttcctgcc tttcctgccc atgtgtcacc cagcacccaa ggttcagtga cacagggtgg    540
tttggagctg gtcactgtca tagcagctgt gatttcacaa ggaagggtgc tgcaggggga    600
cctggttgat ggggagtggg aaggggaagg aataaagaga tcttcctcag gtaaaaaaaa    660
aaaaaaaaaa                                                           670
```

<210> SEQ ID NO 24
<211> LENGTH: 964
<212> TYPE: DNA
<213> ORGANISM: Homo sapiens

<400> SEQUENCE: 24

```
acctcgtttg ctcccagtta cttcttatct ggagcagtaa tgtagtccac ttcactcatg      60
cctaccccgc gtgtctcgtc tcctgacatg tctcacagac gctcctgaag ttaggtcatt     120
acctaaccca tagttattta ccttgaaaga tgggtctccg cacttggaaa ggtttcaaga     180
cttgatactg caataaatta tggctcttca cctgggcgcc aactgctgat caacgaaatg     240
cttgttgaat caggggcaaa cggagtacag acgtctcaag actgaaacgg ccccattgcc     300
tggtctagta gcggatctca ctcagccgca gacaagtaat cactaacccg ttttattcta     360
ttcctatctg tggatgtgta aatggctggg gggccagccc tggataggtt tttatgggaa     420
ttctttacaa taaacatagc ttgtaacttg agatctacaa atccattcat cctgattggg     480
catgaaatcc atggtcaaga ggacaagtgg aaagtgagag gaaggtttg ctagacacct      540 tcgcttgtta tcttgtcaag atagaaaaga tagtatcatt tcacccttgc cagtaaaaac     600
ctttccatcc acccattctc agcagactcc agtattggca cagtcactca ctgccattct     660
cacactataa caagaaaaga aatgaagtgc ataagtctcc tgggaaaaga accttaaccc     720
cttctcgtgc catgactggt gatttcatga ctcataagcc cctccgtagg catcattcaa     780
gatcaatggc ccatgcatgc tgtttgcagc agtcaattga gttgaattag aattccaacc     840
atacatttta aaggtatttg tgctgtgtgt atattttgat aaaatgttgt gacttcatgg     900
caaacaggtg gatgtgtaaa aatggaataa aaaaaaaaaa agagtcaaaa aaaaaaaaaa     960
aatt                                                                  964
```

<210> SEQ ID NO 25
<211> LENGTH: 1568
<212> TYPE: DNA
<213> ORGANISM: Homo sapiens

<400> SEQUENCE: 25

```
ggcgcccaag ccgccgccgc cagatcggtg ccgattcctg ccctgccccg accgccagcg      60
cgaccatgtc ccatcactgg gggtacggca aacacaacgg acctgagcac tggcataagg     120
acttccccat tgccaaggga gagcgccagt ccctgttga catcgacact catacagcca      180
agtatgaccc ttccctgaag cccctgtctg tttcctatga tcaagcaact tccctgagga     240
tcctcaacaa tggtcatgct ttcaacgtgg agtttgatga ctctcaggac aaagcagtgc     300
tcaagggagg accctggat ggcacttaca gattgattca gtttcacttt cactggggtt     360
cacttgatgt acaaggttca gagcatactg tggataaaaa gaaatatgct gcagaacttc     420
acttggttca ctggaacacc aaatatgggg attttgggaa agctgtgcag caacctgatg     480
gactggccgt tctaggtatt tttttgaagg ttggcagcgc taaacgggc cttcagaaag      540 ttgttgatgt gctggattcc attaaaacaa agggcaagag tgctgacttc acaaactttg     600
cagctcgtgg cctccttcct gaatccctgg attactggac ctaccaggc tcactgacca     660 cccctcctct tctggaatgt gtgacctgga ttgtgctcaa ggaacccatc agcgtcagca     720
gcgagcaggt gttgaaattc cgtaaactta acttcaatgg ggagggtgaa cccgaagaac     780
tgatggtgga caactggcgc ccagctcagc cactgaagaa caggcaaatc aaagcttcct     840
tcaaataaga tggtcccata gtctgtatcc aaataatgaa tcttcgggtg tttcccttta     900
gctaagcaca gatctacctt ggtgatttgg accctggttg ctttgtgtct agttttctag     960
acccttcatc tcttacttga tagacttact aataaaatgt gaagactaga ccaattgtca    1020
```

-continued

| | |
|---|---|
| tgcttgacac aactgctgtg gctggttggt gctttgttta tggtagtagt ttttctgtaa | 1080 |
| cacagaatat aggataagaa ataagaataa agtaccttga ctttgttcac agcatgtagg | 1140 |
| gtgatgagca ctcacaattg ttgactaaaa tgctgccttt aaaacatagg aaagtagaat | 1200 |
| ggttgagtgc aaatccatag cacaagataa attgagctag ttaaggcaaa tcaggtaaaa | 1260 |
| tagtcatgat tctatgtaat gtaaaccaga aaaataaat gttcatgatt tcaagatgtt | 1320 |
| atattaaaga aaactttaa aaattattat atatttatag caaagttatc ttaaatatga | 1380 |
| attctgttgt aatttaatga cttttgaatt acagagatat aaatgaagta ttatctgtaa | 1440 |
| aaattgttat aattagagtt gtgatacaga gtatatttcc attcagacaa tatatcataa | 1500 |
| cttaataaat attgtatttt agatatattc tctaataaaa ttcagaattc taaaaaaaaa | 1560 |
| aaaaaaaa | 1568 |

<210> SEQ ID NO 26
<211> LENGTH: 1964
<212> TYPE: DNA
<213> ORGANISM: Homo sapiens

<400> SEQUENCE: 26

| | |
|---|---|
| ggcacgaggc atggaggcgc tgctgctggg cgcggggttg ctgctgggcg cttacgtgct | 60 |
| tgtctactac aacctggtga aggccccgcc gtgcggcggc atgggcaacc tgcggggccg | 120 |
| cacggccgtg gtcacgggtg agtgcggagg cgggtgagtg cgagctggcg gggcgcgcgg | 180 |
| agaggaggcc gggccggcgg tagcagcggc ccgccgggct cagctcagct cggctcccgc | 240 |
| ccgcggtccg caggcgccaa cagcggcatc ggaaagatga cggcgctgga gctggcgcgc | 300 |
| cggggagcgc gcgtggtgct ggcctgccgc agccaggagc gcggggaggc ggctgccttc | 360 |
| gacctccgcc aggagagtgg gaacaatgag gtcatcttca tggccttgga cttggccagt | 420 |
| ctggcctcgg tgcgggcctt tgccactgcc tttctgagct ctgagccacg gttggacatc | 480 |
| ctcatccaca atgccggtat cagttcctgt ggccggaccc gtgaggcgtt taacctgctg | 540 |
| cttcgggtga accatatcgg tccctttctg ctgacacatc tgctgctgcc ttgcctgaag | 600 |
| gcatgtgccc ctagccgcgt ggtggtggta gcctcagctg cccactgtcg gggacgtctt | 660 |
| gacttcaaac gcctggaccg cccagtggtg ggctggcggc aggagctgcg ggcatatgct | 720 |
| gacactaagc tggctaatgt actgtttgcc cgggagctcg ccaaccagct tgaggccact | 780 |
| ggcgtcacct gctatgcagc ccacccaggg cctgtgaact cggagctgtt cctgcgccat | 840 |
| gttcctggat ggctgcgccc acttttgcgc ccattggctt ggctggtgct ccgggcacca | 900 |
| agaggggtg cccagacacc cctgtattgt gctctacaag agggcatcga gcccctcagt | 960 |
| gggagatatt ttgccaactg ccatgtggaa gaggtgcctc cagctgcccg agacgaccgg | 1020 |
| gcagcccatc ggctatggga ggccagcaag aggctggcag ggcttgggcc tggggaggat | 1080 |
| gctgaacccg atgaagaccc ccagtctgag gactcagagg ccccatcttc tctaagcacc | 1140 |
| ccccacccctg aggagcccac agtttctcaa ccttacccca gccctcagag ctcaccagat | 1200 |
| ttgtctaaga tgacgcaccg aattcaggct aaagttgagc ctgagatcca gctctcctaa | 1260 |
| ccctcaggcc aggatgcttg ccatggcact tcatggtcct tgaaaacctc ggatgtgtgc | 1320 |
| gaggccatgc cctggacact gacgggtttg tgatcttgac ctccgtggtt actttctggg | 1380 |
| gccccaagct gtgccctgga catctctttt cctggttgaa ggaataatgg gtgattattt | 1440 |
| cttcctgaga gtgacagtaa ccccagatgg agagataggg gtatgctaga cactgtgctt | 1500 |
| ctcggaaatt tggatgtagt attttcaggc cccacccctta ttgattctga tcagctctgg | 1560 |

| | |
|---|---|
| agcagaggca gggagtttgc aatgtgatgc actgccaaca ttgagaatta gtgaactgat | 1620 |
| cccctttgcaa ccgtctagct aggtagttaa attacccccca tgttaatgaa gcggaattag | 1680 |
| gctcccgagc taagggactc gcctagggtc tcacagtgag taggaggagg gcctgggatc | 1740 |
| tgaacccaag ggtctgaggc cagggccgac tgccgtaaga tgggtgctga gaagtgagtc | 1800 |
| agggcagggc agctggtatc gaggtgcccc atgggagtaa ggggacgcct tccgggcgga | 1860 |
| tgcagggctg gggtcatctg tatctgaagc ccctcggaat aaagcgcgtt gaccgccaaa | 1920 |
| aaaaaaaaaa aaaaaaaaa aaaaaaaaaa aaaaaaaaa aaaa | 1964 |

<210> SEQ ID NO 27
<211> LENGTH: 953
<212> TYPE: DNA
<213> ORGANISM: Homo sapiens

<400> SEQUENCE: 27

| | |
|---|---|
| agcggtggag aaaaggcaga accagagtag agattgacag tgagctgagc caatcaggct | 60 |
| gtgaatctgc agcagtgatc ccaggtcctc caattaatac taagagagtg gaccagggcc | 120 |
| cctgaggaag acagatggca gggacagcgc gccatgaccg agagatggcg atccaggcca | 180 |
| agaaaaagct caccacggcc accaacccca ttgaaagact ccgactgcag tgcctggcca | 240 |
| ggggctctgc tgggatcaaa ggacttggca gagtgtttag aattatggat gacgataata | 300 |
| atcgaaccct tgattttaaa gaatttatga agggttaaa tgattatgct gtggtcatgg | 360 |
| aaaaagaaga ggtggaagaa cttttccgga ggtttgataa agatggaaat ggaacaatag | 420 |
| acttcaatga atttcttctc acattaagac ctccaatgtc cagagccaga aaagaggtaa | 480 |
| tcatgcaagc ttttagaaag ttagacaaga ctggagatgg tgttataaca atcgaagacc | 540 |
| ttcgtgaagt atataatgca aaacaccacc caaagtacca gaatggggaa tggagtgagg | 600 |
| aacaagtatt taggaaattt ctggataact ttgattcacc ctatgacaaa gatggattgg | 660 |
| tgaccccctga ggagttcatg aactactatg caggtgtgag cgcatccatt gacactgatg | 720 |
| tgtacttcat catcatgatg agaaccgcct ggaagcttta agcacatgac ctggggacca | 780 |
| ggccctggga cagccatgtg gctccaaatg actaaatgtc agctcaaaaa ccagaatcgt | 840 |
| atttgatttc acactcatcc taatgttttt ttctgtgtca aaatattgca ttttctgggg | 900 |
| ccaaaaaaca ggcagaaata aaagacattg agtagtcaaa aaaaaaaaaa aaa | 953 |

<210> SEQ ID NO 28
<211> LENGTH: 850
<212> TYPE: DNA
<213> ORGANISM: Homo sapiens

<400> SEQUENCE: 28

| | |
|---|---|
| tagagcatta aaataactat caggcagaag aatctttctt ctcgcctagg atttcagcca | 60 |
| tgcgcgcgct ctctctcttt ctctctcttt tcctctctct ccctctttct agcctggggc | 120 |
| ttgaatttgc atgtctaatt catttactca ccatatttga attggcctga acagatgtaa | 180 |
| atcgggaagg atgggaaaaa ctgcagtcat caacaatgat taatcagctg ttgcaggcag | 240 |
| tgtcttaagg agactggtag gaggaggcat ggaaaccaaa aggccgtgtg tttagaagcc | 300 |
| taattgtcac atcaagcatc attgtcccca tgcaacaacc accaccttat acatcacttc | 360 |
| ctgttttaag cagctctaaa acatagactg aagattatt tttaatatgt tgactttatt | 420 |
| tctgagcaaa gcatcggtca tgtgtgtatt ttttcatagt cccaccttgg agcatttatg | 480 |

| | |
|---|---:|
| tagacattgt aaataaattt tgtgcaaaaa ggactggaaa aatgaactgt attattgcaa | 540 |
| tttttttttg taaaagtagc agtttggtat gagttggcat gcatacaaga tttactaagt | 600 |
| gggataagct aattatactt tttgttgtgg ataaacaaat gcttgttgat agccttttc | 660 |
| tatcaagaaa ccaaggagct aattattaat aacaatcatt gcacactgag tcttagcgtt | 720 |
| tctgatggaa acagtttgga ttgtataata acgccaagcc cagttgtagt cgtttgagtg | 780 |
| cagtaatgaa atctgaatct aaaataaaaa caagattatt tttgtcaaaa aaaaaaaaa | 840 |
| aaaaaaaaaa | 850 |

<210> SEQ ID NO 29
<211> LENGTH: 4670
<212> TYPE: DNA
<213> ORGANISM: Homo sapiens

<400> SEQUENCE: 29

| | |
|---|---:|
| gcggcgcgca cactgctcgc tgggccgcgg ctcccgggtg tcccaggccc ggccggtgcg | 60 |
| cagagcatgg cgggtgcggg cccgaagcgg cgcgcgctag cggcgccggc ggccgaggag | 120 |
| aaggaagagg cgcgggagaa gatgctggcc gccaagagcg cggacggctc ggcgccggca | 180 |
| ggcgagggcg agggcgtgac cctgcagcgg aacatcacgc tgctcaacgg cgtggccatc | 240 |
| atcgtgggga ccattatcgg ctcgggcatc ttcgtgacgc ccacgggcgt gctcaaggag | 300 |
| gcaggctcgc cggggctggc gctggtggtg tgggccgcgt gcggcgtctt ctccatcgtg | 360 |
| ggcgcgctct gctacgcgga gctcggcacc accatctcca aatcgggcgg cgactacgcc | 420 |
| tacatgctgg aggtctacgg ctcgctgccc gccttcctca agctctggat cgagctgctc | 480 |
| atcatccggc cttcatcgca gtacatcgtg gccctggtct tcgccaccta cctgctcaag | 540 |
| ccgctcttcc ccacctgccc ggtgcccgag gaggcagcca agctcgtggc ctgcctctgc | 600 |
| gtgctgctgc tcacggccgt gaactgctac agcgtgaagg ccgccacccg ggtccaggat | 660 |
| gcctttgccg ccgccaagct cctggccctg gccctgatca tcctgctggg cttcgtccag | 720 |
| atcgggaagg gtgatgtgtc caatctagat cccaacttct catttgaagg caccaaactg | 780 |
| gatgtgggga acattgtgct ggcattatac agcggcctct ttgcctatgg aggatggaat | 840 |
| tacttgaatt tcgtcacaga ggaaatgatc aaccctaca gaaacctgcc cctggccatc | 900 |
| atcatctccc tgcccatcgt gacgctggtg tacgtgctga ccaacctggc ctacttcacc | 960 |
| accctgtcca ccgagcagat gctgtcgtcc gaggccgtgg ccgtggactt cgggaactat | 1020 |
| cacctgggcg tcatgtcctg gatcatcccc gtcttcgtgg gcctgtcctg cttcggctcc | 1080 |
| gtcaatgggt ccctgttcac atcctccagg ctcttcttcg tggggtcccg ggaaggccac | 1140 |
| ctgcccctcc atcctctccat gatccaccca cagctcctca ccccgtgcc gtccctcgtg | 1200 |
| ttcacgtgtg tgatgacgct gctctacgcc ttctccaagg acatcttctc cgtcatcaac | 1260 |
| ttcttcagct tcttcaactg gctctgcgtg gccctggcca tcatcggcat gatctggctg | 1320 |
| cgccacagaa agcctgagct tgagcggccc atcaaggtga acctggccct gcctgtgttc | 1380 |
| ttcatcctgg cctgcctctt cctgatcgcc gtctccttct ggaagacacc cgtggagtgt | 1440 |
| ggcatcggct tcaccatcat cctcagcggg ctgcccgtct acttcttcgg ggtctggtgg | 1500 |
| aaaaacaagc ccaagtggct cctccagggc atcttctcca cgaccgtcct gtgtcagaag | 1560 |
| ctcatgcagg tggtccccca ggagacatag ccaggaggcc gagtggctgc ggaggagca | 1620 |
| tgcgcagagc ccagttaaag tagatcacct cctcgaaccc actccggttc cccgcaaccc | 1680 |
| acagctcagc tgcccatccc agtccctcgc cgtccctccc aggtcgggca gtggaggctg | 1740 |

-continued

```
ctgtgaaaac tctggtacga atctcatccc tcaactgagg gccagggacc caggtgtgcc    1800
tgtgctcctg cccaggagca gcttttggtc tccttgggcc cttttttccct tccctccttt    1860 gtttacttat atatatattt ttttttaaact taaattttgg gtcaacttga caccactaag    1920 atgattttt aaggagctgg gggaaggcag gagccttcct ttctcctgcc ccaagggccc    1980
agaccctggg caaacagagc tactgagact tggaacctca ttgctacgac agacttgcac    2040
tgaagccgga cagctgccca gacacatggg cttgtgacat tcgtgaaaac caaccctgtg    2100
ggcttatgtc tctgccttag ggtttgcaga gtggaaactc agccgtaggg tggcactggg    2160 aggggggtggg ggatctgggc aaggtgggtg attcctctca ggaggtgctt gaggccccga    2220
tggactcctg accataatcc tagccctgag acaccatcct gagccaggga acagccccag    2280
ggttgggggg tgccggcatc tccctagct caccaggcct ggcctctggg cagtgtggcc    2340
tcttggctat ttctgtgtcc agttttggag gctgagttct ggttcatgca gacaaagccc    2400
tgtccttcag tcttctagaa acagagacaa gaaaggcaga cacccgcgg ccaggcaccc    2460 atgtgggcgc ccaccctggg ctccacacag cagtgtcccc tgccccagag gtcgcagcta    2520
ccctcagcct ccaatgcatt ggcctctgta ccgcccggca gccccttctg gccggtgctg    2580
ggttcccact cccggcctag gcacctcccc gctctccctg tcacgctcat gtcctgtcct    2640
ggtcctgatg cccgttgtct aggagacaga gccaagcact gctcacgtct gtccgcctg    2700 cgtttggagg cccctgggct ctcacccagt ccccacccgc ctgcagagag ggaactaggg    2760 cacccccttgt ttctgttgtt cccgtgaatt ttttttcgcta tgggaggcag ccgaggcctg    2820
gccaatgcgg cccactttcc tgagctgtcg ctgcctccat ggcagcagcc aaggaccccc    2880
agaacaagaa gaccccccg caggatccct cctgagctcg gggggctctg ccttctcagg    2940
ccccgggctt cccttctccc cagccagagg tggagccaag tggtccagcg tcactccagt    3000
gctcagctgt ggctggagga gctggcctgt ggcacagccc tgagtgtccc aagccgggag    3060
ccaacgaagc cggacacggc ttcactgacc agcggctgct caagccgcaa gctctcagca    3120
agtgcccagc ggagcctgcc gcccccacct gggcaccggg acccctcac catccagtgg    3180 gccccggagaa acctgatgaa cagtttgggg actcaggacc agatgtccgt ctctcttgct    3240
tgaggaatga agacctttat tcaccccctgc ccgttgctt cccgctgcac atggacagac    3300
ttcacagcgt ctgctcatag gacctgcatc cttcctgggg acgaattcca ctcgtccaag    3360
ggacagccca cggtctggag gccgaggacc accagcaggc aggtggactg actgtgttgg    3420 gcaagaccctc ttccctctgg gcctgttctc ttggctgcaa ataaggacag cagctggtgc    3480
cccacctgcc tggtgcattg ctgtgtgaat ccaggaggca gtggacatcg taggcagcca    3540
cggccccggg tccaggagaa gtgctccctg gaggcacgca ccactgcttc ccactggggc    3600 cggcgggggcc cacgcacgac gtcagcctct taccttcccg cctcggctag ggtcctcgg    3660 gatgccgttc tgttccaacc tcctgctctg ggacgtggac atgcctcaag gatacaggga    3720
gccggcggcc tctcgacggc acgcacttgc ctgttggctg ctgcggctgt gggcgagcat    3780
gggggctgcc agcgtctgtt gtggaaagta gctgctagtg aaatggctgg ggccgctggg    3840
gtccgtcttc acactgcgca ggtctcttct gggcgtctga gctggggtgg gagctcctcc    3900
gcagaaggtt ggtggggggt ccagtctgtg atccttggtg ctgtgtgccc cactccagcc    3960
tggggacccc acttcagaag gtaggggccg tgtcccgcgg tgctgactga ggcctgcttc    4020
cccctccccc tcctgctgtg ctggaattcc acagggacca gggccaccgc aggggactgt    4080
```

```
ctcagaagac ttgattttc cgtcccttt tctccacact ccactgacaa acgtccccag    4140
cggtttccac ttgtgggctt caggtgtttt caagcacaac ccaccacaac aagcaagtgc    4200
attttcagtc gttgtgcttt tttgttttgt gctaacgtct tactaattta aagatgctgt    4260
cggcaccatg tttatttatt tccagtggtc atgctcagcc ttgctgctct gcgtggcgca    4320
ggtgccatgc ctgctccctg tctgtgtccc agccacgcag ggccatccac tgtgacgtcg    4380
gccgaccagg ctggacaccc tctgccgagt aatgacgtgt gtggctggga ccttctttat    4440
tctgtgttaa tggctaacct gttacactgg gctgggttgg gtagggtgtt ctggcttttt    4500
tgtgggtttt ttattttaa agaaacactc aatcatccta aaaaaaaaaa aaaaaaaaaa    4560
aaaaaaaaaa aaaaaaaaaa aaaaaaaaaa aaaaaaaaaa aaaaaaaaaa aaaaaaaaaa    4620
aaaaaaaaaa aaaaaaaaaa aaaaaaaaaa aaaaaaaaaa aaaaaaaaaa                4670

<210> SEQ ID NO 30
<211> LENGTH: 176
<212> TYPE: DNA
<213> ORGANISM: Homo sapiens

<400> SEQUENCE: 30
gggacttgga aaggggaact gggatttggg gaggggctgg aggacttccg cacgcttcca      60
cctccttcga cctccactgc gccccacctc cctgcctgtg tgtgttattt caaaggaaaa     120
gaacaaaagg aataaatttt ctaagctctt taaaaaaaaa aaaaaaaaaa aaaaaa         176

<210> SEQ ID NO 31
<211> LENGTH: 2255
<212> TYPE: DNA
<213> ORGANISM: Homo sapiens

<400> SEQUENCE: 31
gcaggctctg cctgtggcca ctagcagaga agctgctgtc cttccaccac cagcaccgga      60
ccacctgctc caagaccagc ctcctggggg gaccaggcac ccggccttca ctggcaccca     120
gggagccgtc ctcagcagcg tcaacatgtc aaggcccagc agcagagcca tttacttgca     180
ccggaaggag tactcccaga acctcacctc agagcccacc ctcctgcagc acagggtgga     240
gcacttgatg acatgcaagc aggggagtca gagagtccag gggcccgagg atgccttgca     300
gaagctgttc gagatggatg cacagggccg ggtgtggagc caagacttga tcctgcaggt     360
cagggacggc tggctgcagc tgctggacat tgagaccaag gaggagctgg actcttaccg     420
cctagacagc atccaggcca tgaatgtggc gctcaacaca tgttcctaca actccatcct     480
gtccatcacc gtgcaggagc cgggcctgcc aggcactagc actctgctct ccagtgcca      540 ggaagtgggg gcagagcgac tgaagaccag cctgcagaag gctctggagg aagagctgga     600
gcaaagcaga cctcgacttg gaggccttca gccaggccag gacagatgga ggggcctgc      660 tatggaaagg ccgctcccta tggagcaggc acgctatctg gagccgggga tccctccaga     720
acagccccac cagaggaccc tagagcacag cctcccacca tccccaaggc ccctgccacg     780
ccacaccagt gcccgagaac caagtgcctt tactctgcct cctccaaggc ggtcctcttc     840
ccccgaggac ccagagaggg acgaggaagt gctgaaccat gtcctaaggg acattgagct     900
gttcatggga aagctggaga aggcccaggc aaagaccagc aggaagaaga aatttgggaa     960
aaaaaacaag gaccagggag gtctcaccca ggcacagtac attgactgct tccagaagat    1020
caagtacagc ttcaacctcc tgggaaggct ggccacctgg ctgaaggaga caagtgcccc    1080
tgagctcgta cacatcctct tcaagtccct gaacttcatc ctggccaggt gccctgaggc    1140
```

```
tggcctagca gcccaagtga tctcacccct cctcacccct aaagctatca acctgctaca    1200
gtcctgtcta agcccacctg agagtaacct ttggatgggg ttgggcccag cctggaccac    1260
tagccgggcc gactggacag gcgatgagcc cctgccctac caacccacat tctcggatga    1320
ctggcaactt ccagagccct ccagccaagc acccttagga taccaggacc ctgtttccct    1380
tcggcgggga agtcataggt tagggagcac ctcacacttt cctcaggaga agacacacaa    1440
ccatgaccct cagcctgggg accccaactc caggccctcc agcccaaaac ctgcccagcc    1500
agccctgaaa atgcaagtct tgtacgagtt tgaagctagg aacccacggg aactgactgt    1560
ggtccaggga gagaagctgg aggttctgga ccacagcaag cggtggtggc tggtgaagaa    1620
tgaggcggga cggagcggct acattccaag caacatcctg gagccctac agccggggac     1680 ccctgggacc cagggccagt caccctctcg ggttccaatg cttcgactta gctcgaggcc    1740
tgaagaggtc acagactggc tgcaggcaga gaacttctcc actgccacgg tgaggacact    1800
tgggtccctg acggggagcc agctactccg cataagacct ggggagctac agatgctatg    1860
tccacaggag gccccacgaa tcctgtcccg gctggaggct gtcagaagga tgctggggat    1920
aagcccttag gcaccagctt agacacctcc aagaaccagg ccccgctgat gcaagatggc    1980
agatctgata cccattagag ccccgagaat tcctcttctg gatcccagtt tgcagcaaac    2040
cccacacccc agctcacaca gcaaaaacaa tggacaggcc cagagggtga agcaaacagt    2100
gtcccttctg gctgtgttgg agcctcccca gtaaccacct atttattta cctctttccc     2160 aaacctggag catttatgcc taggcttgtc aagaatctgt tcagtccctc tccttctcaa    2220
taaaagcatc ttcaagcttg aaaaaaaaaa aaaaa                                2255
```

<210> SEQ ID NO 32
<211> LENGTH: 945
<212> TYPE: DNA
<213> ORGANISM: Homo sapiens
<220> FEATURE:
<221> NAME/KEY: misc_feature
<222> LOCATION: (36)..(36)
<223> OTHER INFORMATION: a or g or c or t/u

<400> SEQUENCE: 32

```
ccttccattg aattccacca gacacattca ggttancttc gtaatgtctt catatgagta      60
tcaatcaaca ccttccccaa ctcaattgta ctaggttgta gagcacaagg atggtctcgt     120
gctgctctgt ggcacctgtg cctacactgc tctgagcttt gaggaggctg ctctctttgc     180
tgaccccatg atcttttctg cccttctgtt aagggcattg ccacagcaa cggggcaaat      240 gccccaagct ggctgtaagt gacccatccc tttggctccc atgattagac caaggagagg     300 catgggtcc agctgagcca ttcagaacca ttccttagca ttttccactc aaaggttaga      360
gatgagattt tctcttccca aggctacctc tggccatggt tccagcttca tggggcaat      420 gggattagga aaatgaggtc aacctgcaaa ggaaagcaga tgcaagagat ggagacagaa     480
tgggggtgtc ctggggatct tggagcctga attcattggc acaaaaggca gcagcatcct    540
cactgtatct gcagtccatt tggactcaat aaaaactttg aaagtcacat gtgttatgga    600
attccttctc agtgacacat tcatctgtgc tcagttgtcc cagcaagggt cagcccctca     660 taccccctgca gcatccgctg ctatgaagca gagctgtaaa cgccctccct gtgtatagga    720
aaagctacat ggagcaaatc ctcctgcctg aagaagtgca tctcagcatc acttcagctg    780
tcggggcatt tgtggggaga accagaccac ctctgcggaa ggcagcagac cctcttccag    840
```

```
ccatggatgg agttgaattc tctataaacg gttcaccagc aaaccaccaa tacattccat    900
tgtttgccta gagagaaatt taaaaataaa taaatgttca cttat                   945
```

<210> SEQ ID NO 33
<211> LENGTH: 736
<212> TYPE: DNA
<213> ORGANISM: Homo sapiens

<400> SEQUENCE: 33

```
tgcggccgcg gcatgaaagg cggcgaggag aggcagcact gctgctcttg acttctgagc     60
agggcttaga gagcctgccc cggcttaagc cgagctgctg gtgctgaccc tgagcgccga    120
gtccgcgagc tctgagtccg gagcctccca gccgtggagc cgtgggatga ggggggcgtt    180
gggggacagg gcaaagtcga tcttggttgt acagccgccc gatcctagcg cggagctgcg    240
agcctgaccg gccgcgtctg gcatggtcag agaaagaatt ttcttttccc aactccggct    300
tttggttttg tgtgtccacc ttgcgcaact ccggagccag ccgacccac atggattctc     360
aacaggtggc cggcacatct tctgagcctc gctctctcat ctgaaagtgg agtgtaagtc    420
caagaagatt catttagaca agaaggtgg aaaaaagga cttctgggc cagcaagtcg       480
gatgaccacc ctccaagggg cagaggaggg cccattttgt gaagaagaaa tcaactaccc    540
ggaaaacgcc acaggaggac atgtttctgc agatgtagtt gccctagaaa cagaagagta    600
tgggggtgtg aatgtcttct cttttggggg caaacactat gtcctttctct ttttctagat   660
acagttaatt cctggaaatt ttagcgagtt tgttcttgtg gatattttga acaataaaga    720
gtgaaaatca aaaaa                                                      736
```

<210> SEQ ID NO 34
<211> LENGTH: 2104
<212> TYPE: DNA
<213> ORGANISM: Homo sapiens

<400> SEQUENCE: 34

```
cccaatcact cctggaatac acagagagag gcagcagctt gctcagcgga caaggatgct     60
gggcgtgagg gaccaaggcc tgccctgcac tcgggcctcc tccagccagt gctgaccagg    120
gacttctgac ctgctggcca gccaggacct gtgtggggag gccctcctgc tgccttgggg    180
tgacaatctc agctccaggc tacagggaga ccggagggat cacagagcca gcatgttaca    240
ggatcctgac agtgatcaac ctctgaacag cctcgatgtc aaaccctgc gcaaaccccg     300
tatccccatg gagaccttca gaaaggtggg gatccccatc atcatagcac tactgagcct    360
ggcgagtatc atcattgtgg ttgtcctcat caaggtgatt ctggataaat actacttcct    420
ctgcgggcag cctctccact tcatcccgag gaagcagctg tgtgacggag agctggactg    480
tccttggggg gaggacgagg agcactgtgt caagagcttc cccgaagggc tgcagtggc     540
agtccgcctc tccaaggacc gatccacact gcaggtgctg gactcggcca cagggaactg    600
gttctctgcc tgtttcgaca acttcacaga agctctcgct gagacagcct gtaggcagat    660
gggctacagc agcaaaccca ctttcagagc tgtggagatt ggcccagacc aggatctgga    720
tgttgttgaa atcacagaaa acagccagga gcttcgcatg cggaactcaa gtgggccctg    780
tctctcaggc tccctggtct ccctgcactg tcttgcctgt gggaagagcc tgaagacccc    840
ccgtgtggtg ggtgggggag aggctcctgt ggattcttgg ccttggcagg tcagcatcca    900
gtacgacaaa cagcacgtct gtgggggag catcctggac ccccactggg tcctcacggc     960
agcccactgc ttcaggaaac ataccgatgt gttcaactgg aaggtgcggg caggctcaga   1020
```

```
caaactgggc agcttcccat ccctggctgt ggccaagatc atcatcattg aattcaaccc     1080
catgtacccc aaagacaatg acatcgccct catgaagctg cagttcccac tcactttctc     1140
aggcacagtc aggcccatct gtctgccctt ctttgatgag gagctcactc cagccacccc     1200
actctggatc attggatggg gctttacgaa gcagaatgga gggaagatgt ctgacatact     1260
gctgcaggcg tcagtccagg tcattgacag cacacggtgc aatgcagacg atgcgtacca     1320
gggggaagtc accgagaaga tgatgtgtgc aggcatcccg gaaggggtg tggacacctg      1380 ccagggtgac agtggtgggc ccctgatgta ccaatctgac cagtggcatg tggtgggcat     1440
cgttagctgg ggctatggct gcgggggccc gagcacccca ggagtataca ccaaggtctc     1500
agcctatctc aactggatct acaatgtctg gaaggctgag ctgtaatgct gctgccccctt    1560 tgcagtgctg ggagccgctt ccttcctgcc ctgcccacct ggggatcccc caaagtcaga     1620
cacagagcaa gagtccccct gggtacaccc ctctgcccac agcctcagca tttcttggag     1680
cagcaaaggg cctcaattcc tgtaagagac cctcgcagcc cagaggcgcc cagaggaagt     1740
cagcagccct agctcggcca cacttggtgc tcccagcatc ccagggagag acacagccca     1800
ctgaacaagg tctcagggt attgctaagc caagaaggaa ctttcccaca ctactgaatg      1860
gaagcaggct gtcttgtaaa agcccagatc actgtgggct ggagaggaga aggaaagggt     1920
ctgcgccagc cctgtccgtc ttcacccatc cccaagccta ctagagcaag aaaccagttg     1980
taatataaaa tgcactgccc tactgttggt atgactaccg ttacctactg ttgtcattgt     2040
tattacagct atggccacta ttattaaaga gctgtgtaac atcaaaaaaa aaaaaaaaa     2100 aaaa                                                                  2104
```

<210> SEQ ID NO 35
<211> LENGTH: 3865
<212> TYPE: DNA
<213> ORGANISM: Homo sapiens

<400> SEQUENCE: 35

```
tttttcaatt ttgaacattt tgcaaaacga ggggttcgag gcaggtgaga gcatcctgca       60
cgtcgccggg gagcccgcgg gcacttggcg cgctctcctg ggaccgtctg cactggaaac      120
ccgaaagttt ttttttaata tatatttta tgcagatgta tttataaaga tataagtaat       180
ttttttcttc ccttttctcc accgccttga gagcgagtac ttttggcaaa ggacggagga     240
aaagctcagc aacatttag ggggcggttg tttctttctt tcttatttct tttttaaggg      300 gaaaaattt gagtgcatcg cgatggagaa aatgtcccga ccgctccccc tgaatcccac      360
ctttatcccg cctccctacg gcgtgctcag gtccctgctg agaacccgc tgaagctccc      420 ccttcaccac gaagacgcat ttagtaaaga taaagacaaa gaaagaagc tggatgatga      480 gagtaacagc ccgacggtcc cccagtcggc attcctgggg cctaccttat gggacaaaac    540
ccttccctat gacggagata cttttccagt ggaatacatg gacctggagg agttttttgtc    600 agaaaatggc attccccca gcccatctca gcatgaccac agccctcacc ctcctgggct     660
gcagccagct tcctcggctg cccccctcggt catggacctc agcagccggg cctctgcacc    720 cccttcaccct ggcatcccat ctccgaactg tatgcagagc cccatcagac caggtcagct    780
gttgccagca aaccgcaata caccaagtcc cattgatcct gacaccatcc aggtcccagt     840
gggttatgag ccagacccag cagatcttgc cctttccagc atccctggcc aggaaatgtt    900
tgaccctcgc aaacgcaagt tctctgagga agaactgaag ccacagccca tgatcaagaa     960
```

-continued

```
agctcgcaaa gtcttcatcc ctgatgacct gaaggatgac aagtactggg caaggcgcag    1020
aaagaacaac atggcagcca agcgctcccg cgacgcccgg aggctgaaag agaaccagat    1080
cgccatccgg gcctcgttcc tggagaagga gaactcggcc ctccgccagg aggtggctga    1140
cttgaggaag gagctgggca aatgcaagaa catacttgcc aagtatgagg ccaggcacgg    1200
gcccctgtag gatggcattt ttgcaggctg gctttggaat agatggacag tttgtttcct    1260
gtctgatagc accacacgca aaccaacctt tctgacatca gcactttacc agaggcataa    1320
acacaactga ctcccatttt ggtgtgcatc tgtgtgtgtg tgcgtgtata tgtgcttgtg    1380
ctcatgtgtg tggtcagcgg tatgtgcgtg tgcgtgttcc tttgctcttg ccattttaag    1440
gtagccctct catcgtcttt tagttccaac aaagaaaggt gccatgtctt tactagactg    1500
aggagccctc tcgcgggtct cccatcccct ccctccttca ctcctgcctc ctcagctttg    1560
cttcatgttc gagcttacct actcttccag gactctctgc ttggattcac taaaaagggc    1620
cctggtaaaa tagtggatct cagtttttaa gagtacaagc tcttgtttct gtttagtccg    1680
taagttacca tgctaatgag gtgcacacaa taacttagca ctactccgca gctctagtcc    1740
tttataagtt gctttcctct tactttcagt tttggtgata atcgtcttca aattaaagtg    1800
ctgtttagat ttattagatc ccatatttac ttactgctat ctactaagtt tcctttt aat    1860 tctaccaacc ccagataagt aagagtacta ttaatagaac acagagtgtg tttttgcact    1920
gtctgtacct aaagcaataa tcctattgta cgctagagca tgctgcctga gtattactag    1980
tggacgtagg atattttccc tacctaagaa tttcactgtc ttttaaaaaa caaaaagtaa    2040
agtaatgcat ttgagcatgg ccagactatt ccctaggaca aggaagcaga gggaaatggg    2100
aggtctaagg atgaggggtt aatttatcag tacatgagcc aaaaactgcg tcttggatta    2160
gcctttgaca ttgatgtgtt cggttttgtt gttccccttc cctcacaccc tgcctcgccc    2220
ccacttttct agttaacttt ttccatatcc ctcttgacat tcaaaacagt tacttaagat    2280 tcagtttttcc cacttttttgg taatatatat attttttgtga attatacttt gttgttttta    2340
aaaagaaaat cagttgatta agttaataag ttgatgtttt ctaaggccct ttttcctagt    2400
ggtgtcattt ttgaatgcct cataaattaa tgattctgaa gcttatgttt cttattctct    2460
gtttgctttt gaacgtatgt gctcttataa agtggacttc tgaaaaatga atgtaaaaga    2520
cactggtgta tctcagaagg ggatggtgtt gtcacaaact gtggttaatc caatcaattt    2580
aaatgtttac tatagaccaa aaggagagat tattaaatcg tttaatgttt atacagagta    2640
attataggaa gttctttttt gtacagtatt tttcagatat aaatactgac aatgtatttt    2700
ggaagacata tattatatat agaaaagagg agaggaaaac tattccatgt tttaaaatta    2760
tatagcaaag atatatattc accaatgttg tacagagaag aagtgcttgg gggttttga    2820 agtctttaat attttaagcc ctatcactga cacatcagca tgttttctgc tttaaattaa    2880
aattttatga cagtatcgag gcttgtgatg acgaatcctg ctctaaaata cacaaggagc    2940
tttcttgttt cttattaggc ctcagaaaga agtcagttaa cgtcacccaa aagcacaaaa    3000
tggattttag tcaaatattt attggatgat acagtgtttt ttaggaaaag catctgccac    3060
aaaaatgttc acttcgaaat tctgagttcc tggaatggca cgttgctgcc agtgcccag    3120 acagttcttt tctaccctgc gggcccgcac gttttatgag gttgatatcg gtgctatgtg    3180
tttggtttat aatttgatag atgtttgact taaagatga ttgttctttt gtttcattaa    3240
gttgtaaaat gtcaagaaat tctgctgtta cgacaaagaa acattttacg ctagattaaa    3300
atatcctttc atcaatggga ttttctagtt tcctgccttc agagtatcta atccttt aat    3360
```

```
gatctggtgg tctcctcgtc aatccatcag caatgcttct ctcatagtgt catagacttg    3420
ggaaacccaa ccagtaggat atttctacaa ggtgttcatt ttgtcacaag ctgtagataa    3480
cagcaagaga tgggggtgta ttggaattgc aatacattgt tcaggtgaat aataaaatca    3540 aaaactttg caatcttaag cagagataaa taaaagatag caatatgaga cacaggtgga     3600
cgtagagttg gccttttac aggcaaagag gcgaattgta gaattgttag atggcaatag     3660
tcattaaaaa catagaaaaa tgatgtcttt aagtggagaa ttgtggaagg attgtaaacat   3720 ggaccatcca aatttatggc cgtatcaaat ggtagctgaa aaaactatat ttgagcactg    3780
gtctctcttg gaattagatg tttatatcaa atgagcatct caaatgtttt ctgcagaaaa    3840
aaataaaaag attctaataa aaaaa                                          3865
```

<210> SEQ ID NO 36
<211> LENGTH: 359
<212> TYPE: DNA
<213> ORGANISM: Homo sapiens
<220> FEATURE:
<221> NAME/KEY: misc_feature
<222> LOCATION: (17)..(17)
<223> OTHER INFORMATION: a or g or c or t/u

<400> SEQUENCE: 36

```
ttccttccct ccctccnttc ctcaggagcc gccagtcccc aagttggctg tggttgggca     60
cctggtttgg gtcctgcaga gctgggctca ggccctgggc tctgaacctg tgaacccttg    120
ctgtgttacg aaactttcct tcctctgagg gccttgaacc ctctccttt cttctttgg      180 gggtgggggt taactttatt ttctcttccc tgtatctgcc tctcccttcc ctcaatttcc    240
tgttttaaaa ctgaatggca cgaaattgtt ttcctcaact cggagattcc tgtatggaga    300
gaatcaattt ctatatttgc aataaatttc ttatttaaag ctaaaaaaaa aaaaaaaa      359
```

<210> SEQ ID NO 37
<211> LENGTH: 1848
<212> TYPE: DNA
<213> ORGANISM: Homo sapiens

<400> SEQUENCE: 37

```
ggcacgaggg ccatctgtgg gggctttggg ccaggggtct ccggacagca tgagcgtggg     60
cttcatcggc gctggccagc tggcttttgc cctggccaag ggcttcacag cagcaggcgt    120
cttggctgcc cacaagataa tggctagctc cccagacatg gacctggcca cagtttctgc    180
tctcaggaag atgggggtga agttgacacc ccacaacaag gagacggtgc agcacagtga    240
tgtgctcttc ctggctgtga agccacacat catcccctc atcctggatg aaataggcgc    300
cgacattgag gacagacaca ttgtggtgtc ctgcgcggcc ggcgtcacca tcagctccat    360
tgagaagaag ctgtcagcgt ttcggccagc ccccagggtc atccgctgca tgaccaacac    420
tccagtcgtg gtgcgggagg gggccaccgt gtatgccaca ggcacgcacg cccaggtgga    480
ggacgggagg ctcatggagc agctgctgag cagcgtgggc ttctgcacgg aggtggaaga    540
ggacctgatt gatgccgtca cggggctcag tggcagcggc cccgcctacg cattcacagc    600
cctggatgcc ctggctgatg ggggcgtgaa gatgggactt ccaaggcgcc tggcagtccg    660 cctcgggggcc caggccctcc tgggggctgc caagatgctg ctgcactcag aacagcaccc    720
aggccagctc aaggacaacg tcagctctcc tggtggggcc accatccatg ccttgcatgt    780
gctggagagt gggggcttcc gctccctgct catcaacgct gtggaggcct cctgcatccg    840
```

```
cacacgggag ctgcagtcca tggctgacca ggagcaggtg tcaccagccg ccatcaagaa      900
gaccatcctg gacaaggtga agctggactc ccctgcaggg accgctctgt cgccttctgg      960
ccacaccaag ctgctccccc gcagcctggc cccagcgggc aaggattgac acgtcctgcc     1020
tgaccaccat cctgccacca ccttctcttc tcttgtcact aggggactag ggggtcccc      1080
aaagtggccc actttctgtg gctctgatca gcgcaggggc cagccaggga catagccagg     1140
gaggggccac atcactttcc actggaaatc tctgtggtct gcaagtgctt cccagcccag     1200
aacaggggtg gattccccaa cctcaacctc ctttcttctc tgctcccaaa ccatgtcagg     1260
accaccttcc tctagagctc gggagcccgg agggtcttca cccactccta ctccagtatc     1320
agctggcacg ggctccttcc tgagagcaaa ggtcaaggac cccctctgtg aaggctcagc     1380
agaggtggga tcccacgccc cctcccggcc cctccctgcc ctccattcag ggagaaacct     1440
ctccttcccg tgtgagaagg gccagagggt ccaggcatcc caagtccagc gtgaagggcc     1500
acagcccctc ttggctgcca agcacgcaga tcccatggac atttggggaa agggctcctt     1560
gggctgctgg tgaacttctg tggccaccac ctcctgctcc tgacctccct gggagggtgc     1620
tatcagttct gtcctggccc tttcagtttt ataagttggt ttccagcccc cagtgtcctg     1680
acttctgtct gccacatgag gagggaggcc ctgcctgtgt ggggagggtgg ttactgtggg    1740
tggaatagtg gaggccttca actgattaga caaggcccgc ccacatcttg gagggcatct     1800
gccttactga ttaaaatgtc aatgtaatct aaaaaaaaaa aaaaaaaa               1848

<210> SEQ ID NO 38
<211> LENGTH: 3003
<212> TYPE: DNA
<213> ORGANISM: Homo sapiens

<400> SEQUENCE: 38
gataaatgcg gagggacggt ccagctttag ctctctgctc gccgccgccg ctgtcgccgc       60
cacctcctct gatctacgaa agtcatgtta cccaacaccg ggaggctggc aggatgtaca      120
gtttttatca caggtgcaag ccgtggcatt ggcaaagcta ttgcattgaa agcagcaaag      180
gatggagcaa atattgttat tgctgcaaag accgcccagc cacatccaaa acttctaggc      240
acaatctata ctgctgctga agaaattgaa gcagttggag gaaaggcctt gccatgtatt      300
gttgatgtga gagatgaaca gcagatcagt gctgcagtgg agaaagccat caagaaattt      360
ggagcttata ccattgctaa gtatggtatg tctatgtatg tgcttggaat ggcagaagaa      420
tttaaaggtg aaattgcagt caatgcatta tggcctaaaa cagccataca cactgctgct      480
atggatatgc tgggaggacc tggtatcgaa agccagtgta gaaagttga tatcattgca      540
gatgcagcat attccatttt ccaaaagcca aaaagttta ctggcaactt tgtcattgat      600
gaaaatatct taaagaaga aggaatagaa attttgacg tttatgcaat taaaccaggt      660
catcctttgc aaccagattt cttcttagat gaatacccag aagcagttag caagaaagtg      720
gaatcaactg gtgctgttcc agaattcaaa gaagagaaac tgcagctgca accaaaacca      780
cgttctggag ctgtggaaga acatttaga attgttaagg actctctcag tgatgatgtt      840
gttaaagcca ctcaagcaat ctatctgttt gaactctccg gtgaagatgg tggcacgtgg      900
tttcttgatc tgaaaagcaa gggtgggaat gtcggatatg gagagccttc tgatcaggca      960
gatgtggtga tgagtatgac tactgatgac tttgtaaaaa tgttttcagg gaaactaaaa     1020
ccaacaatgg cattcatgtc agggaaattg aagattaaag taacatggcc ctagcaatc     1080
aaattggaga agctaatgaa tcagatgaat gccagactgt gaaggaaaat ataaaaaaaa     1140
```

```
agtcgactgc tatgctcaaa aagtaaaaaa agctcaacag ttaaaatcta atgtttgttt    1200
tctttcctgt tatattataa ggatatgcac gtttgttctg gaaagatag aatttgtctc     1260 taaaagactt gaaattgtaa ttaaaatggc aagctaatca acataagct tcattaagtg     1320 ggattctaag acagtctgtg tttttatatt tcaagggttt aaccctttga gccttacatc    1380
tcattcactg tctttctcca agaaagtat tttgggcgga cagtcagatc aagcagtaaa     1440
attagctctt tcaaatcttc ttgtcatgta aatgaagct agtctgtttt aaaattttta     1500
gttttggatt gtatactaat gaaaatctta atgatgtttt tgattttat atacttattt     1560 taaagaaaat cttatatagt acattttaca aaaattataa aaaatgaatt agtactggcg    1620
aggactaaat gaaacaataa ttttcattt tgataactag ctttccaggt ggacttagcc     1680
ataggaaaat attactaatg taatttaaca aattgctgca tgtattccat ttaaaaatat    1740
gtttaaattg tcctaaaaca aaataatttt ctccctagga gtatgcattt ggctacagtg    1800
ttttgaaaca gaaaccttag aataggtcat tggtatgggc tgaactgtgt atcccccaat    1860
tcatttgttg aggtcctaac tcccatttct tttgaatgtg actgttcgga gatgaggcct    1920
ttaaagaggt gacttaagtt caaaggaggc tgttagtcta atccaacatg gtgtcctttg    1980
gacataagag ataccagcaa tgtgtgcaca gaacaaagac caggagagga cacagtgaga    2040
aggcagttat ctgcaagcaa agagagaggc ttcagaagaa acaaaatcac cagcaccttg    2100
atctttgact tctaatctcc agaatagtga gaaataaatt tctgttgtta agccgtccac    2160
tgtgggaggc cgacgcagga ggattgcttg aggccaggag ttcaaggcca gcctggacaa    2220
catagtaaga ccctatctct accccccctaa taaattaatt taaaaagccc cccaatctgt   2280
ggtattttat tatggcagcc ctagcaagct aatacagtgg tttgagaggc tgggagggtt    2340
gaggggaaga taaactttta aaaagctctt atctttcatt tcaatcagtt aaaaatactt    2400
gctcagtgta acaattttgc ttctcagctt ccactctaat attgttgtgc cattaagcaa    2460
tttagctaat cctgacattt cttagattca taatgttagg agcatttaat ctgtatttta    2520
caagttagga agcagaggat cagagatggg aaaggactag cccaaggcca acattaacaa    2580
gccctctaac aaaaacttta caatacattt atgttgaatg gaactccaag atctcacctc    2640
tccatccagg aatggagtcc atgtaatcaa agtgaactta aaaataggac agtttcaaca    2700
agtcaggaga ttcacagcaa ctgatcaaag ggagtccagt caacgtgagc aagcgtgatt    2760
atgatgagga agcccctct gctttaatcc acacaaggaa cgtaacctga agtaacctga     2820
tgttaaccaa tctgctgtgt ctactatgct gttccttgt tcctgctagt gctgctttac     2880
aaatgcagac cattctatca tacctggcag ggcttctgtt ttattttgta ggctggatgc    2940
tacccagttc atgaatcgct aataaaagcc aattagatct ttaaaaaaaa aaaaaaaaa    3000 aaa                                                                  3003
```

<210> SEQ ID NO 39
<211> LENGTH: 1824
<212> TYPE: DNA
<213> ORGANISM: Homo sapiens
<400> SEQUENCE: 39

```
tattaaaagt accccatgga tggacctcca aatgagttta gggtaattgc gcttaaaata     60
ttaggaccaa agtacatttta tttttatagat ggaggagggg aggagacgag tggggaccag   120
cttgacatcc agtcttcacc tggacatatg gaaagaacaa atgtgcgatc tgctcgttcc    180
```

```
ctctgaaggt ctctgttacg tatttcctcc tctcctccag agcataataa ccaatgactg        240
ctctcagaaa ggtactgtga ccaccacttg cttggctctc caacttcctc ccccatttcc        300
ctcttgactc ctgtttgcca taacaccttc tgtcccctag ccttgcctca ggtccccgac        360
gaatcctgcc cttaatctgt gggggtggta ggtggcactg gtttgaagag cttactggat        420
ctccctcagt gagtcagcct ggagttgtgt ttgaaaacca caggccctga ctgtggctgt        480
aagacctccc agacaccacc tgctgctgcc tatcatcatc ttcaggtgct gggctccct        540 gtgggcctcg tctgcccgcc ctctgctgca gctgtcccat gggcgcccgc cctctctgac        600
accacaagag agcccatcta gattccagga aaaaactcat cttttatttgc cttcttccca       660 ctgaaggtaa aagcaacatt aataaccaca acaaatactt agtgagtgct tactattatt        720
catttaattg taggcccttc catccctggc catgatgaga gacatgccat agcttactcc        780
taaagagacc tgaggacaca cgtgcacaaa catattgggc atatcatcaa tggcatcaaa        840
actgattttc cctgtctacc cagaacaggc ctgagggaga gggaaaagcg gatacccacc        900
tgtgtcgctg tttgcgtgcc aagtccagga acagtccata cagccctgct gcatcccacg        960
acgctgtcac aaagcaggag ttcatccgag gccaaggtat ggagaaactg aggcccagaa       1020
attgatgtcc agaatgcttt gctcttagcc actgtactat tatggcatat tttatcttta       1080
tgtattgcat catttcatgg attcaagttt atcaatgtcc tttgacaagt ttaaaaatct       1140
gtctgctaaa atctatcaaa tacattaagg aaaagtccca cttggcacat ctcccacacc       1200
agatgttaat tattcatact gcatgactga ggattttgga ggcagagaga gattcatctg       1260
caatatttgg aacaccaatg gaggtctatg tcaacacaga atttatacag cagctggtgc       1320
tagtcagagc taatgacaga atttcagttt aataaaaaga cccccaactg agcacaccat       1380
cttgaaaaaa gtatacttat caaacagctt tcaatcagtt caagagagac accttaattg       1440
gggagaggaa gaattgcaga gtagtttgta atcatgccaa ttccagatca ataactgcat       1500
gtctgttctt tggtagaaat agcttttgct ttatattaag taatcacata tatattctct       1560
ctatttggat aaggaaacct tcgctttatt tgacaatgta taatgatata ctcttctaat       1620
tcacctctgt gtcttcacaa taaacatgag taaaatttag acaagtgatg gtaaaggtca       1680
atataattat ttattttttaa aataaatttt gtatctaaca ggaaagcagt tcttatgaaa       1740
tttttatatt ttcaaaaatt gttttgttca aataaaattt tatgagtaaa gttaaaaaaa       1800
aaaaaaaaaa aaaaaaaaa aaaa                                                1824

<210> SEQ ID NO 40
<211> LENGTH: 630
<212> TYPE: DNA
<213> ORGANISM: Homo sapiens

<400> SEQUENCE: 40
gggtacctgg tggggccaat caccgagcca tgaacatcag taacgtactc taaagaccaa         60
ggctacgatg gctatgatgg tcagaattac taccaccacc agtgaagctc cagcctggga        120
tgaattcatc cattctggct ttgcatccgg ctaccatttt cgaagttcaa ctcaggaagg        180
tgcaatataa caaatgtgca tattataatg aggaatggta ctaccgttcc agattttctg        240
taattgcttc tgcaaagtaa taggcttctt gtccctttttt tttctggcat gttatggaat        300
gatcattgta aatcaggacc atttatcaag cagtacacca actcataaga tcaaatttca        360
ttgaatggtt tgaggttgta gctctataaa tagtagtttt taacatgcct gtagtattgc        420
taactgcaaa aacatactct ttgtacaaga agtgcttcta agaatttcat tgacattaat        480
```

```
gacactgtat acaataaatg tgtagtttct taatcgcact acctatgcaa cactgtgtat    540
taggtttatc atcctcatgt attttatgt gacctgtatg tatattctaa tctacgagtt    600
ttatcacaaa taaaaatgca atccttcaaa                                    630
```

<210> SEQ ID NO 41
<211> LENGTH: 970
<212> TYPE: DNA
<213> ORGANISM: Homo sapiens

<400> SEQUENCE: 41

```
aaggtgggct tcattgtgaa ttttgttct gttgcagtaa tataggagca catttttggcc     60 attgtaatta cagggaacaa agggattgcg acacatatc tggacttctt ttcctcccctt   120 attgttgtgg aagagacact agaaatgctc aaacacctgc aatatacaga atatacacaa   180
ttttattcca gtatttccct aacatatggt ttaaaattat tccaggtata cagtgtatgc   240
aattctgcat tatcacagag gaacaacttc ttttttaaaa aataaatagg tcagccattt   300
ttattaacgt gcaaaaactt tatcactcta acatgctcta ggtagttgag gaaaagaggt   360
ctgatcactg tttgtattt attttctttg tgggaacatt tcacctgctg agtgtacatg   420 aattgcttt ctataaaagg cttttatgag tttacagtag aatcagtgga aggaagagtt   480
aataagggct gttttaaaa aacaaacaa acaaacaaaa caataatta aaaaaaaatt     540 ttacattcct tcctattctc taactacact tgggaagtgc acttcagata agttgcagt   600 gtgactgaga gatgaaggaa atccatgaaa aaggtcctct tagtgaacaa aattagtta   660 ttaactttat agctatgaaa ttccccgggg catttgtttt tgttcaaaca gactttaacc   720
tctgcatcat acttaaccct gcgacatgcg tacagtatgc atattttgtt ttgaaaaaaa   780
atgtttcgtt ccagtctgtt aagaatattc aaaaataata aaggtattgc ttaataaaat   840
tgctagaatt gtttagcagt acatgcacaa tattttacta gattctttgt tttaatagtg   900
ttttgttgag actgaaaatc ttaaaatggt ctgcgcaaat acaaaaaaaa agaaaacacc   960
aaaaaaaaaa                                                           970
```

<210> SEQ ID NO 42
<211> LENGTH: 1743
<212> TYPE: DNA
<213> ORGANISM: Homo sapiens

<400> SEQUENCE: 42

```
ggtgttgttc cggacacata gaaagataac gacgggaaga gcggggcccg ctttggggtc     60
caggcaggtt ttggggcctc ctgtctggtg ggaggaggcc gcagcgcagc accctgctcg   120
tcacttggga tggagaccgg ctttcccgca atcatgtacc ctggatcttt tattgggggc   180
tggggagaag agtatctcag ctgggaagga ccggggctcc cagatttcgt cttccagcag   240
cagcccgtgg agtctgaagc aatgcactgc agcaacccca agagtggagt tgtgctggct   300
acagtggccc gaggtcccga tgcttgtcag atactcacca gagccccgct gggccaggat   360 ccccccgcaga ggacagtgct agggctgcta actgcaaatg ggcagtacag gaggacctgt   420
ggccagggga tcaagaat caggtgttat tctggatcag aaaatgcctt ccctccagct   480
ggaaagaaag cactccctga ctgtggggtc caagagcccc ccaagcaagg gtttgacatc   540
tacatggatg aactagagca gggggacaga gacagctgct cggtcagaga ggggatggca   600
tttgaggatg tgtatgaagt agacaccggc acactcaagt cagacctgca cttcctgctg   660
```

| | |
|---|---|
| gatttcaaca cagtttcccc tatgctggta gattcatctc tcctctccca gtctgaagat | 720 |
| atatccagtc ttggcacaga tgtgataaat gtgactgaat atgctgaaga aatttatcag | 780 |
| taccttaggg aagctgaaat aaggcacaga cccaaagcac actacatgaa gaagcagcca | 840 |
| gacatcacgg aaggcatgcg cacgattctg gtggactggc tggtggaggt tggggaagaa | 900 |
| tataaacttc gagcagagac cctgtatctg gctgtcaact tcctggacag gttcctttca | 960 |
| tgtatgtctg ttctgagagg gaaactgcag ctcgtaggaa cagcagctat gcttttggct | 1020 |
| tcgaaatatg aagagatata tcctcctgaa gtagacgagt ttgtctatat caccgatgat | 1080 |
| acatacacaa aacgcaact gttaaaaatg gaacacttgc ttctgaaagt tctagctttt | 1140 |
| gatctgacag taccaaccac caaccagttt ctccttcagt acttgaggcg acaaggagtg | 1200 |
| tgcgtcagga ctgagaacct ggctaagtac gtagcagagc tgagtctact tgaagcagat | 1260 |
| ccattcttga aatatcttcc ttcactgata gctgcagcag cttttgcct ggcaaactat | 1320 |
| actgtgaaca agcacttttg gccagaaacc cttgctgcat ttacagggta ttcattaagt | 1380 |
| gaaattgtgc cttgcctgag tgagcttcat aaagcgtacc ttgatatacc ccatcgacct | 1440 |
| cagcaagcaa ttagggagaa gtacaaggct tcaaagtacc tgtgtgtgtc cctcatggag | 1500 |
| ccacctgcag ttcttcttct acaataagtt tctgaatgga agcacttcca gaacttcacc | 1560 |
| tccatatcag aagtgccaat aatcgtcata ggcttctgca cgttggatca actaatgttg | 1620 |
| tttacaatat agatgacatt ttaaaaatgt aaatgaattt agtttccctt agactttagt | 1680 |
| agtttgtaat atagtccaac attttttaaa caataaactg cttgtcttat gacaaaaaaa | 1740 |
| aaa | 1743 |

<210> SEQ ID NO 43
<211> LENGTH: 697
<212> TYPE: DNA
<213> ORGANISM: Homo sapiens

<400> SEQUENCE: 43

| | |
|---|---|
| tccaagccat taaggactgt ggaacttgct atgatcatgg acgtgctgta tggtggcgtt | 60 |
| tgttatgcag gaattgatac agatcctgag ctaaaatacc caaaaggtgc tgggcgagtt | 120 |
| gcttctctcca atcagcagag ctatattgct gccattagtg ctcggtttgt tcagcttcag | 180 |
| catggtgata ttgataaacg tgtggaggta aagccatatg tgctagatga ccagatgtgt | 240 |
| gatgaatgcc agggcgcacg ctgtggtgga aaatttgctc cctttttttg tgccaatgtc | 300 |
| acttgcctgc agtattactg tgagttttgt tgggcaaata tccactctcg tgctggacgt | 360 |
| gagttccata agccattggt aaaggaaggt gctgatcgcc cacgtcagat ccacttccgc | 420 |
| tggaactaag aatagcaaac tggcctctgt ttaacaagga aagaagggt gcatgtggct | 480 |
| tactgtgtct gaagatactg acatgcagaa gaaataagtg cattcttctg cttttcaccc | 540 |
| cagctatcaa tacatgcatc tttatcagca gccaaaacac tacaagcctc ttgttttttca | 600 |
| ccaaaaccct acatctcagg cttactaatt tttgtgatat tttcatgttc aaataaaatg | 660 |
| ttttttttgta ttttcaaaaa aaaaaaaaaa aaaaaaa | 697 |

<210> SEQ ID NO 44
<211> LENGTH: 2227
<212> TYPE: DNA
<213> ORGANISM: Homo sapiens

<400> SEQUENCE: 44

| | |
|---|---|
| ctcgatgtag aggggttggt agcagacagg tggttacatt agaatagtca cacaaactgt | 60 |

```
tcagtgttgc aggaaccttt tcttgggggt gggggagttt cccttttcta aaaatgcaat    120
gcactaaaac tattttaaga atgtagttaa ttctgcttat tcataaagtg ggcatcttct    180
gtgttttagg tgtaatatcg aagtcctggc ttttctcgtt ttctcacttg ctctcttgtt    240
ctctgttttt ttaaaccaat tttactttat gaatatattc atgacatttg taataaatgt    300
cttgagaaag aatttgtttc atggcttcat ggtcatcact caagctcccg taaggatatt    360
accgtctcag gaaaggatca ggactccatg tcacagtcct gccatcttac tttcctcttg    420
tcgagttctg agtggaaata actgcattat ggctgcttta acctcagtca tcaaaagaaa    480
cttgctgttt tttaggcttg atcttttttcc tttgtggtta attttcctgt atattgtgaa    540
aatgggggat tttccctctg ctcccaccca cctaaacaca gcagccattt gtacctgttt    600
gcttcccatc ccacttggca cccactctga cctcttgtca gtttcctgtt cctggttcca    660 tcttttttgaa aaaggccctc ctttgagcta caaacatctg gtaagacaag tacatccact    720
catgaatgca gacacagcag ctggtggttt tgtgtatacc tgtaaagaca agctgagagg    780
cttacttttt ggggaagtaa aagaagatgg aaatggatgt ttcatttgta tgagtttgga    840
gcagtgctga aggccaaagc cgcctactgg tttgtagtta acctagagaa ggttgaaaaa    900
ttaatcctac ctttaaaggg atttgaggta ggctggattc catcgccaca ggactttagt    960
tagaattaaa ttcctgcttg taatttatat ccatgtttag gcttttcata agatgaaaca   1020
tgccacagtg aacacactcg tgtacatatc aagagaagaa ggaaaggcac aggtggagaa   1080
cagtaaaagg tgggcagatg tctttgaaga aatgctcaat gtctgatgct aagtgggaga   1140
aggcagagaa caaggatgt ggcataatgg tcttaacatt atccaaagac ttgaagctcc   1200
atgtctgtaa gtcaaatgtt acacaaaaaa aaatgcaaat ggtgtttcat tggaattacc   1260
aagtgcttag aacttgctgg cttcccata ggtggtaaag gggtctgagc tcacaccgag   1320
ttgtgcttgg cttgcttgtg cagctccagg cacccggtgg gcactctggt ggtgtttgtg   1380
gtgaactgaa ttgaatccat tgttgggctt aagttactga aattggaaca ccctttgtcc   1440
ttctcggcgg gggcttcctg gtctgtgctt tacttggctt ttttccttcc cgtcttagcc   1500
tcaccccctt gtcaaccaga ttgagttgct atagcttgat gcaggaccc agtgaagttt   1560 ctccgttaaa gattgggagt cgtcgaaatg tttagattct tttaggaaag gaattatttt   1620
cccccctttt acagggtagt aacttctcca cagaagtgcc aatatggcaa aattacacaa   1680
gaaaacagta ttgcaatgac accattacat aaggaacatt gaactgttag aggagtgctc   1740
ttccaaacaa aacaaaaatg tctctaggtt tagtcagagc tttcacaagt aataaccttt   1800
ctgtattaaa atcagagtaa ccctttctgt attgagtgca gtgttttta ctcttttctc   1860 atgcacatgt tacgttggag aaaatgttta caaaaatggt tttgttacac taatgcgcac   1920
cacatattta tggtatattt taagtgactt tttatgggtt attttaggttt tcgtcttagt   1980 tgtagcacac ttaccctaat tttgccaatt attaatttgc taaatagtaa tacaaatgac   2040
aactgcatta aatttactaa ttataaaagc tgcaagcaga ctggtggcaa gtacacagcc   2100 ctttttttg cagtgctaac ttgtctactg tgtattatga aaattactgt tgtcccccca   2160 ccctttttc cttaaataaa gtaaaaatga caccctaaaa aaaaaaaaa aaaaaaaaa   2220 aaaaaaa                                                           2227
```

<210> SEQ ID NO 45  
<211> LENGTH: 267  
<212> TYPE: DNA

<213> ORGANISM: Homo sapiens

<400> SEQUENCE: 45

| | | |
|---|---|---|
| tatacggctg ctagaagacg acagaaggtg gcttgggggt ggatatcttt gggttgctgg | 60 |
| aaaaggtgtg ggaaggttca ggatggtggg agggactgag gtccctgagg tgaagaggcc | 120 |
| cttggtcctg acgggtttga cccgtgcctg gacccttgga gcagtgttgt gtgaacttgc | 180 |
| ctagaactct gccttctccg ttgtcaataa agcctccccc tcatgaccta aaaaaaaaa | 240 |
| aaaaaaaaaa aaaaaagtc gtatcga | 267 |

<210> SEQ ID NO 46
<211> LENGTH: 4415
<212> TYPE: DNA
<213> ORGANISM: Homo sapiens

<400> SEQUENCE: 46

| | |
|---|---|
| gagcaggaaa atatataccc taaacagaaa ctcttacttg ttttatgagc aagtctgagt | 60 |
| gagtcctaaa atggctggcg aagagctacc aatactgact gacaggtcac cttaaagcct | 120 |
| ctaggtgtgc caagtttgat ttatcttagg gactagaacc tagtcttcta aatgtgattt | 180 |
| tgccttgctg tttcgtcctg atgtgaaggt aaccacacag agagattggg ctgcatcagt | 240 |
| aatgatatgc ataccctttcg tgcatcagtg agcttcttcc ctgttaactg tatgaccaca | 300 |
| aaatttagct ggagtaaata aatatgcgac agaaatcctg aacaagatg gtgaaattgc | 360 |
| ttaagaatcg agacttcagg gctcaatgac ctctgagcat gtttcccaaa gtgtgaccca | 420 |
| catgaccatc tgtctctcag tctcctggtc cctccgtaga gcttctgaaa ctgaatcttt | 480 |
| gtggggtggg ggtagcgttc aagaatcaaa agttgaacca agctctttgg gtgatactta | 540 |
| tgtatactga ggttcaggaa ctgctggaga gatgactggg caccaagagg atgacagtga | 600 |
| ctcagctggc atcccttagc tggttcatgg cagagctgag tgggcactcc tgtctctgac | 660 |
| cccagcttca gtgctcttta tctcctccat gcctcctcag tcgtgctgct ctaagactgc | 720 |
| ttactggctt tccttcatgt cctgggcaca gagcagttct tttggtagca gatttgagtc | 780 |
| cacttccccc gtgcacagat cactgctcag gacccagaga ggagcagctc tgctccagca | 840 |
| gggttttcca ttgcatcaca cacccaaacg gtaggatcca acagtcacac ttgaaagcaa | 900 |
| ccataattgt gaggtttctg atgctgtaga cttccttaca tttctcacaa cctagttaga | 960 |
| gagtcacatg ggggtgaagt gtggctcgcg acctgcccca acaagtgcgt gcagaagcca | 1020 |
| ggaaacaaag gagtaaattc acttcaaatg ggatgcacat ggtgtccgtg atgaagagac | 1080 |
| acattcagaa ttgcccaagg acaggaaaat gaccagagag agccagagct gagctggtaa | 1140 |
| taaagagact ccgagactga gtggagttaa tgagggaagc atgcaacgag tggggcaatt | 1200 |
| tcagttggtt tctctcattg ctttaagcga aatgaactat acggacagga gaacagcctg | 1260 |
| cttgccccag tctctccttg gccgccctct gttgtccctg tcaactcagg tgcccacggt | 1320 |
| gctcagagga ggtgctggca aagcccctgg agccttatgt aggccatggg ggctcctaaa | 1380 |
| aggaacctga atgaatcatt tacagcaggt ctctcttgta aagcccagcc acagtaactc | 1440 |
| gtacactgac tgtttcaaaa gacagccttt cttaatcatt taattgtttc atattcaaat | 1500 |
| atatctccta attgttttta ttttttcctg atctagaaga tatgacaaca gggtagaact | 1560 |
| tgggaagagg gaataggaag ctcgcccttc ctccttccct cctcccctct ctactttcct | 1620 |
| tccttccttg gtcatcaggt accttctttg tgcctgctgt tgtaggctac accctatgtt | 1680 |
| tggtggaagg caaaaagaaa aatcagtagg atacaactca gtagggaaga cagagatatt | 1740 |

```
caagcccctt gtcctcccag tgtgataagt gtggtggttg aggtgtgaac aagggctct    1800 gtgaacagag aggacgaaag aggagctcct cctgaggctg ttgggaaaag catcactgaa   1860
gagtgacttt cagaagaaga gaagaaaaag aggagaacat gcgtgatttt ataatgaaat   1920
agattagata aggggaaaaa aggcatttaa acaaggcaaa agaacagga gaatagagaa    1980 gagatgtgga ggagaaggag cactgtagta aacacgcaga aggacaggaa cacttagaca   2040
tgcaacccac tcccaccctc cgtcttgggg gaggaaagca cactactgtc ccaaagaact   2100
aatactgaac cagtgctgcc ttgtggagag aggcatggcc aaggcgttca gagacctggg   2160
cctggtccca ccgctgccca cagcactcag cctctgagca cagcctgggg tcatctgtgt   2220
gccctctggc caaggctgat ggtagttctc tgagtaattg agagtcattg cctgtctgtg   2280
cagtattgtg aaaacaagtc accttttaac tttaaaacta ctttaaaaaa ctttaaagtt   2340
ttaaaaaaac ttcttttaaaa actactcatg agatgacagt ttctctgacc ctcagaggaa  2400
ggctgggctg cgcatacgtg aggaatttt acatgaacat cccaggactt gctgttcgca    2460
ggtgataaac tgcacctccc caggactccc gctgcactca catgcagctc cctggacttc   2520
tggtatctga cccggcccat ttctgtgttt caggggagaa tttggcttgc gggagtactc   2580
agaagttaag acggtgacag taaagatccc ccagaagaac tcctaagaag gccaagaagg   2640
aggatgaagc ccagcctgca cgtcgtccc tctctgcttt ctctgtaggg cccagctctc    2700
aggaatacaa agttgagcca cggtccttac ttaaagattg aaaagataac atgtaggcca   2760
ggcaggtcac tgcacaacta aagcaaacca gctgggtaca gtttcttggc actctgtaag   2820
gggccacctt aatcatacca aatattgggg aaagtgggat aaagggagga ggaggagcta   2880
gcagacacat ccagtatctc cttctggagc acaggatgaa ataagggagc tgtattattt   2940
catgtctttg tcacaaagaa cttcctctc aaggaaaggt gacctttctc ctgtcttcat    3000
tttcctcctt ccaggccctc ctcgctcacc caccccctccc tctcttccaa ggagatgtca   3060
gctgagctca ttctggggca gatgtttggg ccgggaacaa tttttcaagg ttgtaaagcc   3120
aaattatcat ttcatgttat ccatttcttc aaagcaaaac atgaaatggt tttagctaga   3180
gtcagaccag aatgaaaatg ccaggagctg gtacactaca gatgtagtaa gaacctggga   3240
tattcctgac ccaatctggt tttcttttac ccataaataa catgaatgaa aaagattgg    3300 gacaatagag actggaagtc atcatgtgca gttcaccgct tctgagcttg ctgcagtttt   3360
ggggtgtgtg tgtattagat tccttctcag ttattctgga ataaggcaag gagtgggttg   3420
tttttcatag ctagataaga tcttttccaa agttttttctt agaaccaacc aaaaaacaat  3480
ccgagtaggc ccgagaattt gataatgctg gatgccttgc agacatcatt cagtttctaa   3540
tattgggcaa caattattat taaatgaatt atttctgtag ttggaatctg taccttctga   3600
acctctacac caataactgc tgcaggtgtg attttggtct gtcacactgt acatctatca   3660
taatgtgccc tgtatctatt ggcagtgacc ttggaaaatc tggccaagcc taggggtttc   3720
cttttccatt tgccaagttc cattgtgcca ggactgccgt gctccactga gctcctctgt   3780
cacaccccat tcttgcccct cactgggcag gccatggcct acagcttgca gggagtaaag   3840
caggcccgcc tccctttctt cccatccaca tactcctctt ctgctttcca gtgactccac   3900
cagtttgatg tgggaagtgt tagcttcctt tccttcttcc atcccttctt ccatctttcc   3960
agctgtcaaa tccaatccag tctctaacct aaatgcagat catttattta aaagtaccaa   4020
acataaccca gagtatgtgg aatatgggca acatatatat agccttctgt atttaacgat   4080
```

```
cttctgcttc ttaaccgtac cagttttcta tttataactc ttatctatcc atgatgtttt      4140
aaagtctcca cttgctgtta tttacaaacg acagtgcatt cagcagccca gtgccgtgag      4200
ccctgacaga tgccgtattt ctgagtgctt ccatgtgaat gctgccctcc tgtagcatgt      4260
gtccaagtgg acatagccac taaccaacta gttacctttg gactgcaaca aaaaatgtga      4320
aaatgaagat ttatttcttt taatttactt aaaaagaaac ctctgtgcta gcaataaagc      4380
atttatattg tgcaaaaaaa aaaaaaaaaa aaaac                                 4415

<210> SEQ ID NO 47
<211> LENGTH: 453
<212> TYPE: DNA
<213> ORGANISM: Homo sapiens

<400> SEQUENCE: 47
tgaaaattta tataactgtt gttgataagg aacattatcc aggaattgat acgtttatta       60
ggaaaagata ttttttatagg cttggatgtt tttagttctg actttgaatt tatataaagt      120
atttttataa tgactggtct tccttacctg gaaaaacatg cgatgttagt tttagaatta      180
caccacaagt atctaaattt ggaacttaca aagggtctat cttgtaaata ttgttttgca      240
ttgtctgttg gcaaatttgt gaactgtcat gatacgctta aggtggaaag tgttcattgc      300
acaatatatt tttactgctt tctgaatgta gacggaacag tgtggaagca gaaggctttt      360
ttaactcatc cgtttgccaa tcattgcaaa caactgaaat gtggatgtga ttgcctcaat      420
aaagctcgtc cccattgctt aagccttcaa aaa                                  453

<210> SEQ ID NO 48
<211> LENGTH: 1587
<212> TYPE: DNA
<213> ORGANISM: Homo sapiens

<400> SEQUENCE: 48
cttttagctg ccagccctgg cccatcatgt agctgcagca cagccttccc taacgttgca       60
actgggggaa aaatcacttt ccagtctgtt ttgcaaggtg tgcatttcca tcttgattcc      120
ctgaaagtcc atctgctgca tcggtcaaga gaaactccac ttgcatgaag attgcacgcc      180
tgcagcttgc atctttgttg caaaactagc tacagaagag aagcaaggca aagtcttttg      240
tgctcccctc ccccatcaaa ggaaagggga aaatgtctca gtcgaaaggc aagaagcgaa      300
accctggcct taaaattcca aaagaagcat ttgaacaacc tcagaccagt tccacaccac      360
ctagagattt agactccaag gcttgcattt ctattggaaa tcagaacttt gaggtgaagg      420
cagatgacct ggagcctata atggaactgg gacgaggtgc gtacggggtg gtggagaaga      480
tgcggcacgt gcccagcggg cagatcatgg cagtgaagcg gatccgagcc acagtaaata      540
gccaggaaca gaaacggcta ctgatggatt tggatatttc catgaggacg gtggactgtc      600
cattcactgt cacctttat ggcgcactgt tcgggaggg tgatgtgtgg atctgcatgg      660
agctcatgga tacatcacta gataaattct acaaacaagt tattgataaa ggccagacaa      720
ttccagagga catcttaggg aaaatagcag tttctattgt aaaagcatta gaacatttac      780
atagtaagct gtctgtcatt cacagagacg tcaagcctttc taatgtactc atcaatgctc      840
tcggtcaagt gaagatgtgc gattttggaa tcagtggcta cttggtggac tctgttgcta      900
aaacaattga tgcaggttgc aaaccataca tggccccctga agaataaac ccagagctca      960 accagaaggg atacagtgtg aagtctgaca tttggagtct gggcatcacg atgattgagt     1020
tggccatcct tcgatttccc tatgattcat ggggaactcc atttcagcag ctcaaacagg     1080
```

```
tggtagagga gccatcgcca caactcccag cagacaagtt ctctgcagag tttgttgact   1140
ttacctcaca gtgcttaaag aagaattcca aagaacggcc tacatcccca gagctaatgc   1200
aacatccatt tttcacccta catgaatcca aaggaacaga tgtggcatct tttgtaaaac   1260
tgattcttgg agactaaaaa gcagtggact taatcggttg accctactgt ggattggtgg   1320
gtttcggggt gaagcaagtt cactacagca tcaatagaaa gtcatctttg agataattta   1380
accctgcctc tcagagggtt ttctctccca attttctttt tactccccct cttaaggggg   1440
ccttggaatc tatagtatag aatgaactgt ctagatggat gaattatgat aaaggcttag   1500
gacttcaaaa ggtgattaaa tatttaatga tgtgtcatat gaaaaaaaaa aaaaaaaaa    1560 aaaaaaaaa aaaaaaaaa aaaaaaa                                         1587

<210> SEQ ID NO 49
<211> LENGTH: 558
<212> TYPE: DNA
<213> ORGANISM: Homo sapiens

<400> SEQUENCE: 49
cagtcccacc atgtattttg ctttgtttct aaaaagcttt ttaaaaactg ttatttaata     60
ccaaagggag gaatcgtatg ggttcttctg cccaccgttg tgactaagaa tgcacaggga    120
cttggttctc gttgcacctt tttttagtaa catgtttcat ggggacccac tgtacagccc    180
ttcattctgc tgtgtcagtt tggcctggcc tgacactggc tgccccagcg ggaccacgg     240 aagcagagtg agagccttcg ctgagtcaat gctaccttca gccccagacg catcccattt    300
ccatgtcttc catgctcact gctcatgcac tttttacacg gtttcttcca aacagcccgg    360
tcttgatgca ggagagtctg gaaaaggaag aaaatggttt cagtttcaaa attcaaagga    420
aaaagttgag gacttatttt gtcctgtcaa gattgcaaga acatgtaaaa tgtacggagc    480
ttcataatac gttatattgt tccgaagcag ctcgttgaga aacatttgtt ttcaataaca    540
ttttagctta aaaaaaaa                                                  558

<210> SEQ ID NO 50
<211> LENGTH: 841
<212> TYPE: DNA
<213> ORGANISM: Homo sapiens
<220> FEATURE:
<221> NAME/KEY: misc_feature
<222> LOCATION: (54)..(54)
<223> OTHER INFORMATION: a or g or c or t/u

<400> SEQUENCE: 50
tcacctcgtg gcgtagggga gaggtaacac cgagaagagg cagcggcggt ggcncagaga     60
cgattggtgc caaacagggc agaacgcaac tcagctctgg gtttgtgaat agcacaatgg    120
aagaagctgg actttgtggg ttaagagaga aagcagatat gttgtgtaac tctgaatcac    180
atgatattct tcaacatcaa gactcaaatt gcagtgccac aagtaataaa catttattgg    240
aagatgaaga aggccgtgac tttataacaa agaacaggag ttgggtgagc ccagtgcact    300
gcacacaaga gtcaagaagg gagcttcctg agcaagaagt agcccctccg tctggtcagc    360
aagctttaca attgcaacag gaacaaagaa aaagtcttag gaaaagaagt tttattattg    420
atgcaagccc taaacactct ttccgactcc agaggagaag ctggcagctc tctgtaagaa    480
atatgctgat cttggaaatt cacctcttct atagaagagt ttgttttgaa ctatacgatt    540
tgaaacaaaa ttcttttttt ggagactatg gaaacattct caacagggaa accctactag    600
```

| | |
|---|---|
| actttgtaaa gcaaataatg gaaaagatac agaactttt gaagaatcat gggaaattt | 660 |
| tataattaaa taaatgctaa aattctgttt tgtgaaacat ttatgggaat tatcactgac | 720 |
| agtttttgta cactttcaaa tagtgttaaa gcagcaactc catgttgtaa atgcacaaaa | 780 |
| caaatattta gttaataatc aactccaaga ataaagctgt aacaataata gttaaaaaaa | 840 |
| a | 841 |

<210> SEQ ID NO 51
<211> LENGTH: 2384
<212> TYPE: DNA
<213> ORGANISM: Homo sapiens

<400> SEQUENCE: 51

| | |
|---|---|
| ggcacgaggg tcagcagccg ccagacttcc tgccgaagtc cgagccccct cccggggctg | 60 |
| gagggggggca agcgggttcc gaggtgcaaa gcctggtgcc ccgagccctg cggagctcgg | 120 |
| ggccagcatg gcccccacgc tgcaacaggc gtaccggagg cgctggtgga tggcctgcac | 180 |
| ggctgtgctg gagaacctct tcttctctgc tgtactcctg ggctggggct ccctgttgat | 240 |
| cattctgaag aacgagggct ctattccag cacgtgccca gctgagagca gcaccaacac | 300 |
| cacccaggat gagcagcgca ggtggccagg ctgtgaccag caggacgaga tgctcaacct | 360 |
| gggcttcacc attggttcct tcgtgctcag cgccaccacc ctgccactgg gatcctcat | 420 |
| ggaccgcttt ggccccgac ccgtgcggct ggttggcagt gcctgcttca ctgcgtcctg | 480 |
| caccctcatg gccctggcct cccgggacgt ggaagctctg tctccgttga tattcctggc | 540 |
| gctgtccctg aatggctttg gtggcatctg cctaacgttc acttcactca cgctgcccaa | 600 |
| catgtttggg aacctgcgct ccacgttaat ggccctcatg attggctctt acgcctcttc | 660 |
| tgccattacg ttcccaggaa tcaagctgat ctacgatgcc ggtgtggcct tcgtggtcat | 720 |
| catgttcacc tggtctggcc tggcctgcct tatctttctg aactgcaccc tcaactggcc | 780 |
| catcgaagcc tttcctgccc ctgaggaagt caattacacg aagaagatca agctgagtgg | 840 |
| gctggccctg gaccacaagg tgacaggtga cctcttctac acccatgtga ccaccatggg | 900 |
| ccagaggctc agccagaagg cccccagcct ggaggacggt tcggatgcct tcatgtcacc | 960 |
| ccaggatgtt cggggcacct cagaaaacct tcctgagagg tctgtcccct tacgcaagag | 1020 |
| cctctgctcc cccactttcc tgtggagcct cctcaccatg gcatgaccc agctgcggat | 1080 |
| catcttctac atggctgctg tgaacaagat gctggagtac cttgtgactg gtggccagga | 1140 |
| gcatgagaca aatgaacagc aacaaaaggt ggcagagaca gttgggttct actcctccgt | 1200 |
| cttcggggcc atgcagctgt tgtgccttct cacctgcccc ctcattggct acatcatgga | 1260 |
| ctggcggatc aaggactgcg tggacgcccc aactcagggc actgtcctcg agatgccag | 1320 |
| ggacggggtt gctaccaaat ccatcagacc acgctactgc aagatccaaa agctcaccaa | 1380 |
| tgccatcagt gccttcaccc tgaccaacct gctgcttgtg gttttggca tcacctgtct | 1440 |
| catcaacaac ttacacctcc agtttgtgac ctttgtcctg cacaccattg ttcgaggttt | 1500 |
| cttccactca gcctgtggga gtctctatgc tgcagtgttc ccatccaacc actttgggac | 1560 |
| gctgacaggc ctgcagtccc tcatcagtgc tgtgttcgcc ttgcttcagc agccactttt | 1620 |
| catggcgatg gtgggacccc tgaaaggaga gcccttctgg gtgaatctgg gcctcctgct | 1680 |
| attctcactc ctgggattcc tgttgccttc ctacctcttc tattaccgtg cccggctcca | 1740 |
| gcaggagtac gccgccaatg ggatgggccc actgaaggtg cttagcggct ctgaggtgac | 1800 |
| cgcatagact tctcagacca agggacctgg atgacaggca atcaaggcct gagcaaccaa | 1860 |

-continued

```
aaggagtgcc ccatatggct tttctacctg taacatgcac atagagccat ggccgtagat      1920
ttataaatac aagagaagt tctattttg taaagactgc aaaaaggagg aaaaaaaacc       1980
ttcaaaaacg cccctaagt caacgctcca ttgactgaag acagtccta tcctagaggg       2040 gttgagcttt cttcctcctt gggttggagg agaccaggt gcctcttatc tccttctagc      2100
ggtctgcctc ctggtacctc ttgggggat cggcaaacag ctacccctg aggtcccatg       2160 tgccatgagt gtgcacacat gcatgtgtct gtgtatgtgt gaatgtgaga gagacacagc    2220
cctcctttca gaaggaaagg ggcctgaggt gccagctgtg tcctgggtta ggggttgggg    2280
gtcggcccct tccagggcca ggagggcagg ttccctctct ggtgctgctg cttgcaagtc    2340
ttagaggaaa taaaaaggga agtgagaaaa aaaaaaaaaa aaaa                     2384
```

<210> SEQ ID NO 52
<211> LENGTH: 1923
<212> TYPE: DNA
<213> ORGANISM: Homo sapiens

<400> SEQUENCE: 52

```
ggcacgaggg aggcggcggc tccagccggc gcggcgcgag gctcggcggt gggatccggc       60
gggcggtgct agctccgcgc tccctgcctc gctcgctgcc gggggcggtc ggaaggcgcg     120
gcgcgaagcc cgggtggccc gagggcgcga tggctgctcc tgtcccgtgg gcctgctgtg     180
ctgtgcttgc cgccgccgcc gcagttgtct acgcccagag acacagtcca caggaggcac    240
cccatgtgca gtacgagcgc ctgggctctg acgtgacact gccatgtggg acagcaaact    300
gggatgctgc ggtgacgtgg cgggtaaatg ggacagacct ggcccctgac ctgctcaacg    360
gctctcagct ggtgctccat ggcctggaac tgggccacag tggcctctac gcctgcttcc    420
accgtgactc ctggcacctg cgccaccaag tcctgctgca tgtgggcttg ccgccgcggg    480
agcctgtgct cagctgccgc tccaacactt accccaaggg cttctactgc agctggcatc    540
tgcccacccc cacctacatt cccaacacct tcaatgtgac tgtgctgcat ggctccaaaa    600
ttatggtctg tgagaaggac ccagcccctca agaaccgctg ccacattcgc tacatgcacc    660
tgttctccac catcaagtac aaggtctcca taagtgtcag caatgccctg gccacaatg     720 ccacagctat caccttttgac gagttcacca ttgtgaagcc tgatcctcca gaaaatgtgg    780
tagcccggcc agtgcccagc aaccctcgcc ggctggaggt gacgtggcag accccctcga    840
cctggcctga ccctgagtct tttcctctca gttctttct gcgctaccga cccctcatcc    900
tggaccagtg gcagcatgtg gagctgtccg acggcacagc acaccatc acagatgcct    960 acgccgggaa ggagtacatt atccaggtgg cagccaagga caatgagatt gggacatgga   1020
gtgactggag cgtagccgcc cacgctacgc cctggactga ggaaccgcga cacctccacca   1080 cggaggccca ggctgcggag accacgacca gcaccaccag ctccctggca ccccaccta    1140 ccacgaagat ctgtgaccct ggggagctgg gcagcggcgg gggaccctcg gcacccttct   1200
tggtcagcgt cccccatcact ctggccctgg ctgccgctgc cgccactgcc agcagtctct   1260
tgatctgagc ccggcacccc atgaggacat gcagagcacc tgcagaggag caggaggccg   1320
gagctgagcc tgcagacccc ggtttctatt ttgcacacgg gcaggaggac cttttgcatt   1380
ctcttcagac acaatttgtg gagacccgg cgggcccggg cctgccgccc ccagccctg    1440 ccgcaccaag ctggccctcc ttcctccctc aggggaggtg ggccatgcag ctaacccacc   1500
caccaaagac cccctcaccc tggccccttg ggctggaccc tccaatgcca gcgactccca   1560
```

| | |
|---|---|
| ggagcccttg ggggacgtga ggggagcctc tcacatccga tttctcctcc tgccccagcc | 1620 |
| tcctgtctat cccagggtct ctgttgccac catcagatta taagctcctg atgctggggg | 1680 |
| ggcccagcca tcccctcccc cccagcaccc acaattttca gtccctcccc ctctgccctg | 1740 |
| ttttgtatac ccctccctg accctgctcc tatcccacag tatttaatgc cctgtcagtc | 1800 |
| ccttctagtc tgactcaatg gtaacttgct gtatttgaat ttttttataga tgtatataca | 1860 |
| gggtgggggg agtgggcggt tctcattaaa cgtcaccatt tcatgaaaaa aaaaaaaaa | 1920 |
| aaa | 1923 |

<210> SEQ ID NO 53
<211> LENGTH: 2065
<212> TYPE: DNA
<213> ORGANISM: Homo sapiens

<400> SEQUENCE: 53

| | |
|---|---|
| ggcacgagga gtttcataat ttccgtgggt cgggccgggc gggccaggcg ctgggcacgg | 60 |
| tgatggccac cactggggcc ctgggcaact actacgtgga ctcgttcctg ctgggcgccg | 120 |
| acgccgcgga tgagctgagc gttggccgct atgcgccggg gaccctgggc cagcctcccc | 180 |
| ggcaggcggc gacgctggcc gagcaccccg acttcagccc gtgcagcttc cagtccaagg | 240 |
| cgacggtgtt tggcgcctcg tggaacccag tgcacgcggc gggcgccaac gctgtacccg | 300 |
| ctgcggtgta ccaccaccat caccaccacc ctacgtgca ccccaggcg cccgtggcgg | 360 |
| cggcggcgcc ggacggcagg tacatgcgct cctggctgga gcccacgccc ggtgcgctct | 420 |
| ccttcgcggg cttgccctcc agccggcctt atggcattaa acctgaaccg ctgtcggcca | 480 |
| gaaggggtga ctgtcccacg cttgacactc acactttgtc cctgactgac tatgcttgtg | 540 |
| gttctcctcc agttgataga gaaaacaac ccagcgaagg cgccttctct gaaaacaatg | 600 |
| ctgagaatga gagcggcgga gacaagcccc ccatcgatcc caataaccca gcagccaact | 660 |
| ggcttcatgc gcgctccact cggaaaaagc ggtgccccta caaaacac cagaccctgg | 720 |
| aactggagaa agagtttctg ttcaacatgt acctcaccag ggaccgcagg tacgaggtgg | 780 |
| ctcgactgct caacctcacc gagaggcagg tcaagatctg gttccagaac cgcaggatga | 840 |
| aaatgaagaa aatcaacaaa gaccgagcaa agacgagtg atgccatttg gcttatttta | 900 |
| gaaaaaggg taagctagag agaaaaagaa agaactgtcc gtcccccttc cgccttctcc | 960 |
| cttttctcac ccccaccccta gcctccacca tccccgcaca aagcggctct aaacctcagg | 1020 |
| ccacatcttt tccaaggcaa accctgttca ggctggctcg taggcctgcc gctttgatgg | 1080 |
| aggaggtatt gtaagctttc cattttctat aagaaaaagg aaaagttgag gggggggcat | 1140 |
| tagtgctgat agctgtgtgt gttagcttgt atatatattt ttaaaaatct acctgttcct | 1200 |
| gacttaaaac aaaaggaaag aaactacctt tttataatgc acaactgttg atggtaggct | 1260 |
| gtatagtttt tagtctgtgt agttaattta atttgcagtt tgtgcggcag attgctctgc | 1320 |
| caagatactt gaacactgtg ttttattgtg gtaattatgt tttgtgattc aaacttctgt | 1380 |
| gtactgggtg atgcacccat tgtgattgtg gaagatagaa ttcaatttga actcaggttg | 1440 |
| tttatgaggg gaaaaaaaca gttgcataga gtatagctct gtagtggaat atgtcttctg | 1500 |
| tataactagg ctgttaacct atgattgtaa agtagctgta agaatttccc agtgaaataa | 1560 |
| aaaaaaattt taagtgttct cggggatgca tagattcatc attttctcca ccttaaaaat | 1620 |
| gcgggcattt aagtctgtcc attatctata tagtcctgtc ttgtctattg tatatataat | 1680 |
| ctatatgatt aaagaaaata tgcataatca gacaagcttg aatattgttt ttgcaccaga | 1740 |

```
cgaacagtga ggaaattcgg agctatacat atgtgcagaa ggttactacc tagggtttat    1800
gcttaatttt aatcggagga aatgaatgct gattgtaacg gagttaattt tattgataat    1860
aaattataca ctatgaaacc gccattgggc tactgtagat ttgtatcctt gatgaatctg    1920
gggtttccat cagactgaac ttacactgta tattttgcaa tagttacctc aaggcctact    1980
gaccaaattg ttgtgttgag atgatattta acttttttgcc aaataaaata tattgattct    2040
tttctaaaaa aaaaaaaaaa aaaaa                                          2065

<210> SEQ ID NO 54
<211> LENGTH: 1045
<212> TYPE: DNA
<213> ORGANISM: Homo sapiens

<400> SEQUENCE: 54
aaaccagtgt atccagtcat ggaaaagaag gaggaagatg cacccctgga gcggggcac      60 tggaacaaca agatggagtt tgtgctgtca gtggctgggg agatcattgg cttaggcaac    120
gtctggaggt ttccctatct ctgctacaaa atgggggag gtgagatgag agcccttgtg    180 ccacccccacc cactcctgga aggaggatac ttccatctcc tgcacttacg gcccctctgg    240
ggagtcccat agatgtatag aattctggag gtaggaggac gcttggaggt cattaaggac    300
actctgtaag agactaagac ctagaaaggt tacgtgacta tcccagggct ctttctatta    360
taacgtggca tcgtagaaat atgagcacaa gctggaacca ggtggatgag agtttggatt    420
ctggctctgc tacttaacac tctgtgtgat cttggacaag ttacttaagc tctcagagca    480
tcaattgccg ctcctgcaaa ttgagataat aatgcctgcc tttcaaggtc attgtaagga    540
ttagagacaa tgtgtgtaaa gcacttaata aatagtagct ctgctgatga tgacgttgat    600
aaccaaactg ttctgtggtc ttaagtaata aatagtagct ctgctgatga tgacgttgat    660
aaccaaactg ttctgtggtc ttaagtaata agtagtagct ctgttgatga tgacgttgat    720
aaccaaactg ttctgtggtc ttaagtaata agtagtagct ctgctgatga tgacgttgat    780
aaccaaactg ttctgtggtc ttaagtaata aatagtagct ctgctgatga tgatgttgat    840
aaccaaactg ttctgtggtc ttaagtaata aatagtagct ctgctgatga tgacgttgat    900
aaccaaactg ttctgtggtc ttaagtaata aatagtagct ctgctgatga tgacgttgat    960
aaccaaactg ttctgtggtc ttaagtaata aatagtagct ctgctgatga tgacgttgat   1020
aaaaaaaaaa aaaaaaaaaa aaaaa                                         1045

<210> SEQ ID NO 55
<211> LENGTH: 2024
<212> TYPE: DNA
<213> ORGANISM: Homo sapiens

<400> SEQUENCE: 55
ggaagacatc aggatgtacc atctgcccctt ctgtcggacc ccagggtacg tcccatgagc     60
gcggccgagc tgcgtcgagg gcagcagagc gtgctgcact gctcagggac ccggactctg    120
cagtttctcc tgcactgttt tcacctttgg ccagacgggc tctggaagaa cctacaccct    180
gactggaccc cctccccagg ggagggggt gcctgtaccc ccagcctgg ctggcatcat      240 gcagaggacc ttcgcctggc tgttggaccg cgtgcagcac ctgggtgccc ctgtcaccct    300
tcgcgcctct tatctggaga tctacaatga gcaggttcgg gacttgctga gcctggggtc    360
tccccggccc ctccctgttc gctggaacaa gactcggggc ttctatgtgg agcagctgcg    420
```

```
ggtggtggaa tttgggagtc tggaggccct gatggaactt ttgcaaacgg gtctcagccg    480
tcgaaggaac tcagcccaca ccctgaacca ggcctccagc cgaagccatg ccctgctcac    540
cctttacatc agccgtcaaa ctgcccagca gatgccttct gtggaccctg gggagccccc    600
tgttggtggg aagctgtgct tgtggacct ggcaggcagt gagaaggtag cagccacggg     660
atcccgtggg gagctgatgc ttgaggctaa cagcatcaac cgaagcctgc tggccctggg    720
tcactgcatc tccctgctgc tggacccaca gcggaagcag agccacatcc ctttccggga    780
cagcaagctc accaagttgc tggcagactc actggggagg cgcgggtca ccctcatggt     840 ggcctgcgtg tcccctcag cccagtgcct tcctgagact ctcagcaccc tgcgatatgc      900
aagccgagct cagcgggtca ccacccgacc acaggccccc aagtctcctg tggcaaagca    960
gccccagcgt ttggagacag agatgctgca gctccaggag gagaaccgtc gcctgcagtt    1020
ccagctggac caaatggact gcaaggcctc agggctcagt ggagcccggg tggcctgggc    1080
ccagcggaac ctgtacggga tgctacagga gttcatgcta gagaatgaga ggctcaggaa    1140
agaaaagagc cagctgcaga atagccgaga cctggcccag aatgagcagc gcatcctggc    1200
ccagcaggtc catgcactag agaggcgtct cctctctgcc tgctaccatc accagcaggg    1260
tcctggcctg accccaccgt gtccctgctt gatggcccca gctccccctt gccatgcact    1320
gccacccctc tactcctgcc cctgctgcca catctgccca ctgtgtcgag tgccctggc     1380 ccactgggcc tgcctgccag gggagcacca cctgccccag gtgttggacc ctgaggcctc    1440
aggtggcagg cccccatctg cccggccccc accctgggca ccccatgca gccctggctc     1500 tgccaagtgc ccaagagaga ggagtcacag tgactggact cagacccgag tcctggcaga    1560
gatgttgacg gaggaggagg tggtaccttc tgcacctccc ctgcctgtga ggccccgaa     1620 gacatcacca gggctcagag gtggggccgg ggttccaaac ctggcccaga gactggaggc    1680
cctcagagac cagattggca gctccctgcg acgtggccgc agccagccac cctgcagtga    1740
gggcgcacga gcccaggcc aagtcctccc tccccattga aggccaagtg ggaacccagg     1800
agactgctgt gtgacctcag actgggctcc acactcttgg gcttcagtct gcccatctgc    1860
tgaatggaga cagcagctgc tactccacct gcagctgggc taggggcggg gactgggggt    1920
gctatttagg ggaacaaggg gattcaggag aaaccaggca gcagggggatg aaatacatga    1980 ataaagagag gcatcagctc caaaaaaaaa aaaaaaaaaa aaaa                      2024
```

<210> SEQ ID NO 56
<211> LENGTH: 3334
<212> TYPE: DNA
<213> ORGANISM: Homo sapiens

<400> SEQUENCE: 56

```
ctccccctga gagaggctgg gcagcacccc ccttctgcca ggagtgccag ccaaggtgcc     60
agacccctgt ccagtggcaa gctggaaggc tttcagagca tcgatgaagc tatagcctgg    120
ctcaggaagg aactgacgga gatgcggctg caggaccagc aactggccag acagctcatg    180
cgcctgcgtg gcgacatcaa caagctgaaa atcgaacaca cctgccgcct ccacaggagg    240
atgctcaacg atgccaccta cgagctggag gagcgggatg agctggccga cctcttctgt    300
gactcccctc ttgcctcctc cttcagcctc tccacaccac tcaagcttat tggcgtgacc    360
aagatgaaca tcaactctcg gaggttctct ctctgctgag gagccctcag actgggcgga    420
ggggctggag cggagggctt gggctggagg ggtgtcagag gaagctgagg ccaagttact    480
ccagtgggtc tcccggaggc aggggtccct gggactggcg actcaagggc cccaggacct    540
```

```
attcagtggt gctctcccac ccaggggccc tgggtgtgga tgccagtgtc tctgtgactg    600
gctcttgctt actacccaaa gagctctgca gaagggccgc tccaaccaag atgttaaagg    660
agacctgggt tcccaccata atccatccct ccacggtcac gttcctgttt cctggaatca    720
ctggtgctat gaactgggat tcccaaaggg aggcccccca acaaagctgt cattttttgca   780 gaaggctgtc ccgcaagggc cttggggaa attaggcatg tcagatgtgc ctgtctcacg     840
tgctgttgct gtcctctaag tattgtctca aattcaccct aagtacatga ctcagcaaca    900
ttgacaggga gctactagga agggaaaatc gaaaggcatg acaaatgggc acttggggac    960
gcagccccag tggctggcag ccagtgtctc tggtgagcct gacactacaa ggctgtgtaa   1020
attgtaaatt ctggcgtgtg ctgggacatg tgatggggc actagcgtag cttgggtgca    1080
acaagcacag atgtccccat tgtctcccct ggccacatgc atctccaaag agcctcttca   1140
ctgccaccca caccccaggg tgacagcctg ggagaccact ggtgactgaa ccaggcaggt   1200
cctgaaagca ttttccataa ctgaattctc ctgcaggggc gtgaccgggg cctcctggtg   1260
gattctggtg gtgtcacctt actgccctct ctggaaagac aatctaggga gcccagaggc   1320
ccatcctgag cctcctctga gattttgtgc ctgacctaaa caactagttt taataagact   1380
gttactgatg tgttgttcac ttgttagtaa ctgattttg tccaaatgcg gaagccactt    1440
gtgtaggtca actacagtgc gtaggatttg attttaagag tttctccctc ccaacaggct   1500
tgaggatcag caagttaaga ccccagcagg ttagggaggt cagtctgggg tcatacggca   1560
tggcaggggt ccctcggcca gacccgtaga atcctgagat aaggagtgtt tctgaccttt   1620
ggtgtcatct agtcgagtcc tctcattagt aaaggagcaa agtgaaacct gggggaggag   1680
aaggacttcc ctcaggttgc acagctgttt aggctataga atattgatgt gtgaaaccat   1740
tattgataat gcctagtaga tcacatgtca atgaacttga accccaaaga tggtcgtgat   1800
gctttgccaa acccgcacac tgccaacccc tctactctcc acctcagccc ccacccacat   1860
ctcccagagt attgcaattc agaacatttg ggtcaaggtg gagcaaggca ctgacagtgg   1920
ccccacaggg catgtgtcac taatcactgt cccatggtct acgcacggca tctggctgct   1980
ctgtctactg tgacttcttc ctgtgtaatc tcagtggggc ccgtgtccac ccacacatcg   2040
tgacccacat aggggagagg ttgcttttct tttgtgggct gagagtagga caatgcaaat   2100
gaatgatctc tagtagacag aaaagaactt ggtctctttt ttaaaatttc aaagagccag   2160
aagttctatg cctccttcaa agtaggcaga acaacgcagc caagatctac tgtctgccat   2220
gctctgtgca atgaagtctg caggcctgag gaccatgtac tgctgtcctt cctcagagct   2280
ctgcacaaac actgccaagt cctgaagacg cattcctttc ctgccaacct cttccagat    2340 aagcccttga ggtctcgggc tgacctacac acacacacac acacacacac acacacacac   2400 acaccccac acacacacac acacgacaga gaacatgcca taaacatcct tgaacccatg    2460
caggaaagcc catcccatat tctgaaaaaa tgccaaatta ggttttctt tcttttttgga   2520 aatcagtcat tacagtaacc gaaaccattg ggttcagcga aaatggaaag atttagctga   2580
atgtagtcag tccaattaag ttggatgcaa ctgagtgatt tagttgcttg ggtaacccag   2640
tgcttgcttg ctttcttcat tctctgggtg gaaactaaga tcaagacaca tgtttgggaa   2700
taagttaaat gtctgagcta ttttgctcgg tttatcctaa gagaacttta ttatgggatg   2760
aggaggtgac ccaagatgag aagtggaggg ggacagcgat gttttctaaa catcgtccag   2820
tgttgactgg cttccttact ttgcacagtg aacacaacta accacattaa ttcagctttg   2880
```

-continued

| | |
|---|---|
| tgaagtccct gctctctgtg ggttctatga gtcagcagca acattggcct aacctccgtc | 2940 |
| ccagcctcct ggctcaccac atgtgtacag tgctgtttgc agttgtactc attatccatc | 3000 |
| catctctctg ccatccccaa gcatcgctgg gtgtaaaacg caaactctcc accgacactg | 3060 |
| ccatgcgtgg tcatgtcttg atgccttcag gggctcagta gctatcaaag aggcctggag | 3120 |
| ggcctgggca ggcttgacga tgcctgaccg agttcaagac ccacaccctg tagcaatacc | 3180 |
| aagtgctatt acataatcaa tggacgattt atacttttat tttttatgat tatttgtttc | 3240 |
| tatattgctg ttagaaaaag tgaaataaaa atacttcaaa agaaaaaaaa aaaaaaaaa | 3300 |
| aaaaaaaaaa aaaagaaaaa aaaaaaaaaa aaaa | 3334 |

<210> SEQ ID NO 57
<211> LENGTH: 573
<212> TYPE: DNA
<213> ORGANISM: Homo sapiens
<220> FEATURE:
<221> NAME/KEY: misc_feature
<222> LOCATION: (567)..(569)
<223> OTHER INFORMATION: a or g or c or t/u

<400> SEQUENCE: 57

| | |
|---|---|
| tgaaggaccg cgatcctaaa gagattgaat gggacgacct ggcccagctg cccttcctga | 60 |
| ccatgtgcgt gaaggagagc ctgaggttac atcccccagc tcccttcatc tcccgatgct | 120 |
| gcacccagga cattgttctc ccagatggcc gagtcatccc caagggcatt acctgcctca | 180 |
| tcgatattat aggggtccat cacaacccaa ctgtgtggcc ggatcctgag tctacgaccc | 240 |
| cttccgcttt gacccagaga acagcaaggg gaggtcacct ctggctttta attcccttct | 300 |
| ccgcagggcc caggaactgc atcgggccag cgtttcccat ggcggagatg aaagtggttc | 360 |
| ctggcgttga tgctgctgca cttccggttc ctgccagacc acactgagcc ccgcaggaag | 420 |
| ctggaactga tcattgcggc cgagggcggg ctttggctgc gggtggagcc cctgaatgta | 480 |
| ggcttgcagt gactttctga cccatccacc tgtttttttg cagattgtca tgaataaaac | 540 |
| ggtgctgtca cctcaaaaaa aaaaaannna aaa | 573 |

<210> SEQ ID NO 58
<211> LENGTH: 2534
<212> TYPE: DNA
<213> ORGANISM: Homo sapiens

<400> SEQUENCE: 58

| | |
|---|---|
| gagtcctctc gttggtcccg gaggtggggt tgcgctcaca aggggcgacc gtcgccacgg | 60 |
| tggcggccac tgcatcgcgt cccacctccg cggccctggg cgccgtggtg tcgacgggcc | 120 |
| ccgagcctat gacgggccag ggccagtcgg cgtccgggtc gtcggcgtgg agcacggtat | 180 |
| tccgccacgt ccggtatgag aacctgatag cgggcgtgag cggcggcgtc ttatccaacc | 240 |
| ttgcgctgca tccgctcgac ctcgtgaaga tccgcttcgc cgtgagtgat ggattggaac | 300 |
| tgagaccgaa atataatgga attttacatt gcttgactac catttggaaa cttgatggac | 360 |
| tacggggact ttatcaagga gtaaccccaa atatatgggg tgcaggttta tcctggggac | 420 |
| tctactttt cttttacaat gccatcaagt catataaaac agaaggaaga gctgaacatt | 480 |
| tagaggcaac agaatacctt gtctcagctg ctgaagctgg agccatgacc ctctgcatta | 540 |
| caaacccatt atgggtaaca aaaactcgcc ttatgttaca gtatgatgct gttgttaact | 600 |
| ccccacaccg acaatataaa ggaatgtttg atacacttgt gaaatatat aagtatgaag | 660 |
| gtgtgcgtgg attatataag ggatttgttc ctgggctgtt tggaacatcg catggtgccc | 720 |

```
ttcagtttat ggcatatgaa ttgctgaagt tgaagtacaa ccagcatatc aatagattac      780
cagaagccca gttgagcaca gtagaatata tatctgttgc agcactatcc aaaatatttg      840
ctgtcgcagc aacataccca tatcaagtcg taagagctcg tcttcaggat caacacatgt      900
tttacagtgg tgtaatagat gtaatcacaa agacatggag gaaagaaggc gtcggtggat      960
tttacaaggg aattgctcct aatttgatta gagtgactcc agcctgctgt attacctttg     1020
tggtatatga aaacgtctca cattttttac ttgaccttag agaaaagaga agtaagctc      1080 aaagaggaca attccagtat atctgcccaa ggcagcaaca agctcttttg tgtttaaggc     1140
ataaaagaag aattctgcat agaaacatgg ctcatattcg aaattgctct atagtcatta     1200
gaagccagag aactgctaag tctcctgcaa tgttttttctt gcttttttgcc ttccccatat    1260 atatggaact tggctacctc tgcctgaaat ggctgccatc aacacaatgt taaaactgac     1320
acgaaggata gagtttcaca gatttctacg ttttattggt ggaagctgat ttgcaacatt     1380
tgctaaatgg attagatgaa tgtacttctt tttgtgagct tacttgcctg gattgcttta     1440 aaattaaccct ttgtgcaata ccaagaaaat agctctttaa aagaatgtct ttgtatgtct     1500
caaggtaaat taaggattta ctgaataagg tgttgaccaa atccagacca ttttatttta     1560 ttttttttatt tatttatttt ttgagatgga gtcttgcttt gtcgcccagg ctggagtgca     1620
gtggcgtgat ctcagctcac tgcaacctcc acctcccggg ttcacgccat tctcctgcct     1680
cagcctcctg agtagctggg actacaggca cctgccacca cgcctggcta actttttttt     1740
atattttgag tagaaatggg gtttcaccat gttagccagg atggtctcaa tctcctgacc     1800
ttgtgatccg cctgccttgg cctcccaaag tgctgggatt acaggcgtga gccactgcgc     1860
ctggccagac cattttagaa ttgggaaatt ttagtgagaa aaaatgcact gtaaatatgc     1920
tttagtttta attcagttgg gatgcactac ctagcgaaaa ttgagaaact atatacttct     1980
cagagaaata tctgacatct attgtcattc cattgctatt ttttttcccc agagacttcc     2040
ataattaaaa ataaaatcct agatccagtt cttgtttttt ggcataaaata cttaatctat     2100 tttaaattta taaatctga gcttctagga tccagctgtg tcaacccttta tttagcatat     2160 ataactataa atcacttatt acagatgcta aatagatcac cttttacaga tgctgaaatg     2220
tttgggatat gtttgttgac aaggtaaatg gaaatgagaa actttatact tcagttttca     2280
gatatatgga tctagatccc aaataaatga ttaatcttca ttggtttctc aaattcaggt     2340
tgaaatacaa attaatagcc tttattgatt ttacttttat gagtcattgt agacatctat     2400
aaatataaaa gggcctgtac ccaaaggatg ccagaatact agtattttta tttatcgtaa     2460
acatccacga gtgctgttgc actaccatct atttgttgta aataaaagtg ttgttttcaa     2520
aaaaaaaaaa aaaa                                                       2534

<210> SEQ ID NO 59
<211> LENGTH: 1232
<212> TYPE: DNA
<213> ORGANISM: Homo sapiens

<400> SEQUENCE: 59
ctagaggggc ggaaagtaac aaggaggtgg gggtacaaat cctcagctcc tgcttccgca       60
agcactaacc tgctctgaag tgagccaggc agctctggcc atcttttccc agccacagaa      120
tcaggtgatg gtccagaatt aagagctgtc acctgtgtca ttcactcaca atggaagaaa      180
tgaagaagac tgccatccgg ctgcccaaag gcaaacagaa gcctataaag acggaatgga      240
```

```
attcccggtg tgtccttttc acctacttcc aaggggacat cagcagcgta gtggatgaac      300
acttctccag agctctgagc aatatcaaga gcccccagga attgacccc tcgagtcaga       360 gtgaaggtgt gatgctgaaa acgatgata gcatgtctcc aaatcagtgg cgttactcgt       420
ctccatggac aaagccacaa ccagaagtac ctgtcacaaa ccgtgccgcc aactgcaact      480
tgcatgtgcc tggtcccatg gctgtgaatc agttctcacc gtccctggct aggagggcct      540
ctgttcggcc tggggagctg tggcatttct cctccctggc gggcaccagc tccttagagc      600
ctggctactc tcatcccttc cccgctcggc acctggttcc agagcccag cctgatggga       660 aacgtgagcc tctcctaagt ctcctccagc aagacagatg cctagcccgt cctcaggaat      720
ctgccgccag ggagaatggc aaccctggcc agatagctgg aagcacaggg ttgctcttca      780
acctgcctcc cggctcagtt cactataaga actatatgt atctcgtgga tctgccagta       840
ccagccttcc aaatgaaact cttttcagagt tagagacacc tgggaaatac tcacttacac     900 caccaaaccca ctggggccac ccacatcgat acctgcagca tctttagtca agttggagga    960
gaaagacaac acttggtcta agacacggca gcaagcatc cctgcatatt gttccagata      1020
aaaatgaaag ctgctcacac ccacttgcct ccccaatctg ttaaacagct tcgtgtctag     1080
tatgagctca gtacttgccc tgtgaaaatc ccagaagccc ccgctgtcaa tgttccccat     1140
ccacaccctg cttgctcctg tgtaacagct cagatgatga ataataa aactgtactt        1200 ttttggatgg tgaaaaaaaa aaaaaaaaaa aa                                    1232
```

<210> SEQ ID NO 60
<211> LENGTH: 3551
<212> TYPE: DNA
<213> ORGANISM: Homo sapiens

<400> SEQUENCE: 60

```
ttgccttgtg ttagctagca ataagaaaag aagctttgtt tggattaaca tatataccct      60
cttcattctg cataacctat ttttccccaa taatttgcag cttaggtccg aggacaccac      120
aaactctgct taaagggcct ggaggctctc aaggcatggc cagacgctct gtcttgtact     180
tcatcctgct gaatgctctg atcaacaagg gccaagcctg cttctgtgat cactatgcat     240
ggactcagtg gaccagctgc tcaaaaactt gcaattctgg aacccagagc agacacagac    300
aaatagtagt agataagtac taccaggaaa acttttgtga acagatttgc agcaagcagg     360
agactagaga atgtaactgg caaagatgcc ccatcaactg cctcctggga gattttggac     420
catggtcaga ctgtgaccct tgtattgaaa acagtctaa agttagatct gtcttgcgtc      480
ccagtcagtt tggggacag ccatgcactg agcctctggt agccttttcaa ccatgcattc     540 catctaagct ctgcaaaatt gaagaggctg actgcaagaa taaatttcgc tgtgacagtg     600
gccgctgcat tgccagaaag ttagaatgca atggagaaaa tgactgtgga gacaattcag     660
atgaaaggga ctgtgggagg acaaaggcag tatgcacacg gaagtataat cccatcccta    720
gtgtacagtt gatgggcaat gggtttcatt ttctggcagg agagcccaga ggagaagtcc     780
ttgataactc tttcactgga ggaatatgta aaactgtcaa aagcagtagg acaagtaatc    840
cataccgtgt tccggccaat ctggaaaatg tcggctttga ggtacaaaact gcagaagatg     900 acttgaaaac agatttctac aaggatttaa cttctcttgg acacaatgaa aatcaacaag    960
gctcattctc aagtcagggg gggagctctt tcagtgtacc aatttttat tcctcaaaga    1020 gaagtgaaaa tatcaaccat aattctgcct tcaaacaagc cattcaagcc tctcacaaaa   1080
aggattctag ttttattagg atccataaag tgatgaaagt cttaaacttc acaacgaaag    1140
```

```
ctaaagatct gcacctttct gatgtctttt tgaaagcact taaccatctg cctctagaat    1200
acaactctgc tttgtacagc cgaatattcg atgactttgg gactcattac ttcacctctg    1260
gctccctggg aggcgtgtat gaccttctct atcagtttag cagtgaggaa ctaaagaact    1320
caggtttaac cgaggaagaa gccaaacact gtgtcaggat tgaaacaaag aaacgcgttt    1380
tatttgctaa gaaaacaaaa gtggaacata ggtgcaccac caacaagctg tcagagaaac    1440
atgaaggttc atttatacag ggagcagaga aatccatatc cctgattcga ggtggaagga    1500
gtgaatatgg agcagctttg gcatgggaga agggagctc tggtctggag gagaagacat     1560
tttctgagtg gttagaatca gtgaaggaaa atcctgctgt gattgacttt gagcttgccc    1620
ccatcgtgga cttggtaaga aacatcccct gtgcagtgac aaaacggaac aacctcagga    1680
aagctttgca agagtatgca gccaagttcg atccttgcca gtgtgctcca tgccctaata    1740
atggccgacc caccctctca gggactgaat gtctgtgtgt gtgtcagagt ggcacctatg    1800
gtgagaactg tgagaaacag tctccagatt ataaatccaa tgcagtagac ggacagtggg    1860
gttgttggtc ttcctggagt acctgtgatg ctacttataa gagatcgaga acccgagaat    1920
gcaataatcc tgccccccaa cgaggaggga acgctgtga gggggagaag cgacaagagg     1980
aagactgcac attttcaatc atggaaaaca atggacaacc atgtatcaat gatgatgaag    2040
aaatgaaaga ggtcgatctt cctgagatag aagcagattc cgggtgtcct cagccagttc    2100
ctccagaaaa tggatttatc cggaatgaaa agcaactata cttggttgga gaagatgttg    2160
aaatttcatg ccttactggc tttgaaactg ttggatacca gtacttcaga tgcttaccag    2220
acgggacctg gagacaaggg gatgtggaat gccaacggac ggagtgcatc aagccagttg    2280
tgcaggaagt cctgacaatt acaccatttc agagattgta tagaattggt gaatccattg    2340
agctaacttg ccccaaaggc tttgttgttg ctgggccatc aaggtacaca tgccagggga    2400
attcctggac accacccatt tcaaactctc tcacctgtga aaagatact ctaacaaaat     2460
taaaaggcca ttgtcagctg ggacagaaac aatcaggatc tgaatgcatt tgtatgtctc    2520
cagaagaaga ctgtagccat cattcagaag atctctgtgt gtttgacaca gactccaacg    2580
attactttac ttcacccgct tgtaagtttt tggctgagaa atgtttaaat aatcagcaac    2640
tccatttct acatattggt tcctgccaag acggccgcca gttagaatgg ggtcttgaaa      2700
ggacaagact ttcatccaac agcacaaaga aagaatcctg tggctatgac acctgctatg    2760
actgggaaaa atgttcagcc tccacttcca aatgtgtctg cctattgccc ccacagtgct    2820
tcaagggtgg aaaccaactc tactgtgtca aatgggatc atcaacaagt gagaaaacat     2880
tgaacatctg tgaagtggga actataagat gtgcaaacag gaagatggaa atactgcatc    2940
ctggaaagtg tttggcctag cacaattact gctaggccca gcacaatgaa cagatttacc    3000
atcccgaaga accaactcct acaaatgaga attcttgcac aaacagcaga ctggcatgct    3060
caaagttact gacaaaaatt attttctgtt agtttgagat cattattctc ccctgactct    3120
cctgtttggg catgtcttat tcagttccag ctcatgacgc cctgtagcat accctaggt     3180
accaacttcc acagcagtct cgtaaattct cctgttcaca ttgtacaaaa ataatgtgac    3240
ttctgaggcc cttatgtagc ctgtgacatt aagcattctc acaattagaa ataagaataa    3300
aacccataat tttcttcaat gagttaataa acagaaatct ccagaacctc tgaaacacat    3360
tcttgaagcc cagctttcat atcttcattc aacaaataat ttctgagtgt gtatacagga    3420
tgtcaagtac tgaccaaagt cctgagaact cggcagataa taaaacagac aaaagccttt    3480
```

| | |
|---|---:|
| gccttcatga agcatacatt cattcagggg tagacacaca aaaaatgaaa taaacaggta | 3540 |
| aaatatgtag c | 3551 |

<210> SEQ ID NO 61
<211> LENGTH: 1673
<212> TYPE: DNA
<213> ORGANISM: Homo sapiens

<400> SEQUENCE: 61

| | |
|---|---:|
| ctctcctcgc ccgctgggtg ctgaagttgg gcggatggca gcaaaccggc tccgctagag | 60 |
| gaccgagccg cccagcccg ctcccccgga cccatcggcg cgctgcccac acctccaggc | 120 |
| gaccggccaa ctgggtcctg aagtagctga atgcgaaaa aggcagcagt cccaaaatga | 180 |
| aggaacacct gccgtgtctc aagctcctgg aaaccagagg cccaacaaca cctgttgctt | 240 |
| tgttggtgc tgttgttgca gctgctcctg cctcactgtg aggaatgaag aaagagggga | 300 |
| aaatgcggga agaccacac acactacaaa aatggagagt atccaggtcc tagaggaatg | 360 |
| ccaaaacccc actgcagagg aagtcttgtc ctggtctcaa aattttgaca agatgatgaa | 420 |
| ggccccagca ggaagaaacc ttttcagaga gttcctccga acagaataca gtgaagagaa | 480 |
| cctactttttc tggcttgctt gtgaagactt aagaaggag cagaacaaaa aagtaattga | 540 |
| agaaaaggct aggatgatat atgaagatta catttctata ctatcaccaa agaggtcag | 600 |
| tcttgattct cgagttagag aggtgatcaa tagaaatctg ttggatccca atcctcacat | 660 |
| gtatgaagat gcccaacttc agatatatac tttaatgcac agagattctt ttccaaggtt | 720 |
| tttgaactct caaattttata agtcatttgt tgaaagtact gctggctctt cttctgaatc | 780 |
| ttaatgttca tttaaaaaca atcatttttgg agggctgaga tgggaaataa agtagttaa | 840 |
| ataacatcag aaactgagtt cctggagaac tacagtttag cattcctcag gctactgtga | 900 |
| aaacacaacc gttatggtct ttgtctccat ttttatcaag gttttccatg gttaagtttg | 960 |
| gagaaaatac cacacaaaac aatgaattgc caaattgttt gttttattca agactcattc | 1020 |
| tacttgcaag caaagtgtat ttgtagtcct atgaacagtc tcctcgtgta tctccagaga | 1080 |
| ctgcatgtgc aaagtaaaat gcttcatttg ccacatagtt gttgtaatat ttaatccagt | 1140 |
| agcataactt atatctgtat ttaaggactt ttgtgcaata tggtcttaag aaataattgc | 1200 |
| caaaaaaatc ggccatggtt ctgcattttt aacataatct aagacagaaa aaagcaatt | 1260 |
| tttactatgt aacaatggta ttcaacattc tatatactgt gtttagtaca ctaattttga | 1320 |
| agccaatatt tctgtacatg aaaaagagct atttatctct gtttgttgga aaatcctaat | 1380 |
| ggggattcct ctggttgttc actgccaaaa ctgtggcatt ttcattacag agagtttac | 1440 |
| tatgctaaaa gcaaaaaca aaaaaaaaaa aaagggaag aaggaaaaa gcaaaaaaca | 1500 |
| atttgaagat atcctatctc aatgacaaat caaaagagtg atattgcttt taactgtaat | 1560 |
| agaagaaaat gaatttatgt atatatcaga tgtccaatac tgtaattaat ttattaaaga | 1620 |
| ctggctctcc agttttaaaa aaaaaaaaaa aaaaaaaaaa aaaaaaaaaa aaa | 1673 |

<210> SEQ ID NO 62
<211> LENGTH: 1867
<212> TYPE: DNA
<213> ORGANISM: Homo sapiens

<400> SEQUENCE: 62

| | |
|---|---:|
| aaaagaacca ggattgcatt tgaagttaag ctgcaaaaaa ccagtcgatc aacagatttt | 60 |
| cgagtcccac agtcaatatg caccatgttt aatgttatgg ttgatgccaa agctcaatca | 120 |

```
acaaaacttt gcagcatgga aatgggccaa gagtttgcta aaatgtggca tcaataccat    180
tcaaaaatag acgaactaat tgaagaaact gttaaagaaa tgataacact cttggttgca    240
aagttcgtta ctatcttgga aggagtgctg gcaaaattat ccagatatga cgaagggact    300
ttgttttctt cttttctgtc atttaccgtg aaggcagctt ccaaatatgt ggatgtacct    360
aaacccggga tggacgtggc cgacgcctac gtgactttcg tccgccattc tcaggatgtc    420
ctgcgtgata aggtcaatga ggagatgtac atagaaaggt tatttgatca atggtacaac    480
agctccatga acgtgatctg cacctggttg acggaccgga tggacttaca gcttcatatt    540
tatcagttga aaacactaat taggatggta agaaaaccct acagagattt ccgattgcaa    600
ggggtcctgg actccacctt aaacagcaag acctatgaaa cgatccggaa ccgtctcact    660
gtggaggaag ccacagcatc agtgagtgaa ggtgggggac tgcagggcat cagcatgaag    720
gacagcgatg aggaagacga agaagacgat tagaccattt ggtcctagag tctgctggga    780
cagagtcctg taatcagtgc atgtccttag tctgttagtt aaacccatta ggaattttct    840
gtcaactacc atgcccatga gatgtttatc aatacaactg ccattttagc tatgtggtac    900
caagattagc aaatgacctt catatccact gatttcctga tgtccatgtc tatatgttta    960
caagcaatat ggagcaccat tctttaaata ctgttcatgg agaatacata gtctaaccac   1020
taggcgtgtc cctgttatca gcaaagatca atgatgcttc attcatgtac tatgtatgca   1080
ttggtggtaa atggatgtga gggcaagtac atcaagtaca ttcactctgt tcacgtatg    1140 tggatgccag ttaattaaat gagtacgtaa ataaattaat taaaacacat agatctgctt   1200
tgtgttttta ttttatttt tgaaaaaca aaggcaagt ctccaacaat taactttga     1260 tgctttctgt tcccctaaaa ccaaaaaatg aaccccttgt gtcgttgtta acccatcctt   1320
tcatttactc atataattag ccaaaaaaaa aaggatggct acataccaat ggattgattc   1380
tcttaattgc cacggcaagg gggcgatcct atcatgactt aacatcaagc gcgcagttca   1440
aaactactgt cttctgtcaa agtttctcc tcttaaatgt tattttgctt ttacgtctca   1500
actgtgtatg taaaaaaaac gaatatttaa attacaaccc tagactaaaa atgtgtttat   1560
aataagatgt ggatatttcc ttcagtagat tgtaaccata atttaaatta ttttgttcca   1620
cactgttttt tatatctgtc atgtacattg cattttgatc tgtaactgca caaccctggg   1680
gtttgctgca gagctatttc tttccatgta agtagtgga tccatcttgc ttttgcctta   1740
tataaagcct acagttatgg aagtgtggaa aactgtggct tctcaataaa tattcagatg   1800
tcctaagaaa aaaaaaaaa aaaaaaaaa aaaaaaaaa aaaaaaaaa aaaaaaaaa       1860 aaaaaaa                                                           1867
```

<210> SEQ ID NO 63
<211> LENGTH: 601
<212> TYPE: DNA
<213> ORGANISM: Homo sapiens

<400> SEQUENCE: 63

```
acctgaactg tctaagatat tctaagcaaa gttgacaaag acaattctcc acttgagccc     60
ttaaaaatgt aaccactata aaggtttcac gcggtggttc ttattgattc gctgtgtcat    120
cacatcagct ccactgttgc caaactttgt cgcatgcata atgtatgatg gaggcttgga    180
tgggaatatg ctgattttgt tctgcactta aaggcttctc ctcctggagg gctgcctagg    240
gccacttgct tgatttatca tgagagaaga ggagagagag agagactgag cgctaggagt    300
```

```
gtgtgtatgt gtgtgtgtgt gtgtgtgtgt gtgtgtgtat gtgtgtagcg ggagatgtgg      360
gcggagcgag agcaaaagga ctgcggcctg atgcatgctg gaaaaagaca cgcttttcat      420
ttctgatcag ttgtacttca tcctatatca gcacagctgc catacttcga cttatcagga      480
ttctggctgg tggcctgcgc gagggtgcag tcttacttaa aagactttca gttaattctc      540
actggtatca tcgcagtgaa cttaaagcaa agacctctta gtaaaaaata aaaaaaataa      600
a                                                                      601

<210> SEQ ID NO 64
<211> LENGTH: 367
<212> TYPE: DNA
<213> ORGANISM: Homo sapiens

<400> SEQUENCE: 64
gcttctcttt aaaattgacc caaggcatga gccactgcgc ctggccagca aatgcttttt       60
gtgcagaata cacttctttc aggcattgtc aggtgctgtt ttgtttaagc tctaactcac      120
ccctggaata caggggaatg atgacaacca gcccagccag gcctgactca tcatggtcac      180
atccagcccc caccccggc caactaacca ctgcaggctc ctcttccaga ctcaccaggg       240
ggcctcgagg ccccggcatc tcccttggcc ctgggtgtgg gttttacaag actgtgtctt      300
tcatgacatc atagcccaac catgtgagaa gaaggagaag ccccccttt cttcattaat       360 ctgaaaa                                                                367

<210> SEQ ID NO 65
<211> LENGTH: 2484
<212> TYPE: DNA
<213> ORGANISM: Homo sapiens

<400> SEQUENCE: 65
ggcacgagga agggcctgtg ggtttattat aaggcggagc tcggcgggag aggtgcgggc       60
cgaatccgag ccgagcggag aggaatccgg cagtagagag cggactccag ccggcggacc      120
ctgcagccct cgcctgggac agcggcgcgc tgggcaggcg cccaagagag catcgagcag      180
cggaacccgc gaagccggcc cgcagccgcg acccgcgcag cctgccgctc tcccgccgcc      240
ggtccgggca gcatgaggcg cgcggcgctc tggctctggc tgtgcgcgct ggcgctgagc      300
ctgcagccgg ccctgccgca aattgtggct actaatttgc cccctgaaga tcaagatggc      360
tctggggatg actctgacaa cttctccggc tcaggtgcag gtgctttgca agatatcacc      420
ttgtcacagc agaccccctc cacttggaag gacacgcagc tcctgacggc tattcccacg      480
tctccagaac ccaccggcct ggaggctaca gctgcctcca cctccaccct gccggctgga      540
gaggggccca aggagggaga ggctgtagtc ctgccagaag tggagcctgg cctcaccgcc      600
cgggagcagg aggccacccc ccgacccagg agaccacac agctcccgac cactcatcag      660
gcctcaacga ccacagccac cacggcccag gagcccgcca cctcccaccc ccacagggac      720
atgcagcctg gccaccatga gacctcaacc cctgcaggac ccagccaagc tgaccttcac      780
actccccaca cagaggatgg aggtccttct gccaccgaga gggctgctga ggatggagcc      840
tccagtcagc tccagcagc agagggctct ggggagcagg acttcacctt tgaaaacctcg      900 ggggagaata cggctgtagt ggccgtggag cctgaccgcc ggaaccagtc cccagtggat      960
caggggccca gggggcctc acagggcctc ctgacagga aagaggtgct ggggggtc         1020 attgccgtag gcctcgtggg gctcatcttt gctgtgtgcc tggtgggttt catgctgtac     1080
cgcatgaaga agaaggacga aggcagctac tccttggagg agccgaaaca agccaacggc     1140
```

```
ggggcctacc agaagcccac caaacaggag gaattctatg cctgacgcgg gagccatgcg    1200
ccccctccgc cctgccactc actaggcccc cacttgcctc ttccttgaag aactgcaggc    1260
cctggcctcc cctgccacca ggccacctcc ccagcattcc agcccctctg gtcgctcctg    1320
cccacggagt cgtggggtgt gctgggagct ccactctgct tctctgactt ctgcctggag    1380
acttagggca ccaggggttt ctcgcatagg acctttccac cacagccagc acctggcatc    1440
gcaccattct gactcggttt ctccaaactg aagcagcctc tccccaggtc cagctctgga    1500
ggggaggggg atccgactgc tttggaccta aatggcctca tgtggctgga agatcctgcg    1560
ggtgggcttt gggcctcaca cacctgtagc acttactggt aggaccaagc atcttggggg    1620
ggtggccgct gagtggcagg ggacaggagt ccactttgtt tcgtggggag gtctaatcta    1680
gatatcgact tgttttttgca catgtttcct ctagttcttt gttcatagcc cagtagacct    1740
tgttacttct gaggtaagtt aagtaagttg attcggtatc cccccatctt gcttccctaa    1800
tctatggtcg ggagacagca tcaggggttaa gaagactttt ttttttttttt tttttaaact    1860 aggagaacca aatctggaag ccaaaatgta ggcttagttt gtgtgttgtc tcttgagttt    1920
gtcgctcatg tgtgcaacag ggtatggact atctgtctgg tggccccgtt tctggtggtc    1980
tgttggcagg ctggccagtc caggctgccg tggggccgcc gcctctttca agcagtcgtg    2040
cctgtgtcca tgcgctcagg gccatgctga ggcctgggcc gctgccacgt ggagaagcc    2100 cgtgtgagaa gtgaatgctg ggactcagcc ttcagacaga gaggactgta gggagggcgg    2160
caggggcctg gagatcctcc tgcagaccac gcccgtcctg cctgtggcgc cgtctccagg    2220
ggctgcttcc tcctggaaat tgacgagggg tgtcttgggc agagctggct ctgagcgcct    2280
ccatccaagg ccaggttctc cgttagctcc tgtggcccca ccctgggccc tgggctggaa    2340
tcaggaatat tttccaaaga gtgatagtct tttgcttttg gcaaaactct acttaatcca    2400
atgggttttt ccctgtacag tagattttcc aaatgtaata aactttaata taaagtaaaa    2460
aaaaaaaaaa aaaaaaaaa aaaa                                          2484

<210> SEQ ID NO 66
<211> LENGTH: 1989
<212> TYPE: DNA
<213> ORGANISM: Homo sapiens

<400> SEQUENCE: 66
cggatgggga aaaaaaaga tgtcagctcc tccgctgtag tattgctcct taaaaccccc      60
tctctctgaa aatgacatgc cctcgcaatg taactccgaa ctcgtacgcg gagcccttgg    120
ctgcgcccgg cggaggagag cgctatagcc ggagcgcagg catgtatatg cagtctggga    180
gtgacttcaa ttgcggggtg atgaggggct gcgggctcgc gccctcgctc tccaagaggg    240
acgagggcag cagccccagc ctcgccctca cacctatccc gtcctacctc tcgcagctgg    300
actcctgggg cgaccccaaa gccgcctatc gcctggaaca acctgttggc aggccgctgt    360
cctcctgctc ctacccacct agtgtcaagg aggagaatgt ctgctgcatg tacagcgcag    420
agaagcgggc gaaaagtggc cccgaggcag ctctctactc ccaccccttg ccggagtcct    480
gccttgggga gcacgaggta cccgtgccca gctactaccg cgccagcccg agctactccg    540
cgctggacaa gacgcccac tgttctgggg ccaacgactt cgaagcccct ttcgagcagc    600
gggccagtct caacccgcgc gccgaacatc tggaatcgcc tcagctgggg ggcaaagtga    660
gtttccctga gaccccaag tccgacagcc agaccccag ccccaatgaa atcaagacgg    720
```

| | |
|---|---|
| agcagagcct ggcgggccct aaagggagcc cctcggagag cgaaaaggag agggccaaag | 780 |
| ctgccgactc cagcccagac acctcggata cgaagcgaa agaggagata aaggcagaaa | 840 |
| acaccacagg aaattggctg acagcaaaga gcggaaggaa gaagaggtgc ccctatacta | 900 |
| aacaccagac gctggaattg gagaaagaat ttctgttcaa tatgtatttg acgcgagagc | 960 |
| gccgcctgga gattagcaag accattaacc ttacagacag acaagtcaaa atctggtttc | 1020 |
| aaaatcgcag aatgaaactc aagaaaatga accgagagaa tcggatccgg gaactgacct | 1080 |
| ccaattttaa tttcacctga gagcgcggcc tctcctcctc ccttcccgct ccttcctctc | 1140 |
| cccgcccctc ctccctttgt gcctggtgat atatttttt ttcctcccctg agtataaatg | 1200 |
| caatgcgact gcaaaaaagg caaagacctc agactctcct tccaagggac ctgtggttcg | 1260 |
| tgctgcgaag atgcttccac ttaaagcatg agaaatgggg tgccgggatg tggggtgtgg | 1320 |
| tgtgtgccct catagatggg ggtgggagtg tggctggtgt gtgtgtcaaa ccctcactca | 1380 |
| cccacgcact cacacacagc attctgttct ccatgcaaag ttaagatcga atccatccgc | 1440 |
| ttgtaggga aaaaaaggaa aaaaattaac cagagagggt ctgtaatctc gcagagcaca | 1500 |
| ggcagaatcg ttccttcctt gctgcatttc ctccttagac taatagacgt tttggaaagt | 1560 |
| tcggctagtg ttcgtgtgtt tgtcgtagca cccagagcct ccaccaaacc ctctccatgt | 1620 |
| ctttacctcc cagtcgctct aagaatctgc ttgaagtctc gtatttgtac tgctttctgc | 1680 |
| ttttctccca cccctcctag cacccccaca tcccccatct agtaacatct cagaaatttc | 1740 |
| atccagagga acaaaaaaat taaaaataga acatagcaaa gcaagacag aatgcccccc | 1800 |
| cccaaatatt gtcctgtccc tgtctgggag ttgtgttatt taaagatatt ctgtatgttg | 1860 |
| tatctttgc atgtagcttc cttaatggag aaaaaaaaat cctaataaat ttccagaatc | 1920 |
| ataatcctca aaaaaaaaa aaaaaaaaa aaaaaaaaa aaaaaaaaa aaaaaaaaa | 1980 |
| aaaaaaaaa | 1989 |

```
<210> SEQ ID NO 67
<211> LENGTH: 2125
<212> TYPE: DNA
<213> ORGANISM: Homo sapiens

<400> SEQUENCE: 67
```

| | |
|---|---|
| gcagtggcca cgagaggcag gctggctggg acatgaggtt ggcagagggc aggcaagctg | 60 |
| gcccttggtg ggcctcgtcc tgagcactcg gaggcactcc tatgcttgga aagctcgcta | 120 |
| tgctgctgtg ggtccagcag gcgctgctcg ccttgctcct ccccacactc ctggcacagg | 180 |
| gagaagccag gaggagccga acaccacca ggcccgctct gctgaggctg tcggattacc | 240 |
| ttttgaccaa ctacaggaag ggtgtgcgcc ccgtgaggga ctggaggaag ccaaccaccg | 300 |
| tatccattga cgtcattgtc tatgccatcc tcaacgtgga tgagaagaat caggtgctga | 360 |
| ccacctacat ctggtaccgg cagtactgga ctgatgagtt tctccagtgg aaccctgagg | 420 |
| actttgacaa catcaccaag ttgtccatcc ccacggacag catctgggtc ccggacattc | 480 |
| tcatcaatga gttcgtggat gtggggaagt ctccaaatat cccgtacgtg tatattcggc | 540 |
| atcaaggcga agttcagaac tacaagcccc ttcaggtggt gactgcctgt agcctcgaca | 600 |
| tctacaactt cccccttcgat gtccagaact gctcgctgac cttcaccagt tggctgcaca | 660 |
| ccatccagga catcaacatc tctttgtggc gcttgccaga aaaggtgaaa tccgacagga | 720 |
| gtgtcttcat gaaccaggga gagtgggagt tgctgggggg gctgccctac tttcgggagt | 780 |
| tcagcatgga aagcagtaac tactatgcag aaatgaagtt ctatgtggtc atccgccggc | 840 |

```
ggcccctctt ctatgtggtc agcctgctac tgcccagcat cttcctcatg gtcatggaca        900
tcgtgggctt ctacctgccc cccaacagtg gcgagagggt ctctttcaag attacactcc        960
tcctgggcta ctcggtcttc ctgatcatcg tttctgacac gctgccggcc actgccatcg       1020
gcactcctct cattggtgtc tactttgtgg tgtgcatggc tctgctggtg ataagtttgg       1080
ccgagaccat cttcattgtg cggctggtgc acaagcaaga cctgcagcag cccgtgcctg       1140
cttggctgcg tcacctggtt ctggagagaa tcgcctggct actttgcctg agggagcagt       1200
caacttccca gaggccccca gccacctccc aagccaccaa gactgatgac tgctcagcca       1260 tgggaaaacca ctgcagccac atgggaggac cccaggactt cgagaagagc ccagggaca       1320 gatgtagccc tcccccacca cctcgggagg cctcgctggc ggtgtgtggg ctgctgcagg       1380
agctgtcctc catccggcaa ttcctggaaa agcgggatga gatccgagag gtggcccgag       1440
actggctgcg cgtgggctcc gtgctggaca agctgctatt ccacatttac ctgctggcgg       1500
tgctggccta cagcatcacc ctggttatgc tctggtccat ctggcagtac gcttgagtgg       1560
gtacagccca gtggaggagg gggtacagtc ctggttaggt ggggacagag gatttctgct       1620
taggcccctc aggacccagg gaatgccagg gacattttca agacacagac aaagtcccgt       1680
gccctgtttc caatgccaat tcatctcagc aatcacaagc caaggtctga acccttccac       1740
caaaaactgg gtgttcaagg cccttacacc cttgtcccac ccccagcagc tcaccatggc       1800
tttaaaacat gctctcttag atcaggagaa actcgggcac tccctaagtc cactctagtt       1860
gtggactttt ccccattgac cctcacctga ataagggact ttggaattct gcttctcttt       1920
cacaactttg cttttaggtt gaaggcaaaa ccaactctct actacacagg cctgataact       1980
ctgtacgagg cttctctaac ccctagtgtc ttttttttct tcacctcact tgtggcagct       2040
tccctgaaca ctcatccccc atcagatgat gggagtggga agaataaaat gcagtgaaac       2100
cctaaaaaaa aaaaaaaaaa aaaaa                                             2125

<210> SEQ ID NO 68
<211> LENGTH: 574
<212> TYPE: DNA
<213> ORGANISM: Homo sapiens

<400> SEQUENCE: 68
tcttcgctcc tctaccccat aaaattccct acaaatgcaa aaattcgaga tagaagaagc         60
cgtccctgaa attgctgtct aacattcacc ggaaacctct ccataaacaa ggagaaacga        120
atgcacacgc attttgctaa agaagcccgg gattaagatt taaggataca agctgaaaga        180
aaaaatgaaa aatgcttctc cgcgcgtcaa tcgaggggtg gatgcgccac gcagctgagc        240
ccagctcaca gccacgcgta agaccaaaag ctgccatggg ttctgcgcgc ggagacctca        300
gagccgaaga gagaagtccc cgcgtcagaa acgctgcgga tgccaggtct tgaaaatgct        360
gacttctgag gctaagaatt atttcaaaga caaaagaaa agactggtga ggaggccttc        420
cggtgcaagg gcgcctatcc gctaattttg gatggggaag tagggattat tcgtttaaat        480
tcaatcgcga gcaccaagtc ggactggccg gggatggaga agggcaaccc ccacctttag        540
aaaaataaaa gatctcgaag gccaaaaaaa aaaa                                    574

<210> SEQ ID NO 69
<211> LENGTH: 3697
<212> TYPE: DNA
<213> ORGANISM: Homo sapiens
```

<400> SEQUENCE: 69

```
agggagtgtt cccggggag atactccagt cgtagcaaga gtctcgacca ctgaatggaa      60
gaaaaggact tttaaccacc attttgtgac ttacagaaag gaatttgaat aaagaaaact    120
atgatacttc aggcccatct tcactccctg tgtcttctta tgctttattt ggcaactgga    180
tatggccaag aggggaagtt tagtggaccc ctgaaaccca tgacattttc tatttatgaa    240
ggccaagaac cgagtcaaat tatattccag tttaaggcca atcctcctgc tgtgactttt    300
gaactaactg gggagacaga caacatattt gtgatagaac gggagggact tctgtattac    360
aacagagcct tggacaggga acaagatct actcacaatc tccaggttgc agccctggac    420
gctaatggaa ttatagtgga gggtccagtc cctatcacca tagaagtgaa ggacatcaac    480
gacaatcgac ccacgtttct ccagtcaaag tacgaaggct cagtaaggca gaactctcgc    540
ccaggaaagc ccttcttgta tgtcaatgcc acagacctgg atgatccggc cactcccaat    600
ggccagcttt attaccagat tgtcatccag cttcccatga tcaacaatgt catgtacttt    660
cagatcaaca acaaaacggg agccatctct cttacccgag agggatctca ggaattgaat    720
cctgctaaga atccttccta taatctggtg atctcagtga aggacatggg aggccagagt    780
gagaattcct tcagtgatac cacatctgtg atatctag tgacagagaa tatttggaaa     840
gcaccaaaac ctgtggagat ggtggaaaac tcaactgatc ctcaccccat caaaatcact    900
caggtgcggt ggaatgatcc cggtgcacaa tattccttag ttgacaaaga gaagctgcca    960
agattcccat tttcaattga ccaggaagga gatatttacg tgactcagcc cttggaccga   1020
gaagaaaagg atgcatatgt tttttatgca gttgcaaagg atgagtacgg aaaaccactt   1080
tcatatccgc tggaaattca tgtaaaagtt aaagatatta atgataatcc acctacatgt   1140
ccgtcaccag taaccgtatt tgaggtccag gagaatgaac gactgggtaa cagtatcggg   1200
acccttactg cacatgacag ggatgaagaa aatactgcca acagttttct aaactacagg   1260
attgtggagc aaactcccaa acttcccatg gatggactct tcctaatcca aacctatgct   1320
ggaatgttac agttagctaa acagtccttg aagaagcaag atactcctca gtacaactta   1380
acgatagagg tgtctgacaa agatttcaag acccttgtt ttgtgcaaat caacgttatt    1440
gatatcaatg atcagatccc catctttgaa aaatcagatt atggaaacct gactcttgct   1500
gaagacacaa acattgggtc caccatctta accatccagg ccactgatgc tgatgagcca   1560
tttactggga gttctaaaat tctgtatcat atcataaagg gagacagtga gggacgcctg   1620
ggggttgaca cagatcccca taccaacacc ggatatgtca taattaaaaa gcctcttgat   1680
tttgaaacag cagctgtttc caacattgtg ttcaaagcag aaaatcctga gcctctagtg   1740
tttggtgtga agtacaatgc aagttctttt gccaagttca cgcttattgt gacagatgtg   1800
aatgaagcac ctcaatttc ccaacacgta ttccaagcga aagtcagtga ggatgtagct    1860
ataggcacta aagtgggcaa tgtgactgcc aaggatccag aaggtctgga cataagctat   1920
tcactgaggg gagacacaag aggttggctt aaaattgacc acgtgactgg tgagatcttt   1980
agtgtggctc cattggacag agaagccgga agtccatatc gggtacaagt ggtggccaca   2040
gaagtagggg ggtcttcctt gagctctgtg tcagagttcc acctgatcct tatggatgtg   2100
aatgacaacc ctcccaggct agccaaggac tacacgggct tgttcttctg ccatcccctc   2160
agtgcacctg gaagtctcat tttcgaggct actgatgatg atcagcactt atttcggggt   2220
ccccatttta cattttccct cggcagtgga agcttacaaa cgactggga agtttccaaa    2280
atcaatggta ctcatgccg actgtctacc aggcacacag agtttgagga gagggagtat   2340
```

```
gtcgtcttga tccgcatcaa tgatgggggt cggccaccct tggaaggcat tgtttcttta    2400
ccagttacat tctgcagttg tgtggaagga agttgtttcc ggccagcagg tcaccagact    2460
gggataccca ctgtgggcat ggcagttggt atactgctga ccacccttct ggtgattggt    2520
ataattttag cagttgtgtt tatccgcata agaaggata aaggcaaaga taatgttgaa     2580
agtgctcaag catctgaagt caaacctctg agaagctgaa tttgaaaagg aatgtttgaa    2640
tttatatagc aagtgctatt tcagcaacaa ccatctcatc ctattacttt tcatctaacg    2700
tgcattataa ttttttaaac agatattccc tcttgtcctt taatatttgc taaatatttc    2760 tttttttgagg tggagtcttg ctctgtcgcc caggctggag tacagtggtg tgatcccagc   2820
tcactgcaac ctccgcctcc tgggttcaca tgattctcct gcctcagctt cctaagtagc    2880
tgggtttaca ggcacccacc accatgccca gctaattttt gtattttaa tagagacggg     2940 gtttcgccat ttggccaggc tggtcttgaa ctcctgacgt caagtgatct gcctgccttg    3000
gtctcccaat acaggcatga accactgcac ccacctactt agatatttca tgtgctatag    3060
acattagaga gattttttcat ttttccatga cattttttcct ctctgcaaat ggcttagcta  3120
cttgtgtttt tccctttttgg ggcaagacag actcattaaa tattctgtac attttttctt   3180
tatcaaggag atatatcagt gttgtctcat agaactgcct ggattccatt tatgtttttt    3240
ctgattccat cctgtgtccc cttcatcctt gactcctttg gtatttcact gaatttcaaa    3300
catttgtcag agaagaaaaa cgtgaggact caggaaaaat aaataaataa agaacagcc     3360 ttttccctta gtattaacag aaatgttttct gtgtcattaa ccatctttaa tcaatgtgac   3420
atgttgctct ttggctgaaa ttcttcaact tggaaatgac acagacccac agaaggtgtt    3480
caaacacaac ctactctgca aaccttggta aaggaaccag tcagctggcc agatttcctc    3540
actacctgcc atgcatacat gctgcgcatg ttttcttcat tcgtatgtta gtaaagttttt  3600 ggttattata tatttaacat gtggaagaaa acaagacatg aaaagagtgg tgacaaatca    3660
agaataaaca ctggttgtag tcagttttgt ttgttaa                            3697

<210> SEQ ID NO 70
<211> LENGTH: 2530
<212> TYPE: DNA
<213> ORGANISM: Homo sapiens

<400> SEQUENCE: 70
aaatccttct tccaatgttc ctcccctctc tgtatgaacc ctgtgttggg gggcagaaga     60
tggaagccct tggcaagctc gatcgaacca agctactaaa ttgctgagct cgttttaact   120
gaagtgtgag aaggaggttt aaggcaagta gacaacatcc tgttgttggg gtgcttctct   180
cttttttgca catctggctg aactgggagt caggtggttg acttgtgcct ggctgcagta   240
gcagcggcat ctcccttgca cagttctcct cctcggcctg cccaagagtc caccaggcca   300
tggacgcagt ggctgtgtat catggcaaaa tcagcaggga aaccggcgag aagctcctgc   360
ttgccactgg gctggatggc agctatttgc tgagggacag cgagagcgtg ccaggcgtgt   420
actgcctatg tgtgctgtat cacggttaca tttatacata ccgagtgtcc cagacagaaa   480
caggttcttg gagtgctgag acagcacctg gggtacataa aagatatttc cggaaaataa   540
aaaatctcat ttcagcattt cagaagccag atcaaggcat tgtaatacct ctgcagtatc   600
cagttgagaa gaagtcctca gctagaagta cacaaggtac tacagggata agagaagatc   660
ctgatgtctg cctgaaagcc ccatgaagaa aaataaaaca ccttgtactt tatttttctat 720
```

```
aatttaaata tatgctaagt cttatatatt gtagataata cagttcggtg agctacaaat        780
gcatttctaa agccattgta gtcctgtaat ggaagcatct agcatgtcgt caaagctgaa        840
atggactttt gtacatagtg aggagctttg aaacgaggat tgggaaaaag taattccgta        900
ggttattttc agttattata tttacaaatg ggaaacaaaa ggataatgaa tactttataa        960
aggattaatg tcaattcttg ccaaatataa ataaaaataa tcctcagttt ttgtgaaaag       1020
ctccattttt agtgaaatat tattttatag ctactaattt taaaatgtct tgcttgattg       1080
tatggtggga agttggctgg tgtcccttgt ctttgccaag ttctccacta gctatggtgt       1140
cataggctct tttgggattt ttgaagctgt atactgtgtg ctaaaacaag cactaaacaa       1200
agagtgaagg atttatgttt aattctgaaa gcaaccttct tgcctagtgt tctgatattg       1260
gacagtaaaa tccacagacc aacctggagt tgaaaatctt ataatttaaa atatgctcta       1320
aacatgttta tcgtatttga tgctacagga tttgaaattg tattacaaat ccaatgaaat       1380 gagttttttct tttcatttac ctctgcccca gttgtttcta ctacatggaa gacctcattt       1440
tgaagggaaa tttcagcagc tgcagctcat gagtaactga tttgtaacaa gcctcctttt       1500
aaagtaaccc tacaaaacca ctggaaagtt tatggttgta ttatttttta aaaaaattcc       1560
aagtgattga aacctacacg agatacagaa ttttatgcgg cattttcttc tcacatttat       1620 attttttgtga ttttgtgatt gattatatgt cactttgcta cagggctcac agaattcatt       1680
cactcaacaa acataatagg gcgctgaggg catagaagta aaaacacctg gtccctgctc       1740
tcagttcact gtcttgttgg acgagaaaag aaacaataac gataaaagac agtgaaagaa       1800
aataacgata aagacagtg aaagaaaata acaataaaag acaaggaaaa aataacaatg       1860
aaagttgata agtacatgat aagcgaggtt ccccgtgtgt aggtagatct ggtctttaga       1920
ggcagataga taggtcagtg caaatactct ggtccatggg ccatatgaaa aggctaagct       1980
tcactgtaaa ataataactg ggaattctgg attgtgtatg ggtgttggtg aacttggttt       2040
taattagtga actgctgaga gacagagcta ttctccatgt actggcaaga cctgatttct       2100
gagcatttaa tatggatgcc gtgggagtac aaaagtggag tgtggcctga gtaatgcatt       2160
atgggtggtt taccattcct tgaggtaaaa gcatcacatg aacttgtaaa ggaatttaaa       2220
aatcctactt tcataataag ttgcataggt ttaataattt ttaattatat ggcttgagtt       2280
taaattgtaa taggcgtaac taattttaac tctataatgt gttcattctg gaataatcct       2340
aaacatatga attatgtttg catgttcact tccaagagcc ttttttttgaa aaaaagcttt       2400 ttttgaatca tcaagtcttt cacatttaaa taaagtgttt gaaagcttta tttaaaaaaa       2460
aaaaaaaaaa aaaaaaaaaa aaaaaaaaaa aaaaaaaaaa aaaaaaaaaa aaaaaaaaaa       2520
aagaaaaaaa                                                              2530
```

<210> SEQ ID NO 71
<211> LENGTH: 601
<212> TYPE: DNA
<213> ORGANISM: Homo sapiens

<400> SEQUENCE: 71

```
aattgttttc taagtaattg ctgcctctat tatggcactt catttttgca ctgtcttttg         60
agattcaaga aaaatttcta ttcttttttt tgcatccaat tgtgcctgaa cttttaaaat        120
atgtaaatgc tgccatgttc caaacccatc gtcagtgtgt gtgtttagag ctgtgcaccc        180
tagaaacaac atattgtccc atgagcaggt gcctgagaca cagacccctt tgcattcaca        240
gagaggtcat tggttataga gacttgaatt aataagtgac attatgccag tttctgttct        300
```

```
ctcacaggtg ataaacaatg cttttttgtgc actacatact cttcagtgta gagctcttgt    360
tttatgggaa aaggctcaaa tgccaaattg tgtttgatgg attaatatgc ccttttgccg    420
atgcatacta ttactgatgt gactcggttt tgtcgcagct ttgctttgtt taatgaaaca    480
cacttgtaaa cctcttttgc actttgaaaa agaatccagc gggatgctcg agcacctgta    540
aacaattttc tcaacctatt tgatgttcaa ataagaatt aaactaaaaa aaaaaaaaa    600 a                                                                     601
```

<210> SEQ ID NO 72
<211> LENGTH: 1286
<212> TYPE: DNA
<213> ORGANISM: Homo sapiens

<400> SEQUENCE: 72

```
ggcgccgcgg acgctgctgg agtcgcctgg caacgatgtc gcctggcaac tgaataggtt     60
ggccagtggc gcgggctact ggaagcagaa agggctgcgg aggcagtgag tggtttctgc    120
agagcttcat ttggaaaggc ctctgtagtt ggggaaagat ggcccattcc cagaactcct    180
tggagcttcc cattaacatc aatgccaccc agattaccac tgcctatggc catcgggccc    240
tgcccaagct gaaggaggag ctgcagtcag aggacctcca gacgaggcag aaagccctca    300
tggccctgtg tgacctcatg catgaccccg agtgtatcta caggccatg aacataggct    360 gtatggagaa cctgaaagct tgctgaagg atagcaacag tatggtgcgc ataaagacca    420
ccgaggtgct ccacatcacg gcaagccata gcgtgggcag atacgccttt ctagagcacg    480
acatcgtcct tgccctgtcc ttcctgctga atgacccag cccagtctgc cggggggaacc    540 tgtacaaggc atacatgcag ctggtccagg tgcctagagg ggcccaagag atcatcagca    600
aaggtctgat tcctcactg gtatggaagc tgcaggtgga ggtggaggag gaggagttcc    660
aggagttcat cctggacaca ctggtcctct gcctgcagga ggatgccacc gaggccctgg    720
gcagcaatgt ggtgcttgtc ctgaagcaga agctcctcag cgccaaccag aacatccgca    780
gcaaggccgc ccgtgcgctc cttaatgtca gcatatctcg agagggcaag aaacaggtgt    840
gtcattttga cgtcatcccc atcctggtcc atctgctgaa agacccagtg gagcatgtga    900
agtctaacgc tgccggtgcc ctgatgttcg ccacagtgat cactgaaggg aagtatgcgg    960
ccctggaggc acaagccatc ggcctgctcc tggagctgct gcactccccc atgaccatag   1020
cgcgcctgaa tgccaccaag gcccttacca tgctggcaga ggcccccgag ggccgcaagg   1080
ccctgcagac gcacgtgccc actttccgtg ccatggaggt ggagacttac gaaaagcctc   1140
aagtggccga agccttacag cgggcagccc ggatcgccat cagtgtcatc gagttcaaac   1200
cctgagccct tcattcacct ctgtgagtga ataaatgtgc taagtctctt taaaaaaaa   1260 aaaaaaaaa aaaaaaaaa aaaaaa                                         1286
```

<210> SEQ ID NO 73
<211> LENGTH: 2651
<212> TYPE: DNA
<213> ORGANISM: Homo sapiens

<400> SEQUENCE: 73

```
agagcagtaa gcttgtgata aaggccaatt ccaggtagct cttgaaggtg atagccatct     60
actttccagt ggctgccaac cacagggagt gccagttaac actggaagga ttaaggcaag    120
gtcccttctc ttgagactcc cctctgagat ctgaaaaatg aagtggctta ggaacatcag    180
```

```
cagtgaagaa ctgccaagag ttggtgaagg ttgtctcttc cgagggcctt ctgaagacag    240
ggctcttgaa cagacaagtg gaagggctgt accagggata aaggaaagaa gtgcctgtcc    300
agcagggagc ttgaatttaa gttccatgta tgaagtcatt ggctctatct gcattttct    360 gtcattctct tcatttgttt taaggtggaa aattttctta cagttgatgc aaagtatcaa    420
ctactttacc ctaccttctc cccttttaga tgggttcttc ctgagttttg gagtcttgta    480
tgattatcag tattcccctg tcaaaatcaa atctattcag gtttcttcac tgttgagaac    540
acctaaatgt ttttattttt gagaagtggg gacagagtct cactatgtca cccaggctgg    600
agtgcaatgg catgatctca gctcactgca accttcgcct cctgggttca gcgattctc    660 ctgcctccgc ctcctgagta gctgggatta taggcacgca ccaccacgcc cagctaattt    720
tttgtatttt tagtagagac agagtttcac catgttggcc aggctggtct tgaactcctg    780
accttgtgat ccacccacct cggcctccca gagtgctggg attacaggca tgagccacca    840
cgcttggcta agaacaccta aatttttatg tttcttggct caaaaaccag ttccatttct    900
aatgttgtcc tcacaagaag gctaattggt ggtgagacag caggggagga ggaagagctg    960
tggtttgtaa cttgttcaac tcaggcaata agcgatttta gctttattta aagtcttctg   1020
tccagcttta agcactttgt aagacatggc tgaaagtagc ttttctatca gaattgcaga   1080
tagtcatgtt gggctaacag tcaattggat atattccttt acctcacatg accccagcaa   1140
ctgtggtggt atctagaggt gaaacaggca agtgaaatgg acacctctgc tgtgaatgtt   1200
ttagagaagg aaattcaaaa aatgttgtaa ctgaaagcac tgttgaatat gggtatcggc   1260 tttcttttc actttgactc ttaacattat cagtcaactt ccacattaat gaaagttgac   1320
catagttatt tccaaataaa aagaaaccaa ctcttaccag gtcttggact gtgatgtcat   1380
attattcagt tttatgcttg ttcctgagca gaactcataa gagtgacata gtcagctgct   1440
gacggcacct cagccacgcc actcttactc agttcagtgg gtgtgcttgc gtggtaggat   1500
gtggtgcagc cctctctacg ctcttctatt tttggtatat ttcctatcta accttcaaat   1560
agcttccaat tctttttttc ttggactggc ttcattctga atttgtgcta aaataatctt   1620
tcataaagag acctcagttt atagcgtaac agactacaca atgcactgat gttttcataa   1680
tgtttaaggg acccactgca agaagcttgc tgcctccttt taattgtatt catttagatt   1740
ttgattttcc atgttaagaa ggtgaggtcc atgttggtgc ccttcagagt agagaaccat   1800
gtaaacatta ggaatgaaca gaggccttag gaatgaatag agagtttgcc ttatacaatt   1860
tcctgttaca aagctctccc tctcatgcaa agtagggaac accttttgag catctttgaa   1920
tttgacaaat ggtgctgttg caaacacttt tttttgaga tgaagtctcg cggttgtcac   1980
ccgggctgga gtgcagtggc gtgatctcgg ctcactgcaa cttccacctc ctgggttcca   2040
gcagttctcc tgcctcagcc tcccaagtag ctgagattac aggcgcctgc caccccacct   2100
ggctgatttt tgtaattta gtagagacgg ggtttcacca tgttggccag gctgattaac   2160
tcctgacctc aggtgatcca cctttctcgg cctcccaaag tgctgggatt acgggtgtga   2220
gccaccgtgc ccggcctgca aacacatttt aattgacaac actagggctg ttgtacaaaa   2280
tagtaatgat agccatggaa gttttacctt attctgtgag aagtgttctt aaacttatta   2340
agtgtctaaa ctaaggttta gtgcttttt aaaggaaagt tgtcccagga ttcatcctaa   2400
agaaagcaaa agttaattca actgatccac caatggaatt agatgggtag agttgggttc   2460
ttgagtttta ccaccactta gttcccactg aattttgtaa cttcctgtgt ttgcatcctc   2520
tgttcctatt ctgcccttgc tctgtgtcat ctcagtcatt tgacttagaa agtgcccttc   2580
```

```
aaaaggaccc tgttcactgc tgcactttc  aatgaattaa aatttatttc tgttctaaaa    2640
aaaaaaaaaa a                                                          2651

<210> SEQ ID NO 74
<211> LENGTH: 3403
<212> TYPE: DNA
<213> ORGANISM: Homo sapiens

<400> SEQUENCE: 74
tgatcaacaa ctgtcagctc ccagtcagag agaaagggcc tcttcagtct gtctcaggag      60
actgggagaa acagcataaa ggaccccaca aggaagggag aggtaccctg ggtcaggcgc     120
ttgtggagag agggcttcgc atgtaaagtg acgtcaggga aaatagaaca gaaaaaaagc     180
cagggccagc ccagaggcac ctgagaagaa tcagacccac agctcagccc agccctggca     240
cagagaagag acaggcctgg cagcacccag gaccccctt  tcctcagcct ccacctgcag     300
gacagcagga gcactgatgc gctgaaggta cgttctggag tctggaagca gcagaactga     360
aggaagtaaa cacgggtgtc tgggaagacc cctcaagctg cagtaaagcc caggactgaa     420
ttggccacct gaggccaagg gtggcactcc aacctcctcc taaaggctgg ctagagccac     480
aggaaagggc cagaagccag agaaagggca aggtggacc  cctgcctcca aacctcctct     540
ggagactgac ctcctctttc ctgtgcctta ttgtttctcc ctcttctctt tgttcgccac     600
tgggcggtga cctcagggat cctggcctaa cctggtgatt gtgcaggcaa ctgtgtccga     660 gaagacccctt tctctggaaga ttgaaccca attcagccat ggtgactcct ttgatgtcaa     720
actggtaagg gctgagccgt gggcacagga taccactcct tccagctctt ctgctgtgac     780
ctgcccatgg aagtccctgt ggacacgaaa tcctgtttgg atcatctaac tggaggctct     840
ctgttcttca cctccacgcg ccctcttgac cccaggaggt tcaggggagg aagtacgcca     900
ctctccactg gcaccctcct tggcctacac agagtcaccc ctgagcccct caatgtgtgc     960
tgaggtgggc cctgctctct gcaggggtat ggagagaaat agcttgggt  gctgtgaggc    1020 cccgaagaag ctgggcctgt ccttctccat cgaggcgatc ctaaagaggc ctgccaggag    1080
gagtgatatg gacagaccag aagggccagg tgaagagggc cccggagaag ctgcggcctc    1140
aggctctggg ctagaaaagc ctccaaagga ccagccccag gaaggaagga agagcaagcg    1200
gagggttcgt accaccttca ccactgagca gctgcatgag ctggagaaga tcttccactt    1260
tacccactac ccagacgttc acatccgcag ccagctggca gccaggatca acctcccaga    1320
agctcgggtg cagatctggt tccagaatca gcgagccaag tggcggaagc aggagaagat    1380
tggcaacctg ggggctccac agcagctgag tgaagccagt gtggtcctgc ccacaaatct    1440
ggatgtggct gggcccacgt ggacatccac tgctctgcgc aggctggctc ctcccacgag    1500
ctgttgtcca tcggctcaag atcagctggc ctctgcctgg ttccctgcct ggatcaccct    1560
cctcccagcg cacccatggg aaacacagcc tgtcccaggt cttcccatcc atcaaacttg    1620
catccctgtg ctatgcatcc ttccacctcc acccccaaa  tggggcagca tctgtgctac    1680
ttcaacatag agattggaca tgctctcccc aaatgagcca ctttcctctc caggtgaagg    1740
caggtagcag atgtgccctg ggcctctggg gaaatcgatc tcacaatcca aaatggccc     1800 acagcccagg aagctaccct gaacatgcca gttggaaggc tgcaccagac tcaaaagcaa    1860
actaaacaat aaaggacagc tctcttctct cctggctaaa gctgctctcc tggttcagaa    1920
gacaggctgg atgagatctc aggccgagct ctgaaatagg gaggtaatcc tccagcacct    1980
```

```
gtgtttcctc taacttgctg tgtgacctcc agccggtcac tcaccctctc tggacctcat    2040
ctgtaagagg agccagctgg ataagatgat ttctgaagac gcttccatgg tgggcactga    2100
ggcacagagg aggccaagga gaggttgttt gttcatgcat gcattcatcc gtgacacatg    2160
agtacctact gaggactcca taaacagaac gggatacaga gataaacaat ttgggttctg    2220
tccacgtttg tcaaaaggtg gtgctggccc acctctgaaa gcagaacact tgctcaacaa    2280
ccttgctgtt ggcccaagtc taacacattc tttatgactg tgagcatctc agagtgagag    2340
aaaaatgtag aaagtttttt aaattctaaa caggatttag tgtctttagt tatcttgctg    2400
gatgggaaag ggatgttgtc atttctggca caaatgaaaa gtaggacgga aagctccttt    2460
cattcagttt atctttccag gatatatgaa aagggaccag ctggaagact agcctcactc    2520
tgtcctcgaa agcctgagct ttcattcaac tccctatttc catgcaaaga cgctgggcaa    2580
accacatgtt ctgtctgagc ctcagttttc ctatccataa aatgaaggta gccaggcctg    2640
cctcaaagag cattcaggag gctctgagag gacatgagag tattttgcaa agtgagggca    2700
aggcccagtg tggagtgata ttgttattcc aagattccac tgcaaaagtg gctgctttgg    2760
atgccagccc aggatgagta gttcctgttc tcagggaggt catccgctga gcatcccttc    2820
tgcacagatg tctctgattc ttgtccttgc aggtggagga cagggcctgc tcccctaagc    2880
tgggaagcct ggaatgacct cttgcacaag cctaaattcc aggaatcttc cccaaatccc    2940
agatcctctg caatctacct gcaccccctga cccacccagg agttggaccg ggagttggga    3000
agcctaggtc ttagtcctac actccttcta atttgctgtg taaccttacc attaatctct    3060
ctgggtctca gttttctcat ctgtattgga ggtagcagtg ctagctctgc cttcaggcat    3120
gcaatatgcc agaactacag acaacagccc acaggatgca aaagtgcttt gccatcttaa    3180 aaaatgccaga tcactcagag cctatgaatg tggatatcaa caccaggtct ctagcaccgc    3240
tggatgaaag gagaaggcta gaggctgagg gaggaaagag cagttaacaa acaaaggcag    3300
tagctcatca cttgggtagc aggtacccat tttaggaccc tacactcaaa tgtgcaaaat    3360
aaaatttcta tcattttgct ataaaaaaaa aaaaaaaaaa aaa                      3403
```

<210> SEQ ID NO 75
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 75

```
cccggatcgc catcagtgtc atcgagttca aaccctgagc ccttcattca cctctgtgag    60
```

<210> SEQ ID NO 76
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 76

```
tgcccttgct ctgtgtcatc tcagtcattt gacttagaaa gtgcccttca aaaggaccct    60
```

<210> SEQ ID NO 77
<211> LENGTH: 60
<212> TYPE: DNA
<213> ORGANISM: Artificial Sequence
<220> FEATURE:
<223> OTHER INFORMATION: Synthetic construct - oligonucleotide -continued

<400> SEQUENCE: 77
ggagggaggg ctaattatat attttgttgt tcctctatac tttgttctgt tgtctgcgcc    60

<210> SEQ ID NO 78
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 78
cagtttggat tgtataataa cgccaagccc agttgtagtc gtttgagtgc agtaatgaaa    60

<210> SEQ ID NO 79
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 79
aaatcagagt aaccctttct gtattgagtg cagtgttttt tactcttttc tcatgcacat    60

<210> SEQ ID NO 80
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 80
tgcctggcac aaagaaggaa gaatataaat gatagttcga ctcgtctgtg gaagaactta    60

<210> SEQ ID NO 81
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 81
agtcttttgc ttttggcaaa actctactta atccaatggg ttttccctg tacagtagat     60

<210> SEQ ID NO 82
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 82
ggttactgtg ggtggaatag tggaggcctt caactgatta dacaaggccc gcccacatct    60

<210> SEQ ID NO 83
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 83
taaaatgcac tgccctactg ttggtatgac taccgttacc tactgttgtc attgttatta    60

<210> SEQ ID NO 84

```
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 84
ttctcttttg ggggcaaaca ctatgtcctt ttcttttctc agatacagtt aattcctgga    60

<210> SEQ ID NO 85
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 85
aagacccaca ccctgtagca ataccaagtg ctattacata atcaatggac gatttatact    60

<210> SEQ ID NO 86
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 86
agtgttgcaa gtttccttta aaaccaacaa agcccacaag tcctgaattt cccattctta    60

<210> SEQ ID NO 87
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 87
gtcactgtca tagcagctgt gatttcacaa ggaagggtgc tgcaggggga cctggttgat    60

<210> SEQ ID NO 88
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 88
tttcatccag tgttatgcac tttccacagt tggtgttagt atagccagag ggtttcatta    60

<210> SEQ ID NO 89
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 89
gggaagtagg gattattcgt ttaaattcaa tcgcgagcac caagtcggac tggccgggga    60

<210> SEQ ID NO 90
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 90
```
gggaccaggc cctgggacag ccatgtggct ccaaatgact aaatgtcagc tcaaaaacca    60

<210> SEQ ID NO 91
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 91
tccgtttatg gaggcaattc catatccttt cttgaacgca cattcagctt accccagaga    60

<210> SEQ ID NO 92
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 92
agagttaagc cacttcctgg gtctccttct tatgactgtc tatgggtgca ttgccttctg    60

<210> SEQ ID NO 93
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 93
gtggcctgag taatgcatta tgggtggttt accatttctt gaggtaaaag catcacatga    60

<210> SEQ ID NO 94
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 94
acacatgcat gtgtctgtgt atgtgtgaat gtgagagaga cacagccctc ctttcagaag    60

<210> SEQ ID NO 95
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 95
tctgtaactg cacaaccctg gggtttgctg cagagctatt tctttccatg taaagtagtg    60

<210> SEQ ID NO 96
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 96
aaacactctt tccgactcca gaggagaagc tggcagctct ctgtaagaaa tatgctgatc    60

<210> SEQ ID NO 97
<211> LENGTH: 60
<212> TYPE: DNA

```
<213> ORGANISM: Artificial Sequence
<220> FEATURE:
<223> OTHER INFORMATION: Synthetic construct - oligonucleotide

<400> SEQUENCE: 97
gcttcctcta tcgcccaatg caaaatcgat gaaatgggga gttctctggg ccaggccaca        60

<210> SEQ ID NO 98
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 98
gtagaatcct ctgttcataa tgaacaagat gaaccaatgt ggattagaaa gaagtccgag        60

<210> SEQ ID NO 99
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 99
ctgttttaaa actgaatggc acgaaattgt tttcctcaac tcggagattc ctgtatggag        60

<210> SEQ ID NO 100
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 100
aataaatagt agctctgctg atgatgacgt tgataaccaa actgttctgt ggtcttaagt        60

<210> SEQ ID NO 101
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 101
caaacagccc ggtcttgatg caggagagtc tggaaaagga agaaaatggt ttcagtttca        60

<210> SEQ ID NO 102
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 102
aacatggacc atccaaattt atggccgtat caaatggtag ctgaaaaaac tatatttgag        60

<210> SEQ ID NO 103
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 103
ttgtaatcat gccaattcca gatcaataac tgcatgtctg ttctttggta gaaatagctt        60
```

<210> SEQ ID NO 104
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 104
aaagattatt aacccaaatc acctttcttg cttactccag atgcctcagc ctctgatata    60

<210> SEQ ID NO 105
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 105
gacttccttt aggatctcag gcttctgcag ttctcatgac tcctactttt catcctagtc    60

<210> SEQ ID NO 106
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 106
ctgtatattt tgcaatagtt acctcaaggc ctactgacca aattgttgtg ttgagatgat    60

<210> SEQ ID NO 107
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 107
tgttcaaaca gactttaacc tctgcatcat acttaaccct gcgacatgcg tacagtatgc    60

<210> SEQ ID NO 108
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 108
tgagtcatat acatttactg accactgttg cttgttgctc actgtgctgc ttttccatga    60

<210> SEQ ID NO 109
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 109
ctgaaatgtg gatgtgattg cctcaataaa gctcgtcccc attgcttaag ccttcaaaaa    60

<210> SEQ ID NO 110
<211> LENGTH: 60
<212> TYPE: DNA
<213> ORGANISM: Artificial Sequence
<220> FEATURE:

<223> OTHER INFORMATION: Synthetic construct - oligonucleotide

<400> SEQUENCE: 110
atcaagaaaa cctaatcttc tgactcccag gccaggatgt tttatttctc acatcatgtc    60

<210> SEQ ID NO 111
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 111
ttcatttcca aacatcatct ttaagactcc aaggattttt ccaggcacag tggctcatac    60

<210> SEQ ID NO 112
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 112
agttagaaat agaatctgaa tttctaaagg gagattctgg cttgggaagt acatgtagga    60

<210> SEQ ID NO 113
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 113
caattttctt tttactcccc ctcttaaggg ggccttggaa tctatagtat agaatgaact    60

<210> SEQ ID NO 114
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 114
gggtggagtt tcagtgagaa taaacgtgtc tgcctttgtg tgtgtgtata tatacagaga    60

<210> SEQ ID NO 115
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 115
ctcgctcatt ttttaccatg ttttccagtc tgtttaactt ctgcagtgcc ttcactacac    60

<210> SEQ ID NO 116
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 116
ctttgggccg agcactgaat gtcttgtact ttaaaaaaat gtttctgaga cctctttcta    60

```
<210> SEQ ID NO 117
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 117 ctggacccctt ggagcagtgt tgtgtgaact tgcctagaac tctgccttct ccgttgtcaa    60

<210> SEQ ID NO 118
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 118
ccacctcctt cgacctccac tgcgccccac ctccctgcct gtgtgtgtta tttcaaagga    60

<210> SEQ ID NO 119
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 119
tctggctggt ggcctgcgcg agggtgcagt cttacttaaa agactttcag ttaattctca    60

<210> SEQ ID NO 120
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 120
agatgctgtc ggcaccatgt ttatttattt ccagtggtca tgctcagcct tgctgctctg    60

<210> SEQ ID NO 121
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 121
tccttcctct tcggtgaatg caggttattt aaactttggg aaatgtactt ttagtctgtc    60

<210> SEQ ID NO 122
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 122
gtcctgtccc tgtctgggag ttgtgttatt taaagatatt ctgtatgttg tatcttttgc    60

<210> SEQ ID NO 123
<211> LENGTH: 60
<212> TYPE: DNA
<213> ORGANISM: Artificial Sequence
<220> FEATURE:
<223> OTHER INFORMATION: Synthetic construct - oligonucleotide
```

<400> SEQUENCE: 123
attatatttc aggtgtcctg aacaggtcac tagactctac attgggcagc ctttaaatat    60

<210> SEQ ID NO 124
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 124
aggaatggta ctaccgttcc agattttctg taattgcttc tgcaaagtaa taggcttctt    60

<210> SEQ ID NO 125
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 125
ctgtacccaa aggatgccag aatactagta tttttattta tcgtaaacat ccacgagtgc    60

<210> SEQ ID NO 126
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 126
attgcccccc taaccaatca tgcaaacttt tccccccctg gggtaattca ccagttaaaa    60

<210> SEQ ID NO 127
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 127
cccacagtat ttaatgccct gtcagtccct tctagtctga ctcaatggta acttgctgta    60

<210> SEQ ID NO 128
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 128
aaaaccaact ctctactaca caggcctgat aactctgtac gaggcttctc taacccctag    60

<210> SEQ ID NO 129
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 129
ctcagactgg gctccacact cttgggcttc agtctgccca tctgctgaat ggagacagca    60

<210> SEQ ID NO 130
<211> LENGTH: 60

```
<212> TYPE: DNA
<213> ORGANISM: Artificial Sequence
<220> FEATURE:
<223> OTHER INFORMATION: Synthetic construct - oligonucleotide

<400> SEQUENCE: 130
cctaatgggg attcctctgg ttgttcactg ccaaaactgt ggcatttca ttacaggaga      60

<210> SEQ ID NO 131
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 131
cactcacaat tgttgactaa aatgctgcct ttaaaacata ggaaagtaga atggttgagt      60

<210> SEQ ID NO 132
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 132
ctttgaaggg ctgctgcaca ttgttgaatc catcgacctt tagctgcaat gggatctcta      60

<210> SEQ ID NO 133
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 133
tgcctcatcg atattatagg ggtccatcac aacccaactg tgtggccgga tcctgagtct      60

<210> SEQ ID NO 134
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 134
aaaacagaca aaagcctttg ccttcatgaa gcatacattc attcagggga agacacacaa      60

<210> SEQ ID NO 135
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 135
taacaaacaa aggcagtagc tcatcacttg ggtagcaggt acccatttta ggaccctaca      60

<210> SEQ ID NO 136
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 136
```
atatcagaag tgccaataat cgtcataggc ttctgcacgt tggatcaact aatgttgttt    60

<210> SEQ ID NO 137
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 137
atcatagccc aaccatgtga gaagaaggag aaggccccccc tttcttcatt aatctgaaaa    60

<210> SEQ ID NO 138
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 138
gcagaccatt ctatcatacc tggcagggct tctgttttat tttgtaggct ggatgctacc    60

<210> SEQ ID NO 139
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 139
actacaagcc tcttgttttt caccaaaacc ctacatctca ggcttactaa tttttgtgat    60

<210> SEQ ID NO 140
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 140
gccatgcata catgctgcgc atgttttctt cattcgtatg ttagtaaagt tttggttatt    60

<210> SEQ ID NO 141
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 141
cacctattta ttttacctct ttcccaaacc tggagcattt atgcctaggc ttgtcaagaa    60

<210> SEQ ID NO 142
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 142
gtggacatag ccactaacca actagttacc tttggactgc aacaaaaaat gtgaaaatga    60

<210> SEQ ID NO 143
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 143
acttgtaaac ctcttttgca ctttgaaaaa gaatccagcg ggatgctcga gcacctgtaa    60

<210> SEQ ID NO 144
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 144
aattctctat aaacggttca ccagcaaacc accaatacat tccattgttt gcctagagag    60

<210> SEQ ID NO 145
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 145
aatggcccat gcatgctgtt tgcagcagtc aattgagttg aattagaatt ccaaccatac    60

<210> SEQ ID NO 146
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 146
gagctcagta cttgccctgt gaaaatccca gaagcccccg ctgtcaatgt tccccatcca    60

<210> SEQ ID NO 147
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 147
atgaagcgga attaggctcc cgagctaagg gactcgccta gggtctcaca gtgagtagga    60

<210> SEQ ID NO 148
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 148
agtggctata tcaacatcag ggctagcaca tctttctcta ttatccttct attggaattc    60

<210> SEQ ID NO 149
<211> LENGTH: 1108
<212> TYPE: DNA
<213> ORGANISM: Homo sapiens

<400> SEQUENCE: 149
gagtgagtga gagggcagag gaaatactca atctgtgcca ctcactgcct tgagcctgct    60
tcctcactcc aggactgcca gaggctcact cccttgagcc tgcttcctca ctccaggact   120

| | |
|---|---|
| gccagaggaa gcaatcacca aaatgaagac tgctttaatt ttgctcagca tttttgggaat | 180 |
| ggcctgtgct ttctcaatga aaaatttgca tcgaagagtc aaaatagagg attctgaaga | 240 |
| aaatggggtc tttaagtaca ggccacgata ttatctttac aagcatgcct acttttatcc | 300 |
| tcatttaaaa cgatttccag ttcagggcag tagtgactca tccgaagaaa atggagatga | 360 |
| cagttcagaa gaggaggagg aagaagagga gacttcaaat gaaggagaaa acaatgaaga | 420 |
| atcgaatgaa gatgaagact ctgaggctga gaataccaca ctttctgcta caacactggg | 480 |
| ctatggagag gacgccacgc ctggcacagg gtatacaggg ttagctgcaa tccagcttcc | 540 |
| caagaaggct ggggatataa caaacaaagc tacaaaagag aaggaaagtg atgaagaaga | 600 |
| agaggaggaa gaggaaggaa atgaaaacga agaaagcgaa gcagaagtgg atgaaaacga | 660 |
| acaaggcata aacggcacca gtaccaacag cacagaggca gaaaacggca acggcagcag | 720 |
| cggaggagac aatggagaag aagggggaaga agaaagtgtc actggagcca atgcagaagg | 780 |
| caccacagag accggagggc agggcaaggg cacctcgaag acaacaacct ctccaaatgg | 840 |
| tgggtttgaa cctacaaccc caccacaagt ctatagaacc acttccccac ctttgggaa | 900 |
| aaccaccacc gttgaatacg aggggagta cgaatacacg ggcgtcaatg aatacgacaa | 960 |
| tggatatgaa atctatgaaa gtgagaacgg ggaacctcgt ggggacaatt accgagccta | 1020 |
| tgaagatgag tacagctact ttaaaggaca aggctacgat ggctatgatg gtcagaatta | 1080 |
| ctaccaccac cagtgaagct ccagcctg | 1108 |

<210> SEQ ID NO 150
<211> LENGTH: 4767
<212> TYPE: DNA
<213> ORGANISM: Homo sapiens

<400> SEQUENCE: 150

| | |
|---|---|
| gcctcccgcc gcctcccgcg cggccatgga ctgagcgccg ccggccaggc cgcggggatg | 60 |
| gggccgccgc tcccgctgct gctgctgcta ctgctgctgc tgccgccacg cgtcctgcct | 120 |
| gccgcccctt cgtccgtccc ccgcggccgg cagctcccgg ggcgtctggg ctgcctgctc | 180 |
| gaggagggcc tctgcggagc gtccgaggcc tgtgtgaacg atggagtgtt tggaaggtgc | 240 |
| cagaaggttc cggcaatgga cttttaccgc tacgaggtgt cgcccgtggc cctgcagcgc | 300 |
| ctgcgcgtgg cgttgcagaa gctttccggc acaggtttca cgtggcagga tgactatact | 360 |
| cagtatgtga tggaccagga acttgcagac ctcccgaaaa cctacctgag gcgtcctgaa | 420 |
| gcatccagcc cagccaggcc tcaaaaacac agcgttggca gcgagaggag gtacagtcgg | 480 |
| gagggcggtg ctgccctggc caacgccctc cgacgccacc tgcccttcct ggaggccctg | 540 |
| tcccaggccc cagcctcaga cgtgctcgcc aggacccata cggcgcagga cagacccccc | 600 |
| gctgagggtg atgaccgctt ctccgagagc atcctgacct atgtggccca cgtctgcg | 660 |
| ctgacctacc ctcccgggcc ccggacccag ctccgcgagg acctcctgcc gcggaccctc | 720 |
| ggccagctcc agccagatga gctcagccct aaggtgaca gtggtgtgga cagacaccat | 780 |
| ctgatggcgg ccctcagtgc ctatgctgcc cagaggcccc cagctccccc ggggagggc | 840 |
| agcctggagc cacagtacct tctgcgtgca ccctcaagaa tgcccaggcc tttgctggca | 900 |
| ccagccgccc cccagaagtg gccttcacct ctgggagatt ccgaagaccc ctccagcaca | 960 |
| ggcgatggag cacggattca taccctcctg aaggacctgc agaggcagcc ggctgaggtg | 1020 |
| aggggcctga gtggcctgga gctggacggc atggctgagc tgatggctgg cctgatgcaa | 1080 |
| ggcgtggacc atggagtagc tcgaggcagc cctgggagag cggccctggg agagtctgga | 1140 |

```
gaacaggcgg atggcccaa ggccaccctc cgtggagaca gctttccaga tgacggagtg   1200
caggacgacg atgatagact ttaccaagag gtccatcgtc tgagtgccac actcgggggc   1260
ctcctgcagg accacgggtc tcgactctta cctggagccc tcccctttgc aaggcccctc   1320
gacatggaga ggaagaagtc cgagcaccct gagtcttccc tgtcttcaga agaggagact   1380
gccggagtgg agaacgtcaa gagccagacg tattccaaag atctgctggg gcagcagccg   1440
cattcggagc ccggggccgc tgcgtttggg gagctccaaa accagatgcc tgggccctcg   1500
aaggaggagc agagccttcc agcgggtgct caggaggccc tcagcgacgg cctgcaattg   1560
gaggtccagc cttccgagga agaggcgcgg ggctacatcg tgacagacag agacccctg    1620 cgccccgagg aaggaaggcg gctggtggag gacgtcgccc gcctcctgca ggtgcccagc   1680
agtgcgttcg ctgacgtgga ggttctcgga ccagcagtga ccttcaaagt gagcgccaat   1740
gtccaaaacg tgaccactga ggatgtggag aaggccacag ttgacaacaa agacaaactg   1800
gaggaaacct ctggactgaa aattcttcaa accggagtcg ggtcgaaaag caaactcaag   1860
ttcctgcctc ctcaggcgga gcaagaagac tccaccaagt tcatcgcgct caccctggtc   1920
tccctcgcct gcatcctggg cgtcctcctg gcctctggcc tcatctactg cctccgccat   1980
agctctcagc acaggctgaa ggagaagctc tcgggactag ggggcgaccc aggtgcagat   2040
gccactgccg cctaccagga gctgtgccgc cagcgtatgg ccacgcggcc accagaccga   2100
cctgagggcc cgcacacgtc acgcatcagc agcgtctcat cccagttcag cgacgggccg   2160
atccccagcc cctccgcacg cagcagcgcc tcatcctggt ccgaggagcc tgtgcagtcc   2220
aacatggaca tctccaccgg ccacatgatc ctgtcctaca tggaggacca cctgaagaac   2280
aagaaccggc tggagaagga gtgggaagcg ctgtgcgcct accaggcgga gcccaacagc   2340
tcgttcgtgg cccagaggga ggagaacgtg cccaagaacc gctccctggc tgtgctgacc   2400
tatgaccact cccgggtcct gctgaaggcg gagaacagcc acagccactc agactacatc   2460
aacgctagcc ccatcatgga tcacgacccg aggaaccccg cgtacatcgc cacccaggga   2520
ccgctgcccg ccaccgtggc tgacttttgg cagatggtgt gggagagcgg ctgcgtggtg   2580
atcgtcatgc tgacacccct cgcggagaac ggcgtccggc agtgctacca ctactggccg   2640
gatgaaggct ccaatctcta ccacatctat gaggtgaacc tggtctccga gcacatctgg   2700
tgtgaggact tcctggtgag gagcttctat ctgaagaacc tgcagaccaa cgagacgcgc   2760
accgtgacgc agttccactt cctgagttgg tatgaccgag gagtccctcc ctcctcaagg   2820
tccctcctgg acttccgcag aaaagtaaac aagtgctaca ggggccgttc ttgtccaata   2880
attgttcatt gcagtgacgg tgcaggccgg agcggcacct acgtcctgat cgacatggtt   2940
ctcaacaaga tggccaaagg tgctaaagag attgatatcg cagcgaccct ggagcacttg   3000
agggaccaga gacccggcat ggtccagacg aaggagcagt ttgagttcgc gctgacagcc   3060
gtggctgagg aggtgaacgc catcctcaag gcccttcccc agtgagcggc agcctcaggg   3120
gcctcagggg agcccccacc ccacggatgt tgtcaggaat catgatctga ctttaattgt   3180
gtgtcttcta ttataactgc atagtaatag ggcccttagc tctcccgtag tcagcgcagt   3240
ttagcagtta aaagtgtatt tttgtttaat caaacaataa taaagagaga tttgtggaaa   3300
aatccagtta cgggtggagg ggaatcggtt catcaatttt cacttgctta aaaaaaatac   3360
tttttcttaa agcacccgtt caccttcttg gttgaagttg tgttaacaat gcagtagcca   3420
gcacgttcga ggcggttttcc aggaagagtg tgcttgtcat ctgccacttt cgggagggtg   3480
```

-continued

| | |
|---|---|
| gatccactgt gcaggagtgg ccggggaagc tggcagcact cagtgaggcc gcccggcaca | 3540 |
| caaggcacgt ttggcatttc tctttgagag agtttatcat tgggagaagc cgcggggaca | 3600 |
| gaactgaacg tcctgcagct tcggggcaag tgagacaatc acagctcctc gctgcgtctc | 3660 |
| catcaacact gcgccgggta ccatggacgg ccccgtcagc cacacctgtc agcccaagca | 3720 |
| gagtgattca ggggctcccc gggggcagac acctgtgcac cccatgagta gtgcccactt | 3780 |
| gaggctggca ctcccctgac ctcacctttg caaagttaca gatgcacccc aacattgaga | 3840 |
| tgtgttttta atgttaaaat attgatttct acgttatgaa aacagatgcc cccgtgaatg | 3900 |
| cttacctgtg agataaccac aaccaggaag aacaaatctg ggcattgagc aagctatgag | 3960 |
| ggtccccggg agcacacgaa ccctgccagg cccccgctgg ctcctccagg cacgtcccgg | 4020 |
| acctgtgggg ccccagagag gggacatttc cctcctggga gagaaggaga tcagggcaac | 4080 |
| tcggagaggg ctgcgagcat ttccctcccg ggagaggaga tcagggcgac ctgcacgcac | 4140 |
| tgcgtagagc ctggaaggga agtgagaaac cagccgaccg gccctgcccc tcttcccggg | 4200 |
| atcacttaat gaaccacgtg ttttgacatc atgtaaacct aagcacgtag agatgattcg | 4260 |
| gatttgacaa ataacatttt gagtatccga ttcgccatca cccctaccc cagaaatagg | 4320 |
| acaattcact tcattgacca ggatgatcac atggaaggcg gcgcagaggc agctgtgtgg | 4380 |
| gctgcagatt cctgtgtggg ggttcagcgt agaaaacgca cctccatccc gcccttccca | 4440 |
| cagcattcct ccatcttaga tagatggtac tctccaaagg ccctaccaga gggaacacgg | 4500 |
| cctactgagc ggacagaatg atgccaaaat attgcttatg tctctacatg gtattgtaat | 4560 |
| gaatatctgc tttaatatag ctatcatttc ttttccaaaa ttacttctct ctatctggaa | 4620 |
| tttaattaat cgaaatgaat ttatctgaat ataggaagca tatgcctact tgtaatttct | 4680 |
| aactccttat gtttgaagag aaacctccgg tgtgagatat acaaatatat ttaattgtgt | 4740 |
| catattaaac ttctgattca aaaaaaa | 4767 |

<210> SEQ ID NO 151
<211> LENGTH: 1148
<212> TYPE: DNA
<213> ORGANISM: Homo sapiens

<400> SEQUENCE: 151

| | |
|---|---|
| ggcacgaggc cacgagctgt tgtgcatcca gaggtggaat tggggcccgg cattccctcc | 60 |
| tcgtcccggg ctggcccttg cccccaccct gcaactcctg gttgagatgg gctcagccaa | 120 |
| gagcgtccca gtcacaccag cgcggcctcc gccgcacaac aagcatctgg ctcgagtggc | 180 |
| ggaccccgt tcacctagtg ctggcatcct gcgcactccc atccaggtgg agagctctcc | 240 |
| acagccaggc ctaccagcag gggagcaact ggagggtctt aaacatgccc aggactcaga | 300 |
| tccccgctct cctactcttg gtattgcacg acacctatg aagaccagca gtggagaccc | 360 |
| cccaagccca ctggtgaaac agctgagtga agtatttgaa actgaagact ctaaatcaaa | 420 |
| tcttccccca gagcctgttc tgcccccaga ggcacctta tcttctgaat tggacttgcc | 480 |
| tctgggtacc cagttatctg ttgaggaaca gatgccacct tggaaccaga ctgagttccc | 540 |
| ctccaaacag gtgttttcca aggaggaagc aagacagccc acagaaaccc ctgtggccag | 600 |
| ccagagctcc gacaagccct caagggaccc tgagactccc agatcttcag gttctatgcg | 660 |
| caatagatgg aaaccaaaca gcagcaaggt actagggaga tccccctca ccatcctgca | 720 |
| ggatgacaac tcccctggca ccctgacact acgacagggt aagcggcctt caccctaag | 780 |
| tgaaaatgtt agtgaactaa aggaaggagc cattcttgga actggacgac ttctgaaaac | 840 |

```
tggaggacga gcatgggagc aaggccagga ccatgacaag gaaaatcagc actttccctt    900
ggtggagagc taggccctgc atggcccag caatgcagtc acccagggcc tggtgatatc    960
tgtgtcctct cacccttct ttcccaggga tactgaggaa tggcttgttt tcttagactc   1020
ctcctcagct accaaactgg gactcacagc tttattgggc tttctttgtg tcttgtgtgt   1080
ttcttttata ttaaaggaag taattttaaa tgttacttta aaaggtaaa aaaaaaaaa    1140 aaaaaaaa                                                           1148
```

<210> SEQ ID NO 152
<211> LENGTH: 539
<212> TYPE: DNA
<213> ORGANISM: Homo sapiens

<400> SEQUENCE: 152

```
gcattcgtag taaaggtgcc aagaaaatta ttttggccat ttattgtttt gtccttttct     60
ttaaagaact gttttttttt cttttgttta cttttagacc aaagattggg ttctagaaaa    120
tgcacttggt atactaagta ttaaaacaaa caaaaggaa agttgtttca gttggcaaca     180
ctgcccattc aattgaatca aaggggaca aaattaacga ttgccttcag tttgtgttgt    240
gtatattttg atgtatgtgg tcactaacag gtcacttta ttttttctaa atgtagtgaa    300
atgttaatac ctattgtact tataggtaaa ccttgcaaat atgtaacctg tgttgcgcaa   360
atgccgcata aatttgagtg attgttaatg ttgtcttaaa atttcttgat tgtgatactg   420
tggtcatatg cccgtgtttg tcacttacaa aaatgtttac tatgaacaca cagaaataaa   480
aaataggcta aattcatata aaaaaaaaaa aaaaaaaaa aaaaaaaaaa aaaaaaaa     539
```

<210> SEQ ID NO 153
<211> LENGTH: 1673
<212> TYPE: DNA
<213> ORGANISM: Homo sapiens

<400> SEQUENCE: 153

```
gaggcagtaa ggacttggac tcctctgtcc agcttttaac aatctaagtt acggttaccc     60
tcttctgggt cacgctagaa tcagatctgc tctccagcat cttctgtttc ctggcaagtg    120
tttcctgcta cttttggattg gccacgatgg gctggagctg ccttgtgaca ggagcaggag   180
ggcttctggg tcagaggatc gtccgcctgt tggtggaaga gaaggaactg aaggagatca    240
gggccttgga caaggccttc agaccagaat tgagagagga attttctaag ctccagaaca    300
ggaccaagct gactgtactt gaaggagaca ttctggatga gccattcctg aaaagagcct    360
gccaggacgt ctcggtcgtc atccacaccg cctgtatcat tgatgtcttt ggtgtcactc    420
acagagagtc catcatgaat gtcaatgtga aaggtacca gctactgttg gaggcctgtg    480
tccaagccag tgtgccagtc ttcatctaca ccagtagcat agaggtagcc gggcccaact    540
cctacaagga aatcatccag aacgccacg aagaagagcc tctggaaaac acatggccca    600
ctccataccc gtacagcaaa aagcttgctg agaaggctgt gctggcggct aatgggtgga    660
atctaaaaaa tggtgatacc ttgtacactt gtgcgttaag acccacatat atctatgggg    720
aaggaggccc attcctttct gccagtataa atgaggccct gaacaacaat gggatcctgt    780
caagtgttgg aaagttctct acagtcaacc cagtctatgt tggcaacgtg gcctgggccc   840
acattctggc cttgagggct ctgcgggacc ccaagaaggc cccaagtgtc cgaggtcaat    900
tctattacat ctcagatgac acgcctcacc aaagctatga taaccttaat tacatcctga    960
```

```
gcaaagagtt tggcctccgc cttgattcca gatggagcct tcctttaacc ctgatgtact    1020
ggattggctt cctgctggaa gtagtgagct tcctactcag cccaatttac tcctatcaac    1080
cccccttcaa ccgccacaca gtcacattat caaatagtgt gttcaccttc tcttacaaga    1140
aggctcagcg agatctggcg tataagccac tctacagctg ggaggaagcc aagcagaaaa    1200
ccgtggagtg ggttggttcc cttgtggacc ggcacaagga gaccctgaag tccaagactc    1260
agtgatttaa ggatgacaga gatgtgcatg tgggtattgt taggaaatgt catcaaactc    1320
cacccacctg gcttcataca aaggcaaca ggggcacaag cccaggtcct gctgcctctc    1380
tttcacacaa tgcccaactt actgtcttct tcatgtcatc aaaatctgca cagtcactgg    1440
cccaaccaga actttctgtc ctaatcatac accagaagac aaacaatatg atttgctgtt    1500
accaaatctc agtggctgat tctgaacaat tgtggtctct cttaacttga ggttctcttt    1560
tgactaatag agctccattt cccctcttaa atgagaaagc atttcttttc tctttaatct    1620
cctattcctt cacacagttc aacataaaga gcaataaatg ttttaatgct taa           1673

<210> SEQ ID NO 154
<211> LENGTH: 518
<212> TYPE: DNA
<213> ORGANISM: Homo sapiens

<400> SEQUENCE: 154
aaattttgac cccatataaa gaaatgtgtt atgtatgttg tgcctcctta gagacataaa      60
tttagtgtca aaacatggga gatggcttac tcagaagcat actccactta acataccatg     120
gcctgagcta agtaccatgt cctgtttgtg tcttattttt aaatattttc tttgtccaca     180
tgggccgttg accttagagt taaggcggtt gcttttttga agaaatcacc aaagtttctg     240
ggaaactatg ttcaaggttg aaatggagag tagatttaat tttatttgtc ttgtagggaa     300
gaaatcttcc tttgaaccgc ttttcttgct ttttcccttt ttcccaaact aggttacagg     360
ttcttatctg caaggttcaa gttgcttaga cattgttttc cagtattctg cagggccagt     420
cagttgtaca gaagttggaa tattctgttc cagaattaaa gaagttttta gattatgaaa     480
tattatgata ataaagctat atttctgaaa aaaaaaaa                             518

<210> SEQ ID NO 155
<211> LENGTH: 2833
<212> TYPE: DNA
<213> ORGANISM: Homo sapiens

<400> SEQUENCE: 155
gaaggagctc tcttcttgct tggcagctgg accaagggag ccagtcttgg gcgctggagg      60
gcctgtcctg accatggtcc ctgcctggct gtggctgctt tgtgtctccg tcccccaggc     120
tctccccaag gcccagcctg cagagctgtc tgtggaagtt ccagaaaact atggtggaaa     180 tttccctttta tacctgacca agttgccgct gcccgtgag ggggctgaag gccagatcgt     240
gctgtcaggg gactcaggca aggcaactga gggcccattt gctatggatc cagattctgg     300
cttcctgctg gtgaccaggg ccctggaccg agaggagcag gcagagtacc agctacaggt     360
caccctggag atgcaggatg acatgtcttg tggggtccca cagcctgtgc ttgtgcacgt     420
gaaggatgag aatgaccagg tgccccattt ctctcaagcc atctacagag ctcggctgag     480
ccggggtacc aggcctggca tccccttcct cttccttgag gcttcagacc gggatgagcc     540
aggcacagcc aactcggatc ttcgattcca catcctgagc caggctccag cccagccttc     600
cccagacatg ttccagctgg agcctcggct gggggctctg gcccctcagcc caaggggag     660
```

```
caccagcctt gaccacgccc tggagaggac ctaccagctg ttggtacagg tcaaggacat      720
gggtgaccag gcctcaggcc accaggccac tgccaccgtg gaagtctcca tcatagagag      780
cacctgggtg tccctagagc ctatccacct ggcagagaat ctcaaagtcc tatacccgca      840
ccacatggcc caggtacact ggagtggggg tgatgtgcac tatcacctgg agagccatcc      900
cccgggaccc tttgaagtga atgcagaggg aaacctctac gtgaccagag agctggacag      960
agaagcccag gctgagtacc tgctccaggt gcgggctcag aattcccatg gcaggactaa     1020
tgcggcccct ctggagctgc acgtgctggt gatggatgag aatgacaacg tgcctatctg     1080
ccctccccgt gaccccacag tcagcatccc tgagctcagt ccaccaggta ctgaagtgac     1140
tagactgtca gcagaggatg cagatgcccc cggctccccc aattcccacg ttgtgtatca     1200
gctcctgagc cctgagcctg aggatggggt agaggggaga gccttccagg tggaccccac     1260
ttcaggcagt gtgacgctgg gggtgctccc actccgagca ggccagaaca tcctgcttct     1320
ggtgctggcc atggacctgg caggcgcaga gggtggcttc agcagcacgt gtgaagtcga     1380
agtcgcagtc acagatatca atgatcacgc ccctgagttc atcacttccc agattgggcc     1440
tataagcctc cctgaggatg tggagcccgg gactctggtg gccatgctaa cagccattga     1500
tgctgacctc gagcccgcct ccgcctcat ggattttgcc attgagaggg agacacaga      1560 agggacttttt ggcctggatt gggagccaga ctctgggcat gttagactca gactctgcaa     1620
gaacctcagt tatgaggcag ctccaagtca tgaggtggtg gtggtggtgc agagtgtggc     1680
gaagctggtg gggccaggcc caggccctgg agccaccgcc acggtgactg tgctagtgga     1740
gagagtgatg ccaccccca agttggacca ggagagctac gaggccagtg tccccatcag     1800
tgccccagcc ggctctttcc tgctgaccat ccagccctcc gacccatca gccgaaccct      1860 caggttctcc ctagtcaatg actcagaggg ctggctctgc attgagaaat tctccgggga     1920
ggtgcacacc gcccagtccc tgcagggcgc ccagcctggg acacctaca cggtgcttgt      1980 ggaggcccag gatacagatg agccgagact gagcgcttct gcacccctgg tgatccactt     2040
cctaaaggcc cctcctgccc cagccctgac tcttgcccct gtgccctccc aatacctctg     2100 cacacccgc caagaccatg gcttgatcgt gagtggaccc agcaaggacc ccgatctggc      2160
cagtgggcac ggtccctaca gcttcaccct tggtcccaac ccacggtgc aacgggattg      2220 gcgcctccag actctcaatg gttcccatgc ctacctcacc ttggccctgc attgggtgga     2280
gccacgtgaa cacataatcc ccgtggtggt cagccacaat gcccagatgt ggcagctcct     2340
ggttcgagtg atcgtgtgtc gctgcaacgt ggaggggcag tgcatgcgca aggtgggccg     2400
catgaagggc atgcccacga agctgtcggc agtgggcatc cttgtaggca ccctggtagc     2460
aataggaatc ttcctcatcc tcattttcac ccactggacc atgtcaagga agaaggaccc     2520
ggatcaacca gcagacagcg tgccctgaa ggcgactgtc tgaatggccc aggcagctct     2580
agctgggagc ttggcctctg gctccatctg agtccctgg agagagccc agcacccaag      2640 atccagcagg ggacaggaca gagtagaagc ccctccatct gccctgggt ggaggcacca      2700 tcaccatcac caggcatgtc tgcagagcct ggacaccaac tttatggact gcccatggga     2760
gtgctccaaa tgtcagggtg tttgcccaat aataaagccc cagagaactg ggctgggccc     2820
tatgggattg gta                                                        2833
```

<210> SEQ ID NO 156
<211> LENGTH: 592
<212> TYPE: DNA

<213> ORGANISM: Homo sapiens

<400> SEQUENCE: 156

```
tctttaccta tgtgaagcga ggtgacgtga tacgtcactg gcgccgtctt ataatttaga     60
tgtaaaaatc tttagaaaca aataaaactc tctatatatg tgtatgtctg tgtacaaaaa    120
aatgacagag ctgatggcca gtgtatacag agcgtggccc gcggtgtaca atacccatat    180
aaggtacatt gtgcaggagg ggaattgctg gctgctttta cttcctgacc aagactgaaa    240
aattatttac tgaaatctgt aaacctttt atgaaacttt taagcaccag gctgtttact     300
tacacaattt aggtctgcca gaaaattcta tctgtgatag atctgtaaag agggtcaggg    360
gttagagttt actattttg aagtttacat tgttacatat gaaatggaaa cattattttg     420
aaacgttgtc ataacccaat ggtgcattct gtaaccatgg agtcttctgt ttcctggggg    480
aaagggcat tcatgacctg aacttttag caaattatta ttctcagttt ccattacctg      540
tttggccaaa cagattaata aaatatttga aaagaagca ataaaaaaaa aa             592
```

<210> SEQ ID NO 157
<211> LENGTH: 818
<212> TYPE: DNA
<213> ORGANISM: Homo sapiens
<220> FEATURE:
<221> NAME/KEY: misc_feature
<222> LOCATION: (60)..(60)
<223> OTHER INFORMATION: a or g or c or t/u
<220> FEATURE:
<221> NAME/KEY: misc_feature
<222> LOCATION: (80)..(80)
<223> OTHER INFORMATION: a or g or c or t/u
<220> FEATURE:
<221> NAME/KEY: misc_feature
<222> LOCATION: (114)..(114)
<223> OTHER INFORMATION: a or g or c or t/u
<220> FEATURE:
<221> NAME/KEY: misc_feature
<222> LOCATION: (121)..(121)
<223> OTHER INFORMATION: a or g or c or t/u

<400> SEQUENCE: 157

```
ctgagaaagt ccggtcccta taaggggaca tcagtgcgag acctgctccg tgctgtgagn     60
acaagaggca ccatacaagn aagctcccag ttgaggtgcg acaggcactc gccnaagtcc    120
ntgatggctt cgtccagtac tcacaaaacg gctccccccg gctggtcctt cacacgcacc    180
gagccatgag gagctggcgc ctctgagagc ctcttcctgc cctactaccc gccagactca    240
gaggccagga ggccatgccc tggggccaca gggaggtgag gtgggctgga tgccacacag    300
atggtctccg tgctggctca ctgaagagct gagcctgtgg ctggcctcag aatcaggctg    360
ggtgcagtgg ctcacacctg taatcccagc attttgggag gctgagtgag aggatcactt    420
gagctcagga gttcgagacc agcctggcca acatggcaac ccccatttc tacaaaaaat     480
ttgtaaaatt agccaggcat ggtggcgcac gcctgtagtc ccagctgctt gggaggctga    540
ggtgggagaa tcacttgagc ccaggagttc gaggctgcag tgagccagga tcatgccact    600
gcactccagc ctggtccaca gagagacact gtcaccccct tcccccaca agactggcag     660
aggctgggca gctggggct gatgaagcag agatgttcgc tggatcccag gccctggcac     720
ccctcaggaa atacaagaaa aagaatattc acatctgttt aatgtgcata agccaagga    780
aaggacagtt ccgaattcaa aaaaaaaaa aaaaaaaa                             818
```

<210> SEQ ID NO 158
<211> LENGTH: 753

<212> TYPE: DNA
<213> ORGANISM: Homo sapiens

<400> SEQUENCE: 158

```
tttttttttt ttttttttaaa tatttaactt atttatttaa caaagtagaa gggaatccat      60
tgctagcttt tctgtgttgg tgtctaatat ttgggtaggg tggggatcc ccaacaatca       120
ggtcccctga gatagctggt cattgggctg atcattgcca gaatcttctt ctcctggggt     180
ctggcccccc aaaatgccta acccaggacc ttgggaattc tactcatccc aaatgataat     240
tccaaatgct gttacccaag gttagggtgt tgaaggaagg tagagggtgg ggcttcaggt     300
ctcaacggct tccctaacca cccctcttct cttggcccag cctggttccc cccacttcca     360
ctcccctcta ctctctctag gactgggctg atgaaggcac tgcccaaaat ttcccctacc     420
cccaactttc ccctacccccc aactttcccc accagctcca caaccctgtt tggagctact   480
gcaggaccag aagcacaaag tgcggtttcc caagcctttg tccatctcag cccccagagt     540
atatctgtgc ttggggaatc tcacacagaa actcaggagc accccctgcc tgagctaagg    600
gaggtcttat ctctcagggg gggtttaagt gccgtttgca ataatgtcgt cttatttatt    660
tagcggggtg aatattttat actgtaagtg agcaatcaga gtataatgtt tatggtgaca    720
aaattaaagg ctttcttata tgtttaaaaa aaa                                  753
```

<210> SEQ ID NO 159
<211> LENGTH: 516
<212> TYPE: DNA
<213> ORGANISM: Homo sapiens

<400> SEQUENCE: 159

```
gccttataaa gcaccaagag gctgccagtg ggacattttc tcggccctgc cagcccccag      60
gaggaaggtg ggtctgaatc tagcaccatg acggaactag agacagccat gggcatgatc     120
atagacgtct tttcccgata ttcgggcagc gagggcagca cgcagaccct gaccaagggg     180
gagctcaagg tgctgatgga gaaggagcta ccaggcttcc tgcagagtgg aaaagacaag    240
gatgccgtgg ataaattgct caaggacctg gacgccaatg gagatgccca ggtggacttc    300
agtgagttca tcgtgttcgt ggctgcaatc acgtctgcct gtcacaagta ctttgagaag    360
gcaggactca aatgatgccc tggagatgtc acagattcct ggcagagcca tggtcccagg    420
cttcccaaaa gtgtttgtgg caattattcc cctaggctga gcctgctcat gtacctctga    480
ttaataaatg cttatgaaat gaaaaaaaaa aaaaaa                               516
```

<210> SEQ ID NO 160
<211> LENGTH: 354
<212> TYPE: DNA
<213> ORGANISM: Homo sapiens

<400> SEQUENCE: 160

```
ccagcaaagt ctcttttgac cacacgcttt atccgagatg cttagaagta tatttggctg      60
ttttatttgc atctttgatt aagatgtcta tcattgtaaa aaggtattca aaacaaaagt    120
gtactctttt attattatga atcacattgt actgagctgt gaagtcagtg tttaaaaat     180
gtagagttta ttcatggagc atgccattga ggtttggatg gtgcaggta aaacagaaag    240
gcaagatgtc atctgacatt aggctactta taaataaatg tttatctagc ttttatttca   300
tgccctaatg aataaaacat gcttcgaaaa agaaagtaaa aaaaaaaaac aaaa           354
```

<210> SEQ ID NO 161

<211> LENGTH: 2904
<212> TYPE: DNA
<213> ORGANISM: Homo sapiens

<400> SEQUENCE: 161

```
ggcgagagag acgctcccgc tcgccgccag ctctgattgg cccagcggta ggaaaggtta      60
aaccaaaaat tttttacag ccctagtgtg cgcctgtagc tcggaaaatt aattgtggct     120
atagccgcct cgatcgctgt ctccccagcc tcgccgcgga cgctccggga cgcgcccgcc     180
cgccgcccgg ttctcccccc ctttgggctg gtgctgctgc tgctgtgact gctgctgcga     240
aaggaggagg aggaggagga agcagcgggg ggggagcgg tgggtgtggg ggaaaccaag     300
agtacagtgg acgaggactc accccggcgt ggtgttcttt ttcttcttc ttttctttc     360
ctttttttt tttttttcta attcctgagg ggtggttgct gcttttgcta catgacttgc     420
cagcgcccga gcctgcggtc caactgcgct gctgccggag cgctcagtgc cgccgctgcc     480
gcccgtgccc cccgcgcccc gttcggcacc caccggtcgc cgccccgccc gcgcgccgct     540
gtcccgctcc cgcgccgccg ccgccgtttc ccccgacga ctgggtgatg ctggacatgg     600
gagataggaa agaggtgaaa atgatcccca agtcctcgtt cagcatcaac agcctggtgc     660
ccgagggcct ccagaacgac aaccaccacg cgagccacgg ccaccacaac agccaccacc     720
cccagcacca ccaccaccac caccaccatc accaccaccc gccgccgccc gccccgcaac     780
cgccgccgcc gccgcagcag cagcagccgc cgccgccgcc gagacgcggg gcccggcgcc     840
gacgacgacg aggccccagc agttgttgtt ccgccgcgca cgcacacggc gcgcctgagg     900
gccaacggca gctggcgcaa ggcgaccggc gcggccgggg gatctgcccc gtcgggccgg     960
acgagaagga gaaggcccgc gccgggggg aggagaagaa ggggcgggc gagggcggca    1020
aggacgggga gggggcaag gagggcgaga agaagaacgg caagtacgag aagccgccgt    1080
tcagctacaa cgcgctcatc atgatggcca tgcggcagag ccccgagaag cggctcacgc    1140
tcaacggcat ctacgagttc atcatgaaga acttcccctta ctaccgcgag aacaagcagg    1200
gctggcagaa ctccatccgc cacaatctgt ccctcaacaa gtgcttcgtg aaggtgccgc    1260
gccactacga cgacccgggc aagggcaact actggatgct ggaccgtcg agcgacgacg    1320
tgttcatcgg cggcaccacg ggcaagctgc ggcgctccac cacctcgccg ccaagccgg    1380
ccttcaagcg cggtgccgcg ctcacctcca ccggcctcac cttcatggac gcgcggctc    1440
cctctactgg cccatgtcgc ccttcctgtc cctgcaccac ccccgccagc agcactttga    1500
gttacaacgg gaccacgtcg gcctacccca gccaccccat gccctacagc tccgtgttga    1560
ctcaaaactc gctgggcaac aaccactcct cctccaccgc caacgggctg agcgtggacc    1620
ggctggtcaa cggggaatc ccgtacgcca cgcaccacct cacggccgcc gcgctaaccg    1680
cctcggtgcc ctgcggcctg ctggtgccct gtctgggac ctactccctc aaccctgct    1740
ccgtcaacct gctcgcgggc cagaccagtt acttttccc ccacgtcccg cacccgtcaa    1800
tgacttcgca gagcagcacg tccatgagcg ccagggccgc gtcctcctcc acgtcgccgg    1860
caggcccccc tcgacccctg ccctgtgagt ctttaagacc ctctttgcca gttttacga    1920
cgggactgtc tggggactg tctgattatt cacacatca aaatcagggg tcttcttcca    1980
accctttaat acattaacat ccctgggacc agactgtaag tgaacgtttt acacacattt    2040
gcattgtaaa tgataattaa aaaaataagt ccaggtattt tttattaagc cccccctcc    2100
catttctgta cgtttgttca gtctctaggg ttgtttatta ttctaacaag gtgtggagtg    2160
tcagcgaggt gcaatgtggg gagaatacat tgtagaatat aaggtttgga agtcaaatta    2220
```

```
tagtagaatg tgtatctaaa tagtgactgc tttgccattt cattcaaacc tgacaagtct   2280
atctctaaga gccgccagat ttccatgtgt gcagtattat aagttatcat ggaactatat   2340
ggtggacgca gaccttgaga acaacctaaa ttatggggag aattttaaaa tgttaaactg   2400
taatttgtat ttaaaaagca ttcgtagtaa aggtgcccaa gaaattattt tggccattta   2460
ttgttttctc cttttcttta aagaactgtt ttttttttctt ttgtttactt ttagaccaaa   2520
gattgggcgg ttctagaaaa tgcgccttgg tatactaagt attaaaacaa acaaaaagga   2580
aagttgtttc agttaacgct gcccattcaa ttgaatcaga aggggacaaa attaacgatt   2640
gccttcagtt tgtgttgtgt atattttgat gtatgtggtc actaacaggt cacttttatt   2700
ttttctaaat gtagtgaaat gttaatacct attgtactta taggtaaacc ttgcaaatat   2760
gtaacctgtg ttgcgcaaat gccgcataaa tttgagtgat tgttaatgtt gtcttaaaat   2820
ttcttgattg tgactatgtg gtcatatgcc cgtgtttgtc acttacaaaa atgtttacta   2880
tgaacacaca taaataaaaa atag                                           2904
```

<210> SEQ ID NO 162
<211> LENGTH: 2327
<212> TYPE: DNA
<213> ORGANISM: Homo sapiens

<400> SEQUENCE: 162

```
aaaatgctta ctcttgtggg ctacttgttg tgtggaaaaa ggaaaacgga ttcattttcc     60
catcggcgac tttatgacga cagaaatgaa ccagttctgc gattagacaa tgcaccggaa    120
ccttatgatg tgagttttgg gaattctagc tactacaatc aactttgaa tgattcagcc    180 atgccagaaa gtgaagaaaa tgcacgtgat ggcattccta tggatgacat acctccactt    240
cgtacttctg tatagaacta acagcaaaaa ggcgttaaac agcaagtgtc atctacatcc    300
tagccttttg acaaattcat ctttcaaaag gttacacaaa attactgtca cgttggattt    360
tgtcaaggag aatcataaaa gcaggagacc agtagcagaa atgtagacag gatgtatcat    420
ccaaaggttt tctttcttac aattttttggc catcctgagg catttactaa gtagccttaa    480
tttgtatttt agtagtattt tcttagtaga aaatatttgt ggaatcagat aaaactaaaa    540
gatttcacca ttacagcccct gcctcataac taaataataa aaattattcc accaaaaaat    600
tctaaaacaa tgaagatgac tctttactgc tctgcctgaa gccctagtac cataattcaa    660
gattgcattt tcttaaatga aaattgaaag ggtgcttttt aaagaaaatt tgacttaaag    720
ctaaaaagag gacatagccc agagtttctg ttattgggaa attgaggcaa tagaaatgac    780
agacctgtat tctagtacgt tataattttc tagatcagca cacacatgat cagcccactg    840
agttatgaag ctgacaatga ctgcattcaa cggggccatg gcaggaaagc tgaccctacc    900
caggaaagta atagcttctt taaagtctt caaaggtttt gggaatttta acttgtctta    960
atatatctta ggcttcaatt atttgggtgc cttaaaaact caatgagaat catggtaaaa   1020
aaaaaaagtt aaccaaagaa tatacctgta cataatttgt acagttttaa gttgttagat   1080
aggaactgga tttcttatgt attagacatt attgctcaat cataatggaa tagattctgc   1140
atccctaaat gtatgaacca taggttaaa aaagatgaat ggaaatatca acaacttt    1200 cactgagcat cagtttcata atcaataata taagaagatt aatttggatt ctagtatgtt   1260
tcagtttgtt tttaattacc accttccttt ggtagaaaaa atatgttcct tgatgtagga   1320
aagtctaggt tttagagatt agaggatgag atcaagagtt aaattcctaa agaagcactg   1380
```

| | |
|---|---|
| aatatatgaa gagagcaaac aaatcaagta ccaacctaga ggctttattt ttgaattgat | 1440 |
| tcatggtgtg tgtgtgtgtg tgtgtgtgtg tgtgtgtgtg tgtgtaacac agaaacagct | 1500 |
| ttcagaaaat aagggataga aagtaatgaa gaaagtactt accccatatt gccataaaaa | 1560 |
| tagcaaagaa gactgtccct ccattatcga acaaatatgt cacctgagta gaaaacaaac | 1620 |
| agaaatatta gtcatgcaaa ttgattataa taagccagtg aatactgttt gcactcaggt | 1680 |
| actatgattt tttctcaaat agaatcatat tattttatag tacagaaata ttatatatga | 1740 |
| attcctttca tgggtcttgc aacaatttca catgattttt ctcatgggga gaggtgaaga | 1800 |
| aacaacatta gccctcttct ctcctctctt gattcccttt ataccccacc atcatttctg | 1860 |
| attataaata attctaccat tctatggaag tatttgtggg tcacagattg tcaaactact | 1920 |
| taatgaaagt tgtatgaaat tagtttttca ggtgaggcat tcctagttgc aattcctgtt | 1980 |
| agcaaaactt ctaggagtgg ggaagttgga aaatgcagga ttcttccagt gagccagcat | 2040 |
| ttcccatagc taaccctatt ctcttagtct ttcaaaatgt agaatgggtc caataatggc | 2100 |
| tataagatgt aataaatccc atcttaattt gttttaaaag tttcataaat cactgaacac | 2160 |
| ttatgaaaca aagtgttttt taatcagata tcaactgaaa cttcataaag gatgcatagt | 2220 |
| tttataatgt tattgaatca aattttaagg cttgtattgt ttgattttaa taagtataa | 2280 |
| tctccttttt aaaaaaaaaa aaaaaaaaaa aaaaaaaaaa aaaaaaa | 2327 |

<210> SEQ ID NO 163
<211> LENGTH: 1841
<212> TYPE: DNA
<213> ORGANISM: Homo sapiens

<400> SEQUENCE: 163

| | |
|---|---|
| ggcacgaggc tgcctgcccc ccgggtgggg ctgcggctct ggcctcccag gcccatcctc | 60 |
| aacagctacc ccagccaaca ccaaggccac aaggggaccc cggcctagga ggcaggaagc | 120 |
| caaggtacag agagcagcct ggccctcacc agtgcgcaag ctggggcagc aaggctgaca | 180 |
| gttgctgcat gcccagggca gggtgtggta ctggcaccca agttcagcat ggcagagctg | 240 |
| gccaacagct tgtccccgat ctgcctccag ccccaagatg cctacagccc caggccccct | 300 |
| tcggcagcac tgcctctgcc cacctgcctt taagagactc cagggctgct cctgtcatgc | 360 |
| agcgaaggtt ttgtctgttt caaagttcga gactcaactt gagggactgt ttttgacaat | 420 |
| ccccgctgac ctccgctcct cgtggcgccc tggccctaca cccagcctgg cccagggccg | 480 |
| gctttgcctg gtgaggctgg agggagcacc aggacctgct gtctgctgtc agcccctcct | 540 |
| ggtgctggtg ccctgatgct gtgccttgtc acccattgag ctgcaagagg gaccaagagg | 600 |
| gggccacgca gccagccaga tgcctggccc tgtgctgggg cagacaacgc tgcagagccc | 660 |
| agggagcctg gcgctaggac gtgcgtcctt gtgacactgg cctgtctgaa ctcacctggc | 720 |
| ctggaagcca ccgtctgccc gggcccaagc cctgccccct cagagtccag agccaggaag | 780 |
| gggctgctga gggcgagcat cctgctgggc tctctgcccg gccacccct caagggggct | 840 |
| ggcctgtgag ccttgactgg gattcatgat gtggaggccc ccaacttcca gaagcagctg | 900 |
| gtactctgct cacacaagcg actgggccgg ccggccctgg accctagac cccgagccgc | 960 |
| ctgccgactg cctgcacagg gagagcagtt gaggcccggg cagggccccc acaccagacc | 1020 |
| ccaacatagc ttccccaccc aggcacccc tccggggca gcaggcgtgg gagtcagggc | 1080 |
| tgcatgctcc tcccctccca cctcacaggc ggccttaggc aagtcatttt ctgtcatcac | 1140 |
| aaggtcgcct ctgcctagtc aggtcctggc gtccagagta aggatgtgcg gccccaggc | 1200 |

```
cccccgcacac ctccctcagc accaagaccg ggaccccccc acccacgtgt ctcattgtgg      1260
ctgcctatgg actcccgggc cttgtgtgca ggccaggccc ttccactgat tttttaaagt      1320
gaaccattgc tggatctcag attctgtggc atctaaggcc tagcagggggt gggcacacgg     1380 gtcacccgag gcccatacca agactctgtt cctgccctag gcccagtctc aaaggaagcc     1440
acaaggcgcg ggggccactg aggaaggaaa tgttcatttt catttgtcca aaaccacctt     1500 aagtttaag tatattaatc ttgatgcttt ttaactattg cttttaact tgctgagatt       1560 tagaaatact gttataaaaa cttttttaat ttctgtattt tttttctgta ttgtatcttc      1620
atgggacatt aggggttttc tatggtaagc acacctatgg ttttggtaaa aacattatca    1680
aatatatatc cagacggttc ttccctagaa gaaaacaag tctttacacc tgataaaata      1740
ttttgcgaag agaggtgttc ttttccctta ctggtgctga aaggaaggat ggataacgag     1800
gagaaaataa aactgtgagg ctcaaaaaaa aaaaaaaaa a                           1841

<210> SEQ ID NO 164
<211> LENGTH: 848
<212> TYPE: DNA
<213> ORGANISM: Homo sapiens

<400> SEQUENCE: 164 cctgccccttc tctatatgta ccatctccaa aaccatgta catctccaaa aactggagta       60
gaaagttaga ttgctcaact acaactcctc tagaactcta tagctctgac atacagattc      120
acactctcct ctatttgcta agtatgtaaa gaatgttttc ttttaaaatg ttctcttttg      180
agaacaactg cttatttgtt ataaaagcat ttggttaaaa tgatgtcatc ataaagaaca     240 gtggcttttgt ttcaatacat atttttgaga tgattatcta gaagccagat taataaaatc     300
agcttgtgac cttgctaagc ataaaactg gaaattcaga tacattcaaa attatgggtt     360
catttaaaag tgttctaccct tttgggtatg agactaatat cactaattcc tcaatagtta   420
tcatggctct atcttaatta attagaaaat atgtgtgttt aattctttga gaattaaaat    480
agagaatatt aacagagggt taaaaactgc ttcaactcca ataagataaa ggaagctcaa    540
aatctatgag ctgagtgttc aattagcttt gcctactgag ttcaattta tgtcaataca      600 acagtggatc agacagtacg actttgaact ggtgaatgta aacaattgtt tttcacctaa    660
gctgctttgg aagaactgat gcttgctgct aactaaagtt ttggatgtat cgatttagag    720
aaccaattaa tacctgcaaa ataaagcata ctgtggtact tctgtttgat ctagtatgtg    780
tgattttaga ttgatggatt aaaaattaat aaagatcata cattccatac caaaaaaaaa    840
aaaaaaaa                                                               848

<210> SEQ ID NO 165
<211> LENGTH: 1767
<212> TYPE: DNA
<213> ORGANISM: Homo sapiens

<400> SEQUENCE: 165
ccagaagcct gcatttctgc attctgctta attcccttc cttagatttg aaagaagcca       60
acactaaacc acaaatatac aacaaggcca ttttctcaaa cgagagtcag cctttaacga      120
aatgaccatg gttgacacag agatgccatt ctggcccacc aacttggga tcagctccgt     180 ggatctctcc gtaatggaag accactccca ctcctttgat atcaagccct tcactactgt     240
tgacttctcc agcattttcta ctcccacatta cgaagacatt ccattcacaa gaacagatcc   300
```

| | |
|---|---|
| agtggttgca gattacaagt atgacctgaa acttcaagag taccaaagtg caatcaaagt | 360 |
| ggagcctgca tctccacctt attattctga gaagactcag ctctacaata agcctcatga | 420 |
| agagccttcc aactccctca tggcaattga atgtcgtgtc tgtggagata aagcttctgg | 480 |
| atttcactat ggagttcatg cttgtgaagg atgcaagggt ttcttccgga gaacaatcag | 540 |
| attgaagctt atctatgaca gatgtgatct taactgtcgg atccacaaaa aaagtagaaa | 600 |
| taaatgtcag tactgtcggt ttcagaaatg ccttgcagtg gggatgtctc ataatgccat | 660 |
| caggtttggg cggatgccac aggccgagaa ggagaagctg ttggcggaga tctccagtga | 720 |
| tatcgaccag ctgaatccag agtccgctga cctccgggcc ctggcaaaac atttgtatga | 780 |
| ctcatacata aagtccttcc cgctgaccaa agcaaaggcg agggcgatct tgacaggaaa | 840 |
| gacaacagac aaatcaccat tcgttatcta tgacatgaat tccttaatga tgggagaaga | 900 |
| taaaatcaag ttcaaacaca tcaccccct gcaggagcag agcaaagagg tggccatccg | 960 |
| catctttcag ggctgccagt ttcgctccgt ggaggctgtg caggagatca cagagtatgc | 1020 |
| caaaagcatt cctggttttg taaatcttga cttgaacgac caagtaactc tcctcaaata | 1080 |
| tggagtccac gagatcattt acacaatgct ggcctccttg atgaataaag atggggttct | 1140 |
| catatccgag ggccaaggct tcatgacaag ggagtttcta aagagcctgc gaaagccttt | 1200 |
| tggtgacttt atggagccca gtttgagtt tgctgtgaag ttcaatgcac tggaattaga | 1260 |
| tgacagcgac ttggcaatat ttattgctgt cattattctc agtggagacc gcccaggttt | 1320 |
| gctgaatgtg aagcccattg aagacattca agacaacctg ctacaagccc tggagctcca | 1380 |
| gctgaagctg aaccaccctg agtcctcaca gctgtttgcc aagctgctcc agaaaatgac | 1440 |
| agacctcaga cagattgtca cggaacacgt gcagctactg caggtgatca agaagacgga | 1500 |
| gacagacatg agtcttcacc cgctcctgca ggagatctac aaggacttgt actagcagag | 1560 |
| agtcctgagc cactgccaac atttcccttc ttccagttgc actattctga gggaaaatct | 1620 |
| gacacctaag aaatttactg tgaaaaagca ttttaaaaag aaaaggtttt agaatatgat | 1680 |
| ctattttatg catattgttt ataagacaca atttacaatt tacttttaat attaaaaatt | 1740 |
| accatatatt gaaaaaaaaa aaaaaaa | 1767 |

<210> SEQ ID NO 166
<211> LENGTH: 8448
<212> TYPE: DNA
<213> ORGANISM: Homo sapiens

<400> SEQUENCE: 166

| | |
|---|---|
| gcagtggttt ctcctccttc ctcccaggaa gggccaggaa aatggccctg gtcctggaga | 60 |
| tcttcaccct gctggcctcc atctgctggg tgtcggccaa tatcttcgag taccaggttg | 120 |
| atgcccagcc ccttcgtccc tgtgagctgc agagggaaac ggcctttctg aagcaagcag | 180 |
| actacgtgcc ccagtgtgca gaggatggca gcttccagac tgtccagtgc cagaacgacg | 240 |
| gccgctcctg ctggtgtgtg ggtgccaacg gcagtgaagt gctgggcagc aggcagccag | 300 |
| gacggcctgt ggcttgtctg tcattttgtc agctacagaa acagcagatc ttactgagtg | 360 |
| gctacattaa cagcacagac acctcctacc tccctcagtg tcaggattca ggggactacg | 420 |
| cgcctgttca gtgtgatgtg cagcatgtcc agtgctggtg tgtggacgca gaggggatgg | 480 |
| aggtgtatgg gacccgccag ctggggaggc caaagcgatg tccaaggagc tgtgaaataa | 540 |
| gaaatcgtcg tcttctccac ggggtgggag ataagtcacc accccagtgt tctgcggagg | 600 |
| gagagtttat gcctgtccag tgcaaatttg tcaacaccac agacatgatg attttttgatc | 660 |

```
tggtccacag ctacaacagg tttccagatg catttgtgac cttcagttcc ttccagagga    720
ggttccctga ggtatctggg tattgccact gtgctgacga ccaagggcgg gaactggctg    780
agacaggttt ggagttgtta ctggatgaaa tttatgacac cattttgct ggcctggacc     840
ttccttccac cttcactgaa accaccctgt accggatact gcagagacgg ttcctcgcag    900
ttcaatcagt catctctggc agattccgat gccccacaaa atgtgaagtg gagcggttta    960
cagcaaccag ctttggtcac ccctatgttc caagctgccg ccgaaatggc gactatcagg   1020
cggtgcagtg ccagacggaa gggccctgct ggtgtgtgga cgcccagggg aaggaaatgc   1080
atggaacccg gcagcaaggg gagccgccat cttgtgctga aggccaatct tgtgcctccg   1140
aaaggcagca ggccttgtcc agactctact ttgggacctc aggctacttc agccagcacg   1200
acctgttctc ttccccagag aaaagatggg cctctccaag agtagccaga tttgccacat   1260
cctgcccacc cacgatcaag gagctctttg tggactctgg gcttctccgc ccaatggtgg   1320
agggacagag ccaacagttt tctgtctcag aaaatcttct caagaagcc atccgagcaa    1380
ttttccctc ccgagggctg gctcgtcttg cccttcagtt taccaccaac ccaaagagac    1440
tccagcaaaa ccttttttgga gggaaatttt tggtgaatgt tggccagttt aacttgtctg   1500
gagcccttgg cacaagaggc acatttaact tcagtcaatt tttccagcaa cttggtcttg   1560
caagcttctt gaatggaggg agacaagaag atttggccaa gccactctct gtgggattag   1620
attcaaattc ttccacagga acccctgaag ctgctaagaa ggatggtact atgaataagc   1680
caactgtggg cagctttggc tttgaaatta acctacaaga gaaccaaaat gccctcaaat   1740
tccttgcttc tctcctggag cttccagaat tccttctctt cttgcaacat gctatctctg   1800
tgccagaaga tgtggcaaga gatttaggtg atgtgatgga aacggtactc gactcccaga   1860
cctgtgagca gacacctgaa aggctatttg tcccatcatg cacgacagaa ggaagctatg   1920
aggatgtcca atgcttttcc ggagagtgct ggtgtgtgaa ttcctggggc aaagagcttc   1980
caggctcaag agtcagagat ggacagccaa ggtgccccac agactgtgaa aagcaaaggg   2040
ctcgcatgca aagcctcatg ggcagccagc ctgctggctc caccttgttt gtccctgctt   2100
gtactagtga gggacatttc ctgcctgtcc agtgcttcaa ctcagagtgc tactgtgttg   2160
atgctgaggg tcaggccatt cctggaactc gaagtgcaat agggaagccc aagaaatgcc   2220
ccacgccctg tcaattacag tctgagcaag ctttcctcag gacggtgcag gccctgctct   2280
ctaactccag catgctaccc acccttccg acacctacat cccacagtgc agcaccgatg    2340
ggcagtggag acaagtgcaa tgcaatgggc ctcctgagca ggtcttcgag ttgtaccaac   2400
gatgggaggc tcagaacaag ggccaggatc tgacgcctgc caagctgcta gtgaagatca   2460
tgagctacag agaagcagct tccggaaact tcagtctctt tattcaaagt ctgtatgagg   2520
ctggccagca agatgtcttc ccggtgctgt cacaataccc ttctctgcaa gatgtcccac   2580
tagcagcact ggaagggaaa cggcccagcc cagggagaa tatcctcctg agccctacc    2640
tcttctggca gatcttaaat ggccaactca gccaataccc ggggtcctac tcagacttca   2700
gcactccttt ggcacatttt gatcttcgga actgctggtg tgtggatgag gctggccaag   2760
aactggaagg aatgcggtct gagccaagca agctcccaac gtgtcctggc tcctgtgagg   2820
aagcaaagct ccgtgtactg cagttcatta gggaaacgga agagattgtt tcagcttcca   2880
acagttctcg gttccctctg ggggagagtt tcctggtggc caaggaatc cggctgagga    2940
atgaggacct cggccttcct ccgctcttcc cgccccggga ggctttcgcg gagtttctgc   3000
```

-continued

```
gtgggagtga ttacgccatt cgcctggcgg ctcagtctac cttaagcttc tatcagagac    3060
gccgcttttc cccggacgac tcggctggag catccgccct tctgcggtcg ggcccctaca    3120
tgccacagtg tgatgcgttt ggaagttggg agcctgtgca gtgccacgct gggactgggc    3180
actgctggtg tgtagatgag aaaggagggt tcatccctgg ctcactgact gcccgctctc    3240
tgcagattcc acagtgcccg acaacctgcg agaaatctcg aaccagtggg ctgctttcca    3300
gttggaaaca ggctagatcc caagaaaacc catctccaaa agacctgttc gtcccagcct    3360
gcctagaaac aggagaatat gccaggctgc aggcatcggg ggctggcacc tggtgtgtgg    3420
accctgcatc aggagaagag ttgcggcctg gctcgagcag cagtgcccag tgcccaagcc    3480
tctgcaatgt gctcaagagt ggagtcctct ctaggagagt cagcccaggc tatgtcccag    3540
cctgcagggc agaggatggg ggcttttccc cagtgcaatg tgaccaggcc cagggcagct    3600
gctggtgtgt catggacagc ggagaagagg tgcctgggac gcgcgtgacc gggggccagc    3660
ccgcctgtga gagcccgcgg tgtccgctgc cattcaacgc gtcggaggtg gttggtggaa    3720
caatcctgtg tgagacaatc tcgggcccca caggctctgc catgcagcag tgccaattgc    3780
tgtgccgcca aggctcctgg agcgtgtttc caccagggcc attgatatgt agcctggaga    3840
gcggacgctg gagtcacag ctgcctcagc cccgggcctg ccaacggccc cagctgtggc    3900
agaccatcca gacccaaggg cactttcagc tccagctccc gccgggcaag atgtgcagtg    3960
ctgactacgc gggtttgctg cagactttcc aggttttcat attggatgag ctgacagccc    4020
gcggcttctg ccagatccag gtgaagactt ttggcaccct ggtttccatt cctgtctgca    4080
acaactcctc tgtgcaggtg ggttgtctga ccagggagcg tttaggagtg aatgttacat    4140
ggaaatcacg gcttgaggac atcccagtgg cttctcttcc tgacttacat gacattgaga    4200
gagccttggt gggcaaggat ctccttgggc gcttcacaga tctgatccag agtggctcat    4260
tccagcttca tctggactcc aagacgttcc cagcggaaac catccgcttc ctccaagggg    4320
accactttgg cacctctcct aggacacggt ttgggtgctc ggaaggattc taccaagtct    4380
tgacaagtga ggccagtcag gacggactgg gatgcgttaa gtgccatgaa ggaagctatt    4440
cccaagatga ggaatgcatt ccttgtcctg ttggattcta ccaagaacag gcagggagct    4500
tggcctgtgt cccatgtcct gtgggcagaa cgaccatttc tgccggagct ttcagccaga    4560
ctcactgtgt cactgactgt cagaggaacg aagcaggcct gcaatgtgac cagaatggcc    4620
agtatcgagc cagccagaag gacaggggca gtgggaaggc cttctgtgtg gacggcgagg    4680
ggcggaggct gccatggtgg gaaacagagg cccctcttga ggactcacag tgtttgatga    4740
tgcagaagtt tgagaaggtt ccagaatcaa aggtgatctt cgacgccaat gctcctgtgg    4800
ctgtcagatc caaagttcct gattctgagt tccccgtgat gcagtgcttg acagattgca    4860
cagaggacga ggcctgcagc ttcttcaccg tgtccacgac ggagccagag atttcctgtg    4920
atttctatgc cttggacaagt gacaatgttg cctgcatgac ttctgaccag aaacgagatg    4980
cactgggaa ctcaaaggcc accagctttg gaagtcttcg ctgccaggtg aaagtgagga    5040
gccatggtca agattctcca gctgtgtatt tgaaaaaggg ccaaggatcc accacaacac    5100
ttcagaaacg ctttgaaccc actggtttcc aaaaacatgct ttctgattg tacaacccca    5160
ttgtgttctc agcctcagga gccaatctaa ccgatgctca cctcttctgt cttcttgcat    5220
gcgaccgtga tctgtgttgc gatggcttcg tcctcacaca ggttcaagga ggtgccatca    5280
tctgtgggtt gctgagctca cccagtgtcc tgctttgtaa tgtcaaagac tggatggatc    5340
cctctgaagc ctgggctaat gctacatgtc ctggtgtgac atatgaccag gagagccacc    5400
```

```
aggtgatatt gcgtcttgga gaccaggagt tcatcaagag tctgacaccc ttagaaggaa   5460
ctcaagacac ctttaccaat tttcagcagg tttatctctg gaaagattct gacatggggt   5520
ctcggcctga gtctatggga tgtagaaaaa acacagtgcc aaggccagca tctccaacag   5580
aagcaggttt gacaacagaa cttttctccc ctgtggacct caaccaggtc attgtcaatg   5640
gaaatcaatc actatccagc cagaagcact ggcttttcaa gcacctgttt tcagcccagc   5700
aggcaaacct atggtgcctt tctcgttgtg tgcaggagca ctctttctgt cagctcgcag   5760
agataacaga gagtgcatcc ttgtacttca cctgcaccct ctacccagag gcacaggtgt   5820
gtgatgacat catggagtcc aatacccagg gctgcagact gatcctgcct cagatgccaa   5880
aggccctgtt ccggaagaaa gttatactgg aagataaagt gaagaacttt tacactcgcc   5940
tgccgttcca aaaactgatg gggatatcca ttagaaataa agtgcccatg tctgaaaaat   6000
ctatttctaa tgggttcttt gaatgtgaac gacggtgcga tgcggaccca tgctgcactg   6060
gctttggatt tctaaatgtt tcccagttaa aaggaggaga ggtgacatgt ctcactctga   6120
acagcttggg aattcagatg tgcagtgagg agaatggagg agcctggcgc attttggact   6180
gtggctctcc tgacattgaa gtccacacct atcccttcgg atggtaccag aagcccattg   6240
ctcaaaataa tgctcccagt ttttgccctt tggttgttct gccttccctc acagagaaag   6300
tgtctctgga atcgtggcag tccctggccc tctcttcagt ggttgttgat ccatccatta   6360
ggcactttga tgttgcccat gtcagcactg ctgccaccag caatttctct gctgtccgag   6420
acctctgttt gtcggaatgt tcccaacatg aggcctgtct catcaccact ctgcaaaccc   6480
aactcggggc tgtgagatgt atgttctatg ctgatactca aagctgcaca catagtctgc   6540
agggtcggaa ctgccgactt ctgcttcgtg aagaggccac ccacatctac cggaagccag   6600
gaatctctct gctcagctat gaggcatctg taccttctgt gcccatttcc acccatggcc   6660
ggctgctggg caggtcccag gccatccagg tgggtacctc atggaagcaa gtggaccagt   6720
tccttggagt tccatatgct gccccgcccc tggcagagag gcacttccag gcaccagagc   6780
ccttgaactg gacaggctcc tgggatgcca gcaagccaag ggccagctgc tggcagccag   6840
gcaccagaac atccacgtct cctggagtca gtgaagattg tttgtatctc aatgtgttca   6900
tccctcagaa tgtggcccct aacgcgtctg tgctggtgtt cttccacaac accatggaca   6960
gggaggagag tgaaggatgg ccggctatcg acggctcctt cttggctgct gttggcaacc   7020
tcatcgtggt cactgccagc taccgagtgg gtgtcttcgg cttcctgagt tctggatccg   7080
gagaggtgag tggcaactgg gggctgctgg accaggtggc ggctctgacc tgggtgcaga   7140
cccacatccg aggatttggc ggggaccctc ggcgcgtgtc cctggcagca gaccgtggcg   7200
gggctgatgt ggccagcatc caccttctca cggccagggc caccaactcc caacttttcc   7260
ggagagctgt gctgatggga ggctccgcac tctccccggc cgccgtcatc agccatgaga   7320
gggctcagca gcaggcaatt gctttggcaa aggaggtcag ttgccccatg tcatccagcc   7380
aagaagtggt gtcctgcctc cgccagaagc ctgccaatgt cctcaatgat gcccagacca   7440
agctcctggc cgtgagtggc cctttccact actgggtcc tgtgatcgat ggccacttcc   7500
tccgtgagcc tccagccaga gcactgaaga ggtctttatg ggtagaggtc gatctgctca   7560
ttgggagttc tcaggacgac gggctcatca acagagcaaa ggctgtgaag caatttgagg   7620
aaagtcgagg ccgaccagt agcaaaacag ccttttacca ggcactgcag aattctctgg   7680
gtggcgagga ctcagatgcc cgcgtcgagg ctgctgctac atggtattac tctctggagc   7740
```

```
actccacgga tgactatgcc tccttctccc gggctctgga gaatgccacc cgggactact   7800
ttatcatctg ccctataatc gacatggcca gtgcctgggc aaagagggcc cgaggaaacg   7860
tcttcatgta ccatgctcct gaaaactacg gccatggcag cctggagctg ctggcggatg   7920
ttcagtttgc cttggggctt cccttctacc cagcctacga ggggcagttt tctctggagg   7980
agaagagcct gtcgctgaaa atcatgcagt acttttccca cttcatcaga tcaggaaatc   8040
ccaactaccc ttatgagttc tcacggaaag tacccacatt tgcaacccccc tggcctgact   8100
ttgtaccccg tgctggtgga gagaactaca aggagttcag tgagctgctc cccaatcgac   8160
agggcctgaa gaaagccgac tgctccttct ggtccaagta catctcgtct ctgaagacat   8220
ctgcagatgg agccaagggc gggcagtcag cagagagtga agaggaggag ttgacggctg   8280
gatctgggct aagagaagat ctcctaagcc tccaggaacc aggctctaag acctacagca   8340
agtgaccagc ccttgagctc cccaaaaacc tcacccgagg ctgcccacta tggtcatctt   8400
tttctctaaa atagttactt accttcaata aagtatctac atgcggtg              8448
```

<210> SEQ ID NO 167
<211> LENGTH: 4424
<212> TYPE: DNA
<213> ORGANISM: Homo sapiens

<400> SEQUENCE: 167

```
agatctctcc agatcacact gtcacgtgta cctagcacat ctcgagaact cctttgggcc     60
gtctggggcc cgggaaggaa gcctgagttc tcaagattcc aggactgaga gtgccagctt    120
gtctcaaagc caggtcaatg gtttctttgc cagccattta ggtgaccaaa cctggcagga    180
atcacagcat ggcagccctt ccccatctgt aatatccaaa gccaccgaga aagagacttt    240
cactgatagt aaccaaagca aaactaaaaa gccaggcatt tctgatgtaa ctgattactc    300
agaccgtgga gattcagaca tggatgaagc cacttactcc agcagtcagg atcatcaaac    360
accaaaacag gaatcttcct cttcagtgaa tacatccaac aagatgaatt ttaaaacttt    420
tccttcatca cctcctaggt ctggagatat ctttgaggtt gaactggcta aaaatgataa    480
cagcttgggg ataagtgtca cgggaggtgt gaatacgagt gtcagacatg gtggcattta    540
tgtgaaagct gttattcccc agggagcagc agagtctgat ggtagaattc acaaaggtga    600
tcgcgtccta gctgtcaatg gagttagtct agaaggagcc acccataagc aagctgtgga    660
aacactgaga aatacaggac aggtggttca tctgttatta gaaaagggac aatctccaac    720
atctaaagaa catgtcccgg taaccccaca gtgtaccctt tcagatcaga atgcccaagg    780
tcaaggccca gaaaaagtga agaaaacaac tcaggtcaaa gactacagct tgtcactga    840
agaaaataca tttgaggtaa aattatttaa aaatagctca ggtctaggat tcagttttc    900
tcgagaagat aatcttatac cggagcaaat taatgccagc atagtaaggg ttaaaaagct    960
ctttcctgga cagccagcag cagaaagtgg aaaaattgat gtaggagatg ttatcttgaa   1020
agtgaatgga gcctctttga aaggactatc tcagcaggaa gtcatatctg ctctcagggg   1080
aactgctcca gaagtattct tgcttctctg cagacctcca cctggtgtgc taccggaaat   1140
tgatactgcg cttttgaccc cacttcagtc tccagcacaa gtacttccaa acagcagtaa   1200
agactcttct cagccatcat gtgtggagca agcaccagc tcagatgaaa atgaaatgtc   1260
agacaaaagc aaaaaacagt gcaagtcccc atccagaaaa gacagttaca gtgacagcag   1320
tgggagtgga gaagatgact tagtgacagc tccagcaaac atatcaaatt cgacctggag   1380
ttcagctttg catcagactc taagcaacat ggtatcacag gcacagagtc atcatgaagc   1440
```

```
accaagagtc aagaagatac catttgtacc atgttttact atcctcagga aaaggcccaa   1500
taaaccagag tttgaggaca gtaatccttc ccctctacca ccggatatgg ctcctgggca   1560
gagttatcaa ccccaatcag aatctgcttc ctctagttcg atggataagt atcatataca   1620
tcacatttct gaaccaacta gacaagaaaa ctggacacct tgaaaaatg acttggaaaa    1680 tcaccttgaa gactttgaac tggaagtaga actcctcatt accctaatta aatcagaaaa   1740
aggaagcctg ggttttacag taaccaaagg caatcagaga attggttgtt atgttcatga   1800
tgtcatacag gatccagcca aaagtgatgg aaggctaaaa cctggggacc ggctcataaa   1860
ggttaatgat acagatgtta ctaatatgac tcatacagat gcagttaatc tgctccgggg   1920
atccaaaaca gtcagattag ttattggacg agttctagaa ttacccagaa taccaatgtt   1980
gcctcatttg ctaccggaca taacactaac gtgcaacaaa gaggagttgg gttttcctt    2040 atgtggaggt catgacagcc tttatcaagt ggtatatatt agtgatatta atccaaggtc   2100
cgtcgcagcc attgagggta atctccagct attagatgtc atccattatg tgaacggagt   2160
cagcacacaa ggaatgacct tggaggaagt taacagagca ttagacatgt cacttccttc   2220
attggtattg aaagcaacaa gaaatgatct tccagtggtc cccagctcaa agaggtctgc   2280
tgtttcagct ccaaagtcaa ccaaaggcaa tggttcctac agtgtggggt cttgcagcca   2340
gcctgccctc actcctaatg attcattctc cacggttgct ggggaagaaa taatgaaat    2400 atcgtacccc aaaggaaaat gttctactta tcagataaag ggatcaccaa acttgactct   2460
gcccaaagaa tcttatatac aagaagatga catttatgat gattcccaag aagctgaagt   2520
tatccagtct ctgctggatg ttgtggatga ggagtcccag aatcttttaa acgaaaataa   2580
tgcagcagga tactcctgtg gtccaggtac attaaagatg aatgggaagt tatcagaaga   2640
gagaacagaa gatacagact gcgatggttc acctttacct gagtatttta ctgaggccac   2700
caaaatgaat ggctgtgaag aatattgtga agaaaaagta aaaagtgaaa gcttaattca   2760
gaagccacaa gaaaagaaga ctgatgatga tgaaataaca tggggaaatg atgagttgcc   2820
aatagagaga acaaaccatg aagattctga taaagatcat tcctttctga caaacgatga   2880
gctcgctgta ctccctgtcg tcaaagtgct tccctctggt aaatacacgg gcgccaactt   2940
aaaatcagtc attcgagtcc tgcgggttgc tagatcagga attccttcta aggagctgga   3000
gaatcttcaa gaattaaaac ctttggatca gtgtctaatt gggcaaacta aggaaaacag   3060
aaggaagaac agatataaaa atatacttcc ctatgatgct acaagagtgc ctcttggaga   3120
tgaaggtggc tatatcaatg ccagcttcat taagatacca gttgggaaag aagagttcgt   3180
ttacattgcc tgccaaggac cactgcctac aactgttgga gacttctggc agatgatttg   3240
ggagcaaaaa tccacagtga tagccatgat gactcaagaa gtagaaggag aaaaaatcaa   3300
atgccagcgc tattggccca acatcctagg caaaacaaca atggtcagca acagacttcg   3360
actggctctt gtgagaatgc agcagctgaa gggctttgtg gtgagggcaa tgacccttga   3420
agatattcag accagagagg tgcgccatat ttctcatctg aatttcactg cctggccaga   3480
ccatgataca ccttctcaac cagatgatct gcttactttt atctcctaca tgagacacat   3540
ccacagatca ggcccaatca ttcgcactg cagtgctggc attggacgtt cagggacct    3600 gatttgcata gatgtggttc tgggattaat cagtcaggat cttgattttg acatctctga   3660
tttggtgcgc tgcatgagac tacaaagaca cggaatggtt cagacagagg atcaatatat   3720
tttctgctat caagtcatcc tttatgtcct gacacgtctt caagcagaag aagagcaaaa   3780
```

| | |
|---|---:|
| acagcagcct cagcttctga agtgacatga aaagagcctc tggatgcatt ccatttctc | 3840 |
| tccttaacct ccagcagact cctgctctct atccaaaata aagatcacag agcagcaagt | 3900 |
| tcatacaaca tgcatgttct cctctatctt agaggggtat tcttcttgaa aataaaaaat | 3960 |
| attgaaatgc tgtattttta cagctacttt aacctatgat aattatttac aaaattttaa | 4020 |
| cactaaccaa acaatgcaga tcttagggat gattaaaggc agcatttgat gatagcagac | 4080 |
| attgttacaa ggacatggtg agtctatttt taatgcacca atcttgttta tagcaaaaat | 4140 |
| gttttccaat attttaataa agtagttatt tataggcata cttgaaacca gtatttaagc | 4200 |
| tttaaatgac agtaatattg gcatagaaaa aagtagcaaa tgtttactgt atcaatttct | 4260 |
| aatgtttact atatagaatt tcctgtaata tatttatata cttttttcatg aaaatggagt | 4320 |
| tatcagttat ctgtttgtta ctgcatcatc tgtttgtaat cattatctca ctttgtaaat | 4380 |
| aaaaacacac cttaaaacat gaacaagcca aaaaaaaaaa aaaa | 4424 |

<210> SEQ ID NO 168
<211> LENGTH: 1450
<212> TYPE: DNA
<213> ORGANISM: Homo sapiens

<400> SEQUENCE: 168

| | |
|---|---:|
| ccaggcagca gttagcccgc cgcccgcctg tgtgtcccca gagccatgga gagagccagt | 60 |
| ctgatccaga aggccaagct ggcagagcag gccgaacgct atgaggacat ggcagccttc | 120 |
| ccaggcagca gttagcccgc cgcccgcctg tgtgtcccca gagccatgga gagagccagt | 180 |
| ctgatccaga aggccaagct ggcagagcag gccgaacgct atgaggacat ggcagccttc | 240 |
| atgaaaggcg ccgtggagaa gggcgaggag ctctcctgcg aagagcgaaa cctgctctca | 300 |
| gtagcctata gaacgtggt gggcggccag agggctgcct ggagggtgct gtccagtatt | 360 |
| gagcagaaaa gcaacgagga gggctcggag gagaaggggc ccgaggtgcg tgagtaccgg | 420 |
| gagaaggtgg agactgagct ccagggcgtg tgcgacaccg tgctgggcct gctgacagc | 480 |
| cacctcatca aggaggccgg ggacgccgag agccgggtct tctacctgaa gatgaagggt | 540 |
| gactactacc gctacctggc cgaggtggcc accggtgacg acaagaagcg catcattgac | 600 |
| tcagcccggt cagcctacca ggaggccatg gacatcagca agaaggagat gccgccacc | 660 |
| aaccccatcc gcctgggcct ggccctgaac ttttccgtct tccactacga gatcgccaac | 720 |
| agccccgagg aggccatctc tctggccaag accactttcg acgaggccat ggctgatctg | 780 |
| cacaccctca gcgaggactc ctacaaagac agcaccctca tcatgcagct gctgcgagac | 840 |
| aacctgacac tgtggacggc cgacaacgcc ggggaagagg ggggcgaggc tccccaggag | 900 |
| ccccagagct gagtgttgcc cgccaccgcc ccgccctgcc cctccagtc cccgccctgc | 960 |
| cgagaggact agtatggggt gggaggcccc acccttctcc cctaggcgct gttcttgctc | 1020 |
| caaagggctc cgtggagagg gactggcaga gctgaggcca cctggggctg gggatcccac | 1080 |
| tcttcttgca gctgttgagc gcacctaacc actggtcatg cccccacccc tgctctccgc | 1140 |
| acccgcttcc tcccgacccc aggaccaggc tacttctccc ctcctcttgc ctccctcctg | 1200 |
| cccctgctgc ctcttgattc gtaggaattg aggagtgtct ccgccttgtg gctgagaact | 1260 |
| ggacagtggc aggggctgga gatgggtgtg tgtgtgtgtg tgtgtgtgtg tgtgtgcgcg | 1320 |
| cgcgccagtg caagaccgag actgagggaa agcatgtctg ctgggtgtga ccatgttttcc | 1380 |
| tctcaataaa gttcccctgt gacactcaaa aaaaaaaaaa aaaaaaaaaa aaaaaaaaaa | 1440 |
| aaaaaaaaaa | 1450 |

<210> SEQ ID NO 169
<211> LENGTH: 798
<212> TYPE: DNA
<213> ORGANISM: Homo sapiens

<400> SEQUENCE: 169

```
cggccgcgag gccctgagat gaggctccaa agaccccgac aggccccggc gggtgggagg      60
cgcgcgcccc ggggcgggcg ggctccccc taccggccag accgggggag aggcgcgcgg     120
aggctgcgaa ggttccagaa gggcgggag ggggcgccgc gcgctgaccc tccctgggca     180
ccgctgggga cgatggcgct gctcgccttg ctgctggtcg tggccctacc gcgggtgtgg     240
acagacgcca acctgactgc gagacaacga gatccagagg actcccagcg aacggacgag     300
ggtgacaata gagtgtggtg tcatgttttgt gagagagaaa acactttcga gtgccagaac     360
ccaaggaggt gcaaatggac agagccatac tgcgttatag cggccgtgaa atatttcca     420
cgttttttca tggttgcgaa gcagtgctcc gctggttgtg cagcgatgga gagacccaag     480
ccagaggaga agcggtttct cctggaagag cccatgccct tcttttacct caagtgttgt     540
aaaattcgct actgcaattt agaggggcca cctatcaact catcagtgtt caaagaatat     600
gctgggagca tgggtgagag ctgtggtggg ctgtggctgg ccatcctcct gctgctggcc     660
tccattgcag ccggcctcag cctgtcttga gccacgggac tgccacagac tgagccttcc     720
ggagcatgga ctcgctccag accgttgtca cctgttgcat taaacttgtt ttctgttgat     780
taaaaaaaaa aaaaaaaa                                                    798
```

<210> SEQ ID NO 170
<211> LENGTH: 3726
<212> TYPE: DNA
<213> ORGANISM: Homo sapiens

<400> SEQUENCE: 170

```
ttcagccgga acgttactcc gtgtccaccc ggatcgtgtg tgtgatcgag gctgcggaga      60
cgcctttcac gggggggtgtc gaggtggacg tcttcgggaa actgggccgt tcgcctccca     120
atgtccagtt caccttccaa cagcccaagc ctctcagtgt ggagccgcag cagggaccgc     180
aggcgggcgg caccacactg accatccacg gcacccacct ggacacgggc tcccaggagg     240
acgtgcgggt gaccctcaac ggcgtccccgt gtaaagtgac gaagtttggg gcgcagctcc     300
agtgtgtcac tggcccccag gcgacacggg gccagatgct tctggaggtc tcctacgggg     360
ggtcccccgt gcccaacccc ggcatcttct tcacctaccg cgaaaacccc gtactgcgag     420
ccttcgagcc gctacgaagc tttgccagtg gtggccgcag catcaacgtc acgggtcagg     480
gcttcagcct gatccagagg tttgccatgg tggtcatcgc ggagcccctg cagtcctggc     540
agccgccgcg ggaggctgaa tccctgcagc ccatgacggt ggtgggtaca gactacgtgt     600
tccacaatga caccaaggtc gtcttcctgt ccccggctgt gcctgaggag ccagaggtct     660
acaacctcac ggtgctgatc gagatggacg ggcaccgtgc cctgctcaga acagaggccg     720
gggccttcga gtacgtgcct gaccccaccc ttgagaactt cacaggtggc gtcaagaagc     780
aggtcaacaa gctcatccac gcccggggca ccaatctgaa caaggcgatg acgctgcagg     840
aggccgaggc cttcgtgggt gccgagcgct gcaccatgaa gacgctgacg gagaccgacc     900
tgtactgtga gccccggag gtgcagcccc gcccaagcg gcggcagaaa cgagacacca     960
cacacaacct gccccgagttc attgtgaagt tcggctctcg cgagtgggtg ctgggccgcg    1020
```

```
tggagtacga cacacgggtg agcgacgtgc cgctcagcct catcttgccg ctggtcatcg   1080
tgcccatggt ggtcgtcatc gcggtgtctg tctactgcta ctggaggaag agccagcagg   1140
ccgaacgaga gtatgagaag atcaagtccc agctggaggg cctggaggag agcgtgcggg   1200
accgctgcaa gaaggaattc acagacctga tgatcgagat ggaggaccag accaacgacg   1260
tgcacgaggc cggcatcccc gtgctggact acaagaccta caccgaccgc gtcttcttcc   1320
tgccctccaa ggacgcgac aaggacgtga tgatcaccgg caagctggac atccccgagc   1380
cgcggcggcc ggtggtggag caggccctct accagttctc caacctgctg aacagcaagt   1440
ctttcctcat caatttcatc cacacccctgg agaaccagcg ggagttctcg gcccgcgcca   1500
aggtctactt cgcgtccctg ctgacggtgg cgctgcacgg gaaactggag tactacacgg   1560
acatcatgca cacgctcttc ctggagctcc tggagcagta cgtggtggcc aagaaccccca   1620
agctgatgct gcgcaggtct gagactgtgg tggagaggat gctgtccaac tggatgtcca   1680
tctgcctgta ccagtacctc aaggacagtg ccggggagcc cctgtacaag ctcttcaagg   1740
ccatcaaaca tcaggtggaa aagggcccgg tggatgcgt acagaagaag gccaagtaca   1800
ctctcaacga cacggggctg ctggggatg atgtggagta cgcacccctg acggtgagcg   1860
tgatcgtgca ggacgaggga gtggacgcca tcccggtgaa ggtcctcaac tgtgacacca   1920
tctcccaggt caaggagaag atcattgacc aggtgtaccg tgggcagccc tgctcctgct   1980
ggcccaggcc agacagcgtg gtcctggagt ggcgtccggg ctccacagcg cagatcctgt   2040
cggacctgga cctgacgtca gcgggagg gccggtggaa gcgcgtcaac acccttatgc   2100
actacaatgt ccgggatgga gccacccctca tcctgtccaa ggtgggggtc tcccagcagc   2160
cggaggacag ccagcaggac ctgcctgggg agcgccatgc cctcctggag gaggagaacc   2220
gggtgtggca cctggtgcgg ccgaccacg aggtggacga gggcaagtcc aagagaggca   2280
gcgtgaaaga gaaggagcgg acgaaggcca tcaccgagat ctacctgacg cggctgctct   2340
cagtcaaggg cacactgcag cagtttgtgg acaacttctt ccagagcgtg ctggcgcctg   2400
ggcacgcggt gccacctgca gtcaagtact tcttcgactt cctggacgag caggcagaga   2460
agcacaaacat ccaggatgaa gacaccatcc acatctggaa gacgaacagt ttaccgctcc   2520
ggttctgggt gaacatcctc aagaacccccc acttcatctt tgacgtgcat gtccacgagg   2580
tggtggacgc ctcgctgtca gtcatcgcgc agaccttcat ggatgcctgc acgcgcacgg   2640
agcataagct gagccgcgat ctcccagca acaagctgct gtacgccaag gagatctcca   2700
cctacaagaa gatggtggag gattactaca aggggatccg gcagatggtg caggtcagcg   2760
accaggacat gaacacacac ctggcagaga tttcccgggc gcacacggac tccttgaaca   2820
ccctcgtggc actccaccag ctctaccaat acacgcagaa gtactatgac gagatcatca   2880
atgccttgga ggaggatcct gccgcccaga gacgcagct ggccttccgc ctgcagcaga   2940
ttgccgctgc actggagaac aaggtcactg acctctgacc tacaatctcc agtgctgcct   3000
tgggacatag gtacctgagg tacctgagag ccccctcaggg gaggaggccg agtggctgtg   3060
gctgaggccc ccacccctccc ctggaacgcg ccccaagccg gagtgggtgc agccggaacc   3120
cgcccagcgt ctagactgta gcatcttcct ctgagcaata ccgccgggca ccgcaccagc   3180
accagcccca gccccagctc cctccggccg cagaaccagc atcgggtgtt cactgtcgag   3240
tctcgagtga tttgaaaatg tgccttacgc tgccacgctg ggggcagctg gcctccgcct   3300
ccgcccacgc accagcagcc gcctccatgc cctaggttgg gccccctgggg gatctgaggg   3360
cctgtggccc ccagggcaag ttcccagatc ctatgtctgt ctgtccacca cgagatggga   3420
```

```
ggaggagaaa aagcggtacg atgccttcct gacctcaccg gcctcccaa gggtgccggc    3480 actctgggtg gactcacggc tgctgggccc cacgtcaaag gtcaagtgag acgtaggtca    3540
agtcctacgt cggggcccag acatcctggg gtcctggtct gtcagacagg ctgccctaga    3600
gccccaccca gtccgggggg actgggagca gttccaagac caccccaccc cttttttgtaa   3660 atcttgttca ttgtaaatca aatacagcgt cttttttcact ccgaaaaaaa aaaaaaaaa    3720 aaaaaa                                                                3726

<210> SEQ ID NO 171
<211> LENGTH: 2255
<212> TYPE: DNA
<213> ORGANISM: Homo sapiens

<400> SEQUENCE: 171
gatgtgggca cgcctcagag ccagaagttt atggctccca cctgctcaat ctgacaggaa      60
gcttctgctc cccagttctc cccagccact gtggtctaca gattccagga aacccatccc     120
cctgtgacct cagggtgtgc tctgttctcc accctaggga ccagaaggag ccaggagtaa     180
agaactggct tacttggccg ccactgggaa attctgggta attcgagacg ccctggaatt     240 tggaccccact ccgctgatag gtggtgggca gggttctagg gaacacaaga ggcggagcca     300
ggtggcttcc ctgtgctggc attcttggct ctctctctct ctctttctct ctctctgtct     360
ctctctctct ctctgtctct cagccttgaa gccgtttccc tctgcgattc atgtaagtgt     420
gactcgattt cagggaaagg gaactcgcgt gggctgagga gaccgagtg gacgggctgg       480 ggaaggcacc gtgatgcccg caaccccgtc cctgaaggtg gtccatgagc tgcctgcctg     540
taccctctgt gcggggccgc tggaggatgc ggtgaccgtt ccctgtggac acaccttctg     600
ccggctctgc ctccccgcgc tctcccagat ggggggcccaa tcctcgggca agatcctgct     660
ctgcccgctc tgccaagagg aggagcaggc agagactccc atggcccctg tgccctggg     720 cccgctggga gaaacttact gcgaggagca cggcgagaag atctacttct tctgcgagaa    780
cgatgccgag ttcctctgtg tgttctgcag ggagggtccc acgcaccagg cgcacaccgt    840
ggggttcctg gacgaggcca ttcagcccta ccgggatcgt ctcaggagtc gactggaagc    900
tctgagcacg gagagagatg agattgagga tgtaaagtgt caagaagacc agaagcttca    960
agtgctgctg actcagatcg aaagcaagaa gcatcaggtg gaaacagctt ttgagaggct   1020
gcagcaggag ctggagcagc agcgatgtct cctgctggcc aggctgaggg agctggagca   1080
gcagatttgg aaggagaggg atgaatatat cacaaaggtc tctgaggaag tcacccggct   1140
tggagcccag gtcaaggagc tggaggagaa gtgtcagcag ccagcaagtg agcttctaca   1200
agatgtcaga gtcaaccaga gcaggtgtga gatgaagact tttgtgagtc ctgaggccat   1260
ttctcctgac cttgtcaaga gatccgtga tttccacagg aaaatactca ccctcccaga   1320
gatgatgagg atgttctcag aaaacttggc gcatcatctg gaaatagatt cagggggtcat   1380 cactctggac cctcagaccg ccagccggag cctggttctc tcggaagaca ggaagtcagt   1440
gaggtacacc cggcagaaga gagagcctgcc agacagcccc ctgcgcttcg acggcctccc   1500
ggcggttctg ggcttcccgg gcttctcctc cgggcgccac cgctggcagg ttgacctgca   1560
gctgggcgac ggcggcggct gcacggtggg ggtggccggg gagggggtga ggaggaaggg   1620
agagatggga ctcagcgccg aggacggcgt ctgggccgtg atcatctcgc accagcagtg   1680 ctggggccagc acctcccgg gcaccgacct gccgctgagc gagatcccgc gcggcgtgag   1740
```

```
agtcgccctg gactacgagg cggggcaggt gaccctccac aacgcccaga cccaggagcc      1800
catcttcacc ttcactgcct cttttctccgg caaagtcttc cctttctttg ccgtctggaa    1860
aaaaggttcc tgccttacgc tgaaaggctg aagtggggcg cgcgaagggc ggcgaagcgg     1920
agacggcggc tctccgggat ccagctccgc ccctggccag tgtgcggccc ggggctccc     1980 tgtgcccgcg tgaggcgaga aacaggggga cttgagtctc gaacagcggt tgtttttact     2040
ttatttatct taggccctca gctccctgac gtcctgagcc tccctgtgac gctctggcct    2100
tctctgcacc tcagagtgca gaaccacaga cggcttcggc tgtgcctagg gcaacagcca    2160
acctaggagc cagcgggctt tcggggaaaa aaagaaaaa gacatctaaa ataaaatgtt     2220
taaactgttt caaataaaa aaaaaaaaa aaaaa                                 2255

<210> SEQ ID NO 172
<211> LENGTH: 942
<212> TYPE: DNA
<213> ORGANISM: Homo sapiens

<400> SEQUENCE: 172
tttatacatt ctaaatctcc ccagtttctt tggggctgga agatgcaact tccatttaat      60
agaaactttg aaatcttggg gtaagggagc agtgggggga ctagggagaa ggataagaaa    120
tagaattatt gaaagccccc caccagggac cttcctggcc agaatatgca gagtaattcc    180
tgctggcttc acctttgaaa gtccctcgaa actatgcaga tgaaactgag tctgttttttg   240 atattgtcag atgtattcta ccttggaagt cccaacacct aaactggaat tcttgtatttt  300 acatctcctc cactgtcccc cacaccaccc ctcaattcct gctgccctg ctaatgttaa     360 gcatttttct cttgttatca tcaggttcac attaaaaaca gatacttaca aactgacttg    420
aagcacagat acttttacga atgtgataaa atattttctt aagaaaagga agaggatgt     480 gggtcaaata aaacaccgca tgatgttga ttggtgaata ctggtgtaag aaaagggagc     540
tcaggaattt ttattactgt atttgtaaat gagtttgaag gaatttgtaa atgccactgg    600
tacattttta aggtgacaca tttgctcctt ataaagttat taaaaattac agggtaagct    660
taaatgacgt ttgccagtag ttttactttta tataatcaat attgatattg ttgctgaact   720
atgtaacttt atgatgcatt tttcagtccc ttttcagagc aaatgctttt gcaatggtag    780
taatgtttag tttaaattga cttaataaat tattacctga gcaaaaaaaa aaaaaaaaaa    840 aaaaaaaaa taaaaaaaa aaaaaaaaa aaaaaaaaa taataaaaaa aaaaaaaaca        900
aacaaatcaa taaaacttaa acaaaaaaaa aataaaaaaa aa                        942

<210> SEQ ID NO 173
<211> LENGTH: 1070
<212> TYPE: DNA
<213> ORGANISM: Homo sapiens

<400> SEQUENCE: 173
gcagagatcg ccacatcgtc ggacaaggtc aaggacgggg gcggcgggaa cgagggctct      60
ccatgcccac cgtgtcccgg gcccatagcc gggcaagccc taggaggcag ccgggcgtcg    120
ccggccccgg cgccgtcacg ctcgccctcg gcgcagtgtc cttttccagg cgggacggtg    180
ctgtcccggc ctctctacta caccgcgccc ttctatcccg gctacacgaa ctatggctcc    240
ttcggacacc ttcatggcca ccggggccgg gggccgggcc ccacacccgg tccggggtct    300
catttcaatg gattaaacca gaccgtgttg aaccgagcgg acgctttggc taaagacccg    360
aaaatgttgc ggagccagtc tcagctagac ctgtgcaaag actctcccta tgaattgaag    420
```

```
aaaggtatgt ccgacattta acgcgggctg cgtcggtccc ggacttttct aatttattaa    480
aaacatggcc ttggcagtta ttttccatc accgagagag agagacagag agagaaaata     540
aactacccct cctattcaga agtttatagt ttatggagat ggatgacata aaaatgtaaa    600
catctccaca cacacaaaaa aatgtcttaa ccaaccgaaa agaaaatta aaaaggatt      660 tgtattaaat cttattctgt atatttaatg tagcatttt gtatttaaat tgataattca    720
atatctttga agtaaattat gaaatcaaga cacctgtaca ggcatttaat gttttttgt    780 aatataaata tatcatttg tgtttccccc aaaactgttt catagttaaa aaatacaagt    840
ttaatttaat ttttacacc tattgattct gctgggtatg agctaaagta ttacggaaag    900
gaaacaggtt atactcttag atttaaaaag tgaaagaaac tgcaggcgcc tttgtaaaat   960
gcaaaatatt taattaaaag agattttaac ataatgagag ccactcatta cttttagaa   1020 gcctcaataa actgtccatt gccttggtca aaaaaaaaaa aaaaaaaaa               1070

<210> SEQ ID NO 174
<211> LENGTH: 668
<212> TYPE: DNA
<213> ORGANISM: Homo sapiens
<220> FEATURE:
<221> NAME/KEY: misc_feature
<222> LOCATION: (60)..(60)
<223> OTHER INFORMATION: a or g or c or t/u

<400> SEQUENCE: 174
atatccaaga aatttggaca cctataccta cagaataatg aaatagaaaa gatgaatctn    60
acagtgatgt gtccttctat tgacccacta cattaccacc atttaacata cattcgtgtg   120
gaccaaaata aactaaaaga accaataagc tcatacatct tcttctgctt ccctcatata   180
cacactattt attatggtga acaacgaagc actaatggtc aaacaataca actaaagacc   240
caagttttca ggagatttcc agatgatgat gatgaaagtg aagatcacga tgatcctgac   300
aatgctcatg agagcccaga acaagaagga gcagaagggc actttgacct tcattattat   360
gaaaatcaag aatagcaaga aactatatag gtatacactt acgacttcac aaaacctata   420
cttaatatag taaatctaag taaacatgta ttactcaaag taatatattt agaattatgt   480
attagtataa gatcagaatt gaatttaagt tgttggtgac atctgcatca tttcatagga   540
ttagaactta ctcaaaataa tgtaaatctt taaaaatata aattagaatg acaagtggga   600
atcataaatt aaacgttaat ggtttcttat gctcttttta aatatagaaa tatcatgtta   660
aaaaaaaa                                                            668

<210> SEQ ID NO 175
<211> LENGTH: 2953
<212> TYPE: DNA
<213> ORGANISM: Homo sapiens

<400> SEQUENCE: 175
atgattgcaa cagtggattt aaaagtcaat gaatatgaga aaaccaaaaa atggcttgag    60
atcctaaata agattgaaaa caaaacatac acgaagctca aaatggaca tgtgtttagg   120 aagcaggcac tgatgagtga agaaaggact ctgttatatg atggccttgt ttactggaaa   180
actgctacag gtcgtttcaa agatatccta gctctacttc taactgatgt gctgctcttt   240
ttacaagaaa aagaccagaa atacatcttt gcagccgttg atcagaagcc atcagttatt   300
tcccttcaaa agcttattgc tagagaagtt gctaatgagg agagaggaat gtttctgatc   360
```

| | |
|---|---|
| agtgcttcat ctgctggtcc tgagatgtat gaaattcaca ccaattccaa ggaggaacgc | 420 |
| aataactgga tgagacggat ccagcaggct gtagaaagtt gtcctgaaga aaaggggga | 480 |
| aggacaagtg aatctgatga agacaagagg aaagctgaag ccagagtggc caaaattcag | 540 |
| caatgtcaag aaatactcac taaccaagac caacaaattt gtgcgtattt ggaggagaag | 600 |
| ctgcatatct atgctgaact tggagaactg agcggatttg aggacgtcca tctagagccc | 660 |
| cacctcctta ttaaacctga cccaggcgag cctccccagg cagcctcatt actggcagca | 720 |
| gcactgaaag aagcattagt cacaggaggg agagaaggaa gaggctgttc ggatgtggat | 780 |
| cccgggatcc agggtgtggt aaccgacttg gccgtctctg atgcagggga aaggtggaa | 840 |
| tgtagaaatt ttccaggttc ttcacaatca gagattatac aagccataca gaatttaacc | 900 |
| cgtctcttat acagccttca ggccgccttg accattcagg acagccacat tgagatccac | 960 |
| aggctggttc tccagcagca ggagggcctg tctctcggcc actctatcct ccgaggcggc | 1020 |
| cccttgcagg accagaagtc tcgcgacgcg gacaggcagc atgaggagct ggccaatgtg | 1080 |
| caccagcttc agcaccagct ccagcagggg cagcggcgct ggctgcgcag gtgtgagcag | 1140 |
| cagcagcggg cgcaggcgac cagggagagc tggctgcagg agcggagcg ggagtgccag | 1200 |
| tcgcaggagg agctgctgct gcggagccgg ggcgagctgg acctccagct ccaggagtac | 1260 |
| cagcacagcc tggagcggct gagggagggc cagcgcctgg tggagaggga gcaggcgagg | 1320 |
| atgcgggccc agcagagcct gctgggccac tggaagcacg gccggcagag gagcctgtcc | 1380 |
| gcggtgctcc ttccgggtgg ccccgaggta atggaactta atcgatctga gagtttatgt | 1440 |
| catgaaaact cattcttcat caatgaagct ttagtacaaa tgtcatttaa cacttttcaac | 1500 |
| aaactgaatc catcagttat ccatcaggat gccacttacc ctacaactca atctcattct | 1560 |
| gacttggtga ggactagtga acatcaagta gacctcaagg tggaccctt tcagccttcg | 1620 |
| aatgtcagtc acaaactgtg gacagccgct ggttccggcc atcagatact tcctttccat | 1680 |
| gaaagcagca aggattcttg taaaaatggc tccagtatga caaagtgcag ttgtacgttg | 1740 |
| acatctcccc cgggactgtg gactggaacc acatctactt tgaaggattt ggacacctcc | 1800 |
| cacactgagt ccccaacccc ccatgactca aattcacacc gccctcaact gcaggcgttt | 1860 |
| ataacagaag caaagctaaa tctaccgaca aggacaatga ccagacaaga tggggaaact | 1920 |
| ggagatggag ccaaagaaaa tattgtttac ctctaattgt gttgtcattt ttccaaacaa | 1980 |
| aacaaaacac tggcactttt gggagaaact ttttgtctcc attccttatg tatgtgtgat | 2040 |
| tgtctgtgtc caaattgctt taagaataat atttaatatt tcctggaagc tcattttttt | 2100 |
| ggcatgagtc taattaaatt attgaaagcc accctgtttg tataatcttt aacttatcaa | 2160 |
| atctaatttc agatttctgg aggagaaact aacttgaata agcaggacta ttttaaaagt | 2220 |
| tgttttgacg ctagagtaaa attccatgtc acattttcta cccaatcatc tggatttcaa | 2280 |
| gattcctttt aagatctcaa tgaagcaatt tggatttaaa gagtggtatt cacaaggggt | 2340 |
| gaactttcac agtcagggca gttgcctcag tgcccacata ggcagaggag gatgtgggaa | 2400 |
| agggcttttc tcagctagtt tttgtgtgct catttcttct gggagcatta aaagtggtga | 2460 |
| tctgttacag tcactattca actgggcacg tgttgtgatt ggtcagtcac tgagccaggg | 2520 |
| atacagtccg gacttgctta gtacctaagc ctaatgctgg tggggtttca agacatggtt | 2580 |
| cagcatcatc ttttaacaag gcccagaggc ccagagcccg catcaagtca ttttgatgta | 2640 |
| aatagtgaac tttgttagag ccctcacttc tatcaatcag ctgtcctgtc cctgccagca | 2700 |
| cctggagcac caactaccac tccctggaaa gaacccttcc ctgcagtttt ttaaggacaa | 2760 |

```
aactgcccac tcctcattaa gtttgctgcc tggatacact tttccacaaa ggaaaactgg    2820
catatcctgc cttccgagta gtatgggtct ctgtgtgaga aaccaggaga tattttcatc    2880
ttgttcggaa atacttgtat gtatttggt gtcaataaat atcttgtacc tcattaaaaa     2940
aaaaaaaaaa aaa                                                       2953

<210> SEQ ID NO 176
<211> LENGTH: 4157
<212> TYPE: DNA
<213> ORGANISM: Homo sapiens

<400> SEQUENCE: 176
ctgagccgca tctgcaatag cacacttgcc cggccacctg ctgccgtgag cctttgctgc     60
tgaagcccct ggggtcgcct ctacctgatg aggatgtgca cccccattag ggggctgctc    120
atggcccttg cagtgatgtt tgggacagcg atggcatttg cacccatacc ccggatcacc    180
tgggagcaca gagaggtgca cctggtgcag tttcatgagc cagacatcta caactactca    240
gccttgctgc tgagcgagga caaggacacc ttgtacatag gtgcccggga ggcggtcttc    300
gctgtgaacg cactcaacat ctccgagaag cagcatgagg tgtattggaa ggtctcagaa    360
gacaaaaaag caaatgtgc agaaaagggg aaatcaaaac agacagagtg cctcaactac    420
atccgggtgc tgcagccact cagcgccact tcccttttacg tgtgtgggac caacgcattc    480
cagccggcct gtgaccacct gaacttaaca tcctttaagt ttctggggaa aaatgaagat    540
ggcaaaggaa gatgtccctt tgacccagca cacagctaca catccgtcat ggttgatgga    600
gaactttatt cggggacgtc gtataatttt ttgggaagtg aacccatcat ctcccgaaat    660
tcttcccaca gtcctctgag gacagaatat gcaatccctt ggctgaacga gcctagtttc    720
gtgtttgctg acgtgatccg aaaaagccca gacagccccg acggcgagga tgacagggtc    780
tacttcttct tcacggaggt gtctgtggag tatgagtttg tgttcagggt gctgatccca    840
cggatagcaa gagtgtgcaa gggggaccag ggcggcctga ggaccttgca gaagaaatgg    900
acctccttcc tgaaagcccg actcatctgc tcccggccag acagcggctt ggtcttcaat    960
gtgctgcggg atgtcttcgt gctcaggtcc ccgggcctga aggtgcctgt gttctatgca   1020
ctcttcaccc cacagctgaa caacgtgggg ctgtcggcag tgtgcgccta caacctgtcc   1080
acagccgagg aggtcttctc ccacgggaag tacatgcaga gcaccacagt ggagcagtcc   1140
cacaccaagt gggtgcgcta taatggcccg gtacccaagc cgcggcctgg agcgtgcatc   1200
gacagcgagg cacgggccgc caactacacc agctccttga atttgccaga caagacgctg   1260
cagttcgtta aagaccaccc tttgatggat gactcggtaa ccccaatata caacaggccc   1320
aggttaatca agaaagatgt gaactacacc cagatcgtgg tggaccggac ccaggccctg   1380
gatgggactg tctatgatgt catgtttgtc agcacagacc ggggagctct gcacaaagcc   1440
atcagcctcg agcacgctgt tcacatcatc gaggagaccc agctcttcca ggactttgag   1500
ccagtccaga ccctgctgct gtcttcaaag aagggcaaca ggtttgtcta tgctggctct   1560
aactcgggcg tggtccaggc cccgctggcc ttctgtggga agcacggcac ctgcgaggac   1620
tgtgtgctgg cgcgggaccc ctactgcgcc tggagcccgc ccacagcgac ctgcgtggct   1680
ctgcaccaga ccgagagccc cagcagggt ttgattcagg agatgagcgg cgatgcttct   1740
gtgtgcccga taaaagtaa aggaagttac cggcagcatt ttttcaagca cggtggcaca   1800
gcggaactga aatgctccca aaaatccaac ctggcccggg tcttttggaa gttccagaat   1860
```

```
ggcgtgttga aggccgagag ccccaagtac ggtcttatgg gcagaaaaaa cttgctcatc    1920
ttcaacttgt cagaaggaga cagtggggtg taccagtgcc tgtcagagga gagggttaag    1980
aacaaaacgg tcttccaagt ggtcgccaag cacgtcctgg aagtgaaggt ggttccaaag    2040
cccgtagtgg cccccacctt gtcagttgtt cagacagaag gtagtaggat tgccaccaaa    2100
gtgttggtgg catccaccca agggtcttct ccccaaccc cagccgtgca ggccacctcc    2160
tccggggcca tcacccttcc tcccaagcct gcgcccaccg gcacatcctg cgaaccaaag    2220
atcgtcatca acacggtccc ccagctccac tcggagaaaa ccatgtatct taagtccagc    2280
gacaaccgcc tcctcatgtc cctcttcctc ttcttctttg ttctcttcct ctgcctcttt    2340
ttctacaact gctataaggg ataccctgccc agacagtgct tgaaattccg ctcggcccta    2400
ctaattggga agaagaagcc caagtcagat ttctgtgacc gtgagcagag cctgaaggag    2460
acgttagtag agccagggag cttctcccag cagaatgggg agcaccccaa gccagccctg    2520
gacaccggct atgagaccga gcaagacacc atcaccagca aagtccccac ggatagggag    2580
gactcacaga ggatcgacga ccttctgcc agggacaagc cctttgacgt caagtgtgag    2640
ctgaagttcg ctgactcaga cgcagatgga gactgaggcc ggctgtgcat ccccgctggt    2700
gcctcggctg cgacgtgtcc aggcgtggag agttttgtgt ttctcctgtt cagtatccga    2760
gtctcgtgca gtgctgcgta ggttagcccg catcgtgcag acaacctcag tcctcttgtc    2820 tatttctct tgggttgagc ctgtgacttg gtttctcttt gtccttttgg aaaaatgaca    2880
agcattgcat cccagtcttg tgttccgaag tcagtcggag tacttgaaga aggcccacgg    2940
gcggcacgga gttcctgagc cctttctgta gtgggggaaa ggtggctgga cctctgttgg    3000
ctgagaagag catcccttca gcttcccctc cccgtagcag ccactaaaag attatttaat    3060
tccagattgg aaatgacatt ttagtttatc agattggtaa cttatcgcct gttgtccaga    3120
ttggcacgaa ccttttcttc cacttaatta ttttttttagg attttgcttt gattgtgttt    3180
atgtcatggg tcattttttt ttagttacag aagcagttgt gttaatattt agaagaagat    3240
gtatatcttc cagattttgt tatatatttg gcataaaata cggcttacgt tgcttaagat    3300
tctcagggat aaacttcctt ttgctaaatg cattcttttct gcttttagaa atgtagacat    3360
aaacactccc cggagcccac tcacctttttt tcttttcctt ttttttttttt taactttatt    3420 ccttgaggga agcattgttt ttggagagat ttctcttctg tacttcgttt tacttttctt    3480 ttttttttaac ttttactctc tcgaagaaga ggaccttccc acatccacga ggtgggtttt    3540
gagcaaggga aggtagcctg gatgagctga gtggagccag gctggcccag agctgagatg    3600
ggagtgcggt acaatctgga gcccacagct gtcggtcaga acctcctgtg agacagatgg    3660
aaccttcaca agggcgcctt tggttctctg aacatctcct ttctcttctt gcttcaattg    3720
cttacccact gcctgcccag actttctatc cagcctcact gagctgccca ctactggaag    3780
ggaactgggc ctcggtggcc ggggccgcga gctgtgacca cagcaccctc aagcatacgg    3840
cgctgttcct gccactgtcc tgaagatgtg aatgggtggt acgatttcaa cactggttaa    3900
tttcacactc catctccccg ctttgtaaat accatcgggg aagagacttt ttttccatgg    3960
tgaagagcaa taaactctgg atgtttgtgc gcgtgtgtgg acagtcttat cttccagcat    4020
gataggattt gaccattttg gtgtaaacat ttgtgttta taagatttac cttgttttta    4080
tttttctact ttgaattgta tacatttgga aagtacccaa ataaatgaga agcttctatc    4140
cttaaaaaaa aaaaaaa                                                   4157
```

<210> SEQ ID NO 177
<211> LENGTH: 1023
<212> TYPE: DNA
<213> ORGANISM: Homo sapiens
<220> FEATURE:
<221> NAME/KEY: misc_feature
<222> LOCATION: (4)..(4)
<223> OTHER INFORMATION: a or g or c or t/u
<220> FEATURE:
<221> NAME/KEY: misc_feature
<222> LOCATION: (23)..(23)
<223> OTHER INFORMATION: a or g or c or t/u
<220> FEATURE:
<221> NAME/KEY: misc_feature
<222> LOCATION: (28)..(28)
<223> OTHER INFORMATION: a or g or c or t/u
<220> FEATURE:
<221> NAME/KEY: misc_feature
<222> LOCATION: (47)..(47)
<223> OTHER INFORMATION: a or g or c or t/u
<220> FEATURE:
<221> NAME/KEY: misc_feature
<222> LOCATION: (53)..(53)
<223> OTHER INFORMATION: a or g or c or t/u
<220> FEATURE:
<221> NAME/KEY: misc_feature
<222> LOCATION: (69)..(69)
<223> OTHER INFORMATION: a or g or c or t/u

<400> SEQUENCE: 177

```
cccntcccca gaggcaggaa aancagtntg ccgaaaggat agactgnggt gcngtctttc    60
cccaagttnt gaactagttt taaggtagct taggatgaaa aatggagaat gattgggggt   120
tccaaaccac tttcttctcc cttggcttat atctcttcac catttggtgg tcaactgtgg   180
gcctaccctg gacctcatct actcagcgag aattggacat gaagctagag gcagctgcct   240
tggaagggaa gtcaggctca cttggacagc ccaggccatg gcaggaagaa tcccttcctc   300
ttggggtcct tgatgggcat gtgtgatggg gaaggagcag tctcccagcc ctgggtctgc   360
tccccacatc tctcctaatt ccacttcacc ttttgccacc ccctcccac cagaggccta    420
gccctttgt caccgaaggc ccccagagtg tttctgtgtg aaaccctctc atttacactg    480
tggcatcaaa atccacaaaa gatggattaa ttgcactctg gttaatagca gcagcacaat   540
gattaaaatc tatattccta tcttctctag caccctggtg tggggatggg gcggaagggt   600
gtcttgaggg gcagggagga ccccataaaa caatccctcc tgcattctca ggctaaatag   660
ggcccccagt gactacctgt tcttggctgt ccctctgaa gagctctgcc ttctcacagc    720
caccaccagt tgccccactc ccaggaaaac agcacatgtt cttcttctcc tgccttgaga   780
ctgcgtgtta gtcttccatt cataactcat cagcagctca gtccttctta tgtcagtct    840
cagttcattc agccaaagct cattttgtc ctatccaaag tagaaagggt tcttttagaa    900
aacttgaaga atgtgcctcc tcttagcatc tgtttctgac tcccagttat ttttaaaata   960
aatgatgaat aaaatgcctg ccctgaaggg ttctggagga gtcaggtatc aaaaaaaaaa  1020
aaa                                                                1023
```

<210> SEQ ID NO 178
<211> LENGTH: 550
<212> TYPE: DNA
<213> ORGANISM: Homo sapiens

<400> SEQUENCE: 178

```
tttttaagat gatcttgctc cgtcacccag gctggagtgc agtggcgtaa tcatggcttc    60
ctgcagcctc aaactcctgg gctcaatgag ttccttgaga tcttccatcc tcagcttccc   120
```

| | |
|---|---|
| aagtagctag tagtagtagt ggcttgcacc aacgctcctg ccctaatttt caatattttt | 180 |
| tttgtagaga taggatctca ctgtgttacc caagctagac ttgaactcct ggcctcaagc | 240 |
| gatccttccg ccttggcctc ccaaagtgtt gggattacag cattagcta ccacacctgg | 300 |
| ccaaggccca ggtttcgaca gaaagggaga gaaaacctgc cagagatgcc atttcggagc | 360 |
| cactctgctt ggcagggacc tgtgttcccc tcatgcaggt tcatccttag agggctgcgg | 420 |
| tcttatctgg ttgtgcaaaa gtcccacaac ctttctggat tgatagtttg tggtgaaata | 480 |
| aacaatttta gtttgtttgg agaatctttt gtatacaaaa tacaaataaa acctaaatca | 540 |
| aagaaacaga | 550 |

<210> SEQ ID NO 179
<211> LENGTH: 2798
<212> TYPE: DNA
<213> ORGANISM: Homo sapiens

<400> SEQUENCE: 179

| | |
|---|---|
| gaggggccgg aggcgtcccc gctcccgctc gctactagcc cgcgggccag cgccgcgtcc | 60 |
| cgagccccgg cgggagccat ggctctaaaa ggacaagaag attatattta tcttttcaag | 120 |
| gattcaacac atccagtgga tttctctgat gcattcagaa cattttactt ggatggatta | 180 |
| tttactgata ttactcttca gtgtccttca ggcataattt tccattgtca ccgagccgtt | 240 |
| ttagctgctt gcagcaatta ttttaaggca atgttcacag ctgacatgaa agaaaaattt | 300 |
| aaaaataaaa taaaactctc tggcatccac catgatattc tggaaggcct tgtaaattat | 360 |
| gcatacactt cccaaattga aataactaaa agaaatgttc aaagcctgct tgaggcagcg | 420 |
| gatctgctac agttcctttc agtaaagaag gcttgtgagc ggttttttggt aaggcacttg | 480 |
| gatattgata attgtattgg aatgcactcc tttgcagaat tcatgtgtg tccagaacta | 540 |
| gagaaggaat ctcgaagaat tctatgttca aagtttaagg aagtgtggca acaagaagaa | 600 |
| tttctggaaa tcagccttga aaagtttctc tttatcttgt ccagaaagaa tctcagtgtt | 660 |
| tggaaagaag aagctatcat agagccagtt attaagtgga ctgctcatga tgtagaaaat | 720 |
| cgaattgaat gcctctataa tctactgagc tatatcaaca ttgatataga tccagtgtac | 780 |
| ttaaaaacag ccttaggcct tcaaagaagc tgcctgctca ccgaaaataa gatccgctcc | 840 |
| ctaatataca atgccttgaa tcccatgcat aaagagattt cccagaggtc cacagccaca | 900 |
| atgtatataa ttggaggcta ttactggcat cctttatcag aggttcacat atgggatcct | 960 |
| ttgacaaatg tttggattca gggagcagaa ataccagatt ataccaggga gagctatggt | 1020 |
| gttacatgtt taggacccaa catttatgta actgggggct acaggacgga taacatagaa | 1080 |
| gctcttgaca cagtgtggat ctataacagt gaaagtgatg aatggacaga aggttttgcca | 1140 |
| atgctcaatg ccaggtatta ccactgtgca gtcaccttgg gtggctgtgt ctatgcttta | 1200 |
| ggtggttaca gaaaagggggc tccagcagaa gaggctgagt ctatgatcc tttaaaagag | 1260 |
| aaatggattc ctattgcaaa catgattaaa ggtgtgggaa atgctactgc ctgtgtctta | 1320 |
| catgatgtta tctacgtcat tggtggccac tgtggctaca gaggaagctg cacctatgac | 1380 |
| aaagttcaga gctacaattc cgatatcaac gaatggagcc tcatcacctc cagtccacat | 1440 |
| ccagaatatg gattgtgctc agttccgttt gaaaataagc tctatctagt cggtggacaa | 1500 |
| actacaatca gaatgctaa tgaccctgaa caaaatgaat ggagagagat agctcccatg | 1560 |
| atggaaagga ggatggagtg cggtgccgtc atcatgaatg gatgtattta tgtcactgga | 1620 |
| ggatactcct actcaaaggg aacgtatctt cagagcattg agaaatatga tccagatctt | 1680 |

```
aataagtggg aaatagtggg taatcttccc agtgccatgc ggtctcatgg gtgtgtttgt    1740
gtgtataatg tctaattgaa tctgcagaaa tgaccaagca atcacttttt tggagtatag    1800
ttttataaaa aaagaatgca gggtttgaag ttccttacct gataattgtg tctggcacat    1860 gatagggat  cagtaaattg taattcctaa ccctactgta ctcccaaaca tggtgattca    1920
tggtcaagaa aaatcttata tatatatata cacacacata tatatgtgtt catatatatg    1980
tatacatata tgtgtatata tacgcatgta tgtatacata tatgtgtata tatacgcatg    2040
tatgtatgca tatgtgtgta tatatacgta tgtatgtata catatgtgta tatatacgta    2100
tgtatgtata catatatgtg tatatatgcg tatgtatgta tacatatatg tgtatatata    2160
cgtatgtatg tatacatata tgtgtatata tacgtatgta tgtatacata tatgtgtata    2220
tatacgtatg tatgtataca tatatgtgtg tatatacgtg tgtatgtata catatatgtg    2280
tatatatacg tgtgtatgta tacatatatg tgtatatatg cgtgtgtatg tatacatata    2340
tgtgtatata tacgtgtgta tgtatacata tatgtgtata tatacgtgtg tatgtataca    2400
tatatgtgta tatatgcgtg tgtatatata tacacatata tacgtatata tgtatatata    2460
tatacacagt tgaatcagtg ggattaatac ctataatctc tggttttcaa aggtaatatg    2520
gaatatttga cacttggtaa aaggtgaact acctttgtag tgaatctttt cctcttggta    2580
gcatcaacac tggggataaa tcagaaccat tctgtggaat gaaatgtttc tcaagagcct    2640
ataatatagt agatagtgca tattaagatg tctggctggg catggtggct catgcctgta    2700
atcccagcac tttgggaggc tgaggcggga ggatcacttg agcctagaag ttggagacta    2760
acctggcgag accctgtctc aaaaaaaaaa aaaaaaaa                            2798

<210> SEQ ID NO 180
<211> LENGTH: 439
<212> TYPE: DNA
<213> ORGANISM: Homo sapiens

<400> SEQUENCE: 180
acccttttgt gaccagctgc atacccaaa accttttgga atctgggcta actggctgtg      60
cctacatcaa cagcacccgt gaaccccgt gtgctatgct ctgtgcaaca aaacattcag     120
aacccacttt caagatgctg ctgctgtgcc agtgtgacaa aaaaaagagg cgcaagcagc    180
agtaccagca gagacagtcg gtcattttc acaagcgcgc acccgagcag gccttgtaga    240
atgaggttgt atcaatagca gtgacaaaac gcacacatca acccacagac cttaggagga    300
ggaaggcgag ggcggggtga cttctggtga tgataaaaat ggttttatca cccagatgtg    360
aaagaagctg cctgtttact gatccattga ataaacccat tttaatagaa aaagtcaata    420
ccaattcagc aaaaaaaaa                                                 439

<210> SEQ ID NO 181
<211> LENGTH: 1309
<212> TYPE: DNA
<213> ORGANISM: Homo sapiens

<400> SEQUENCE: 181
tatctatgta acaaatcgca gcacaggagt ccctgggct ccctcaggct ctggtatgac      60
atatttgagc catataaatt cagcttctcc tctggcatct gttagccgac tcacttgcaa    120
ctccacctca gcagtggtct ctcagtcctc tcaaagcaag gaaagagtac tgtgtgctga    180
gagaccatgg caaagaatcc tccagagaat tgtgaagact gtcacattct aaatgcagaa    240
```

```
gcttttaaat ccaagaaaat atgtaaatca cttaagattt gtggactggt gtttggtatc      300
ctgaccctaa ctctaattgt cctgttttgg gggagcaagc acttctggcc ggaggtaccc      360
aaaaaagcct atgacatgga gcacactttc tacagcagtg gagagaagaa gaagatttac      420
atggaaattg atcctgtgac cagaactgaa atattcagaa gcggaaatgg cactgatgaa      480
acattggaag tacacgactt taaaaacgga tacactggca tctacttcgt gggtcttcaa      540
aaatgtttta tcaaaactca gattaaagtg attcctgaat tttctgaacc agaagaggaa      600
atagatgaga atgaagaaat taccacaact ttctttgaac agtcagtgat ttgggtccca      660
gcagaaaagc ctattgaaaa ccgagatttt cttaaaaatt ccaaaattct ggagatttgt      720
gataacgtga ccatgtattg atcaatccc actctaatat cagtttctga gttacaagac      780
tttgaggagg agggagaaga tcttcacttt cctgccaacg aaaaaaagg gattgaacaa      840
aatgaacagt gggtggtccc tcaagtgaaa gtagagaaga cccgtcacgc cagacaagca      900
agtgaggaag aacttccaat aaatgactat actgaaaatg gaatagaatt tgatcccatg      960
ctggatgaga gaggttattg ttgtatttac tgccgtcgag gcaaccgcta ttgccgccgc     1020
gtctgtgaac ctttactagg ctactaccca tatccatact gctaccaagg aggacgagtc     1080
atctgtcgtg tcatcatgcc ttgtaactgg tgggtggccc gcatgctggg gagggtctaa     1140
taggaggttt gagctcaaat gcttaaactg ctggcaacat ataataaatg catgctattc     1200
aatgaatttc tgcctatgag gcatctggcc cctggtagcc agctctccag aattacttgt     1260
aggtaattcc tctcttcatg ttctaataaa cttctacatt atcaaaaaa                 1309

<210> SEQ ID NO 182
<211> LENGTH: 1477
<212> TYPE: DNA
<213> ORGANISM: Homo sapiens

<400> SEQUENCE: 182
gcggatcgct gctccctctc gccatggcgc aggtgctgat cgtgggcgcc gggatgacag       60
gaagcttgtg cgctgcgctg ctgaggaggc agacgtccgg tcccttgtac cttgctgtgt      120
gggacaaggc tgacgactca gggggaagaa tgactacagc ctgcagtcct cataatcctc      180
agtgcacagc tgacttgggt gctcagtaca tcacctgcac tcctcattat gccaaaaaac      240
accaacgttt ttatgatgaa ctgttagcct atggcgtttt gaggcctcta agctcgccta      300
ttgaaggaat ggtgatgaaa gaaggagact gtaactttgt ggcacctcaa ggaatttctt      360
caattattaa gcattacttg aaagaatcag gtgcagaagt ctacttcaga catcgtgtga      420
cacagatcaa cctaagagat gacaaatggg aagtatccaa acaaacaggc tcccctgagc      480
agtttgatct tattgttctc acaatgccag ttcctgagat tctgcagctt caaggtgaca      540
tcaccacctt aattagtgaa tgccaaaggc agcaactgga ggctgtgagc tactcctctc      600
gatatgctct gggcctcttt tatgaagctg gtacgaagat tgatgtccct tgggctgggc      660
agtacatcac cagtaatccc tgcatacgct tcgtctccat tgataataag aagcgcaata      720
tagagtcatc agaaattggg ccttccctcg tgattcacac cactgtccca tttggagtta      780
catacttgga acacagcatt gaggatgtgc aagagttagt cttccagcag ctggaaaaca      840
ttttgccggg tttgcctcag ccaattgcta ccaaatgcca aaaatggaga cattcacagg      900
ttacaaatgc tgctgccaac tgtcctggcc aaatgactct gcatcacaaa cctttccttg      960
catgtggagg ggatggattt actcagtcca actttgatgg ctgcatcact tctgccctat     1020
gtgttctgga agctttaaag aattatattt agtgcctata tccttattct ctatatgtgt     1080
```

```
attgggtttt tattttcaca attttctgtt attgattatt ttgttttcta ttttgctaag    1140
aaaaattact ggaaaattgt tcttcactta ttatcatttt tcatgtggag tataaaatca    1200
attttgtaat tttgatagtt acaacccatg ctagaatgga aattcctcac accttgcacc    1260
ttccctactt ttctgaattg ctatgactac tccttgttgg aggaaaagtg gtacttaaaa    1320
aataacaaac gactctctca aaaaattac attaaatcac aataacagtt tgtatgccaa    1380
aaacttgatt atccttatga aaatttcaat tctgaataaa gaataatcac attatcaaag    1440
ccccatcaaa aaaaaaaaaa aaaaaaaaaa aaaaaaa                             1477

<210> SEQ ID NO 183
<211> LENGTH: 3100
<212> TYPE: DNA
<213> ORGANISM: Homo sapiens

<400> SEQUENCE: 183
actcgtctct ggtaaagtct gagcaggaca gggtggctga ctggcagatc cagaggttcc      60
cttggcagtc cacgccaggc cttcaccatg gatcagttcc ctgaatcagt gacagaaaac     120
tttgagtacg atgatttggc tgaggcctgt tatattgggg acatcgtggt ctttgggact     180
gtgttcctgt ccatattcta ctccgtcatc tttgccattg gcctggtggg aaatttgttg     240
gtagtgtttg ccctcaccaa cagcaagaag cccaagagtg tcaccgacat ttacctcctg     300
aacctggcct tgtctgatct gctgtttgta gccactttgc ccttctggac tcactatttg     360
ataaatgaaa agggcctcca caatgccatg tgcaaattca ctaccgcctt cttcttcatc     420
ggcttttttg gaagcatatt cttcatcacc gtcatcagca ttgataggta cctggccatc     480
gtcctggccg ccaactccat gaacaaccgg accgtgcagc atggcgtcac catcagccta     540
ggcgtctggg cagcagccat tttggtggca gcaccccagt tcatgttcac aaagcagaaa     600
gaaaatgaat gccttggtga ctaccccgag gtcctccagg aaatctggcc cgtgctccgc     660
aatgtggaaa caaattttct tggcttccta ctcccctgc tcattatgag ttattgctac     720
ttcagaatca tccagacgct gttttcctgc aagaaccaca gaaagccaa agccattaaa     780 ctgatccttc tggtggtcat cgtgttttc tcttctgga caccctacaa cgttatgatt     840
ttcctggaga cgcttaagct ctatgacttc tttcccagtt gtgacatgag gaaggatctg     900
aggctggccc tcagtgtgac tgagacggtt gcatttagcc attgttgcct gaatcctctc     960
atctatgcat tgctgggga aagttcaga agatacctt accacctgta tgggaaatgc    1020
ctggctgtcc tgtgtgggcg ctcagtccac gttgatttct cctcatctga atcacaaagg    1080
agcaggcatg gaagtgttct gagcagcaat tttacttacc acacgagtga tggagatgca    1140
ttgctccttc tctgaaggga atcccaaagc cttgtgtcta cagagaacct ggagttcctg    1200
aacctgatgc tgactagtga ggaaagattt ttgttgttat ttcttacagg cacaaaatga    1260
tggacccaat gcacacaaaa caaccctaga gtgttgttga gaattgtgct caaaatttga    1320
agaatgaaca aattgaactc tttgaatgac aaagagtaga catttctctt actgcaaatg    1380
tcatcagaac ttttttggttt gcagatgaca aaaattcaac tcagactagt ttagttaaat    1440
gagggtggtg aatattgttc atattgtggc acaagcaaaa gggtgtctga gccctcaaag    1500
tgagggaaaa ccagggcctg agccaagcta gaattccctc tctctgactc tcaaatcttt    1560
tagtcattat agatccccca gactttacat gacacagctt tatcaccaga gagggactga    1620
cacccatgtt tctctggccc caagggaaaa ttcccaggga agtgctctga taggccaagt    1680
```

```
ttgtatcagg tgcccatccc tggaaggtgc tgttatccat ggggaaggga tatataagat   1740
ggaagcttcc agtccaatct catggagaag cagaaataca tatttccaag aagttggatg   1800
ggtgggtact attctgatta cacaaaacaa atgccacaca tcacccttac catgtgcctg   1860
atccagcctc tccctgatt acaccagcct cgtcttcatt aagccctctt ccatcatgtc    1920
cccaaacctg caagggctcc ccactgccta ctgcatcgag tcaaaactca aatgcttggc   1980
ttctcatacg tccaccatgg ggtcctacca atagattccc cattgcctcc tccttcccaa   2040
aggactccac ccatcctatc agcctgtctc ttccatatga cctcatgcat ctccacctgc   2100
tcccaggcca gtaagggaaa tagaaaaacc ctgcccccaa ataagaaggg atggattcca   2160
accccaactc cagtagcttg ggacaaatca agcttcagtt tcctggtctg tagaagaggg   2220
ataaggtacc tttcacatag agatcatcct ttccagcatg aggaactagc caccaactct   2280
tgcaggtctc aacccttttg tctgcctctt agacttctgc tttccacacc tgcactgctg   2340
tgctgtgccc aagttgtggt gctgacaaag cttggaagag cctgcaggtg ccttggccgc   2400
gtgcatagcc cagacacaga agaggctggt tcttacgatg gcacccagtg agcactccca   2460
agtctacaga gtgatagcct tccgtaaccc aactctcctg gactgccttg aatatcccct   2520
cccagtcacc ttgtgcaagc ccctgcccat ctgggaaaat accccatcat tcatgctact   2580
gccaacctgg ggagccaggg ctatgggagc agcttttttt tcccccctag aaacgtttgg   2640
aacaatgtaa aactttaaag ctcgaaaaca attgtaataa tgctaaagaa aaagtcatcc   2700
aatctaacca catcaatatt gtcattcctg tattcacccg tccagacctt gttcacactc   2760
tcacatgttt agagttgcaa tcgtaatgta cagatggttt tataatctga tttgttttcc   2820
tcttaacgtt agaccacaaa tagtgctcgc tttctatgta gtttggtaat tatcattta    2880 gaagactcta ccagactgtg tattcattga agtcagatgt ggtaactgtt aaattgctgt   2940
gtatctgata gctctttggc agtctatatg tttgtataat gaatgagaga ataagtcatg   3000
ttccttcaag atcatgtacc ccaatttact tgccattact caattgataa acatttaact   3060
tgtttccaat gtttagcaaa tacatatttt atagaacttc                        3100
```

<210> SEQ ID NO 184
<211> LENGTH: 662
<212> TYPE: DNA
<213> ORGANISM: Homo sapiens
<400> SEQUENCE: 184

```
tgaacatatt caggctgatt ggggacgtgt cccacctggc ggccatcgtc atcttgatgg     60
tagagatctg gaagacgcgc tcctgcgccg gtatttctgg aaaagccag cttctgtctg    120 cactggtctt cacaactcgt gacctggatc ttttcacttc attatttca gtgtatcaca    180 catctatcaa ggttatctac gttgcctgct cgtatgccac agtgtacctg atctacctta   240
aatttaaggc aacatcggat ggaaatcatg ataccttccg agtggagttt ctggtggtcc   300
ctgtgggagg cctcctcatt tttagttaat cacgatttct ctcctcttga gtactcaagg   360
gaaagaagct cagtttgcca gcataagtgc caaagaccat cgccagcatc tgtccttcag   420
ggtgttcgga cagaattctt accacagcaa aggcataaga tgcttgatac ggaaaatcaa   480
gaacttaact tttttgttgc agatagtcat cagtggttct gtaaaaacgc agaggaaaag   540
agccagaagg tttctgttta atgcatcttg ccttatcttt ttttattact gtgcacaaag   600 attttttttac acaaacatcc ttaatgctgt tttaataaat tcagtgtgta gcttcaaaaa   660
aa                                                                  662
```

<210> SEQ ID NO 185
<211> LENGTH: 5920
<212> TYPE: DNA
<213> ORGANISM: Homo sapiens

<400> SEQUENCE: 185

| | | | | | |
|---|---|---|---|---|---|
| ggcaggtctc | gctctcggca | ccctcccggc | gcccgcgttc | tcctggccct | gcccggcatc | 60 |
| ccgatggccg | ccgctgggcc | ccggcgctcc | gtgcgcggag | ccgtctgcct | gcatctgctg | 120 |
| ctgaccctcg | tgatcttcag | tcgtgatggt | gaagcctgca | aaaggtgat | acttaatgta | 180 |
| ccttctaaac | tagaggcaga | caaaataatt | ggcagagtta | atttggaaga | gtgcttcagg | 240 |
| tctgcagacc | tcatccggtc | aagtgatcct | gatttcagag | ttctaaatga | tgggtcagtg | 300 |
| tacacagcca | gggctgttgc | gctgtctgat | aagaaaagat | catttaccat | atggctttct | 360 |
| gacaaaagga | aacagacaca | gaaagaggtt | actgtgctgc | tagaacatca | gaagaaggta | 420 |
| tcgaagacaa | gacacactag | agaaactgtt | ctcaggcgtg | ccaagaggag | atgggcacct | 480 |
| attccttgct | ctatgcaaga | gaattccttg | ggccctttcc | cattgtttct | tcaacaagtt | 540 |
| gaatctgatg | cagcacagaa | ctatactgtc | ttctactcaa | taagtggacg | tggagttgat | 600 |
| aaagaacctt | taaatttgtt | ttatatagaa | agagacactg | gaaatctatt | ttgcactcgg | 660 |
| cctgtggatc | gtgaagaata | tgatgttttt | gatttgattg | cttatgcgtc | aactgcagat | 720 |
| ggatattcag | cagatctgcc | cctcccacta | cccatcaggg | tagaggatga | aaatgacaac | 780 |
| caccctgttt | tcacagaagc | aatttataat | tttgaagttt | tggaaagtag | tagacctggt | 840 |
| actacagtgg | gggtggtttg | tgccacagac | agagatgaac | cggacacaat | gcatacgcgc | 900 |
| ctgaaataca | gcattttgca | gcagacacca | aggtcacctg | ggctcttttc | tgtgcatccc | 960 |
| agcacaggcg | taatcaccac | agtctctcat | tatttggaca | gagaggttgt | agacaagtac | 1020 |
| tcattgataa | tgaaagtaca | agacatggat | ggccagtttt | ttggattgat | aggcacatca | 1080 |
| acttgtatca | taacagtaac | agattcaaat | gataatgcac | ccactttcag | acaaaatgct | 1140 |
| tatgaagcat | ttgtagagga | aaatgcattc | aatgtggaaa | tcttacgaat | acctatagaa | 1200 |
| gataaggatt | taattaacac | tgccaattgg | agagtcaatt | ttaccatttt | aaagggaaat | 1260 |
| gaaaatggac | atttcaaaat | cagcacagac | aaagaaacta | atgaaggtgt | tctttctgtt | 1320 |
| gtaaagccac | tgaattatga | agaaaaccgt | caagtgaacc | tggaaattgg | agtaaacaat | 1380 |
| gaagcgccat | ttgctagaga | tattcccaga | gtgacagcct | tgaacagagc | cttggttaca | 1440 |
| gttcatgtga | gggatctgga | tgaggggcct | gaatgcactc | ctgcagccca | atatgtgcgg | 1500 |
| attaaagaaa | acttagcagt | ggggtcaaag | atcaacggct | ataaggcata | tgaccccgaa | 1560 |
| aatagaaatg | gcaatggttt | aaggtacaaa | aaattgcatg | atcctaaagg | ttggatcacc | 1620 |
| attgatgaaa | tttcagggtc | aatcataact | tccaaaatcc | tggataggga | ggttgaaact | 1680 |
| cccaaaaatg | agttgtataa | tattacagtc | ctggcaatag | acaaagatga | tagatcatgt | 1740 |
| actggaacac | ttgctgtgaa | cattgaagat | gtaaatgata | atccaccaga | atacttcaa | 1800 |
| gaatatgtag | tcatttgcaa | accaaaaatg | gggtataccg | acattttagc | tgttgatcct | 1860 |
| gatgaacctg | tccatggagc | tccatttat | ttcagtttgc | ccaatacttc | tccagaaatc | 1920 |
| agtagactgt | ggagcctcac | caaagttaat | gatacagctg | cccgtctttc | atatcagaaa | 1980 |
| aatgctggat | tcaagaata | taccattcct | attactgtaa | aagacagggc | cggccaagct | 2040 |
| gcaacaaaat | tattgagagt | taatctgtgt | gaatgtactc | atccaactca | gtgtcgtgcg | 2100 |

```
acttcaagga gtacaggagt aatacttgga aaatgggcaa tccttgcaat attactgggt    2160
atagcactgc tctttcctgt attgctaact ttagtatgtg gagttttttgg tgcaactaaa    2220 gggaaacgtt ttcctgaaga tttagcacag caaaacttaa ttatatcaaa cacagaagca    2280
cctggagacg atagagtgtg ctctgccaat ggatttatga cccaaactac caacaactct    2340
agccaaggtt tttgtggtac tatgggatca ggaatgaaaa atggagggca ggaaaccatt    2400
gaaatgatga aaggaggaaa ccagaccttg gaatcctgcc gggggctgg gcatcatcat    2460 accctggact cctgcagggg aggacacacg gaggtggaca actgcagata cacttactcg    2520
gagtggcaca gttttactca accccgtctc ggtgaagaat ccattagagg acacactggt    2580
taaaaattaa acataaaaga aattgcatcg atgtaatcag aatgaagacc gcatgccatc    2640
ccaagattat gtcctcactt ataactatga gggaagagga tctccagctg ttctgtggg    2700 ctgctgcagt gaaaagcagg aagaagatgg ccttgacttt ttaaataatt tggaacccaa    2760
atttattaca ttagcagaag catgcacaaa gagataatgt cacagtgcta caattaggtc    2820
tttgtcagac attctggagg tttccaaaaa taatattgta aagttcaatt tcaacatgta    2880
tgtatatgat gattttttttc tcaatttga attatgctac tcaccaattt atattttttaa    2940 agccagttgt tgcttatctt ttccaaaaag tgaaaaatgt taaaacagac aactggtaaa    3000
tctcaaactc cagcactgga attaaggtct ctaaagcatc tgctcttttt ttttttttacg    3060 gatatttag taataaatat gctggataaa tattagtcca acaatagcta agttatgcta    3120
atatcacatt attatgtatt cactttaagt gatagtttaa aaaataaaca agaaatattg    3180
agtatcacta tgtgaagaaa gttttggaaa agaaacaatg aagactgaat taaattaaaa    3240
atgttgcagc tcataaagaa ttgggactca ccctactgc actaccaaat tcatttgact    3300
ttggaggcaa aatgtgttga agtgcccttat gaagtagcaa ttttctatag gaatatagtt    3360
ggaaataaat gtgtgtgtgt atattattat taatcaatgc aatatttaaa atgaaatgag    3420
aacaaagagg aaaatggtaa aaacttgaaa tgaggctggg gtatagtttg tcctacaata    3480
gaaaaaagag agagcttcct aggcctgggc tcttaaatgc tgcattataa ctgagtctat    3540
gaggaaatag ttcctgtcca atttgtgtaa tttgtttaaa attgtaaata aattaaactt    3600
ttctggtttc tgtgggaagg aaatagggaa tccaatggaa cagtagcttt gctttgcagt    3660
ctgtttcaag atttctgcat ccacaagtta gtagcaaact ggggaatact cgctgcagct    3720
ggggttccct gcttttttggt agcaagggtc cagagatgag gtgttttttt cggggagcta    3780
ataacaaaaa catttttaaaa cttacctttta ctgaagttaa atcctctatt gctgtttcta    3840
ttctctctta tagtgaccaa catctttta atttagatcc aaataaccat gtcctcctag    3900
agtttagagg ctagggggag ctgaggggag gatcttactg aaagcacccct ggggagattg    3960 attgtccttaa aacctaagcc ccacaaactt gacacctgat caggtctggg agctacaaaa    4020 tttcatttttt ctcctcactg cccttcttct gagtggcatt ggcctgaatc aaggaaagcc    4080
aggccttgtg ggccccctttc tttcggcttt ctgctaaagc aacacctcca gcagagattc    4140
ccttaagtga ctccaggttt tccaccatcc ttcagcgtga attaatttttt aatcagtttg    4200 ctttctccag agaaatttta aaataataga agaaatagaa attttgaatg tataaaagaa    4260
aaagatcaag ttgtcatttt agaacagagg gaactttggg agaaagcagc ccaagtaggt    4320
tatttgtaca gtcagagggc aacaggaaga tgcaggcctt caaggcaag agagggccac    4380 aaggaatatg ggtgggagta aaagcaacat cgtctgcttc atacttttttc ctaggcttgg    4440 cactgccttt tcctttctca ggccaatggc aactgccatt tgagtccggt gagggatcag    4500
```

```
ccaacctctt ctctatggct caccttattt ggagtgagaa atcaaggaga cagagctgac    4560
tgcatgatga gtctgaaggc atttgcagga tgagcctgaa ctggttgtgc agaacaaaca    4620
aggcattcat gggaattgtt gtattccttc tgcagccctc cttctgggca ctaagaaggt    4680
ctatgaatta aatgcctatc taaaattctg atttattcct acattttctg ttttctaatt    4740
tgaccctaaa atctatgtgt tttagactta gactttttat tgccccccccc ccctttttttt    4800 ttgagacgga gtctcgctct gacgcacagg ctggagtgca gtggctccga tctctgctca    4860
ctgaaagctc cgcctcccgg gttcatgcca ttctcctgcc tcagcctcct gagtagctgg    4920
gactacaggc gcccaccacc acgcccggct aattttttgt attttttaata gagacggggt    4980 ttcactgtgt tagccaggat ggtctcgatc tcctgacctc gtgatccgcc tgcctcggcc    5040
tcccaaagtg ctgggattac aggcatgacc caccgctccc ggccttgttt ccgtttaaa     5100 gtcgtcttct tttaatgtaa tcattttgaa catgtgtgaa agttgatcat acgaattgga    5160
tcaatcttga aatactcaac caaaagacag tcgagaagcc aggggagaa agaactcagg     5220 gcacaaaata ttggtctgag aatggaattc tctgtaagcc tagttgctga aatttcctgc    5280
tgtaaccaga agccagtttt atctaacggc tactgaaaca cccactgtgt tttgctcact    5340
cccactcacc gatcaaaacc tgctacctcc ccaagacttt actagtgccg ataaactttc    5400
tcaaagagca accagtatca cttcccgtt tataaaacct ctaaccatct ctttgttctt      5460
tgaacatgct gaaaaccacc tggtctgcat gtatgcccga atttgtaatt cttttctctc    5520
aaatgaaaat ttaattttag ggattcattt ctatattttc acatatgtag tattattatt    5580
tccttatatg tgtaaggtga aatttatggt atttgagtgt gcaagaaaat atattttttaa   5640 agctttcatt tttcccccag tgaatgattt agaattttt atgtaaatat acagaatgtt     5700
ttttcttact tttataagga agcagctgtc taaaatgcag tggggtttgt tttgcaatgt    5760
tttaaacaga gttttagtat tgctattaaa agaagttact ttgcttttaa agaaacttgg    5820
ctgcttaaaa taagcaaaaa ttggatgcat aaagtaatat ttacagatgt ggggagatgt    5880
aataaaacaa tattaacttg gaaaaaaaaa aaaaaaaaa                           5920
```

<210> SEQ ID NO 186
<211> LENGTH: 696
<212> TYPE: DNA
<213> ORGANISM: Homo sapiens
<220> FEATURE:
<221> NAME/KEY: misc_feature
<222> LOCATION: (8)..(8)
<223> OTHER INFORMATION: a or g or c or t/u

<400> SEQUENCE: 186

```
gactcagnct tcagccgctc tcctccccct gggcaaacag gactcatctg atgatgtgag      60
aagagttcag aggagggaga aaaatcgtat tgccgcccag aagagccgac agaggcagac    120
acagaaggcc gacaccctgc acctggagag cgaagacctg gagaaacaga acgcggctct    180
acgcaaggag atcaagcagc tcacagagga actgaagtac ttcacgtcgg tgctgaacag    240
ccacagcccc ctgtgctcgg tgctggccgc cagcacgccc tcgccccccg aggtggtgta    300
cagcgcccac gcattccacc aacctcatgt cagctccccg cgcttccagc cctgagcttc    360
cgatgcgggg agagcagagc ctcgggaggg gcacacagac tgtggcagag ctgcgcccat    420
cccgcagagg cccctgtcca cctggagacc cggagacaga ggcctggaca aggagtgaac    480
acgggaactg tcacgactgg aagggcgtga ggcctcccag cagtgccgca gcgtttcgag    540
```

| gggcgtgtgc tggaccccac cactgtgggt tgcaggccca atgcagaaga gtattaagaa | 600 |
| agatgctcaa gtcccatggc acagagcaag gcgggcaggg aacggttatt tttctaaata | 660 |
| aatgctttaa aagaaaaaaa aaaaaaaaaa aaaaaa | 696 |

<210> SEQ ID NO 187
<211> LENGTH: 586
<212> TYPE: DNA
<213> ORGANISM: Homo sapiens
<220> FEATURE:
<221> NAME/KEY: misc_feature
<222> LOCATION: (9)..(10)
<223> OTHER INFORMATION: a or g or c or t/u
<220> FEATURE:
<221> NAME/KEY: misc_feature
<222> LOCATION: (31)..(31)
<223> OTHER INFORMATION: a or g or c or t/u
<220> FEATURE:
<221> NAME/KEY: misc_feature
<222> LOCATION: (44)..(45)
<223> OTHER INFORMATION: a or g or c or t/u
<220> FEATURE:
<221> NAME/KEY: misc_feature
<222> LOCATION: (116)..(116)
<223> OTHER INFORMATION: a or g or c or t/u
<220> FEATURE:
<221> NAME/KEY: misc_feature
<222> LOCATION: (130)..(130)
<223> OTHER INFORMATION: a or g or c or t/u

<400> SEQUENCE: 187

| atgcaaggnn taggcaaaga ttgttgaccc nggagataga ggtnncaatg agccagatca | 60 |
| ttccattgca ttccagcttg ggcgacagaa tgagactctg tctcaaaatt aaaaancaaa | 120 |
| aaaccaaaan caaatagatg aaaaagtaga ctggagacaa ataaaagtga gtttctaaag | 180 |
| gaaattcaca gtaatgctgc attaaacact aagctcactt aggtcacttt ctagtgagct | 240 |
| aaccgtaaca gagagcctac aggatacacg tgagataatg tcacgtgtag aagatcgttg | 300 |
| tgaattaaag ttcaaaatta agacttctta gattatgatg tagattttag agctccttaa | 360 |
| aacataaagc gaatcttata aatgttcaat tctaaagtta ttccacttgg aaaaattagc | 420 |
| ttttgggaca attttttaaga acttttgtgt aaaatgcagc tccatgttta gcataatcta | 480 |
| aaaataattt caagcaatcc agaatcttcc aagaatgtta ttaaagcttt aaaacaaagc | 540 |
| aaaacaaaaa gacccttttg tgccttatat gggaagacta aaaaaa | 586 |

<210> SEQ ID NO 188
<211> LENGTH: 1359
<212> TYPE: DNA
<213> ORGANISM: Homo sapiens

<400> SEQUENCE: 188

| accgggcacc ggacggctcg ggtactttcg ttcttaatta ggtcatgccc gtgtgagcca | 60 |
| ggaaagggct gtgtttatgg gaagccagta acactgtggc ctactatctc ttccgtggtg | 120 |
| ccatctacat ttttgggact cgggaattat gaggtagagg tggaggcgga gccggatgtc | 180 |
| agaggtcctg aaatagtcac catggggaa atgatccgc ctgctgttga agcccccttc | 240 |
| tcattccgat cgcttttttgg ccttgatgat ttgaaaataa gtcctgttgc accagatgca | 300 |
| gatgctgttg ctgcacagat cctgtcactg ctgccattga agttttttcc aatcatcgtc | 360 |
| attgggatca ttgcattgat attagcactg gccattggtc tgggcatcca cttcgactgc | 420 |
| tcagggaagt acagatgtcg ctcatccttt aagtgtatcg agctgatagc tcgatgtgac | 480 |
| ggagtctcgg attgcaaaga cggggaggac gagtaccgct gtgtccgggt gggtggtcag | 540 |

```
aatgccgtgc tccaggtgtt cacagctgct tcgtggaaga ccatgtgctc cgatgactgg      600
aagggtcact acgcaaatgt tgcctgtgcc caactgggtt tcccaagcta tgtgagttca      660
gataacctca gagtgagctc gctggagggg cagttccggg aggagtttgt gtccatcgat      720
cacctcttgc cagatgacaa ggtgactgca ttacaccact cagtatatgt gagggaggga      780
tgtgcctctg ccacgtggt taccttgcag tgcacagcct gtggtcatag aagggctac       840 agctcacgca tcgtgggtgg aaacatgtcc ttgctctcgc agtggccctg gcaggccagc      900
cttcagttcc agggctacca cctgtgcggg ggctctgtca tcacgcccct gtggatcatc      960
actgctgcac actgtgttta tgacttgtac ctccccaagt catggaccat ccaggtgggg     1020
ctagtttccc tgttggacaa tccagcccca tcccacttgg tggagaagat tgtctaccac     1080
agcaagtaca agccaaagag gctgggcaat gacatcgccc ttatgaagct ggccgggcca     1140
ctcacgttca atggtacatc tgggtctcta tgtggttctg cagctcttcc tttgtttcaa     1200
gaggatttgc aattgctcat tgaagcattc ttatgatggc tgctttataa tccttgtcag     1260
atattaataa ttccaactcc tgattcatgt tggtgttggc atcagttgat tatctttttct    1320 cattaaaatt gtgatgctcc taaaaaaaaa aaaaaaaaa                           1359

<210> SEQ ID NO 189
<211> LENGTH: 2711
<212> TYPE: DNA
<213> ORGANISM: Homo sapiens

<400> SEQUENCE: 189
ttcagaagga ggagagacac cgggcccagg gcaccctcgc gggcgggcgg acccaagcag       60
tgagggcctg cagccggccg gccagggcag cggcaggcgc ggcccggacc tacgggagga      120
agccccgagc cctcggcggg ctgcgagcga ctccccggcg atgcctcaca actccatcag      180
atctggccat ggagggctga accagctggg aggggccttt gtgaatgcca gacctctgcc      240
ggaagtggtc cgccagcgca tcgtagacct ggcccaccag ggtgtaaggc cctgcgacat      300
ctctcgccag ctccgcgtca gccatggctg cgtcagcaag atccttggca ggtactacga      360
gactggcagc atccggcctg gagtgatagg gggctccaag cccaaggtgg ccacccccaa      420
ggtggtggag aagattgggg actacaaacg ccagaaccct accatgtttg cctgggagat      480
ccgagaccgg ctcctggctg agggcgtctg tgacaatgac actgtgccca gtgtcagctc      540
cattaataga atcatccgga ccaaagtgca gcaaccattc aacctcccta tggacagctg      600
cgtggccacc aagtccctga gtcccggaca cacgctgatc cccagctcag ctgtaactcc      660
cccggagtca ccccagtcgg attccctggg ctccacctac tccatcaatg ggctcctggg      720
catcgctcag cctggcagcg acaagaggaa aatggatgac agtgatcagg atagctgccg      780
actaagcatt gactcacaga gcagcagcag cggaccccga aagcaccttc gcacggatgc      840
cttcagccag caccacctcg agccgctcga gtgcccattt gagcggcagc actacccaga      900
ggcctatgcc tcccccagcc acaccaaagg cgagcagggc ctctacccgc tgcccttgct      960
caacagcacc ctggacgacg ggaaggccac cctgaccccct tccaacacgc cactggggcg     1020
caacctctcg actcaccaga cctaccccgt ggtggcagat cctcactcac ccttggccat     1080
aaagcaggaa accccgagg tgtccagttc tagctccacc ccttgctctt tatctagctc     1140 cgccttttg gatctgcagc aagtcggctc cgggtccccg cccttcaatg cctttccccca    1200 tgctgcctcc gtgtacgggc agttcacggg ccaggccctc ctctcagggc gagagatggt    1260
```

```
ggggcccacg ctgcccggat acccacccca catccccacc agcggacagg gcagctatgc    1320
ctcctctgcc atcgcaggca tggtggcagg aagtgaatac tctggcaatg cctatggcca    1380
caccccctac tcctcctaca gcgaggcctg gggcttcccc aactccagct tgctgagttc    1440
cccatattat tacagttcca catcaaggcc gagtgcaccg cccaccactg ccacggcctt    1500
tgaccatctg tagttgccat ggggacagtg ggagcgactg agcaacagga ggactcagcc    1560
tgggacaggc cccagagagt cacacaaagg aatctttatt attacatgaa aaataaccac    1620
aagtccagca ttgcggcaca ctccctgtgt ggttaattta atgaaccatg aaagacagga    1680
tgaccttgga caaggccaaa ctgtcctcca agactcctta atgaggggca ggagtcccag    1740
ggaaagagaa ccatgccatg ctgaaaaaga caaaattgaa gaagaaatgt agccccagcc    1800
ggtaccctcc aaaggagaga agaagcaata gccgaggaac ttgggggggat ggcgaatggt    1860
tcctgcccgg gcccaagggt gcacagggca cctccatggc tccattatta acacaactct    1920
agcaattatg gaccataagc acttccctcc agcccacaag tcacagcctg gtgccgaggc    1980
tctgctcacc agccacccag ggagtcacct ccctcagcct cccgcctgcc ccacacggag    2040
gctctggctg tcctctttcc tccactccat ttgcttggct ctttctacac ctccctcttg    2100
gatgggctga gggctggagc gagtccctca gaaattccac caggctgtca gctgacctct    2160
ttttcctgct gctgtgaagg tatagcacca cccaggtcct cctgcagtgc ggcatcccct    2220
tggcagctgc cgtcagccag gccagcccca gggagcttaa aacagacatt ccacagggcc    2280
tgggcccctg ggaggtgagg tgtggtgtgc ggcttcaccc agggcagaac aaggcagaat    2340
cgcaggaaac ccgcttcccc ttcctgacag ctcctgccaa gccaaatgtg cttcctgcag    2400
ctcacgccca ccagctactg aagggaccca aggcaccccc tgaagccagc gatagagggt    2460
ccctctctgc tccccagcag ctcctgcccc caaggcctga ctgtatatac tgtaaatgaa    2520
actttgtttg ggtcaagctt ccttcttttct aaccccccaga cttttggcctc tgagtgaaat    2580
gtctctcttt gccctgtggg gcttctctcc ttgatgcttc tttcttttttt taaagacaac    2640
ctgccattac cacatgactc aataaaccat tgctcttcaa aaaaaaaaaa aaaaaaaaa    2700
aaaaaaaaaa a                                                         2711

<210> SEQ ID NO 190
<211> LENGTH: 3323
<212> TYPE: DNA
<213> ORGANISM: Homo sapiens

<400> SEQUENCE: 190
tgcttcataa aatttaccta agcaagtggt cttgcttgcc tcaaatccaa gcagtcttga     60
acacttggag gcaattaatg agtatatctt agtcaaaaga attgttggag cttttttatta    120
aagctgcagt ttcagttctg cttttgggga attgtgctat gaaagcagct gccaaaataa    180
gctcatttat tttcttcaat cccactcagt gctcagtcac tatattctgt ttccttttt     240
tttttcaagt tgcatatttg gtttcccctt atgattggga aagatgaatt ttcagcagaa    300
aacagtgttt gttcactttc aaagagtgat agtttctaaa acatttagag caataaatat    360
tcatcagagg taccaagtaa gccagcagaa gagttaaggg ttagagaaat cccttatttc    420
atgtcttgac tctaaaatga tcaaagtact tttccttgta atgtggatt cttcttatgc      480
ggatatgcaa aaacttcagt tatacgtagt aatgctagca ggtaatttta gtggacattt    540
tataacaact gtcactttgt tttgccacat gtagagtttg ttcagctatt ttccagatat    600
ctcccacaa aaggaggcaa agggtaccag ctttcaatg agcattacct attacttggc       660
```

```
aaagatgatg aagactctat taatagttca tttgataaat gttgacataa ccaacaatag      720
agattaggaa gttagtttta agaaatcaat agcatataga cattaccctc atggagtttg      780
tattctacta cttgaactga ttgtagctat aaaagcatag ttagatagct gaatagttag      840
atcataagca aagaaggcca gaacacatct cttatcaaga aatcaatgaa tagtttatct      900 cattttaaa gcaactttat ccttctttaa ttccttcctt tcttctagtg caaaactact       960
taataaggtt ggtgtttagg ttagtgttca caccattcct catctggtgt gaattacctt     1020
ctctttcttt actatttact accaacctag tacatgtgtt gactgaattc ttttcaaaca     1080
atgttgagtt atcatggtgc acctaataaa ttaacaccac agattacagc atccttgctg     1140
attttctcag caaagccaga ttagatggaa ataaacaaag aaaatgatcc tagagtgaat     1200
ttttctagaa aatatctatt atgaaccatg ctgtttaaag tattagcttg aaggtgatgg     1260
atccagctat tcagaaaata actttcatat aaccatgatt ttgcacagta tgaggtctta     1320
aatgtgtgga aagagataaa ttttttatca ttaccacaaa cccctttta agattcaaag      1380 gtggaagaaa gtgatttatt ttttctcttc agcatacata tataaaagac ttgtcagatg     1440
tttaatttgg ggaggttgat aatgaaacat atcaacagag tatagtagtt atagtagtgt     1500
ttgtgggtaa ataatttcct ggggtcagac atatataaac atatttgctt caaaatgata     1560
aaggcatgaa atcagtctta aaaattgaaa tgggggtgat gggggagaaa aagaagaaca     1620
aatttgaagt gcccttcaa atctgctgga tacaagtatt gaagttttaa gtcatcttat      1680
tctgtctgaa agtgtatttt tcattctaca atagacccaa tcaacaagac gtataacttg     1740
agttgcatga tgttcagttt atgtaatcta ctgttgggat ggtaagaatt gatgtaggct     1800
gtggtgtaag aatgaattaa aatatagttt cactggcttt tctctacata tccactatca     1860
caatggctag gtttcctgtt gctcactgtt ggattctgga gaaaaattta atgaaagatg     1920
atatcagagg aagaataagt ggaggtagag aagaaaggag tgatagagga ggggaaaaaa     1980
acaaaacata ttttgtgtt atccaaagga gcttttcct tattctgtca agcattgaga       2040
tcttcttcag ctttcaatgt agttgctaaa tacaaataat gctactaggt agtgactaaa     2100
tatagcaaac acttcatcag atattagaat taggtcacac tattgaggtt ataatctgaa     2160
ggttgtgtta catagaaacc actttagatt attatcaact tgggctaggc tttattttat     2220
aatagcatag taagtaatat ctattgtgtc atttcttcaa ccattttatt ctaagatcca     2280
tgaagcttct tgaggccaaa taaaataata agtttagaca agaagtagat tgtgacttt      2340 tttcccttag agatactatt tactatctcc tatcctgata ggtggaaggt ttactgaatt     2400
ggaaattggt tgactattag ttttaacta aatgtgcaa taacacattg cagtttcctc       2460
aaactagttt cctatgatca ttaaactcat tctcagggtt aagaaggaa tgtaaatttc      2520 tgcctcaatt tgtacttcat caataagttt ttgaagagtg cagatttta gtcaggtctt      2580 aaaaataaac tcacaaatct ggatgcattt ctaaattctg caaatgtttc ctggggtgac     2640
ttaacaagga ataatcccac aatataccta gctacctaat acatggagct ggggctcaac     2700
ccactgtttt taaggatttg cgcttacttg tggctgagga aaaataagta gttcgaggaa     2760
gtagttttta aatgtgagct tatagataga aacagaatat caacttaatt atgaaattgt     2820
tagaacctgt tctcttgtat ctgaatctga ttgcaattac tattgtactg atagactcca     2880
gccattgcaa gtctcagata tcttagctgt gtagtgattc ttgaaattct ttttaagaaa     2940
aattgagtag aaagaaataa acccttgta aatgaggctt ggcttttgtg aaagatcatc     3000
```

```
cgcaggctat gttaaaagga ttttagctca ctaaaagtgt aataatggaa atgtggaaaa      3060
tatcgtaggt aaaggaaact acctcatgct ctgaaggttt tgtagaagca caattaaaca      3120
tctaaaatgg ctttgttaca ccagagccat ctggtgtgaa gaactctata tttgtatgtt      3180
gagagggcat ggaataattg tattttgctg gcaatagaca cattctttat tatttgcaga      3240
ttcctcatca aatctgtaat tatgcacagt ttctgttatc aataaaacaa aagaatcctg      3300
ttaaaaaaaa aaaaaaaaaa aaa                                             3323

<210> SEQ ID NO 191
<211> LENGTH: 671
<212> TYPE: DNA
<213> ORGANISM: Homo sapiens
<220> FEATURE:
<221> NAME/KEY: misc_feature
<222> LOCATION: (21)..(21)
<223> OTHER INFORMATION: a or g or c or t/u
<220> FEATURE:
<221> NAME/KEY: misc_feature
<222> LOCATION: (49)..(49)
<223> OTHER INFORMATION: a or g or c or t/u

<400> SEQUENCE: 191
tggctctctc cttcaaaagg nccaggccct gtcccccttt ctccccgant ccaaccccag        60
ctcccctgtg aagaaaaaag ttaaaaaatt tgttatttat ttgcttttg cgttgggatg       120 ggttcgtgtc cagtcccggg ggtctgatat ggccatcaca ggctgggtgt cccagcagc       180 cctggcttgg gggcttgacg cccttcccct tgcccaggc catcatctcc ccacctctcc       240
tcccctctcc tcagttttgc cgactgcttt tcatctgagt caccatttac tccaagcatg       300
tattccagac ttgtcactga ctttccttct ggagcaggtg gctagaaaaa gaggctgtgg       360
gcaggaaaga aaggctcctg tttctcattt gtgaggccag cctctggctt ttctgccgtg       420
gattctcccc ctgtcttctc ccctcagcaa ttcctgcaaa gggttaaaaa tttaactggt       480
ttttactact gatgacttga tttaaaaaaa atacaaagat gctggatgct aacttgatac       540
taaccatcag attgtacagt ttggttgttg ctgtaaatat ggtagcgttt tgttgttgtt       600
gttttttcat gccccatact actgaataaa ctagttctgt gcgggtaaaa aaaaaaaaa       660 aaaaaaaaaa a                                                            671

<210> SEQ ID NO 192
<211> LENGTH: 3485
<212> TYPE: DNA
<213> ORGANISM: Homo sapiens

<400> SEQUENCE: 192
cacaaagaaa aagaaatac ctgtagaagc gcatcgaaag ctcctggaac agagttgtgt        60
ctcatatttg caaagatgca gaaaaaataa acccgggaca tccagctttc ttttccttc       120 ttctttgact attctgagaa gctatgcgac taggagcaca ttttaggtaa acacgtggct       180
tgagtagcca taaggccact cttccctgtc gtgtgacccg cgcctgggcc tttaagagat       240
attggtgttt gaaaagggag gaatctgttt gccctcagat atttagttca actgcctgca       300
ttgcttccta ttttgttgtc caactctgta gtagttagca ctggcttac caacatgtaa       360 agaaattttc tttactgccc catgagtagt tggaggcaaa gagaaatttt taaagcgcag       420
aaaaaggcct gcagggagat ggaatttgtt ctgccagaga aacgagatga tagctgtatt       480
taataaagtt actgacctct tgtcaaaatt taaaacgcaa aagaagatgt ttcaaaatgc       540
agagaatgtc agaaaacaaa aactacaggg accagaccag tataatgttt agttttcatt       600
```

```
atactaactt ttgtctagac tggagttgat tcactatttt ttctttaact cctcaggaag    660
caaaccttcc cgatgatgaa gacttcttga aggatttcat gggtgatttg ggatcccagg    720
accatttggc tagtgtgcct aggtgaccac atgattgctg ttttaccagg aatgcagcat    780
cccattgaca aaacaagtgc tctgagaagg tttaaaatac tacagagaat atgggaacac    840
agaccttgaa atttagctga gttgtaacag ctgaaactcc aagaggtgtc ttccttgttt    900
gaggtgaaac tagtgttgct tccagagggc agctggaaac cgtaaagctg tttggaaatc    960
tttttgactg acttgctgac aaagaggtac tgtgatgcat tttaacaata tctaagttga   1020
ttttttttta aatcaaggaa aataaaaacc aagcatgaat gctatggtat gtgcccettt   1080
tgaccatcct gggctgatta acatcattta aatcaaagta atcataaaaa ggcatattct   1140
acttcaatta tgtggtcaaa taagagtaaa cacacacact cacacatgct gaccccaatt   1200
gccagagcat tactgcacta taaattacgg ttaattccca aattatacta ctgtttatct   1260
tatttaacaa gtcagaaagc acttttaaaa taacttgagg gctacaaggt cattctatta   1320
atgtcattct ccattcgggt tgtaggcatg tggaagtacc cattaaaaga taagttagag   1380
tttaaatact gataaacaaa acctttatt gcaactggac agtttctgga gagttagcgg    1440
aagaatcttg gagtttcctt tggtcagatg aatacaacat ttcacttttg cagcactatt   1500
tagaatgtac tccatggttc tcttgttccc aacttccaaa aagaacagaa actttggtt    1560
tacacagaac acgggcatct gaggcaggac ctcttccctg cccttgatc tgactcacac    1620
ctccacatat gacgtaatca acccaaattt gacaccaatt cactctttc tgcaaagggc    1680
atattttgaa acaagggaca gcctgagggc ggctataatg agaatgttca tgggggttac   1740
tgggtcccta attctgaact tgcttatgac acccagagtg aatagattca gattcagaac   1800
cttctgagaa ataacccaaa gaaaatttgt tacccagcca attcttcgaa agcttaatat   1860
caaaatatat ctttttcaaga agaaaatcgt tagagagaag aatgtggagg ggagagaaat   1920
gggtttctca ttgatatgat attttgttaa ccatttcatt ttgaattatt caagttttgg   1980
ttaatattgt attctttttt cgtaactatt ttaccgtgag agtaggtcat tgggttactt   2040
agatatttat ttttacacag ttattagtct tcagatagtt ttattttact tcatatgatt   2100
ttagttttg tcagtataat tttaaatcat gttttttcttg gtcatctctt tgtgtatatt   2160
gtgtaattgg attttcattg actgcaagtg gagtgtttgc cactcaattc agtactcagt   2220
actatggtga cttgttttca aataagtctc agatacacat ttagggagcc tttgctggcc   2280
gaatatagac tctgtcagga cagcaggtcc cctgatctaa gaattttccc caatggttgc   2340
tctaaaaatg ctgctatttt gctgttcact gtattgcact tagttaaaaa gaagataatg   2400
tgaaagatga gagcagtttt ttaaaggatc ttttcatata cccaattccc ttattttcag   2460
atgtcccatc aatttttagat atgaaagctt taagtaaaag tgtgtatgcc tttctactgt   2520
cagaacagga tggatgcagc ctgggtcaga tttatttaag ataaaaatca tgcagactca   2580
tcattcatat cataggtgaa aaatgtaaaa accaaatggt ttccactaaa gccaccaaga   2640
tcttttagaa atgttttgcac ctttggtggt ggcacaggaa aagagaagaa ttcagctgga   2700
gtgaattcta gaagtagata tcagaaacgg ggcatgaaga acaggggaac tgggtggcat   2760
cagactccta aagaagtgag ttaatttttcc ttcccttcca ttcagattca tgccacagct   2820
ccatatcttg agtatgtgta agaggtgagt tccttcttca gccaggggcg gtggctcatg   2880
cctttaatcc caatgctttg ggaggccaag gtgggaggat cacttgtgcc ttggggttca   2940
```

```
aggttgcagt gaaccatgat tgcaccactg cactccagcc tgagtgacag agcaagaccc    3000
tgtctctaaa aatatatata aaaagtaaaa ctaaagaact tcttgcctaa acctgaatta    3060
ccgcaatttg ctgagtgact ttgagaaaaa tcagactgtt tagttcagtc gggatgaaaa    3120
gcttgcgatt gcttcccaca agaatgggca atagtgacgg ctgcaaggta cttttatttg    3180
ttcatgaaag aacgacaatt tttcaaaatg taattaaaca taatagaatg ttttaaacta    3240
ctgggcactg aaactggaag aaaaaggagg ctttattgaa cattcccctt tttcagttgg    3300
ttcaaagttc agcactgtgg ttatcattgg tgatgccaga aaacattagt agacttagac    3360
aattgctatg gcagtttcta aacagagctt tttctataca ctatttgcaa ctggagtgca    3420
atattgtata ttctgtgtta aagaaataaa gtatttttat catttattaa aaaaaaaaa     3480 aaaaa                                                                3485

<210> SEQ ID NO 193
<211> LENGTH: 1915
<212> TYPE: DNA
<213> ORGANISM: Homo sapiens

<400> SEQUENCE: 193
ccatccagaa cgatgaggcc gtggccccgc tcatgaagta cctggatgag aagctggccc      60
tgctgaacgc ctcgctggtg aaggggaacc tgagcagggt gctggaggcc ctgtgggagc     120
tactcctcca ggccattctg caggcgctgg gtgcaaaccg tgacgtctct gctgatttct     180
acagccgctt ccatttcacg ctggaggccc tggtcagttt tttccacgca gagggtcagg     240
gtttgccccT ggagagcctg agggatggaa gctacaagag gctgaaggag gagctgcggc     300
tgcacaaatg ttccacccgc gagtgcatcg agcagttcta cctggacaag ctcaaacaga     360
ggaccctgga gcagaaccgg tttggacgcc tgagcgtccg ttgccattac gaggcggctg     420
agcagcggct ggccgtggag gtgctgcacg ccgcggacct gctccccctg gatgccaacg     480
gcttaagtga cccctttgtg attgtggagc tgggcccacc gcatctcttt ccactggtcc     540
gcagccagag gacccaggtg aagacccgga cgctgcaccc tgtatacgac gaactcttct     600
acttttccgt gcctgccgag gcgtgccgcc gccgcgcggc ctgtgtgttg ttcaccgtca     660
tggaccacga ctggctgtcc accaacgact tcgctgggga ggcggccctc ggcctaggtg     720
gcgtcactgg tgtcgcccgg cccaggtgg gcggggtgc aagggctggg cagcctgtca      780
ccctgcacct gtgccggccc agagcccagg tgagatctgc gctgaggagg ctggaaggcc     840
gcaccagcaa ggaggcgcag gagttcgtga agaaactcaa ggagctggag aagtgcatgg     900
aggcggaccc ctgagtccat cagctgccag ccccggccct ggcccccacc ccaagttccc     960
tgaagcatcc tccagctcac tgtggccagc tttgtgcaac cagggcccac ggcgcccctc    1020
ctgtgctgtg acgtgtgtgt cgtggctggc cccgcggcgc ctaccgccct ggccgtgtct    1080
gtctggtgtg tgctgtgaac ccctgcaccc aaccccacat ctgggtggcc aacttggcag    1140
gacttggcca gcagctgccc aggacacagt gcaggccaga gcgggcttga ccacctggtg    1200
ggcctccctg cccgcttcct tgggctcccc ggccctgggt gggcggtgcg cagctggtct    1260
ccagggactc agtgagtggc tgtgctctct gcacaacggg caatgtgcag acgcatttt     1320 ggtaatcaca gctggggagt gaaaagggtg ccactggcac cactgggtgg atggtccaga    1380
gcctccaccc acagagggga tgcaaagggc aggtgagtca agaaccgcat aggtctccag    1440
tccccacggg gctcccaggc cggggaaagg ttccctgag gtcactctga ggccagggac     1500
gtcacccaag gctggtggtc agtgtgaagg gctccgtgcc aactggtcag ctgtccttca    1560
```

```
cgcacatatc cgtggccacc tgagacctgc tccacgaccc ttccaggcag agccgagagt    1620
tcgccccaac ccttccccag gcccagtgtg aaaaacagac tcacaagggg cttcttggcc    1680
tgcagcttca tttgcgagag cgccgaggca ggacacagag cacagctgtg ctggaagtgt    1740
ggggagaacc cggacagctc agtcctgcca gcagccgcaa agagccgagg ctgccaggcc    1800
catttatgtc cctcatgtct ctagattttc tcgtcaccca gcctcaaaaa tatatgtgtc    1860
tgcaaccctc aaaaaaaaaa aaaaaaaaaa aaaaaaaaaa aaaaaaaaaa aaaaa         1915

<210> SEQ ID NO 194
<211> LENGTH: 2681
<212> TYPE: DNA
<213> ORGANISM: Homo sapiens

<400> SEQUENCE: 194 ggggggggctc cgtgacagcc aacgcagtga ccctcgcccc ttccttggca gcacatcatg    60
cttgtgcagc ggcagatgtc tgtgatggaa gaggacctgg aagaattcca gctcgctctg   120
aaacactacg tggagagtgc ttcctcccaa agtggatgct gcgtatttc tatacagaag     180 cttcaaatg aatctcgcta catgatctat gagttctggg agaatagtag tgtatggaat     240
agccaccttc agacaaatta tagcaagaca ttccaaagaa gtaatgtgga tttcttggaa    300
actccagaac tcacatctac aatgctagtt cctgcttcgt ggtggatcct gaacaactag    360
atgttcctag acattttctt tatggttcca agtgcaaaac aggtgttctt atctaaaacg    420
tcaattagaa aattatctgc ggttgttaat ctactgtata tttttgtttg gtatatttac    480
taagtgcact ctttcaaaac ttattctata actttatcaa ttcatgtgaa ttttagctca    540
attttcaaag ttcactaata ttctcaatat ttaatgctaa atgctttgct acattgtaac    600
tcacctaaaa ccttttagtg acaaaatcct aatatgtgga aaaagcata tgcataaagg     660 aataatattg tgaaaatgaa tctgttatga taaagaaaaa ataagtggaa actttttaga    720
gtattacttc atagggcaga ttttgtaaac tgtcgtatac tgtaaagggt taaatcagcg    780
ttttgtgatt tttaagtaac tgtgagtgaa gtttattctt caacaatgtc tactccatcc    840
ccaacccaac tcacagccct atgactacta tctttgcatt agttaaaaag ttagtatata    900
ggcatcaaac aaccttggct gtaacctata gaatctctat ccatgtatca ggttatagac    960 tggttttca aaagtgaaca atcctgtgat aagttggagt accatttagt aatacagcaa    1020
cattgtgtca tttattagca tcataattct ttgttatgta agttaaatat atcaagaaag    1080
aagagactgt ttggaaaaat gtggttcaag ttttatgcta tatagttttg gtatgcgata    1140
cagacagcta acttttctta tgaaaaatac atatttgcat gtaaacaatg atttcaaaat    1200
acttgaaaaa taaatttta acccaaatga ataactaaga aatataaaac aagcacaaaa     1260
tcttagggaa gtcataaaat agtagtgaaa gtattagaca gaagacatct gttttcgaat    1320
ttcaacacta gaatgactaa aactatctac ctatagaact atctgtagat agtatactat    1380
ctacactctg ctcaacaagc tcagaaatta aatattttta gtaataaaaa tctgttctgg    1440
ttataaacct tgctaatgaa aatacaaatac atataaaaat gtatagccat gttattttct    1500
agtataaatt cctttgaaac tataagtctt tgaggaaaat tataaggtaa attttcctg     1560 tttttccccc tttgaaaaac tcaggaaaaa aggaagattg aactaataaa attttatttc    1620
ttaaatataa atttgaccta aaatattttc tcaaactaat tcatgaaaca gcaacttta    1680 ccaataccttt tgtatactct cagttctcat tcagtataaa taaaatttta aaatcctttc   1740
```

```
atagttctat tagaaataag tagtaaattt tgatatattg tacatacaca cgtgtgtgtg    1800
tgtgtgtgtg tgtgtgtgta tttgtgtgcc tctggtcaac tctaaggatg acagacactg    1860
tgtaacaaca cctgggtcaa ctcttttaat ttatatacaa agcaaagaac aacattaatg    1920
gagatgcaca atgattattc aaacaagcta tatatatgta caaaggcaaa cagacacata    1980
acagtctctg cagactgatt gtatatagta agaaaagatc aaaagacttt aaaacctaaa    2040
tgacttttga catacaaact cttcttgaga atgtttgttg taaatggttt caaaaataca    2100
aattatagcc aatcaaaaca ttgctttggt tggtgcattt aagtatccaa ctcaaaaagc    2160
atatcaaata ttttgggtac taggcagttt ccaaagtagc atggtagtat tacttgttaa    2220
aagggttctg ttttcattaa cagtactaag tggaagggat ctgcagattc caaattggaa    2280
taagctctat catattctga aacaagaatt agaatgactt gagaacgggc aaataacaaa    2340
gcaaaccaat ataattatat ggtcattctg accccagctc ttatacaaat tatacatgta    2400
tttttgtgta tgtttgtgag agttgtatgt atgtgaatgt gtgtgagtgt gtattcacat    2460
acacatatat actggaacct atagtagaaa aggaaactag tagggccaaa aaaaaaaaga    2520 aaagaaaaa gaaaaagaa aaaaaagaa aaaactggga cctaagtata aatatctcat    2580
cctaaagtaa acaataagtt tatagttaac gaagattttt ttctatttaa aaccccattt    2640
tcctaaagaa caaaaaaaaa aaaaaaaaa aaaaaaaaaa a                        2681
```

<210> SEQ ID NO 195
<211> LENGTH: 2805
<212> TYPE: DNA
<213> ORGANISM: Homo sapiens

<400> SEQUENCE: 195

```
ggcacgaggg caggggaag ggaagtgcgg ctcggtcggc gcgggtggag ggggcgtgag      60
gccgccctac ggtggccgtc gagggacggc gctacggctc ccacgctagg ccaaacgcct     120
ccggcggccg cgcccgagag ccccttcacc tgcaggggcga ccccagccgg cgacgcgtga    180
accacgccct cagccgcctt gccagcgccc ccagccgcgc gccccagcac catgcggccg    240
ccctgcgcac ggagccccga gggacagggg caccccgcagg cccggcccct agcaccgccg    300
gccggccccg aggtccggga cgccggcgcc gccgcggaga gggcaccggg ccgacgcctc    360
cccccagggt cagctgcggg ctcccaggcc taggcgccca tgaccctac gccaaccgcc    420 gcctggacac cgccgccgcc actgcgacct agcgccgccg ccgccggggc ccaatgccgg    480
tcatgcccat tccgcggcgg gtgcgctcct tccacgcccc gcacaccacc tgcctgcatg    540
cggcctgcgg gcccgtgcgc gcctcccacc tggcccgcac caagtacaac aacttcgacg    600
tgtacatcaa gacgcgctgg ctgtacggct tcatccgctt cctactctac tttagctgca    660
gcctgttcac tgcggcgctc tggggtgcgc tggccgccct cttctgccta cagtacctgg    720
gcgttcgcgt cctgctgcgc ttccagcgca agctgtcggt gctgctgctg ctgctgggcc    780
gccggcgcgt ggacttccgc ctggtgaacg agctgctcgt ctatggcatc cacgtcacca    840
tgctgctggt cggggggcctg ggctggtgct tcatggtctt cgtggacatg tgagggccgt    900
gggtgcgagc ttgatgtatc gtcccggcct gtggctgtgt tctctccatg ggtgggtcg    960 gccagcgcct tcccttcgcc catcccccag gcagtcgctg ctgcccggcg cccacggaga   1020
gaaaagaaag ggctgagact tctgtgatgg gggcgcggac accacccta ggctggcttc   1080 ctggaccac cctcccgta tgcactctca ggggcagcgc ccacctgccg gtggctcctg    1140
ctcacatgtc ttcgggtcgt actgcggggt gggccctccg ttccgcctct ctgtgggcct    1200
```

```
ctctccagga ccacagctgc cagggacttt agacatcacc ctgggaggcc cctggacaca    1260
gagggctgtg tgcccaggag caattccgga ggggggccct cctggctgca cagccccttc    1320
tgcgtgccct ggccccagcc ccagccaacg ggacacggaa ggctcccctc gctgacacac    1380
cacactgcca caaagctgct tactctgccc tgggccgcct gaggcctggc actgcccgcg    1440
gaccaccctg tgtgtgtcat cctgaggggc tgtgtgggtc ctgagtcccc agccagcctt    1500
cagggtcccc ttggattgtg tagatgcagt ctagcggggg gccggagaag ggctcaggtg    1560 ggagggggcct cagcaggctc ccagctcagg ggctggcctg gggggaaccc tgggagccag    1620
gggctgactc cagcaacact ggcctgtctg cctgttctgg gagggctgtg aggatgtctt    1680
gcagatgctc tggatttctg cggaggcacc tccattcctt tctggctttt tttgcggggg    1740
agggctttgg gcctctttct ttgagggaac accgtcaaag aaagcctggg agatcgaggc    1800
ttcagtgagc caggatggaa acgcgtgtcc caagtgtccg gagcaggcgg cagaggcctc    1860
agtgcggcaa acacagcccc agagcctgtg tggcaccagc agcatcttag agccccaggt    1920
atatgctgag atcttatctc acgctgtcct ccagtgtctg gggggcccaa atgatggcac    1980
agggtcaggt gggctggagg ggcgcagatg cctgtgttca ggagggtgg ccaccatggg     2040 ccgaggtctc acccaggacc ccttgctctg ctcctcagcc ttgcagtcac ggcagcacta    2100
tggtggactg cccatggccg tgtgactttg ggggcaagtg ggagggcgcc ctgaataatg    2160
attgcaagga caacaggcag aggctaccct agagcaggac acagggtgtg gtactgacaa    2220
ccctagtgtc acctcaaatc catgtcccca cactctgggc atgggtggga cttgtgaccc    2280
taccctgtca ggcggaccag tggcccagga gccatgagga cagttgtgtg ccactggaag    2340
agaaactttt tgaaaaaccc taaatcaggt agagaaagca aaaatctct ggccgtaaac      2400 cgtgctctct aatttatcgg cagcttctgt ggatgacctc tgatgagccc gggctgcgtc    2460
cacgccctgg gcaggtaggc gggagcttcc ctgcgtgggc ctcatttctt gctgcagaga    2520
atcttttgca ctaagtcatg ctgtttcctc aaagaagctt tgttttttgt taacgtatta    2580
ctcagagtca cccaagcctc ttggctgagg gtgaaggtgg gacgggaggc gggaggggggc   2640 tggtggtgcc gctcgtgcgg tgtcaacgct gcagggagtt gtggcacctt ggtgccctct    2700
gagcacctgg ccgcctgctg tccccggtgc ctgtgaaatt cgtcatgcca tgacccacct    2760
gcattaaacc tattttttta atgtgttaaa aaaaaaaaa aaaaa                      2805
```

<210> SEQ ID NO 196
<211> LENGTH: 496
<212> TYPE: DNA
<213> ORGANISM: Homo sapiens
<220> FEATURE:
<221> NAME/KEY: misc_feature
<222> LOCATION: (2)..(2)
<223> OTHER INFORMATION: a or g or c or t/u
<220> FEATURE:
<221> NAME/KEY: misc_feature
<222> LOCATION: (26)..(26)
<223> OTHER INFORMATION: a or g or c or t/u
<220> FEATURE:
<221> NAME/KEY: misc_feature
<222> LOCATION: (49)..(49)
<223> OTHER INFORMATION: a or g or c or t/u
<220> FEATURE:
<221> NAME/KEY: misc_feature
<222> LOCATION: (60)..(60)
<223> OTHER INFORMATION: a or g or c or t/u
<220> FEATURE:
<221> NAME/KEY: misc_feature
<222> LOCATION: (88)..(88)

<223> OTHER INFORMATION: a or g or c or t/u
<220> FEATURE:
<221> NAME/KEY: misc_feature
<222> LOCATION: (115)..(115)
<223> OTHER INFORMATION: a or g or c or t/u
<220> FEATURE:
<221> NAME/KEY: misc_feature
<222> LOCATION: (124)..(124)
<223> OTHER INFORMATION: a or g or c or t/u
<220> FEATURE:
<221> NAME/KEY: misc_feature
<222> LOCATION: (159)..(159)
<223> OTHER INFORMATION: a or g or c or t/u
<220> FEATURE:
<221> NAME/KEY: misc_feature
<222> LOCATION: (207)..(207)
<223> OTHER INFORMATION: a or g or c or t/u

<400> SEQUENCE: 196

| | | | | | |
|---|---|---|---|---|---|
| gnggaaacac | gggccaaacc | cgtgantttg | gtgccccttg | taaactcanc | ccctgcaaan | 60 |
| ccaaagaccc | caatggattt | aaagttgntt | ggcatttgta | ctggcaaggc | aaaanatttt | 120 |
| taantacctt | ttcctaatac | ttattgtatg | agcttttgnt | gtttacttgg | aggтттттgтc | 180 |
| тттттactaca | agtttggaac | tatttantat | tgccttggta | tttgtgctct | gtttaagaaa | 240 |
| caggcacttt | tttttattat | ggataaaatg | ttgagatgac | aggaggtcat | ttcaatatgg | 300 |
| cttagtaaaa | таттттаттgт | tcctttattc | tctgtacaag | атттттgggcc | тcттттттттc | 360 |
| cttaatgtca | caatgttgag | ttcagcatgt | gtctgtccat | ttcatttgta | cgcttgttca | 420 |
| aaaccaagtt | tgttctggtt | тcaagтттата | aaaataaatt | ggacatttaa | cttgatctcc | 480 |
| aaaaaaaaaa | aaaaaa | | | | | 496 |

<210> SEQ ID NO 197
<211> LENGTH: 2802
<212> TYPE: DNA
<213> ORGANISM: Homo sapiens

<400> SEQUENCE: 197

| | | | | | |
|---|---|---|---|---|---|
| ggcacgaggc | aatctgagga | gcaggaggac | cggggcgccg | gtgtcctgcc | gcctccttct | 60 |
| ccttgctctc | acctgcgcct | attagtccac | gcgccttcaa | ggccagggc | tacagcccag | 120 |
| acagagaggg | gacagcagag | ggagagagag | cacctgagga | tacagagctg | gcactggact | 180 |
| gccтттттcac | ccccccaggтg | atgagtgagg | тттcgaagaac | ggaagattta | aaaagcagcc | 240 |
| ggggcctccg | tатттgaatga | agacccagt | gcaaagacat | caccatgaac | actagcattc | 300 |
| cttatcagca | gaatccttac | aatccacggg | gcagctccaa | tgtcatccag | tgctaccgct | 360 |
| gtggagacac | ctgcaaaggg | gaagtggtcc | gcgtgcacaa | caaccacttc | cacatcagat | 420 |
| gcttcacctg | тcaagттатgт | ggctgtggcc | tggcccagtc | aggcttcttc | ttcaagaacc | 480 |
| aggagtacat | ctgcaccccag | gactaccagc | aactctatgg | cacccgctgt | gacagctgcc | 540 |
| gggacтттcat | cacaggcgaa | gtcatctcgg | ccttgggccg | cacttaccac | cccaagtgct | 600 |
| tcgtgtgcag | cttgtgcagg | aagccтттттcc | ccattggaga | caaggtgacc | ttcagcggta | 660 |
| aagaatgtgt | gtgccaaacg | tgctcccagt | ccatggccag | cagtaagccc | atcaagattc | 720 |
| gtggaccaag | ccactgtgcc | gggtgcaagg | aggagatcaa | gcacggccag | tcactcctgg | 780 |
| ctctggacaa | gcagtggcac | gtcagctgct | tcaagtgcca | gacctgcagc | gtcatcctca | 840 |
| ccgggggagтa | tatcagcaag | gatggтgтттc | catactgtga | gtccgactac | catgcccagt | 900 |
| ttggcattaa | atgtgagact | tgtgaccgat | acatcagtgg | cagagtcttg | gaggcaggag | 960 |
| ggaagcacta | ccacccaacc | tgtgccaggt | gtgtacgctg | ccaccagatg | ttcaccgaag | 1020 |

| | |
|---|---|
| gagaggaaat gtacctcaca ggttccgagg tttggcaccc catctgcaaa caggcagccc | 1080 |
| gggcagagaa gaagttaaag catagacgga catctgaaac ctccatctca cccctggat | 1140 |
| ccagcattgg gtcacccaac cgagtcatct gcgacatcta cgagaacctg gacctccggc | 1200 |
| agagacgggc ctccagcccg gggtacatag actcccccac ctacagccgg cagggcatgt | 1260 |
| cccccacctt ctcccgctca cctcaccact actaccgctc tggtgatttg tctacagcaa | 1320 |
| ccaagagcaa aacaagtgaa gacatcagcc agacctccaa gtacagtccc atctactcgc | 1380 |
| cagacccta ctatgcttcg gagtctgagt actggaccta ccatgggtcc cccaaagtgc | 1440 |
| cccgagccaa aaggttctcg tctggaggag aggaggatga ttttgaccgc agcatgcaca | 1500 |
| agctccaaag tggaattggc cggctgattc tgaaggaaga aatgaaggcc cggtcgagct | 1560 |
| cctatgcaga tccctggacc cctccccgga gctccaccag cagccgggaa gccctgcaca | 1620 |
| cagctggcta tgagatgtcc ctcaatggct cccctcggtc gcactacctg gctgacagtg | 1680 |
| atcctctcat ctccaaatct gcctccctgc ctgcctaccg aagaaatggg ctgcacagga | 1740 |
| cacccagcgc agacctcttc cactacgaca gcatgaacgc agtcaactgg ggcatgcgag | 1800 |
| agtacaagat ctacccttat gaactgctgc tggtgactac aagaggaaga aaccgactgc | 1860 |
| ccaaggatgt agacaggacc cgtttagagg gaaactttg gaagagtggc tgcttatgag | 1920 |
| attccaaaat gaagtgttgg ccaacaccgc tcatggccat cctggatttt cccagtggct | 1980 |
| tcccttcctg ctcgcctccc tgaacagggg agaaagctta acctctcttc tcctctccaa | 2040 |
| acctttcacc ttgaatgggt aatgtttggt ggggctgtt ccttcttgga gaagccttga | 2100 |
| gtcggaccat tttgagatca tggaggaagg atgaagaagt gaaaatgaca ataatgactc | 2160 |
| tcaagaggct ggcgatgtga catggcaaat gtagaactga cttaaattga acaaacccc | 2220 |
| actgagcacc tctgatgttg agcacctgct gaatactgag cactgaatgg ggagggga | 2280 |
| ggggagcacg gggtgagtca acctgggact cggtctcagg gatatgccta ccaatagcgg | 2340 |
| gtatcgtaag gcatgtaccc aaacataacg gatgtaaggc agaaagtgat cggagaagga | 2400 |
| atgagaaagt gtgcgtgatg ttaatgaaaa gtcatatgca gctagagcag acccaggaaa | 2460 |
| gctttctgga agagattgca tctgaggaaa ttcaggaagg atctttgtag attggggga | 2520 |
| gattctaaat tgaaggggtg atggggtgag gggccagagg gaagtctgct gtgttctcat | 2580 |
| gtaggatgtc agccctccct gcaacttctc tttttggcca atgtcttttc actttcctga | 2640 |
| cccctttagaa tcatccccag ccagacgcaa tcatggaagt tgccttattg tcactggtta | 2700 |
| agaacttggc gagattgaag ggcttttgtt attgttgttg gatattttg tttcccataa | 2760 |
| aagcacatca tttcaacccct aaaaaaaaaa aaaaaaaaa aa | 2802 |

<210> SEQ ID NO 198
<211> LENGTH: 3278
<212> TYPE: DNA
<213> ORGANISM: Homo sapiens

<400> SEQUENCE: 198

| | |
|---|---|
| gaagaattag atacttttga gtgggctttg aagagctggt ctcagtgttc caaaccctgt | 60 |
| ggtggaggtt tccagtacac taaatatgga tgccgtagga aaagtgataa taaaatggtc | 120 |
| catcgcagct tctgtgaggc caacaaaaag ccgaaaccta ttagacgaat gtgcaatatt | 180 |
| caagagtgta cacatccact ctgggtagca gaagaatggg aacactgcac caaaaccctgt | 240 |
| ggaagttctg gctatcagct tcgcactgta cgctgccttc agccactcct tgatggcacc | 300 |

| | |
|---|---|
| aaccgctctg tgcacagcaa atactgcatg ggtgaccgtc ccgagagccg ccggccctgt | 360 |
| aacagagtgc cctgccctgc acagtggaaa acaggaccct ggagtgagtg ttcagtgacc | 420 |
| tgcggtgaag gaacggaggt gaggcaggtc ctctgcaggg ctggggacca ctgtgatggt | 480 |
| gaaaagcctg agtcggtcag agcctgtcaa ctgcctcctt gtaatgatga accatgtttg | 540 |
| ggagacaagt ccatattctg tcaaatggaa gtgttggcac gatactgctc cataccaggt | 600 |
| tataacaagt tatgttgtga gtcctgcagc aagcgcagta gcaccctgcc accaccatac | 660 |
| cttctagaag ctgctgaaac tcatgatgat gtcatctcta accctagtga cctccctaga | 720 |
| tctctagtga tgcctacatc tttggttcct tatcattcag agaccctgc aaagaagatg | 780 |
| tctttgagta gcatctcttc agtgggaggt ccaaatgcat atgctgcttt caggccaaac | 840 |
| agtaaacctg atggtgctaa tttacgccag aggagtgctc agcaagcagg aagtaagact | 900 |
| gtgagactgg tcaccgtacc atcctcccca cccaccaaga gggtccacct cagttcagct | 960 |
| tcacaaatgg ctgctgcttc cttctttgca gccagtgatt caataggtgc ttcttctcag | 1020 |
| gcaagaacct caaagaaaga tggaaagatc attgacaaca gacgtccgac aagatcatcc | 1080 |
| accttagaaa gatgagaaag tgaaccaaaa aggctagaaa ccagaggaaa acctggacaa | 1140 |
| cctctctctt cccatggtgc atatgcttgt ttaaagtgga atctctata gatcgtcagc | 1200 |
| tcatttatc tgtaattgga agaacagaaa gtgctggctc actttctagt tgctttcatc | 1260 |
| ctccttttgt tctgcattga ctcatttacc agaattcatt ggaagaaatc accaaagatt | 1320 |
| attacaaaag aaaaatatgt tgctaagatt gtgttggtcg ctctctgaag cagaaagggg | 1380 |
| actggaacca attgtgcata tcagctgact ttttgtttgt tttagaaaag ttacagtaaa | 1440 |
| aattaaaaag agataccaat ggtttacact ttaacaagaa atttggata tggaacaaag | 1500 |
| aattcttaga cttgtattcc tatttatcta tattagaaat attgtatgag caaatttgca | 1560 |
| gctgttgtgt aaatactgta tattgcaaaa atcagtatta ttttaagaga tgtgttctca | 1620 |
| aatgattgtt tactatatta catttctgga tgttctaggt gcctgtcgtt gagtattgcc | 1680 |
| ttgtttgaca ttctataggt taattttcaa agcagagtat tacaaaagag aagttagaat | 1740 |
| tacagctact gacaatataa agggttttgt tgaatcaaca atgtgatacg taaattatag | 1800 |
| aaaaagaaaa gaaacacaaa agctatagat atacagatat cagcttacct attgccttct | 1860 |
| atacttataa tttaaaggat tggtgtctta gtacacttgt ggtcacaggg atcaacgaat | 1920 |
| agtaaataat gaactcgtgc aagacaaaac tgaaccctc tttccaggac ctcagtaggc | 1980 |
| accgttgagg tgtcctttgt ttttgtgtgt gtgtgttctt ttttaatttt cgcattgttg | 2040 |
| acagatacaa acagttatac tcaatgtact gtaataatcg caaggaaaa agttttggga | 2100 |
| taacttattt gtatgttggt agctgagaaa aatatcatca gtctagaatt gatatttgag | 2160 |
| tatagtagag ctttggggct tgaaggcag gttcaagaaa gcatatgtcg atggttgaga | 2220 |
| tatttatttt ccatatggtt catgttcaaa tgttcacaac cacaatgcat ctgactgcaa | 2280 |
| taatgtgcta ataatttatg tcagtagtca ccttgctcac agcaaagcca gaaatgctct | 2340 |
| ctccagggag tagatgtaaa gtacttgtac atagaattca gaactgaaga tatttattaa | 2400 |
| aagttgattt ttttttcttg atagtatttt tatgtactaa atatttacac taatatcaat | 2460 |
| tacatatttt ggtaaactag agagacataa ttagagatgc atgctttgtt ctgtgcatag | 2520 |
| agacctttaa gcaaactact acagccaact caaaagctaa aactgaacaa atttgatgtt | 2580 |
| atgcaaacat cttgcatttt tagtagttga tattaagttg atgacttgtt tcccttcaag | 2640 |
| gaaacattaa attgtatgga ctcagctagc tgttcaatga aattgtgaat tagaaacatt | 2700 |

```
tttaaaagtt tttgaaagag ataagtgcat catgaattac atgtacatga gaggagatag      2760
tgatatcagc ataatgattt tgaggtcagt acctgagctg tctaaaaata tattatacaa      2820
actaaaatgt agatgaatta acctctcaaa gcacagaatg tgcaagaact tttgcatttt      2880
aatcgttgta aactaacagc ttaaactatt gactctatac ctctaaagaa ttgctgctac      2940
tttgtgcaag aactttgaag gtcaaattag gcaaattcca gatagtaaaa caatccctaa      3000
gccttaagtc tttttttttt tcctaaaaat tcccatagaa taaaattctc tctagtttac      3060
ttgtgtgtgc atacatctca tccacagggg aagataaaga tggtcacaca aacagtttcc      3120
ataaagatgt acatattcat tatacttctg acctttgggc tttctttttct actaagctaa      3180 aaattccttt ttatcaaagt gtacactact gatgctgttt gttgtactga gagcacgtac      3240
caataaaaat gttaacaaaa tataaaaaaa aaaaaaaa                              3278

<210> SEQ ID NO 199
<211> LENGTH: 567
<212> TYPE: DNA
<213> ORGANISM: Homo sapiens

<400> SEQUENCE: 199
tcctgtgttc tagacctctg gaggctgctg tggggaccac actgatcctg gagaaaaggg       60
atggagctga aaaagatgga atgcttgcag agcatgacct gaggagggag gaacgtggtc      120
aactcacacc tgcctcttcc tgcagcctca cctctacctg cccccatcat aagggcactg      180
agcccttccc aggctggata ctaagcacaa agcccatagc actgggctct gatggctgct      240
ccactgggtt acagaatcac agccctcatg atcattctca gtgagggctc tggattgaga      300 ggaggccct gggaggagag aaggggcag agtcttccct accaggtttc tacaccccg       360 ccaggctgcc catcagggcc cagggagccc ccagaggact ttattcggac caagcagagc      420
tcacagctgg acaggtgttg tatatagagt ggaatctctt ggatgcagct tcaagaataa      480 attttttcttc tctttttcaaa aatgtataaa aatcattata catagcatta aagaaacatt      540
tttgagaagt acaaaacaaa aaaaaaa                                          567

<210> SEQ ID NO 200
<211> LENGTH: 2907
<212> TYPE: DNA
<213> ORGANISM: Homo sapiens

<400> SEQUENCE: 200
cgggcgccgc aggagcgagt gagctgggag cgaggggcga aggcgcggag aagcccggcc       60
gcccggtggg cggcagaagg ctcagccgag gcggcggcgc cgactccgtt ccactctcgg      120
cccggatcca ggcctccggg ttcccaggcg ctcacctccc tctgacgcac tttaaagagt      180
ctcccccctt ccacctcagg gcgagtaata gcgaccaatc atcaagccat ttaccaggct      240
tcggaggaag ctgtttatgt gatccccgca ctaattaggc tcatgaacta acaaatcgtt      300
tgcacaactt gtgaagaagc gaacacttcc atggattgtc cttggactta gggcgccctg      360
cccgcctttt gcagaggaga aaaaactttt ttttttttt gcctccccg agaactttcc      420 cccttctcc tccctgcctc taactccgat ccccccacgc catctcgcca aaaaaaaaa      480 aaaaaaaaaa aagaaaaaa aaagaaaaaa aagaaaaaa aattacccca atccacgcct      540
gcaaattctt ctgaaggat tttcccccct ctcttcaggt tgggcgcgtt tggtgcaaga      600
ttctcgggat cctcggcttt gcctctccct ctccctcccc cctcctttcc tttttcctt      660
```

```
cctttcctttt  ctttcttcct   ttccttcccc  ccacccccac  ccccaccccca  aacaaacgag    720 tccccaattc   tcgtccgtcc   tcgccgcggg  cagcgggcgg  cggaggcagc   gtgcggcggt    780
cgccaggagc   tgggagccca   gggcgcccgc  tcctcggcgc  agcatgttcc   agccggcgcc    840
caagcgctgc   ttcaccatcg   agtcgctggt  ggccaaggac  agtcccctgc   ccgcctcgcg    900
ctccgaggac   cccatccgtc   ccgcggcact  cagctacgct  aactccagcc   ccataaatcc    960
gttcctcaac   ggcttccact   cggccgccgc  cgccgccgcc  ggtaggggcg   tctactccaa   1020
cccggacttg   tgttcgccg    aggcggtctc  gcacccgccc  aaccccgccg   tgccagtgca   1080
cccggtgccg   ccgccgcacg   ccctggccgc  ccacccccta  ccctcctcgc   actcgccaca   1140
ccccctattc   gcctcgcagc   agcgggatcc  gtccaccttc  taccctggc    tcatccaccg   1200 ctaccgatat   ctgggtcatc   gcttccaagg  gaacgacact  agccccgaga   gtttcctttt   1260
gcacaacgcg   ctggcccgaa   agcccaagcg  gatccgaacc  gccttctccc   cgtcccagct   1320
tctaaggctg   gaacacgcct   ttgagaagaa  tcactacgtg  gtgggcgccg   aaaggaagca   1380
gctggcacac   agcctcagcc   tcacgaaaac  tcaggtaaaa  gtatggtttc   agaaccgaag   1440
aacaaagttc   aaaaggcaga   agctggagga  agaaggctca  gattcgcaac   aaaagaaaaa   1500
agggacgcac   catattaacc   ggtggagaat  cgccaccaag  caggcgagtc   cggaggaaat   1560
agacgtgacc   tcagatgatt   aaaaacataa  acctaacccc  acagaaacgg   caacatggaa   1620
gcaaaagaga   cagggagagg   tggagaagga  aaaaaccta   caaaacaaaa   acaaaccgca   1680
tacacgttca   ccgagaaagg   gagagggaat  cggagggagc  agcggaatgc   ggcgaagact   1740
ctggacagcg   agggcacagg   gtcccaaacc  gaggccgcgc  caagatggca   gaggatggag   1800
gctccttcat   caacaagcga   ccctcgtcta  aagaggcagc  tgagtgagag   acacagagag   1860
aaggagaaag   agggagggag   agagagaaag  agagagaaag  agagagagag   agagagagag   1920
agaaagctga   acgtgcactc   tgacaagggg  agctgtcaat  caaacaccaa   accggggaga   1980
caagatgatt   ggcaggtatt   ccgtttatca  cagtccactt  aaaaaatgat   gatgatgata   2040
aaaaccacga   cccaaccagg   cacaggactt  ttttgttttt  tgcacttcgc   tgtgtttccc   2100
ccccatctct   aaaaataatt   agtaataaaa  aacaaaaatt  ccatatctag   ccccatccca   2160
cacctgtttc   aaatccttga   aatgcatgta  gcagttgttg  ggcgaatggt   gtttaaagac   2220
cgaaaatgaa   ttgtaatttt   cttttccttt  taaagacagg  ttctgtgtgc   ttttatttt    2280 gatttttttt   cccaagaaat   gtgcagtctg  taaacacttt  ttgatacctt   ctgatgtcaa   2340
agtgattgtg   caagctaaat   gaagtaggct  cagcgatagt  ggtcctctta   cagagaaacg   2400
gggagcagga   cgacgggggg   gctggggtg   gcggggagg   gtgcccacaa   aaagaatcag   2460
gacttgtact   gggaaaaaaa   cccctaaatt  aattatattt  cttggacatt   ccctttccta   2520
acatcctgag   gcttaaaacc   ctgatgcaaa  cttctccttt  cagtggttgg   agaaattggc   2580
cgagttcaac   cattcactgc   aatgcctatt  ccaaacttta  aatctatcta   ttgcaaaacc   2640
tgaaggactg   tagttagcgg   ggatgatgtt  aagtgtggcc  aagcgcacgg   cggcaagttt   2700
tcaagcactg   agtttctatt   ccaagatcat  agacttacta  aagagagtga   caaatgcttc   2760
cttaatgtct   tctataccag   aatgtaaata  tttttgtgtt  ttgtgttaat   ttgttagaat   2820
tctaacacac   tatatacttc   caagaagtat  gtcaatgtca  atattttgtc   aataaagatt   2880
tatcaatatg   ccaaaaaaaa   aaaaaaa                                           2907
```

<210> SEQ ID NO 201
<211> LENGTH: 60

<212> TYPE: DNA
<213> ORGANISM: Artificial Sequence
<220> FEATURE:
<223> OTHER INFORMATION: Synthetic construct - oligonucleotide

<400> SEQUENCE: 201
acttctggtg atgataaaaa tggtttatc acccagatgt gaaagaagct gcctgtttac    60

<210> SEQ ID NO 202
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 202
gtggttctgt aaaacgcag aggaaaagag ccagaaggtt tctgtttaat gcatcttgcc    60

<210> SEQ ID NO 203
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 203
tttataagga agcagctgtc taaaatgcag tggggtttgt tttgcaatgt tttaaacaga    60

<210> SEQ ID NO 204
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 204
cttatgaagc tggccgggcc actcacgttc aatggtacat ctgggtctct atgtggttct    60

<210> SEQ ID NO 205
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 205
gtgagccagc atttcccata gctaacccta ttctcttagt ctttcaaaat gtagaatggg    60

<210> SEQ ID NO 206
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 206
ctttacacct gataaaatat tttgcgaaga gaggtgttct ttttccttac tggtgctgaa    60

<210> SEQ ID NO 207
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 207
gcatacatct catccacagg ggaagataaa gatggtcaca caaacagttt ccataaagat    60

<210> SEQ ID NO 208
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 208
tgagttcagc atgtgtctgt ccatttcatt tgtacgcttg ttcaaaacca agtttgttct    60

<210> SEQ ID NO 209
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 209
aagaccgaga ctgagggaaa gcatgtctgc tgggtgtgac catgtttcct ctcaataaag    60

<210> SEQ ID NO 210
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 210
ggcatctggc ccctggtagc cagctctcca gaattacttg taggtaattc ctctcttcat    60

<210> SEQ ID NO 211
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 211
tggatgtttg tgcgcgtgtg tggacagtct tatcttccag catgatagga tttgaccatt    60

<210> SEQ ID NO 212
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 212
tcctggcaga gccatggtcc caggcttccc aaaagtgttt gtggcaatta ttccctagg    60

<210> SEQ ID NO 213
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 213
tttgatgata gcagacattg ttacaaggac atggtgagtc tattttaat gcaccaatct    60

<210> SEQ ID NO 214
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 214
ttcttccagt tgcactattc tgagggaaaa tctgacacct aagaaattta ctgtgaaaaa    60

<210> SEQ ID NO 215
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 215
gaacaattgt ggtctctctt aacttgaggt tctcttttga ctaatagagc tccatttccc    60

<210> SEQ ID NO 216
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 216
gttaagtgtg gccaagcgca cggcggcaag ttttcaagca ctgagtttct attccaagat    60

<210> SEQ ID NO 217
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 217
cggcctactg agcggacaga atgatgccaa aatattgctt atgtctctac atggtattgt    60

<210> SEQ ID NO 218
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 218
cagggtgttt gcccaataat aaagccccag agaactgggc tgggccctat gggattggta    60

<210> SEQ ID NO 219
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 219
tgtacagttt ggttgttgct gtaaatatgg tagcgttttg ttgttgttgt ttttcatgc    60

<210> SEQ ID NO 220
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 220
taccaaactg ggactcacag ctttattggg ctttcttgt gtcttgtgtg tttcttttat    60

<210> SEQ ID NO 221
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 221
cattgaggtt tggatggtgg caggtaaaac agaaaggcaa gatgtcatct gacattaggc        60

<210> SEQ ID NO 222
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 222
agttcagcac tgtggttatc attggtgatg ccagaaaaca ttagtagact tagacaattg        60

<210> SEQ ID NO 223
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 223
taaaatttct tgattgtgac tatgtggtca tatgcccgtg tttgtcactt acaaaaatgt        60

<210> SEQ ID NO 224
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 224
agccatctgg tgtgaagaac tctatatttg tatgttgaga gggcatggaa taattgtatt        60

<210> SEQ ID NO 225
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 225
cttattgtca ctggttaaga acttggcgag attgaagggc ttttgttatt gttgttggat        60

<210> SEQ ID NO 226
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 226
ctttctagtg agctaaccgt aacagagagc ctacaggata cacgtgagat aatgtcacgt        60

<210> SEQ ID NO 227
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 227
ttgtcttaaa atttcttgat tgtgatactg tggtcatatg cccgtgtttg tcacttacaa    60

<210> SEQ ID NO 228
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 228
cctgggggaa agggcattc atgacctgaa cttttttagca aattattatt ctcagtttcc    60

<210> SEQ ID NO 229
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 229
ttcattaaca gtactaagtg aagggatct gcagattcca aattggaata agctctatca    60

<210> SEQ ID NO 230
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 230
ccaatgcaga agagtattaa gaaagatgct caagtcccat ggcacagagc aaggcgggca    60

<210> SEQ ID NO 231
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 231
caaggctacg atggctatga tggtcagaat tactaccacc accagtgaag ctccagcctg    60

<210> SEQ ID NO 232
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 232
agctcacagc tggacaggtg ttgtatatag agtggaatct cttggatgca gcttcaagaa    60

<210> SEQ ID NO 233
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 233
tccaaagtag aaagggttct tttagaaaac ttgaagaatg tgcctcctct tagcatctgt    60

<210> SEQ ID NO 234

```
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 234 gatgcattt tcagtcccttt ttcagagcaa atgcttttgc aatggtagta atgtttagtt        60

<210> SEQ ID NO 235
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 235
cctgtggggc ttctctcctt gatgcttctt tcttttttta aagacaacct gccattacca        60

<210> SEQ ID NO 236
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 236
ttgcactaag tcatgctgtt tcctcaaaga agctttgttt tttgttaacg tattactcag        60

<210> SEQ ID NO 237
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 237
ctggatccca ggccctggca cccctcagga aatacaagaa aaagaatatt cacatctgtt        60

<210> SEQ ID NO 238
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 238
ttagaggggc cacctatcaa ctcatcagtg ttcaaagaat atgctgggag catgggtgag        60

<210> SEQ ID NO 239
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 239
ggcccattta tgtccctcat gtctctagat tttctcgtca cccagcctca aaaatatatg        60

<210> SEQ ID NO 240
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 240
```

```
tccccaaaaa cctcacccga ggctgcccac tatggtcatc tttttctcta aaatagttac    60
```

<210> SEQ ID NO 241
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 241

```
gaaattcctc acaccttgca ccttccctac ttttctgaat tgctatgact actccttgtt    60
```

<210> SEQ ID NO 242
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 242

```
tgtctgtcca ccacgagatg ggaggaggag aaaaagcggt acgatgcctt cctgacctca    60
```

<210> SEQ ID NO 243
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 243

```
gtcttatctc tcagggggg tttaagtgcc gtttgcaata atgtcgtctt atttatttag    60
```

<210> SEQ ID NO 244
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 244

```
ccgagtagta tgggtctctg tgtgagaaac caggagatat tttcatcttg ttcggaaata    60
```

<210> SEQ ID NO 245
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 245

```
ttgtgcaaaa gtcccacaac ctttctggat tgatagtttg tggtgaaata aacaatttta    60
```

<210> SEQ ID NO 246
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 246

```
tccagtattc tgcagggcca gtcagttgta cagaagttgg aatattctgt tccagaatta    60
```

<210> SEQ ID NO 247
<211> LENGTH: 60
<212> TYPE: DNA

```
<213> ORGANISM: Artificial Sequence
<220> FEATURE:
<223> OTHER INFORMATION: Synthetic construct - oligonucleotide

<400> SEQUENCE: 247
gtctcgaaca gcggttgttt ttactttatt tatcttaggc cctcagctcc ctgacgtcct    60

<210> SEQ ID NO 248
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 248
agtgaatctt ttcctcttgg tagcatcaac actggggata aatcagaacc attctgtgga    60

<210> SEQ ID NO 249
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 249
tgagagccca gaacaagaag gagcagaagg gcactttgac cttcattatt atgaaaatca    60

<210> SEQ ID NO 250
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 250
ggaagaactg atgcttgctg ctaactaaag ttttggatgt atcgatttag agaaccaatt    60

<210> SEQ ID NO 251
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 251
gaatgagaga ataagtcatg ttccttcaag atcatgtacc ccaatttact tgccattact    60

<210> SEQ ID NO 252
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 252
tacggaaagg aaacaggtta tactcttaga tttaaaaagt gaaagaaact gcaggcgcct    60

<210> SEQ ID NO 253
<211> LENGTH: 2888
<212> TYPE: DNA
<213> ORGANISM: Homo sapiens

<400> SEQUENCE: 253
gtggcggcgg aggcggcgga ggccagggag gaagatgtcg taatgagcga tccacagacc    60
agcatggctg ccactgctgc tgtgagtccc agtgactacc tgcagcctgc cgcctccacc   120
```

-continued

| | |
|---|---|
| acccaggact cccagccatc tcccttagcc ctgcttgctg caacatgtag caaaattggc | 180 |
| cctccagcag ttgaagctgc tgtgacacct cctgctcccc cacagccac accgcggaaa | 240 |
| cttgtcccta tcaaacctgc ccctctccct ctcagccccg gcaagaatag ctttggaatc | 300 |
| ttgtcctcca aaggaaatat acttcagatt caggggtcac aactgagcgc ctcctatcct | 360 |
| ggagggcagc tggtgttcgc tatccagaat cccaccatga tcaacaaagg acccgatca | 420 |
| aatgccaata tccagtacca ggcggtccct cagattcagg caagcaattc ccaaaccatc | 480 |
| caagtacagc ccaatctcac caaccagatc cagatcatcc ctggcaccaa ccaagccatc | 540 |
| atcacccct caccgtccag tcacaagcct gtccccatca agccagcccc catccagaag | 600 |
| tcgagtacga ccaccacccc cgtgcagagc ggggccaatg tggtgaagtt gacaggtggg | 660 |
| ggcggcaatg tgacgctcac tctgcccgtc aacaacctcg tgaacgccag tgacaccggg | 720 |
| gccctactc agctcctcac tgaaagcccc caacccgc tgtctaagac taacaagaaa | 780 |
| gcaaggaaga gagccttcc tgcctcccag cccctgtgg ctgtggctga gcaggtggag | 840 |
| acggtgctga tcgagaccac cgcggacaac atcatccagg caggaaataa cctgctcatt | 900 |
| gttcagagcc ctggtggggg ccagccagct gtggtccagc aggtccaggt ggtgccccc | 960 |
| aaggccgagc agcagcaggt ggtacagatc ccccagcagg ctctgcgggt ggtgcaggcg | 1020 |
| gcatctgcca ccctccccac tgtaccccag aagccctccc agaactttca gatccaggca | 1080 |
| gctgagccga cacctactca ggtctacatc cgcacgcctt ccggtgaggt gcagacagtc | 1140 |
| cttgtccagg acagccccc agcaacagct gcagccacct ctaacaccac ctgtagcagc | 1200 |
| cctgcatccc gtgctcccca tctgagtggg accagcaaaa agcactcagc tgcaattctc | 1260 |
| cgaaaagagc gtcccctgcc aaagattgcc ccagccggga gcatcatcag cctgaatgca | 1320 |
| gcccagttgg cggcagctgc ccaggcaatg cagaccatca acatcaatgg tgtccaggtc | 1380 |
| cagggcgtgc ctgtcaccat caccaacaca ggcgggcagc agcagctgac agtgcagaat | 1440 |
| gtttctggga acaacctgac catcagtggg ctgagcccca cccagatcca gctgcaaatg | 1500 |
| gaacaagccc tggccggaga gacccagccc ggggagaagc ggcgccgcat ggcctgcacg | 1560 |
| tgtcccaact gcaaggatgg ggagaagagg tctggagagc agggcaagaa gaagcacgtg | 1620 |
| tgccacatcc ccgactgtgg caagacgttc cgtaagacgt ccttgctgcg tgcccatgtg | 1680 |
| cgcctgcaca ctggcgagcg gcccttgtc tgcaactggt tcttctgtgg gaagaggttc | 1740 |
| acacggagtg acgagctcca acggcatgct cgcacccaca caggggacaa acgcttcgag | 1800 |
| tgcgcccagt gtcagaagcg cttcatgagg agtgaccacc tcaccaagca ttacaagacc | 1860 |
| cacctggtca cgaagaactt gtaaggccaa ctgcggcggg aggccctgaa gatgcagtcc | 1920 |
| cccacctgtg tcctccctgg gcccctggtg gaaaggagcc ctgtggctgc cttgggcctg | 1980 |
| ccctcagccc cactcctgtt ctgcaactgt ccccacagga agggctctg ttccctgtat | 2040 |
| tgtcctcctt ctgaagcccc ttggctctgc cttggccctt cccctcacca cgagctcccg | 2100 |
| gcctgcccag actgtggaca ctggccgtgc ccaatgagac gttctaaacc aggacgcgtg | 2160 |
| ggaacccta tttccaaagg aaaaacatgc atttcactcc gtcgaggagc aaagtgagcc | 2220 |
| cctaccccc accccgatcc ccgctcccaa cactgccgga gtcgcgtcat gcatgcccc | 2280 |
| ctctcctgca cctccctggc cctgccggcc actgtggacg ccctggggct tggcacccac | 2340 |
| ctctggagaa actcggggcc acctccactc catgtgccca gccccgccac aacctctcct | 2400 |
| ccagcacatt ccagctctat ttaaaaagta aagacaccca ccgactcctg atccccctct | 2460 |

| | |
|---|---|
| ttttctatgg agaacgttgc cttatactct ctacttcaga tgatgaacac tgtgtactgt | 2520 |
| gtgtgcttta aagaagtttt atttaattgc tcccttcttc ctttccttgt tattcacctc | 2580 |
| cctgatgcct gctttcagtt gagggttggg ggcaatgatg agcatatgaa ttttttctca | 2640 |
| ctctagcaat tcccttttct aaatgacaca gcatttaaac tcaaatctgg attcagataa | 2700 |
| cagcacctgc acatcctgca cctcctccct ctcccttcac ctcacccctg cccggcccaa | 2760 |
| gctctacttg tgtacagtgt atattgtata atagacaatt gtgtctacta catgttttaaa | 2820 |
| aacacattgc ttgttatttt tgaggctttt aaattaaaca aaaatccaac tttaaaaaaa | 2880 |
| aaaaaaaa | 2888 |

<210> SEQ ID NO 254
<211> LENGTH: 999
<212> TYPE: DNA
<213> ORGANISM: Homo sapiens

<400> SEQUENCE: 254

| | |
|---|---|
| cccgcgtcgg tgcccgcgcc cctccccggg ccccgccatg ggcctcaccg tgtccgcgct | 60 |
| cttttcgcgg atcttcggga agaagcagat gcggattctc atggttggct tggatgcggc | 120 |
| tggcaagacc acaatcctgt acaaactgaa gttgggggag attgtcacca ccatcccaac | 180 |
| cataggcttc aatgtagaaa cagtggaata taagaacatc tgtttcacag tctgggacgt | 240 |
| gggaggccag gacaagattc ggcctctgtg gcggcactac ttccagaaca ctcagggcct | 300 |
| catctttgtg gtggacagta atgaccggga gcgggtccaa gaatctgctg atgaactcca | 360 |
| gaagatgctg caggaggacg agctgcggga tgcagtgctg ctggtatttg ccaacaagca | 420 |
| ggacatgccc aacgccatgc ccgtgagcga gctgactgac aagctggggc tacagcactt | 480 |
| acgcagccgc acgtggtatg tccaggccac ctgtgccacc caaggcacag gtctgtacga | 540 |
| tggtctggac tggctgtccc acgagctgtc aaagcgctaa ccagccaggg gcaggcccct | 600 |
| gatgcccgga agtcctgcg tgcatccccg gatgaccata ctcccggact cctcaggcag | 660 |
| tgccctttcc tcccactttt cctcccccat agccacaggc ctctgctcct gctcctgcct | 720 |
| gcatgttctc tctgttgttg gagcctggag ccttgctctc tgggcacaga ggggtccact | 780 |
| ctcctgcctg ctgggaccta tggaagggc ttcctggcca aggcccctc ttccagagga | 840 |
| ggagcaggga tctgggtttc cttttttttt tctgttttgg gtgtactcta ggggccaggt | 900 |
| tgggaggggg aaggtgaggg cttcgggtgg tgctataatg tggcactgga tcttgagtaa | 960 |
| taaatttgct gtggtttgaa aaaaaaaaa aaaaaaaa | 999 |

<210> SEQ ID NO 255
<211> LENGTH: 3487
<212> TYPE: DNA
<213> ORGANISM: Homo sapiens

<400> SEQUENCE: 255

| | |
|---|---|
| gtggcggtgg ctgcggcgac ggcagaggcg aagggagccg gatcgccgac ctgagcggga | 60 |
| ggcggcggtg gcggccatgg cggcagatgg agagcgttcc ccgctgctgt ctgagcccat | 120 |
| cgacggtggc gcgggcggca acggtttagt ggggcccggc gggagtgggg ctgggcccgg | 180 |
| gggaggcctg accccctccg caccaccgta cggagccggt aaacatgccc cgccccaggg | 240 |
| taagccgggg cggtccgag gtgctccccg gggtactctg aaagccgggg aggggcggg | 300 |
| accgagggcg gaggcgggtc ccagtcgcca ggtgcgggac tgctgcacct gtgactgggc | 360 |
| gaggcttcct tccctccgta atcgcgacca cagcctaggg acggaagggg gttctgagca | 420 |

```
acctgataga agtgccaatt atgagaagcc ctccgagctt ggtcagaggg ttgaagatca      480
gaaggacttc cctaccaccg tggagcatca gtggggtgt aagtgatccc agcccttcta      540
tttgcttcct ctccagcatt tcccccgttt cccgagggc atccagccgt gttgcctggg      600
gaggacccac ccccctattc acccttaact agcccggaca gtgggagtgc ccctatgatc      660
acctgccgag tctgccaatc tctcatcaac gtggaaggca agatgcatca gcatgtagtc      720 aaatgtggt tctgcaatga agccaccgtg agttacacat atctatgaaa tgggccctgt      780
ttcctggatc ctctttctga tgtcttggtt ctagaccctg accttccggc tattagccaa      840
gtgcttttga tgatacccag gtttcagttc caggtgtctc acacagccat tccccagaa      900 gccactcacc aaagctaatg ttcactttct ctcacttta cacctagcct agttcctatt       960
tgcaaatctc atgatatagt ctttctttta tttctccttc ctggttagca ccttattttt      1020
ctgatctcat aaagtgtttt tggagggaag tgagggat tgggattaga ggtttgcttg       1080
ctgatgaccc tattattctc tagccaatca agaatgcacc cccagggaaa aaatatgttc      1140
gatgcccctg taactgtctc cttatctgca aagtgacatc caacggatt gcatgccctc      1200 gtccctactg gtaagaggca taaggtgggg aagggcctaa gtgggaact ggaaagtcaa      1260 aaaaggatga gcgtatacag agaatgtaaa ggtgagagag cctagtgttt atttaggaga      1320
aaaggctttg aagcatgtgc ctcaggaatg ttatagctgt ctttctcgtt tctcaataaa      1380
aatattgaga tgaaatgatg tcgtttcgga gaatagagag ccttggggac tgggtgtgtt      1440
atcctgaggt cggagggga ttggggacct gaagtttaaa cagtgctctt tctttctcaa      1500
ggattcttga gggtatacag ttggggaca gagtatctta agtacagaga agtcgagtga      1560
cttaatagac agggagtggg ggatgtggaa cagggactgt gaagattttt aggattaaaa      1620 attttcaaa cacaagtttg aaaatacaag tctttttctt ttgtatagca aaagaatcat      1680
caacctgggg cctgtgcatc ccggacctct gagtccagaa ccccaaccca tgggtgtcag      1740
ggttatctgt ggacattgca agaatacttt tctggtgagg aaggggtatt gggaagggga      1800
ggggaaagga gactaagagt catttcgagt atatttctta gagtaatggt aatgaccct      1860 gaaaggtctg tcctatggga acatgttctg catccccacc ccaaggttct cattgaggaa      1920
gaccctgctt gtgctattat ttttgttttc tttctccata gtggacagag ttcacagacc      1980
gcactttggc acgttgtcct cactgcagga aagtgtcatc tattgggcgc agatacccac      2040
gtaagagatg tatctgctgc ttcttgcttg gcttgctttt ggcagtcact gccactggcc      2100
ttgccgtgag tacccttgcc ccaacctctt tcattctgca gcctcatctc cataggctaa      2160
gatttgggaa actgctaccc taaaaaaag tggaagaaac ttaggggact agtttgtttt      2220
gttttaagat atggatgagc taagtgcaa agtggctgat caaacagact ttattactac      2280
tacaagagtg aaaaacagcc ttcctttctc tgtaggatga ggataggaca gtgaaattct      2340
taatttaaga gttgctattt ttcaaacctg gctcagttgt cagatattaa gaaaaactga      2400
gatacagtgt gggatgggat gagtatgtta cgcctaaggg aaggaagctg atcagctctg      2460
cctttaagaa ggtccctgag ggtggctaca tgtggataag gaacaaggac tgaagcgtga      2520
gttattactg ttcttagaac taataggagg tagtggagac caacattaac cccatctttc      2580
ttttcttctc cctccttatc ttcatcagtt tggcacatgg aagcatgcac ggcgatatgg      2640
aggcatctat gcagcctggg catttgtcat cctgttggct gtgctgtgtt tgggccgggc      2700
tctttattgg gcctgtatga aggtcagcca ccctgtccag aacttctcct gagcctgatg      2760
```

```
acccacagac tgtgcctggc ccctccctgg tggggacagt gacactacga agggagctgg    2820
ggtagttaaa ggctcccggg gcttctagaa ggaagccaag cagctgcctt ccttttccct    2880
ggggagaggt aggaaggaac caggccctca cttaggtttg gaggggcaga taagagcact    2940
gctgaccatc tgctttcctc caaggggttgc tgtgtctagg gtgaagtagg caaaacgttg    3000
cccttaaaac tgggccctga agacggttcc agccttgtcc ttcctgtgtg ctccctgaga    3060
gccattcctg tcccttacac attccagggc agggtggggg tgggtagccc tgggggttcc    3120
cctccctctt gtgcaccatt aggactttgc tgctgctatt gcacttcacc agaggttggc    3180
tctggcctca gtaccctcag tctcctctcc ccacattgtg tcctgtgggg gtggggtcag    3240
ccgctgctct gtacagaacc acaggaactg atgtgtatat aactatttaa tgtgggatat    3300
gttcccctat tcctgtattt cccttaattc ctcctcccga cctttttttac ccccccagtt    3360 gcagtattta actgggctgg gtagggttgc tcagtctttg ggggaggtta gggacttatc    3420
ctgtgcttgt aaataaataa ggtcatgact ctaaaaaaaa aaaaaaaaaa aaaaaaaaa    3480 aaaaaaa                                                              3487
```

<210> SEQ ID NO 256
<211> LENGTH: 1651
<212> TYPE: DNA
<213> ORGANISM: Homo sapiens

<400> SEQUENCE: 256

```
ctgtcagcac ggggcctggc atgtaattgg tctgcaccca ctggtgcact gaactgccat      60
aacctcaggt tttctttctt gctgataccc ctgggtcatg ttctttggca ataacatga     120 ttcattatga agtagagttc agcaaaggac aaggatgaaa gttgtcattt agagaactgc     180
cattcagact ttcttgtcta ggtaaagagc aaggtcttct ctcttttcaa ctcatttttct    240 aaatttaaac tgacgatgag aatatggatg atgtgtagct tccttctccc ccactgattt     300
ttggttcagg ctctgggttt ttggcaagaa cttacagatc tcacttatta ttggccaccc     360
ttctgcttta agacctgtca gggcttgtct gaaataaaac tggaagcact tctgattcca     420
tcctcactgc tttcctcctt caccgtcaga cagcattact gtatagcact gagtgagggg     480
ccctgacact ggaaggtggc aggtggggcc tggccgccag tgaggtatca tcatttgtgt     540
gtgctcatgt gtgcgttggg cttgttgtat ctgaggcatg acattccat atacacggct      600 taaagagttt tcttcccata ccgaaagcat atattcggag aggacccaac ttattcagca     660
tagccttgtt cccatagtag ccatcctatt cccccacagc ctctacttta ggaaagctcc     720
ccgtccccat atgaaatcca aaccaaaaaa gatatatcac tttcagctca attattccat     780
aattacaaga tattaggcta gtgggctctt tattggttgg gtcttatatt aatgttatat     840
gctagccttg taattttgag ctcctctatg gatgttaatt ttagtgaaac tctatattga     900
agaaaagatg ggactaaggg ggagacagga ggaggaaaga aagcagagac aggcaaagaa     960
tcatagcctg aaattcaaca gcaagcatgg cttatgaaga tcaagttata tttttgcttc    1020
atgaatcatt gtcagacaaa ttaagaacat attgtttctt atttatctat tgtcaaggat    1080
tcactatcag acactaagaa tgaatcttga ttttcataag ctctgttgac accatggagc    1140
cacagagcat aaaacttgca tctaataaag aaagtgcaac atggaacagc agggagtgga    1200
ataccagcac aactcacagc tgcttcctgt tcctcgtccc tgttttcagg aatgtttctt    1260
agcaggaagt tttttaatag accgagaatt tgttatatgt attctaagaa aagttgtagt    1320
tgtagatgca ttactctccc aaatcttaga gatcagggat gattatgttc cattttttgtt   1380
```

| | |
|---|---|
| tggtgagttc ccatctttgt atgtacctcc ttgctcccgg ctgtcctcct ctcctcttcc | 1440 |
| ctagtgagtg gttaatgagt gttaatgcct aaaccatact tgttttatgg acacttctat | 1500 |
| aatggattcg ttgcataatt ttcatgcagt gtatagtgtt actagttgga aattcttgga | 1560 |
| ggactcttag ctgtctgatg aaattcctag tagaaatttt tgttttgaat tcctaaagtt | 1620 |
| gaaatatgaa aattatattt taatttgatt c | 1651 |

<210> SEQ ID NO 257
<211> LENGTH: 2511
<212> TYPE: DNA
<213> ORGANISM: Homo sapiens

<400> SEQUENCE: 257

| | |
|---|---|
| agttttctg gtagaaggcg gggttctcct cgtacgctgc ggagtctctg cggggtgtag | 60 |
| accggaatcc tgctgacggg cagagtggat cagggaggga gggtcgagac acggtggctg | 120 |
| caggtctgag acaaggctgc tccgaggtag tagctctctt gcctggaggt ggccattcat | 180 |
| tcctggagtg ctgctgagga gcgagggccc atctgggtc tctggaagtc ggtgcccagg | 240 |
| cctgaaggat agccccccctt gcgcttccct gggctgcggc cggccttctc agaacgaagg | 300 |
| gcgtccttcc accccgcggc gcaggtgacc gctgccatgg cttttcccca tcggccggac | 360 |
| gcccctgagc tgcctgactt ctccatgctg aagaggctgg ctcgagacca gctcatctat | 420 |
| ctgctggagc agcttcctgg aaaaaaggat ttattcattg aggcagatct catgagccct | 480 |
| ttggatcgaa ttgccaatgt ctccatcctg aagcaacacg aagtagacaa gctatacaag | 540 |
| gtggagaaca agccagccct cagctccaat gaacaattgt gcttcttggt cagaccccgc | 600 |
| atcaagaata tgcgatacat tgccagtctt gtcaatgctg acaaattggc tggccgaact | 660 |
| cgcaaataca agtgatctt cagccctcaa agttctatg cgtgtgagat ggtgcttgag | 720 |
| gaagagggaa tctatggaga tgtgagctgt gatgaatggg ccttctcttt gctgcctctt | 780 |
| gatgtggatc tgctgagcat ggaactacca gaattttca gggattactt tctggaagga | 840 |
| gatcagcgtt ggatcaacac tgtagctcag gccttacacc ttctcagcac tctctatgga | 900 |
| cccttttccaa actgctatgg aattggcagg tgcgccaaga tggcatatga attgtggagg | 960 |
| aacctggagg aggaggagga tggcgaaacc aagggccgaa ggccagagat tggacatatc | 1020 |
| tttctcttgg acagagatgt ggactttgtg acagcacttt gctcccaagt ggtttatgag | 1080 |
| ggcctagtag atgacacctt ccgcatcaag tgtgggagtg tcgactttgg cccagaagtc | 1140 |
| acatcctctg acaagagcct gaaggtgcta ctcaatgccg aggacaaggt gtttaatgag | 1200 |
| attcggaacg agcacttctc caatgtcttt ggcttcttga ccagaaggc ccggaacttg | 1260 |
| caggcccagt atgatcgccg gagaggcatg acattaagc agatgaagaa ttcgtgtcc | 1320 |
| caggagctca agggcctgaa acaggagcac cgcctgctga gtctccatat tggggcctgt | 1380 |
| gaatccatca tgaagaagaa aaccaagcag gatttccagg agctaatcaa gactgagcat | 1440 |
| gcactgctag aggggttcaa catccgggag agcaccagct acattgagga acacatagac | 1500 |
| cggcaggtgt cgcctataga aagcctgcgc ctcatgtgcc ttttgtccat cactgagaat | 1560 |
| ggtttgatcc ccaaggatta ccgatctctg aaaacagt atctgcagag ctatggccct | 1620 |
| gagcacctgc taaccttctc caatctgcga agagctgggc tcctaacgga gcaggccccc | 1680 |
| ggggacaccc tcacagccgt ggagagtaaa gtgagcaagc tggtgaccga caaggctgca | 1740 |
| ggaaagatta ctgatgcctt cagttctctg gccaagagga gcaattttcg tgccatcagc | 1800 |

| | |
|---|---|
| aaaaagctga atttgatccc acgtgtggac ggcgagtatg atctgaaagt gccccgagac | 1860 |
| atggcttacg tcttcagtgg tgcttatgtg cccctgagct gccgaatcat tgagcaggtg | 1920 |
| ctagagcggc gaagctggca gggccttgat gaggtggtac ggctgctcaa ctgcagtgac | 1980 |
| tttgcattca cagatatgac taaggaagac aaggcttcca gtgagtccct gcgcctcatc | 2040 |
| ttggtggtgt tcttgggtgg ttgtacattc tctgagatct cagccctccg gttcctgggc | 2100 |
| agagagaaag gctacaggtt catttttcctg acgacagcag tcacaaacag cgctcgcctt | 2160 |
| atggaggcca tgagtgaggt gaaagcctga tgttttttccc ggccagtgtt gacatcttcc | 2220 |
| ctgaacacat tcctcagtga gatgcaggca tctggcaccc agctgctata accaagtgtc | 2280 |
| caccaactac ctgctaagag ccgggagcat ggaacgtgtt gggatttaga aacattatc | 2340 |
| tgagaaaaga gttcacttcc tgctcccagg atatttctct tttctgttta tgaagtacaa | 2400 |
| cccatgctgc taagatgcga gcaggaagag gcatcctttg ctaaatcctg tttgaatgtc | 2460 |
| attgtaaata aagcctctgc tctcagatgt aaaaaaaaaa aaaaaaaaa a | 2511 |

<210> SEQ ID NO 258
<211> LENGTH: 2401
<212> TYPE: DNA
<213> ORGANISM: Homo sapiens

<400> SEQUENCE: 258

| | |
|---|---|
| ggcacgaggg gtcgcgctgc cgccgtttta tttgaagaca tcgtccagtt ctgaccatgg | 60 |
| actcgcagcc atcggccctt agtttccatc ccctctagtg ggccttcggg ggctctactg | 120 |
| acgtccctcc ttcccttggt accgggccgg ggaagtgttc tcgggcgcgg gaggttccgc | 180 |
| atgcccaggc ctggccaggg gagatgaccg atccgtcgct ggggctgaca gtccccatgg | 240 |
| cgccgcctct ggccccgctc cctccccggg acccaaacgg ggcgggatcc gagtggagaa | 300 |
| agcccggggc cgtgagcttc gccgacgtgg ccgtgtactt ctcccgggag gagtggggct | 360 |
| gcctgcggcc cgcgcagagg gccctgtacc gggacgtgat gcgggagacc tacgccacc | 420 |
| tgggcgcgct cggtgagagc cccacctgct tgcctgggcc ctgcgcctcc acaggccctg | 480 |
| ccgcgcctct gggagctgcg tgtggagttg ggggccccgg ggccgggcag gcggcctcct | 540 |
| cgcagcgtgg ggtttgcgtt cttctccccc aggagtcgga ggcagcaagc cggcgctcat | 600 |
| ctcctgggtg gaggagaagg ccgaactgtg ggatccggct gcccaggatc cggaggtggc | 660 |
| gaagtgtccg acagaagcgg acccagcaga ttccagaaac aaggaagagg aaagacaaag | 720 |
| ggaagggacg ggagccctgg agaagcccga ccctgtggcc gccgggtctc ctgggctgaa | 780 |
| ggctccccaa gccccctttg ccgggttgga gcagctgtcc aaggcccggc gccggagtcg | 840 |
| ccccccgcttt tttgcccacc cccctgtccc ccgagctgac cagcgtcacg gctgctacgt | 900 |
| gtgcgggaag agcttcgcct ggcgctccac actggtggag cacatttaca gccacagggg | 960 |
| cgagaagccc ttccactgcg cagactgcg caagggcttc ggccacgctt cctccctgag | 1020 |
| caaacaccgg gccatccatc gtggggagcg gccccaccgc tgtcccgagt gtggtcgggc | 1080 |
| cttcatgcgc cgcacggcgc tgacttctca cctgcgcgtt cacactggcg agaagcccta | 1140 |
| ccgctgcccg cagtgtggcc gctgcttcgg cctgaagacc ggcatggcca agcaccaatg | 1200 |
| ggtccatcgg cccgggggcg aggggcgtag gggccggcgc cctgggggc tgtctgtgac | 1260 |
| cctgactcct gtccgcgggg acctggaccc gcctgtgggc ttccagctgt atccagagat | 1320 |
| attccaggaa tgtgggtgac ggcctaaaaa gtgaccatct agacattgtg gcggccga | 1380 |
| gatgggctca ggggccccgaa cctctgcagc ggcctgcagg gaggtcccag aatccaccgc | 1440 |

```
aagagctggc ctggggtgcg gacagtctga tcttgggctc tcagcagcct cttctgccag    1500
caccttgctc cccgctgccc tgggctctcc aaggcccct  ttgctgaggc agggctgagg    1560
tgagaacccc ccagacctcc atacagggaa gcaaaagctg tttctcctcc cagagatgct    1620
aagaggattg aggtagagaa gaaccttgtt ttctctgttg tcttttctt  tttacttttt    1680 taatttttg  agacggagtt ttgctcttgt tgcccaggct ggagtgcaat ggtgcgatct    1740
cgactcactg caacttccac ctcctggagt caagcgattc tcctgcctca gcacccaag    1800 tagctggaat tacaggcacc tgccactatg cccggctaac ttttgtatt  tttagtagag    1860 atggggtttc accatgttgg ctaggctggt ctcgaactcc tgccctcagg tgatccaccc    1920
acctctgcct cccaaagtgc tgggattaca ggcgtgagcc acctcacctg gccttttctt    1980
ttttattctt tgaccttccc acaagacaat cccattgtc  tgtttttttt gtttatttat    2040
ttacttatta agacagcatc ttgctcctca cccaggctgg aatgcagtgg tgtgaactgg    2100
gctcactgca gcctagacct gctgggctca aggaatcctc ctgccccagc ctctcagatg    2160
gctgtgacta caggtgggca acactatgcc tggttaattt ttaaattttt ttgcagagat    2220
ggggttccca ctatgttgat caggctggtc tcaaactcct cggttcaagc aattcgccca    2280
ccttggcctc ccaaagtgct gggattacag gggagccact gcactggcct tcattgtctt    2340
tttgctgcac aacctaaaaa accagtgacc ctgtattgga aaaaaaaaa  aaaaaaaaa     2400 a                                                                    2401

<210> SEQ ID NO 259
<211> LENGTH: 2384
<212> TYPE: DNA
<213> ORGANISM: Homo sapiens

<400> SEQUENCE: 259
gccatggccg ccggccccgc gccgccccc  ggccgcccc  gggcgcagat gccgcatctg     60
aggaaggtgc gaggcggatg gagcgggtgg tcgtgagcat gcaggacccc gaccagggcg    120
tgaagatgcg gagccagcgc ctgctggtca ccgtcattcc ccacgcggtg acaggcagcg    180
acgtcgtgca gtggttggcc cagaagttct gcgtctcgga ggaggaggcc ctgcacctgg    240
gcgccgtcct ggtgcagcat ggctacatct acccgctgcg cgaccccgt  agcctcatgc    300 tccggccaga cgagacgccc tacaggttcc agacccgta  cttctggaca agtaccctga    360
ggccggctgc agagctggac tatgccatct acctggccaa gaagaacatc cgaaaacggg    420
ggaccctggt ggattatgag aaggactgct atgaccggct acacaagaag atcaaccacg    480
catgggacct ggtgctgatg caggcgaggg agcagctgag ggcagccaag cagcgcagca    540
agggggacag gctggtcatt gcgtgccagg agcagaccta ctggctggtg aacaggcccc    600
cgcccggggc ccccgatgtg ctggagcagg gtccagggcg gggatcctgc gctgccagcc    660
gtgtgctcat gaccaagagt gcagatttcc ataagcggga gatcgagtac ttcaggaaag    720
cgctgggcag gacccgagtg aagtcctccg tctgccttga ggcgtacctg agtttctgcg    780
gccagcgtgg accccacgat cccctcgtgt cggggtgcct gccagcaat  ccctggatct    840 cagacaatga cgcctactgg gtcatgaatg ccccacggt  ggctgccccc acgaagctcc    900
gtgtggagag atggggcttc agcttccggg agctcctgga ggaccccgtg ggcgggccc    960 acttcatgga ctttctggga aaggagttca gtggagaaaa cctcagcttc tgggaggcat   1020
gtgaggagct tcgatatgga gcgcaggccc aggtccccac cctggtggat gccgtgtacg   1080
```

```
agcagttcct ggcccccgga gctgcccact gggtcaacat cgacagccgg accatggagc    1140
agaccctgga ggggctgcgc cagccccacc gctatgtcct ggatgacgcc cagctgcaca    1200
tatacatgct catgaagaag gactcctacc caaggttcct gaagtctgac atgtacaagg    1260
ccctcctggc agaggctggg atcccgctgg agatgaagag acgcgtgttc ccgtttacgt    1320
ggaggccacg gcactcgagc cccagccctg cactccttcc cacccctgtg gagcccacag    1380
cggcttgtgg ccctggggt ggagatgggg tggcctagtg gacctggccc atctgccact    1440
ctagtccctg cagctcaacg tcctgcgtga atgcagcagc caccccgtc ttggcccagg    1500 tcctgggggc tgctgaaccc agcaccagtg tccccttgtg cccaggggc ccagtcttct    1560 gtggggtgca cagcctccct ccctccagca agccctccct gcccagaagg aatgggtcca    1620
ggtgtggatt cccagggagg gggttcattg gctcagcttg ggtcagggca gagcctgtta    1680
cctgaagaga ggtgagacca aggccacagg gagctccacc ttctctggtc ttcagtccag    1740
cactgggtgc ccatcccat ctctaaaacc agtaaatcag ccagcgaata cccggaagca    1800
agatgcacag gcgggcggct tcccacacac ccgtcacaag acgcggacat gcaggtctcg    1860
gcgcgagctc tgccccgtcc aagagcctct ccgctgtcgc ccagtgtgag cctggaagag    1920
gacccaagag agtgccgtgc tgaggctgcc tcgaggtcac tgccttccgg agctgcgcct    1980
attcctccct cgccaaacgc gttccagaat ttgtccacag gtgcgccggc acctgctttc    2040
ccacctcgag gccgcggcct cccccccgat ttatagacaa ctctgacatt gtcaccccac    2100
tgacgaggcc cgattccata gggtggatcc ttgccaggcg tccctgatcc tccctgccca    2160
agtcttcctt cgtgagctgg ccttgctccc catcccccaa gtgcctcacc agtccccag    2220 actgggtgaa ggtacagctg gctccttcg ggggtgcagc ttcaactctc tcggcggtag    2280
ggcggtgcca tccccaccca tagggctggc tcacatccag tcactcccaa cagcgtccag    2340
cacacaaata aaagacccctt gggccctggc tctgagaaaa aaaa    2384
```

<210> SEQ ID NO 260
<211> LENGTH: 1500
<212> TYPE: DNA
<213> ORGANISM: Homo sapiens

<400> SEQUENCE: 260

```
agactgccga gcagccttga gccgttgagc agctgaacag aggccatgcc ggggcactcc      60
gaggcctgag acgaccacgc ctgtgccgct gaggaccttc atcagggctc cgtccacttg     120
gcccgcttgg ctgtccaatc acactccagt gtcaaccact ggcacccagc agccaagaga     180
ggtgtggcgt ggccctgggg acgcatggct gaggcaggaa caggtgagcc gtcccccagc     240
gtggagggcg aacacgggac ggagtatgac acgctgcctt ccgacacagt ctccctcagt     300
gactcggact ctgacctcag cttgcccggt ggtgctgaag tggaagcact gtccccgatg     360
gggctgcctg ggaggagga ttcaggtcct gatgagccgc cctcacccc gtcaggcctc     420 ctcccagcca cggtgcagcc attccatctg agaggcatga gctccacctt ctcccagcgc     480
agccgtgaca tctttgactg cctggagggg cggccagac gggctccatc ctctgtggcc     540
cacaccagca tgagtgacaa cggaggcttc aagcggcccc tagcgccctc aggccggtct     600
ccagtggaag gcctgggcag ggccatcgg agccctgcct caccaagggt gcctccggtc     660
cccgactacg tggcacaccc cgagcgctgg accaagtaca gcctggaaga tgtgaccgag     720
gtcagcgagc agagcaatca ggccaccgcc ctggccttcc tgggctccca gagcctggct     780
gcccccactg actgcgtgtc ctccttcaac caggatccct ccagctgtgg ggaggggagg    840
```

```
gtcatcttca ccaaaccagt ccgaggggtc gaagccagac acgagaggaa gagggtcctg      900
gggaaggtgg gagagccagg caggggcggc cttgggaatc ctgccacaga caggggcgag      960
ggccctgtgg agctggccca tctggccggg cccggagcc cagaggctga ggagtggggc      1020
agcccccatg gaggcctgca ggaggtggag gcactgtcag ggtctgtcca cagtgggtct     1080
gtgccaggtc tcccgccggt ggaaactgtt ggcttccatg gcagcaggaa gcggagtcga     1140
gaccacttcc ggaacaagag cagcagcccc gaggacccag gtgctgaggt ctgagaggga     1200
gatggcccag cctgacccca ctggccactg ccatcctgct gccttcccag tggggctggt     1260 caggggggcag cctggccact gcctagctgg aatgggagga agcctgcagg tggcaccggt    1320
ggccctggct gcagttctgg gcagcatcct cccaagcaga gaccttgctg aagctcctgg     1380
ggtgtggggt gtgggctgga agcactggct ccctggtagg gacaataaag gttttgggtc     1440
tttcaaaaaa aaaaaaaaaa aaaaaaaaaa aaaaaaaaaa aaaaaaaaaa aaaaaaaaac     1500

<210> SEQ ID NO 261
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 261
tcatcttcac caaaccagtc cgagggggtcg aagccagaca cgagaggaag agggtcctgg     60

<210> SEQ ID NO 262
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 262
ctctgctcct gctcctgcct gcatgttctc tctgttgttg gagcctggag ccttgctctc     60

<210> SEQ ID NO 263
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 263
tgctcccggc tgtcctcctc tcctcttccc tagtgagtgg ttaatgagtg ttaatgccta     60

<210> SEQ ID NO 264
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 264
ccccatctct aaaaccagta atcagccag cgaatacccg gaagcaagat gcacaggcgg      60

<210> SEQ ID NO 265
<211> LENGTH: 60
<212> TYPE: DNA
<213> ORGANISM: Artificial Sequence
<220> FEATURE:
<223> OTHER INFORMATION: Synthetic construct - oligonucleotide
```

```
<400> SEQUENCE: 265
ccagaaacaa ggaagaggaa agacaaaggg aagggacggg agccctggag aagcccgacc    60

<210> SEQ ID NO 266
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 266
aagtacaacc catgctgcta agatgcgagc aggaagaggc atcctttgct aaatcctgtt    60

<210> SEQ ID NO 267
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 267
acctcacccc tgcccggccc aagctctact tgtgtacagt gtatattgta taatagacaa    60

<210> SEQ ID NO 268
<211> LENGTH: 60
<212> TYPE: DNA
<213> ORGANISM: Artificial Sequence
<220> FEATURE:
<223> OTHER INFORMATION: Synthetic construct - oligonucleotide

<400> SEQUENCE: 268
ttcccttaat tcctcctccc gaccttttt accccccag ttgcagtatt taactgggct     60
```

IDENTIFICATION OF TUMORS

RELATED APPLICATIONS

This application is a continuation of U.S. patent application Ser. No. 11/145,307, filed Jun. 3, 2005, which claims benefit of priority from U.S. Provisional Patent Application 60/577,084, filed Jun. 4, 2004,the content of each of which is incorporated herein by reference in its entirety.

FIELD OF THE INVENTION

This invention relates to the use of gene expression to classify human tumors. The classification is performed by use of gene expression profiles, or patterns, of 50 or more expressed sequences that are correlated with tumors arising from certain tissues as well as being correlated with certain tumor types. The invention also provides for the use of 50 or more specific gene sequences, the expression of which are correlated with tissue source and tumor type in various cancers. The gene expression profiles, whether embodied in nucleic acid expression, protein expression, or other expression formats, may be used to determine a cell containing sample as containing tumor cells of a tissue type or from a tissue origin to permit a more accurate identification of the cancer and thus treatment thereof as well as the prognosis of the subject from whom the sample was obtained.

SUMMARY OF THE INVENTION

This invention relates to the use of gene expression measurements to classify or identify tumors in cell containing samples obtained from a subject in a clinical setting, such as in cases of formalin fixed, paraffin embedded (FFPE) samples. The invention provides the ability to classify tumors in the real-world conditions faced by hospital and other laboratories which have to conduct testing on clinical FFPE samples. The invention may also be applied to other samples, such as fresh samples, that have undergone none to little or minimal treatment (such as simply storage at a reduced, non-freezing, temperature), and frozen samples. The samples may be of a primary tumor sample or of a tumor that has resulted from a metastasis of another tumor. Alternatively, the sample may be a cytological sample, such as, but not limited to, cells in a blood sample. In some cases of a tumor sample, the tumors may not have undergone classification by traditional pathology techniques, may have been initially classified but confirmation is desired, or have been classified as a "carcinoma of unknown primary" (CUP) or "tumor of unknown origin" (TUO) or "unknown primary tumor". The need for confirmation is particularly relevant in light of the estimates of 5 to 10% misclassification using standard techniques. Thus the invention may be viewed as providing means for cancer identification, or CID.

In a first aspect of the invention, the classification is performed by use of gene expression profiles, or patterns, of 50 or more expressed sequences. The gene expression profiles, whether embodied in nucleic acid expression, protein expression, or other markers of gene expression, may be used to determine a cell containing sample as containing tumor cells of a tissue type or from a tissue origin to permit a more accurate identification of the cancer and thus treatment thereof as well as the prognosis of the subject from whom the sample was obtained.

In some embodiments, the invention is used to classify among at least 34 or at least 39 tumor types with significant accuracy in a clinical setting. The invention is based in part on the surprising and unexpected discovery that 50 or more expressed sequences in the human genome are capable of classifying among at least 34, or at least 39, tumor types, as well as subsets of those tumor types, in a meaningful manner. Stated differently, the invention is based in part on the discovery that it is not necessary to use supervised learning to identify gene sequences which are expressed in correlation with different tumor types. Thus the invention is based in part on the recognition that any 50 or more expressed sequences, even a random collection of expressed sequences, has the capability to classify, and so may be used to classify, a cell as being a tumor cell of a tissue or tissue origin.

In another aspect, the invention provides for the classifying of a cell containing sample as containing a tumor cell of a tissue type or origin by determining the expression levels of 50 or more transcribed sequences and then classifying the cell containing sample as containing a tumor cell of a plurality (two or more) of tumor types. To classify among at least 34 to at least 39 tumor types, and subsets thereof, as few as any 50 expressed sequences may be used to provide classification in a meaningful manner. The invention is also based in part on the observation that the expressed sequences need not be those the expression levels of which are evidently or highly correlated (directly, or indirectly through correlation with another expressed sequence) with any of the tumor types. Thus the invention provides, in a further embodiment, for the use of the expression levels of genes, the expression levels of which are not strongly correlated with the actual classification of the particular tumor sample, as one of the 50 or more transcribed sequences. All of the genes selected may be such non-correlates, or only a portion of the genes may be non-correlates, typically at least 90%, 85%, 75%, 50% or 25%, as well as portions falling within the ranges created by using any two of the foregoing point examples as endpoints of a range.

The invention is practiced by determining the expression levels of gene sequences where the sequences need not have been selected based on a correlation of their expression levels with the tumor types to be classified. Thus as a non-limiting example, the gene sequences need not be selected based on their correlation values with tumor types or a ranking based on the correlation values. Additionally, the invention may be practice with use of gene expression levels which are not necessarily correlated to one or more other gene expression level(s) used for classification. Thus in additional embodiments, the ability for the expression level of one expressed sequence to function in classification is not redundant with (is independent of) the ability of at least one other gene expression level used for classification.

The invention may be applied to identify the origin of a cancer in a patient in a wide variety of cases including, but not limited to, identification of the origin of a cancer in a clinical setting. In some embodiments, the identification is made by classification of a cell containing sample known to contain cancer cells, but the origin of those cells is unknown. In other embodiments, the identification is made by classification of a cell containing sample as containing one or more cancer cells followed by identification of the origin(s) of those cancer cell(s). In further embodiments, the invention is practiced with a sample from a subject with a previous history of cancer, and identification is made by classification of a cell as either being cancer from a previous origin of cancer or a new origin. Additional embodiments include those where multiple cancers found in the same organ or tissue and the invention is used to determine the origin of each cancer, as well as whether the cancers are of the same origin.

The invention is also based in part on the discovery that the expression levels of particular gene sequences can be used to classify among tumor types with greater accuracy than the expression levels of a random group of gene sequences. In one embodiment, the invention provides for the use of expression levels of 50 to 74 expressed sequences of a first set in the human genome to classify among at least 34 or at least 39 tumor types with significant accuracy. The invention thus provides for the identification and use of gene expression patterns (or profiles or "signatures") based on the 50 to 74 expressed sequences as correlated with at least the 34 or 39 tumor types. The invention also provides for the use of 50 to 74 of these expressed sequences to classify among subsets of the 34 or 39 tumor types. Depending on the number of tumor types, accuracies ranging from over 80% to 100% may be achieved.

In another embodiment, the invention provides for the use of expression levels of 50 to 90 expressed sequences of a second set in the human genome to classify among at least 34 or at least 39 tumor types with significant accuracy. 38 of the sequences in the second set are present in the first set of 74 sequences. The expression levels of the 50 to 90 sequences in the second set may be used in the same manner as described for the first set of 74 sequences. Depending on the number of tumor types, accuracies ranging from about 75% to about 95% may be achieved.

The invention is also based in part upon the discovery that use of 50 or more expressed sequences to classify among 53 tumor types, which include (but are not limited to) the 34 and 39 types described herein, was limited by the number of available samples of some tumor types. As noted hereinbelow, accuracy is linked to the number of available samples of each tumor type such that the ability to classify additional tumor types is readily achieved by the application of increased numbers of each tumor type. Thus while the invention is exemplified by use in classifying among 34 or 39 tumor types as well as subsets of the 34 or 39, 50 or more expressed sequences can also be used to classify among all tumor types with the inclusion of samples of the additional tumor types. Thus the invention also provides for the classification of a tumor as being a type beyond the 34 or 39 types described herein.

The invention is based upon the expression levels of the gene sequences in a set of known tumor cells from different tissues and of different tumor types. These gene expression profiles (of gene sequences in the different known tumor cells/types), whether embodied in nucleic acid expression, protein expression, or other expression formats, may be compared to the expression levels of the same sequences in an unknown tumor sample to identify the sample as containing a tumor of a particular type and/or a particular origin or cell type. The invention provides, such as in a clinical setting, the advantages of a more accurate identification of a cancer and thus the treatment thereof as well as the prognosis, including survival and/or likelihood of cancer recurrence following treatment, of the subject from whom the sample was obtained.

The invention is further based in part on the discovery that use of 50 or more expressed sequences as described herein as capable of classifying among two or more tumor types necessarily and effectively eliminates one or more tumor types from consideration during classification. This reflects the lack of a need to select genes with expression levels that are highly correlated with all tumor types within the range of the classification system. Stated differently, the invention may be practiced with a plurality of genes the expression levels of which are not highly correlated with any of the individual tumor types or multiple types in the group of tumor types being classified. This is in contrast to other approaches based upon the selection and use of highly correlated genes, which likely do not "rule out" other tumor types as opposed to "rule in" a tumor type based on the positive correlation.

The classification of a tumor sample as being one of the possible tumor types described herein to the exclusion of other tumor types is of course made based upon a level of confidence as described below. Where the level of confidence is low, or an increase in the level of confidence is preferred, the classification can simply be made at the level of a particular tissue origin or cell type for the tumor in the sample. Alternatively, and where a tumor sample is not readily classified as a single tumor type, the invention permits the classification of the sample as one of a few possible tumor types described herein. This advantageously provides for the ability to reduce the number of possible tissue types, cell types, and tumor types from which to consider for selection and administration of therapy to the patient from whom the sample was obtained.

The invention thus provides a non-subjective means for the identification of the tissue source and/or tumor type of one or more cancers of an afflicted subject. Where subjective interpretation may have been previously used to determine the tissue source and/or tumor type, as well as the prognosis and/or treatment of the cancer based on that determination, the present invention provides objective gene expression patterns, which may used alone or in combination with subjective criteria to provide a more accurate identification of cancer classification. The invention is particularly advantageously applied to samples of secondary or metastasized tumors, but any cell containing sample (including a primary tumor sample) for which the tissue source and/or tumor type is preferably determined by objective criteria may also be used with the invention. Of course the ultimate determination of class may be made based upon a combination of objective and non-objective (or subjective/partially subjective) criteria.

The invention includes its use as part of the clinical or medical care of a patient. Thus in addition to using an expression profile of genes as described herein to assay a cell containing sample from a subject afflicted with cancer to determine the tissue source and/or tumor type of the cancer, the profile may also be used as part of a method to determine the prognosis of the cancer in the subject. The classification of the tumor/cancer and/or the prognosis may be used to select or determine or alter the therapeutic treatment for said subject. Thus the classification methods of the invention may be directed toward the treatment of disease, which is diagnosed in whole or in part based upon the classification. Given the diagnosis, administration of an appropriate anti-tumor agent or therapy, or the withholding or alternation of an anti-tumor agent or therapy may be used to treat the cancer.

Other clinical methods include those involved in the providing of medical care to a patient based on a classification as described herein. In some embodiments, the methods relate to providing diagnostic services based on expression levels of gene sequences, with or without inclusion of an interpretation of levels for classifying cells of a sample. In some embodiments, the method of providing a diagnostic service of the invention is preceded by a determination of a need for the service. In other embodiments, the method includes acts in the monitoring of the performance of the service as well as acts in the request or receipt of reimbursement for the performance of the service.

The details of one or more embodiments of the invention are set forth in the accompanying drawing and the description below. Other features and advantages of the invention will be apparent from the drawing and detailed description, and from the claims.

Definitions

As used herein, a "gene" is a polynucleotide that encodes a discrete product, whether RNA or proteinaceous in nature. It is appreciated that more than one polynucleotide may be capable of encoding a discrete product. The term includes alleles and polymorphisms of a gene that encodes the same product, or a functionally associated (including gain, loss, or modulation of function) analog thereof, based upon chromosomal location and ability to recombine during normal mitosis.

A "sequence" or "gene sequence" as used herein is a nucleic acid molecule or polynucleotide composed of a discrete order of nucleotide bases. The term includes the ordering of bases that encodes a discrete product (i.e. "coding region"), whether RNA or proteinaceous in nature. It is appreciated that more than one polynucleotide may be capable of encoding a discrete product. It is also appreciated that alleles and polymorphisms of the human gene sequences may exist and may be used in the practice of the invention to identify the expression level(s) of the gene sequences or an allele or polymorphism thereof. Identification of an allele or polymorphism depends in part upon chromosomal location and ability to recombine during mitosis.

The terms "correlate" or "correlation" or equivalents thereof refer to an association between expression of one or more genes and another event, such as, but not limited to, physiological phenotype or characteristic, such as tumor type.

A "polynucleotide" is a polymeric form of nucleotides of any length, either ribonucleotides or deoxyribonucleotides. This term refers only to the primary structure of the molecule. Thus, this term includes double- and single-stranded DNA and RNA. It also includes known types of modifications including labels known in the art, methylation, "caps", substitution of one or more of the naturally occurring nucleotides with an analog, and internucleotide modifications such as uncharged linkages (e.g., phosphorothioates, phosphorodithioates, etc.), as well as unmodified forms of the polynucleotide.

The term "amplify" is used in the broad sense to mean creating an amplification product can be made enzymatically with DNA or RNA polymerases. "Amplification," as used herein, generally refers to the process of producing multiple copies of a desired sequence, particularly those of a sample. "Multiple copies" mean at least 2 copies. A "copy" does not necessarily mean perfect sequence complementarity or identity to the template sequence. Methods for amplifying mRNA are generally known in the art, and include reverse transcription PCR (RT-PCR) and quantitative PCR (or Q-PCR) or real time PCR. Alternatively, RNA may be directly labeled as the corresponding cDNA by methods known in the art.

By "corresponding", it is meant that a nucleic acid molecule shares a substantial amount of sequence identity with another nucleic acid molecule. Substantial amount means at least 95%, usually at least 98% and more usually at least 99%, and sequence identity is determined using the BLAST algorithm, as described in Altschul et al. (1990), J. Mol. Biol. 215:403-410 (using the published default setting, i.e. parameters w=4, t=17).

A "microarray" is a linear or two-dimensional or three dimensional (and solid phase) array of discrete regions, each having a defined area, formed on the surface of a solid support such as, but not limited to, glass, plastic, or synthetic membrane. The density of the discrete regions on a microarray is determined by the total numbers of immobilized polynucleotides to be detected on the surface of a single solid phase support, such as of at least about $50/cm^2$, at least about $100/cm^2$, or at least about $500/cm^2$, up to about $1,000/cm^2$ or higher. The arrays may contain less than about 500, about 1000, about 1500, about 2000, about 2500, or about 3000 immobilized polynucleotides in total. As used herein, a DNA microarray is an array of oligonucleotide or polynucleotide probes placed on a chip or other surfaces used to hybridize to amplified or cloned polynucleotides from a sample. Since the position of each particular group of probes in the array is known, the identities of a sample polynucleotides can be determined based on their binding to a particular position in the microarray. As an alternative to the use of a microarray, an array of any size may be used in the practice of the invention, including an arrangement of one or more position of a two-dimensional or three dimensional arrangement in a solid phase to detect expression of a single gene sequence. In some embodiments, a microarray for use with the present invention may be prepared by photolithographic techniques (such as synthesis of nucleic acid probes on the surface from the 3' end) or by nucleic synthesis followed by deposition on a solid surface.

Because the invention relies upon the identification of gene expression, some embodiments of the invention determine expression by hybridization of mRNA, or an amplified or cloned version thereof, of a sample cell to a polynucleotide that is unique to a particular gene sequence. Polynucleotides of this type contain at least about 16, at least about 18, at least about 20, at least about 22, at least about 24, at least about 26, at least about 28, at least about 30, or at least about 32 consecutive basepairs of a gene sequence that is not found in other gene sequences. The term "about" as used in the previous sentence refers to an increase or decrease of 1 from the stated numerical value. Other embodiments are polynucleotides of at least or about 50, at least or about 100, at least about or 150, at least or about 200, at least or about 250, at least or about 300, at least or about 350, at least or about 400, at least or about 450, or at least or about 500 consecutive bases of a sequence that is not found in other gene sequences. The term "about" as used in the preceding sentence refers to an increase or decrease of 10% from the stated numerical value. Longer polynucleotides may of course contain minor mismatches (e.g. via the presence of mutations) which do not affect hybridization to the nucleic acids of a sample. Such polynucleotides may also be referred to as polynucleotide probes that are capable of hybridizing to sequences of the genes, or unique portions thereof, described herein. Such polynucleotides may be labeled to assist in their detection. The sequences may be those of mRNA encoded by the genes, the corresponding cDNA to such mRNAs, and/or amplified versions of such sequences. In some embodiments of the invention, the polynucleotide probes are immobilized on an array, other solid support devices, or in individual spots that localize the probes.

In other embodiments of the invention, all or part of a gene sequence may be amplified and detected by methods such as the polymerase chain reaction (PCR) and variations thereof, such as, but not limited to, quantitative PCR (Q-PCR), reverse transcription PCR (RT-PCR), and real-time PCR (including as a means of measuring the initial amounts of mRNA copies for each sequence in a sample), optionally real-time RT-PCR or real-time Q-PCR. Such methods would utilize one or two primers that are complementary to portions of a gene sequence, where the primers are used to prime nucleic acid synthesis. The newly synthesized nucleic acids are optionally labeled and may be detected directly or by hybridization to a polynucleotide of the invention. The newly synthesized nucleic acids may be contacted with polynucleotides (containing sequences) of the invention under conditions which allow for their hybridization. Additional methods to detect the expression of expressed nucleic acids include RNAse protection assays, including liquid phase hybridizations, and in situ hybridization of cells.

Alternatively, and in further embodiments of the invention, gene expression may be determined by analysis of expressed protein in a cell sample of interest by use of one or more antibodies specific for one or more epitopes of individual gene products (proteins), or proteolytic fragments thereof, in said cell sample or in a bodily fluid of a subject. The cell sample may be one of breast cancer epithelial cells enriched from the blood of a subject, such as by use of labeled antibodies against cell surface markers followed by fluorescence activated cell sorting (FACS). Such antibodies may be labeled to permit their detection after binding to the gene product. Detection methodologies suitable for use in the practice of the invention include, but are not limited to, immunohistochemistry of cell containing samples or tissue, enzyme linked immunosorbent assays (ELISAs) including antibody sandwich assays of cell containing tissues or blood samples, mass spectroscopy, and immuno-PCR.

The terms "label" or "labeled" refer to a composition capable of producing a detectable signal indicative of the presence of the labeled molecule. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

The term "support" refers to conventional supports such as beads, particles, dipsticks, fibers, filters, membranes and silane or silicate supports such as glass slides.

"Expression" and "gene expression" include transcription and/or translation of nucleic acid material.

As used herein, the term "comprising" and its cognates are used in their inclusive sense; that is, equivalent to the term "including" and its corresponding cognates.

Conditions that "allow" an event to occur or conditions that are "suitable" for an event to occur, such as hybridization, strand extension, and the like, or "suitable" conditions are conditions that do not prevent such events from occurring. Thus, these conditions permit, enhance, facilitate, and/or are conducive to the event. Such conditions, known in the art and described herein, depend upon, for example, the nature of the nucleotide sequence, temperature, and buffer conditions. These conditions also depend on what event is desired, such as hybridization, cleavage, strand extension or transcription.

Sequence "mutation," as used herein, refers to any sequence alteration in the sequence of a gene disclosed herein interest in comparison to a reference sequence. A sequence mutation includes single nucleotide changes, or alterations of more than one nucleotide in a sequence, due to mechanisms such as substitution, deletion or insertion. Single nucleotide polymorphism (SNP) is also a sequence mutation as used herein. Because the present invention is based on the relative level of gene expression, mutations in non-coding regions of genes as disclosed herein may also be assayed in the practice of the invention.

"Detection" or "detecting" includes any means of detecting, including direct and indirect determination of the level of gene expression and changes therein.

Unless defined otherwise all technical and scientific terms used herein have the same meaning as commonly understood to one of ordinary skill in the art to which this invention belongs.

Figure 1:
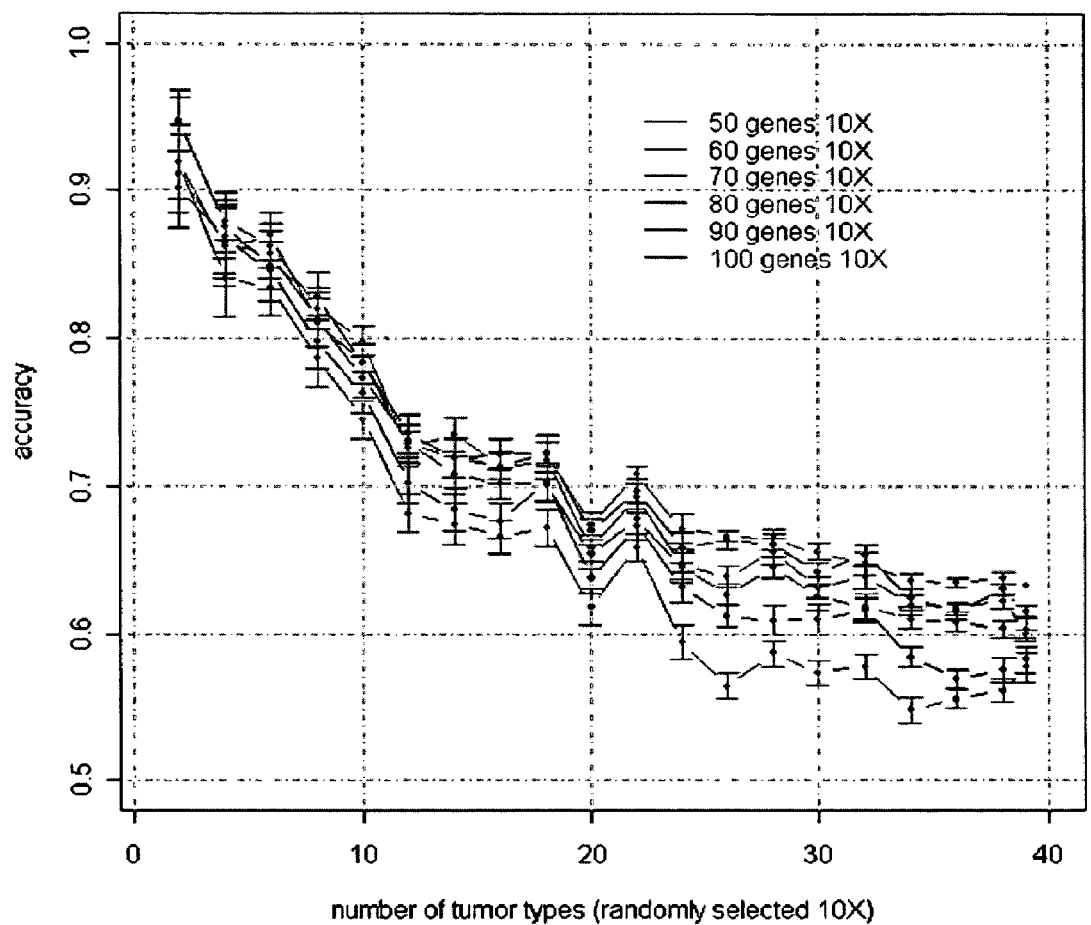
FIG. 1 shows a capacity plot for the ability to use the expression levels of subsets of a set of 100 expressed gene sequences to classify among 39 tumor types and subsets thereof. Expression levels of random combinations of 50, 55, 60, 65, 70, 75, 80, 85, 90, 95 and 100 (each sampled 10 times) of the 100 sequences were used with data from tumor types and then used to predict test random sets of tumor samples (each sampled 10 times) ranging from 2 to 39 types. A plot of numbers of tumor types versus prediction accuracies for results using from 50 to 100 genes are shown as non-limiting examples. Generally, accuracy improves with higher numbers of gene sequences, where 50 gene sequences results in a more noticeable reduction in accuracy when used with about 20 or more tumor types.

If the tumor is of a non-germ cell origin, then it is either of a epithelial or non-epithelial origin. If it is the former, then it is either squamous or non-squamous origin. Squamous origin tumors are of cervix, esophagus, larynx, lung, or skin in origin. Non-squamous origin tumors are of urinary bladder, breast, carcinoid-intestine, cholangiocarcinoma, digestive, kidney, liver, lung, prostate, reproductive system, skin-basal cell, or thyroid-follicular-papillary origin. Among those of digestive origin, the tumors are of small and large bowel, stomach-adenocarcinoma, bile duct, esophagus, gall bladder, and pancreas in origin. The esophagus origin tumors may be of either Barrett's esophagus or adenocarcinoma types. Of the reproductive system origin tumors, they may be of cervix adenocarcinoma type, endometrial tumor, or ovarian origin. Ovarian origin tumors are of the clear, serous, mucinous, and endometroid types.

If the tumor is of non-epithelial origin, then it is of adrenal gland, brain, GIST (gastrointestinal stromal tumor), lymphoma, meningioma, mesothelioma, sarcoma, skin melanoma, or thyroid-medullary origin. Of the lymphomas, they are B cell, Hodgkin's, or T cell type. Of the sarcomas, they are leimyosarcoma, osteosarcoma, soft-tissue sarcoma, soft tissue MFH (malignant fibrous histiocytoma), soft tissue sarcoma synovial, soft tissue Ewing's sarcoma, soft tissue fibrosarcoma, and soft tissue rhabdomyosarcoma types.

DETAILED DESCRIPTION OF MODES OF PRACTICING THE INVENTION

This invention provides methods for the use of gene expression information to classify tumors in a more objective manner than possible with conventional pathology techniques. The invention is based in part on the results of randomly reducing the number of gene sequences used to classify a tumor sample as one of a plurality of tumor types, such as the 34 tumor types described below and in U.S. Provisional Application 60/577,084, filed Jun. 4, 2004. A total number of 16,948 genes, which were filtered down from a larger set based upon removal of genes that display low or constant signals in the samples used was used for both cross-validation and prediction accuracies as described in the examples below. 100 random selections of 50, 100, 150, 200, 250, 300, 400, 500, 600, 700, 800, 900, 1000, 1200, 1400, 1600, 1800, 2000, 2200, 2400, 2600, 2800, 3000 and more genes from the total were selected and used for classification as described herein.

Thus in a first aspect, the invention provides a method of classifying a cell containing sample as including a tumor cell of (or from) a type of tissue or a tissue origin. The method comprises determining or measuring the expression levels of 50 or more transcribed sequences from cells in a cell containing sample obtained from a subject, and classifying the sample as containing tumor cells of a type of tissue from a plurality of tumor types based on the expression levels of said sequences. As used herein, "a plurality" refers to the state of two or more.

In some embodiments of the invention, the expression of more than 50% of said transcribes sequences are not correlated with expression of another one of said transcribed sequences; and/or the 50 or more transcribes sequences are not selected based upon supervised learning using known tumor samples, on the level of correlation between their expression and said plurality of tumor types, or on their rank in a correlation between their expression and said plurality of tumor types.

The classifying is based upon a comparison of the expression levels of the 50 or more transcribed sequences in the cells of the sample to their expression levels in known tumor samples and/or known non-tumor samples. Alternatively, the classifying is based upon a comparison of the expression levels of the 50 or more transcribed sequences to the expression of reference sequences in the same samples, relative to, or based on, the same comparison in known tumor samples and/or known non-tumor samples. Thus as a non-limiting example, the expression levels of the gene sequences may be determined in a set of known tumor samples to provide a database against which the expression levels detected or determined in a cell containing sample from a subject is compared. The expression level(s) of gene sequence(s) in a sample also may be compared to the expression level(s) of said sequence(s) in normal or non-cancerous cells, preferably from the same sample or subject. As described below and in embodiments of the invention utilizing Q-PCR or real time Q-PCR, the expression levels may be compared to expression levels of reference genes in the same sample or a ratio of expression levels may be used.

The selection of 50 or more gene sequences to use may be random, or by selection based on various criteria. As one non-limiting example, the gene sequences may be selected based upon unsupervised learning, including clustering techniques. As another non-limiting example, selection may be to reduce or remove redundancy with respect to their ability to classify tumor type. For example, gene sequences are selected based upon the lack of correlation between their expression and the expression of one or more other gene sequences used for classifying. This is accomplished by assessing the expression level of each gene sequence in the expression data set for correlation, across the plurality of samples, with the expression level of each other gene in the data set to produce a correlation matrix of correlation coefficients. These correlation determinations may be performed directly, between expression of each pair of gene sequences, or indirectly, without direct comparison between the expression values of each pair of gene sequences.

A variety of correlation methodologies may be used in the correlation of expression data of individual gene sequences within the data set. Non-limiting examples include parametric and non-parametric methods as well as methodologies based on mutual information and non-linear approaches.

Non-limiting examples of parametric approaches include Pearson correlation (or Pearson r, also referred to as linear or product-moment correlation) and cosine correlation. Non-limiting examples of non-parametric methods include Spearman's R (or rank-order) correlation, Kendall's Tau correlation, and the Gamma statistic. Each correlation methodology can be used to determine the level of correlation between the expressions of individual gene sequences in the data set. The correlation of all sequences with all other sequences is most readily considered as a matrix. Using Pearson's correlation as a non-limiting example, the correlation coefficient r in the method is used as the indicator of the level of correlation. When other correlation methods are used, the correlation coefficient analogous to r may be used, along with the recognition of equivalent levels of correlation corresponding to r being at or about 0.25 to being at or about 0.5.

The correlation coefficient may be selected as desired to reduce the number of correlated gene sequences to various numbers. In some embodiments of the invention using r, the selected coefficient value may be of about 0.25 or higher, about 0.3 or higher, about 0.35 or higher, about 0.4 or higher, about 0.45 or higher, or about 0.5 or higher. The selection of a coefficient value means that where expression between gene sequences in the data set is correlated at that value or higher, they are possibly not included in a subset of the invention. Thus in some embodiments, the method comprises excluding or removing (not using for classification) one or more gene sequences that are expressed in correlation, above a desired correlation coefficient, with another gene sequence in the tumor type data set. It is pointed out, however, that there can be situations of gene sequences that are not correlated with any other gene sequences, in which case they are not necessarily removed from use in classification.

Thus the expression levels of gene sequences, where more than about 10%, more than about 20%, more than about 30%, more than about 40%, more than about 50%, more than about 60%, more than about 70%, more than about 80%, or more than about 90% of the levels are not correlated with that of another one of the gene sequences used, may be used in the practice of the invention. Correlation between expression levels may be based upon a value below about 0.9, about 0.8, about 0.7, about 0.6, about 0.5, about 0.4, about 0.3, or about 0.2. The ability to classify among classes with exclusion of the expression levels of some gene sequences is present because expression of the gene sequences in the subset is correlated with expression of the gene sequences excluded from the subset. So no information was lost because information based on the expression of the excluded gene sequences is still represented by sequences retained in the subset. Therefore, expression of the gene sequences of the subset has information content relevant to properties and/or characteristics (or phenotype) of a cell. This has application and relevance to the classification of additional tumor type classes not included as part of the original gene expression data set which can be classified by use of a subset of the invention because based on the redundancy of information between expression of sequences in the subset and sequences expressed in those additional classes. Thus the invention may be used to classify cells as being a tumor type beyond the plurality of known classes used to generate the original gene expression data set.

Selection of gene sequences based upon reducing correlation of expression to a particular tumor type may also be used. This also reflects a discovery of the present invention, based upon the observation that expression levels that were most highly correlated with one or more tumor types was not necessarily of greatest value in classification among different tumor types. This is reflected both by the ability to use randomly selected gene sequences for classification as well as the use of particular sequences, as described herein, which are not expressed with the most significant correlation with one or more tumor types. Thus the invention may be practiced without selection of gene sequences based upon the most significant P values or a ranking based upon correlation of gene expression and one or more tumor types. Thus the invention may be practiced without the use of ranking based methodologies, such as the Kruskal-Wallis H-test.

The gene sequences used in the practice of the invention may include those which have been observed to be expressed in correlation with particular tumor types, such as expression of the estrogen receptor, which has been observed to be expressed in correlation with some breast and ovarian cancers. In some embodiments of the invention, however, the invention is practiced with use of the expression level of at least one gene sequence that has not been previously identified as being associated with any of the tumor types being classified. Thus the invention may be practiced without all of the gene sequences having previously been associated or correlated with expression in the 2 or more (up to 39 or more) tumor types to which a cell containing sample may be classified.

While the invention is described mainly with respect to human subjects, samples from other subjects may also be used. All that is necessary is the ability to assess the expression levels of gene sequences in a plurality of known tumor samples such that the expression levels in an unknown or test sample may be compared. Thus the invention may be applied to samples from any organism for which a plurality of expressed sequences, and a plurality of known tumor samples, are available. One non-limiting example is application of the invention to mouse samples, based upon the availability of the mouse genome to permit detection of expressed murine sequences and the availability of known mouse tumor samples or the ability to obtain known samples. Thus, the invention is contemplated for use with other samples, including those of mammals, primates, and animals used in clinical testing (such as rats, mice, rabbits, dogs, cats, and chimpanzees) as non-limiting examples.

While the invention is readily practiced with the use of cell containing samples, any nucleic acid containing sample which may be assayed for gene expression levels may be used in the practice of the invention. Without limiting the invention, a sample of the invention may be one that is suspected or known to contain tumor cells. Alternatively, a sample of the invention may be a "tumor sample" or "tumor containing sample" or "tumor cell containing sample" of tissue or fluid isolated from an individual suspected of being afflicted with, or at risk of developing, cancer. Non-limiting examples of samples for use with the invention include a clinical sample, such as, but not limited to, a fixed sample, a fresh sample, or a frozen sample. The sample may be an aspirate, a cytological sample (including blood or other bodily fluid), or a tissue specimen, which includes at least some information regarding the in situ context of cells in the specimen, so long as appropriate cells or nucleic acids are available for determination of gene expression levels. The invention is based in part on the discovery that results obtained with frozen tissue sections can be validly applied to the situation with fixed tissue or cell samples and extended to fresh samples.

Non-limiting examples of fixed samples include those that are fixed with formalin or formaldehyde (including FFPE samples), with Boudin's, glutaldehyde, acetone, alcohols, or any other fixative, such as those used to fix cell or tissue samples for immunohistochemistry (IHC). Other examples include fixatives that precipitate cell associated nucleic acids and proteins. Given possible complications in handling frozen tissue specimens, such as the need to maintain its frozen state, the invention may be practiced with non-frozen samples, such as fixed samples, fresh samples, including cells from blood or other bodily fluid or tissue, and minimally treated samples. In some applications of the invention, the sample has not been classified using standard pathology techniques, such as, but not limited to, immunohistochemistry based assays.

In some embodiments of the invention, the sample is classified as containing a tumor cell of a type selected from the following 53, and subsets thereof: Adenocarcinoma of Breast, Adenocarcinoma of Cervix, Adenocarcinoma of Esophagus, Adenocarcinoma of Gall Bladder, Adenocarcinoma of Lung, Adenocarcinoma of Pancreas, Adenocarcinoma of Small-Large Bowel, Adenocarcinoma of Stomach, Astrocytoma, Basal Cell Carcinoma of Skin, Cholangiocarcinoma of Liver, Clear Cell Adenocarcinoma of Ovary, Diffuse Large B-Cell Lymphoma, Embryonal Carcinoma of Testes, Endometrioid Carcinoma of Uterus, Ewings Sarcoma, Follicular Carcinoma of Thyroid, Gastrointestinal Stromal Tumor, Germ Cell Tumor of Ovary, Germ Cell Tumor of Testes, Glioblastoma Multiforme, Hepatocellular Carcinoma of Liver, Hodgkin's Lymphoma, Large Cell Carcinoma of Lung, Leiomyosarcoma, Liposarcoma, Lobular Carcinoma of Breast, Malignant Fibrous Histiocytoma, Medulary Carcinoma of Thyroid, Melanoma, Meningioma, Mesothelioma of Lung, Mucinous Adenocarcinoma of Ovary, Myofibrosarcoma, Neuroendocrine Tumor of Bowel, Oligodendroglioma, Osteosarcoma, Papillary Carcinoma of Thyroid, Pheochromocytoma, Renal Cell Carcinoma of Kidney, Rhabdomyosarcoma, Seminoma of Testes, Serous Adenocarcinoma of Ovary, Small Cell Carcinoma of Lung, Squamous Cell Carcinoma of Cervix, Squamous Cell Carcinoma of Esophagus, Squamous Cell Carcinoma of Larynx, Squamous Cell Carcinoma of Lung, Squamous Cell Carcinoma of Skin, Synovial Sarcoma, T-Cell Lymphoma, and Transitional Cell Carcinoma of Bladder.

In other embodiments of the invention, the sample is classified as containing a tumor cell of a type selected from the following 34, and subsets thereof: adrenal, brain, breast, carcinoid-intestine, cervix (squamous cell), cholangiocarcinoma, endometrium, germ-cell, GIST (gastrointestinal stromal tumor), kidney, leiomyosarcoma, liver, lung (adenocarcinoma, large cell), lung (small cell), lung (squamous), lymphoma (B cell), Lymphoma (Hodgkins), meningioma, mesothelioma, osteosarcoma, ovary (clear cell), ovary (serous cell), pancreas, prostate, skin (basal cell), skin (melanoma), small and large bowel; soft tissue (liposarcoma); soft tissue (MFH or Malignant Fibrous Histiocytoma), soft tissue (Sarcoma-synovial), testis (seminoma), thyroid (follicular-papillary), thyroid (medullary carcinoma), and urinary bladder.

In further embodiments of the invention, the sample is classified as containing a tumor cell of a type selected from the following 39, and subsets thereof: adrenal gland, brain, breast, carcinoid-intestine, cervix-adenocarcinoma, cervix-squamous, endometrium, gall bladder, germ cell-ovary, GIST, kidney, leiomyosarcoma, liver, lung-adenocarcinoma-large cell, lung-small cell, lung-squamous, lymphoma-B cell, lymphoma-Hodgkin's, lymphoma-T cell, meningioma, mesothelioma, osteosarcoma, ovary-clear cell, ovary-serous, pancreas, prostate, skin-basal cell, skin-melanoma, skin-squamous, small and large bowel, soft tissue-liposarcoma, soft tissue-MFH, soft tissue-sarcoma-synovial, stomach-adenocarcinoma, testis-other (or non-seminoma), testis-seminoma, thyroid-follicular-papillary, thyroid-medullary, and urinary bladder.

The methods of the invention may also be applied to classify a cell containing sample as containing a tumor cell of a tumor of a subset of any of the above sets. The size of the subset will usually be small, composed of two, three, four, five, six, seven, eight, nine, or ten of the tumor types described above. Alternatively, the size of the subset may be any integral number up to the full size of the set. Thus embodiments of the invention include classification among 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 of the above types. In some embodiments, the subset will be composed of tumor types that are of the same tissue or organ type. Alternatively, the subset will be composed of tumor types of different tissues or organs. In some embodiments, the subset will include one or more types selected from adrenal gland, brain, carcinoid-intestine, cervix-adenocarcinoma, cervix-squamous, gall bladder, germ cell-ovary, GIST, leiomyosarcoma, liver, meningioma, osteosarcoma, skin-basal cell, skin-squamous, soft tissue-liposarcoma, soft tissue-MFH, soft tissue-sarcoma-synovial, testis-other (or non-seminoma), testis-seminoma, thyroid-follicular-papillary, and thyroid-medullary.

Figure 2:
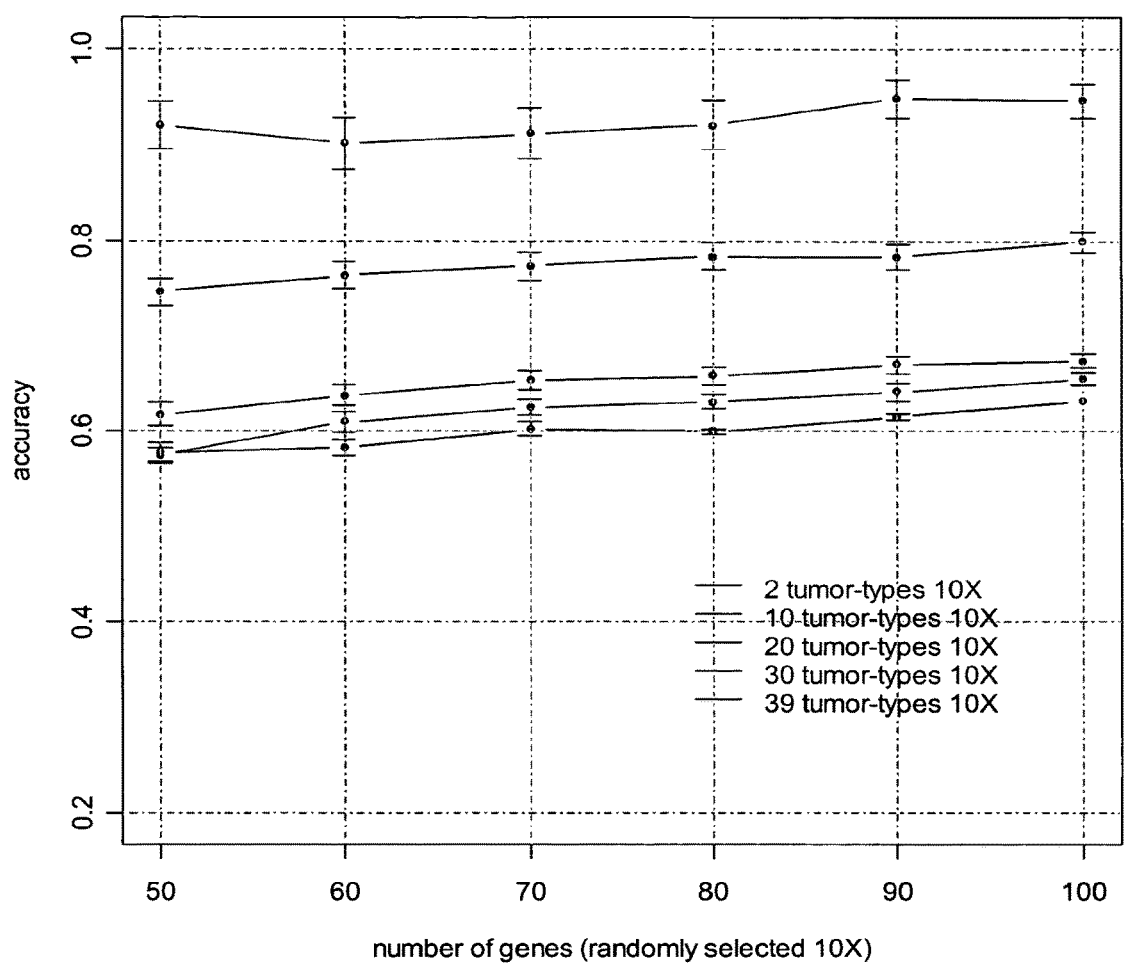
FIG. 2 shows an alternative presentation of the data used with respect to FIG. 1. A plot of numbers of gene sequences used, ranging from 50-100, versus prediction accuracies for various representative numbers of tumor types is shown. The plotted lines, from top to bottom, are of the results from 2, 10, 20, 30, and 39 tumor types, respectively.

Classification among subsets of the above tumor types is demonstrated by the results shown in FIGS. 1 and 2, where the expression levels of as few as 50 or more genes sequences can be used to classify among random samples of 2 tumor types among those in the set of 39 listed above. Expression levels of 50-100 gene sequences (that were randomly selected) can be used to classify among 2 to 39 tumor types with varying degrees of accuracy. The invention may be practiced with the expression levels of 50 or more, about 55 or more, about 60 or more, about 65 or more, about 70 or more, about 75 or more, about 80 or more, about 85 or more, about 90 or more, about 100 or more, about 110 or more, about 120 or more, about 130 or more, about 140 or more, about 150 or more, about 200 or more, about 250 or more, about 300 or more, about 350 or more, or about 400 or more transcribed sequences as found in the human "transcriptome" (transcribed portion of the genome). The invention may also be practiced with expression levels of 50-60 or more, about 60-70 or more, about 70-80 or more, about 80-90 or more, about 90-100 or more, about 100-110 or more, about 110-120 or more, about 120-130 or more, or about 130-140 or more transcribed sequences. In some embodiments of the invention, the transcribed genes may be randomly picked or include all or some of the specific genes sequences disclosed herein. As demonstrated herein, classification with accuracies of about 55%, about 60%, about 65%, about 70%, about 75%, about 80%, about 85%, about 90%, or about 95% or higher can be performed by use of the instant invention.

In other embodiments, the gene expression levels of other gene sequences may be determined along with the above described determinations of expression levels for use in classification. One non-limiting example of this is seen in the case of a microarray based platform to determine gene expression, where the expression of other gene sequences is also measured. Where those other expression levels are not used in classification, they may be considered the results of "excess" transcribed sequences and not critical to the practice of the invention. Alternatively, and where those other expression levels are used in classification, they are within the scope of the invention, where the description of using particular numbers of sequences does not necessarily exclude the use of expression levels of additional sequences. In some embodiments, the invention includes the use of expression level(s) from one or more "excess" gene sequences, such as those which may provide information redundant to one or more other gene sequences used in a method of the invention.

Because classification of a sample as containing cells of one of the above tumor types inherently also classifies the tissue or organ site origin of the sample, the methods of the invention may be applied to classification of a tumor sample as being of a particular tissue or organ site of the patient. This application of the invention is particularly useful in cases where the sample is of a tumor that is the result of metastasis by another tumor. In some embodiments of the invention, the tumor sample is classified as being one of the following 24: Adrenal, Bladder, Bone, Brain, Breast, Cervix, Endometrium, Esophagus, Gall Bladder, Kidney, Larynx, Liver, Lung, Lymph Node, Ovary, Pancreas, Prostate, Skin, Soft Tissue, Small/Large Bowel, Stomach, Testes, Thyroid, and Uterus.

While the invention also provides for classification as one of the above tumor types based upon comparisons to the expression levels of sequences in the 39 tumor types, it is possible that a higher level of confidence in the classification is desired. If an increase in the confidence of the classification is preferred, the classification can be adjusted to identify the tumor sample as being of a particular origin or cell type as shown in FIG. 8. Thus an increase in confidence can be made in exchange for a decrease in specificity as to tumor type by identification of origin or cell type.

The classification of a cell containing sample as having a tumor cell of one of the 39 tumor types above inherently also classifies the tissue or organ site origin of the sample. For example, the identification of a sample as being cervix-squamous necessarily classifies the tumor as being of cervical origin, squamous cell type (and thus epithelial rather than non-epithelial in origin) as shown in FIG. 8. It also means that the tumor was necessarily not germ cell in origin. Thus, the methods of the invention may be applied to classification of a tumor sample as being of a particular tissue or organ site of a subject or patient. This application of the invention is particularly useful in cases where the sample is of a tumor that is the result of metastasis by another tumor.

The practice of the invention to classify a cell containing sample as having a tumor cell of one of the above types is by use of an appropriate classification algorithm that utilizes supervised learning to accept 1) the levels of expression of the gene sequences in a plurality of known tumor types as a training set and 2) the levels of expression of the same genes in one or more cells of a sample to classify the sample as having cells of one of the tumor types. Further discussion of this is provided in the Example section herein. The levels of expression may be provided based upon the signals in any format, including nucleic acid expression or protein expression as described herein.

As would be evident to the skilled practitioner, the range of classification is affected by the number of tumor types as well as the number of samples for each tumor type. But given adequate samples of the full range of human tumors as provided herein, the invention is readily applied to the classification of those tumor types as well as additional types.

Non-limiting examples of classification algorithms that may be used in the practice of the invention include supervised learning algorithms, machine learning algorithms, linear discriminant analysis, attribute selection algorithms, and artificial neural networks (ANN). In preferred embodiments of the invention, a distance-based classification algorithm, such as the k-nearest neighbor (KNN) algorithm, or support vector machine (SVM) are used.

The use of KNN is in some embodiments of the invention and is discussed further as a non-limiting representative example. KNN can be used to analyze the expression data of the genes in a "training set" of known tumor samples including all 39 of the tumor types described herein. The training data set can then be compared to the expression data for the same genes in a cell containing sample. The expression levels of the genes in the sample are then compared to the training data set via KNN to identify those tumor samples with the most similar expression patterns. As a non-limiting example, the five "nearest neighbors" may be identified and the tumor types thereof used to classify the unknown tumor sample. Of course other numbers of "nearest neighbors" may be used. Non-limiting examples include less than 5, about 7, about 9, or about 11 or more "nearest neighbors".

As a hypothetical example, if the five "nearest neighbors" of an unknown sample are four B cell lymphomas and one T cell lymphoma, then the classification of the sample as being of a B cell lymphoma can be made with great accuracy. This has been used with 84% or greater accuracy, such as 90%, as described in the Examples.

The classification ability may be combined with the inherent nature of the classification scheme to provide a means to increase the confidence of tumor classification in certain situations. For example, if the five "nearest neighbors" of a sample are three ovary clear cell and two ovary serous tumors, confidence can be improved by simply treating the tumors as being of ovarian origin and treating the subject or patient (from whom the sample was obtained) accordingly. See FIG. 8. This is an example of trading off specificity in favor of increased confidence. This provides the added benefit of addressing the possibility that the unknown sample was a mucinous or endometroid tumor. Of course the skilled practitioner is free to treat the tumor as one or both of these two most likely possibilities and proceeding in accordance with that determination.

Because the developmental lineage of tumor cells in certain tumor types (e.g., germ cells) can be complex and involve multiple cell types, FIG. 8 may appear to be oversimplified. However, it serves as a good basis to relate known histopathology and to serve as a "guide tree" for analyzing and relating tumor-associated gene expression signatures.

The inherent nature of the classification scheme also provides a means to increase the confidence of tumor classification in cases wherein the "nearest neighbors" are ambiguous. For example, if the five "nearest neighbors" were one urinary bladder, one breast, one kidney, one liver, and one prostate, the classification can simply be that of a non-squamous cell tumor. Such a determination can be made with significant confidence and the subject or patient from whom the sample was obtained can be treated accordingly. Without being bound by theory, and offered solely to improve the understanding of the invention, the last two examples reflect the similarities in gene expression of cells of a similar cell type and/or tissue origin.

Embodiments of the invention include use of the methods and materials described herein to identify the origin of a cancer from a patient. Thus given a sample containing tumor cells, the tissue origin of the tumor cells is identified by use of the present invention. One non-limiting example is in the case of a subject with an inflamed lymph node containing cancer cells. The cells may be from a tissue or organ that drains into the lymph node or it may be from another tissue source. The present invention may be used to classify the cells as being of a particular tumor or tissue type (or origin) which allows the identification of the source of the cancer cells. In an alternative non-limiting example, the sample (such as that from a lymph node) contains cells, which are first assayed by use of the invention to classify at least one cell as being a tumor cell of a tissue type or origin. This is then used to identify the source of the cancer cells in the sample. Both of these are examples of the advantageous use of the invention to save time, effort, and cost in the use of other cancer diagnostic tests.

In further embodiments, the invention is practiced with a sample from a subject with a previous history of cancer. As a non-limiting example, a cell containing sample (from the lymph node or elsewhere) of the subject may be found to contain cancer cells such that the present invention may be used to determine whether the cells are from the same or a different tissue from that of the previous cancer. This application of the invention may also be used to identify a new primary tumor, such as the case where new cancer cells are found in the liver of a subject who previously had breast cancer. The invention may be used to identify the new cancer cells as being the result of metastasis from the previous breast cancer (or from another tumor type, whether previously identified or not) or as a new primary occurrence of liver cancer. The invention may also be applied to samples of a tissue or organ where multiple cancers are found to determine the origin of each cancer, as well as whether the cancers are of the same origin.

While the invention may be practiced with the use of expression levels of a random group of expressed gene sequences, the invention also provides exemplary gene sequences for use in the practice of the invention. The invention includes a first group of 74 gene sequences from which 50 or more may be used in the practice of the invention. The 50 to 74 gene sequences may be used along with the determination of expression levels of additional sequences so long as the expression levels of gene sequences from the set of 74 are used in classifying. A non-limiting example of such embodiments of the invention is where the expression of the 74 gene sequences, or at least 50 (or 50 to about 90) members thereof, is measured along with the expression levels of a plurality of other sequences, such as by use of a microarray based platform used to perform the invention. Where those other expression levels are not used in classification, they may be considered the results of "excess" transcribed sequences and not critical to the practice of the invention. Alternatively, and where those other expression levels are used in classification, they are within the scope of the invention, where the use of the above described sequences does not necessarily exclude the use of expression levels of additional sequences.

mRNA sequences corresponding to a set of 74 gene sequences for use in the practice of the invention are provided in the attached Sequence Listing. A listing of the SEQ ID NOs, with corresponding identifying information, including accession numbers and other information, is provided by the following.

>Hs.73995_mRNA_1 gi|190403|gb|M60502.1|HUMPROFILE Human profilaggrin mRNA, 3' end polyA = 1 (SEQ ID NO: 1)
>Hs.75236_mRNA_4 gi|14280328|gb|AY033998.1| *Homo sapiens* polyA = 3 (SEQ ID NO: 2)
>Hs.299867_mRNA_1 gi|4758533|ref|NM_004496.1| *Homo sapiens* hepatocyte nuclear factor 3, alpha (HNF3A), mRNA polyA = 3 (SEQ ID NO: 3)
>Hs.285401_contig1
AI147926|AI880620|AA768316|AA761543|AA279147|AI216016|AI738663|N79248|AI684489|
AA960845|AI718599|AI379138|N29366|BF002507|AW044269|R34339|R66326|H04648|
R67467|AI523112|BF941500 polyA = 2 polyA = 3 (SEQ ID NO: 4)
>Hs.182507_mRNA_1 gi|15431324|ref|NM_002283.2| *Homo sapiens* keratin, hair, basic, 5 (KRTHB5), mRNA polyA = 3 (SEQ ID NO: 5)
>Hs.292653_contig1
AI200660|AW014007|AI341199|AI692279|AI393765|AI378686|AI695373|AW292108|T10352|
R44346|AW470408|AI380925|BF938983|AW003704|H08077|F03856|H08075|F08895|
AW468398|AI865976|H22568|AI858374|AI216499 polyA = 2 polyA = 3 (SEQ ID NO: 6)
>Hs.97616_mRNA_3 gi|12654852|gb|BC001270.1|BC001270 *Homo sapiens* clone MGC: 5069 IMAGE: 3458016 polyA = 3 (SEQ ID NO: 7)
>Hs.123078_mRNA_3 gi|14328043|gb|BC009237.1|BC009237 *Homo sapiens* clone MGC: 2216 IMAGE: 2989823 polyA = 3 (SEQ ID NO: 8)
>Hs.285508_contig1 AW194680|BF939744|BF516467 polyA = 1 polyA = 1 (SEQ ID NO: 9)
>Hs.183274_contig1
BF437393|BF064008|BF509951|AW134603|AI277015|AI803254|AA887915|BF054958|AI004413|
AI393911|AI278517|AW612644|AI492162|AI309226|AI863671|AA448864|AI640165|
AA479926|AA461188|AA780161|BF591180|AI918020|AI758226|AI291375|BF001845|
BF003064|AI337393|AI522206|BE856784|BF001760|AI280300 FLAG = 1 polyA = 2 WARN polyA = 3 (SEQ ID NO: 10)
>Hs.334841_mRNA_3 gi|14290606|gb|BC009084.1|BC009084 *Homo sapiens* clone MGC: 9270 IMAGE: 3853674 polyA = 3 (SEQ ID NO: 11)
>Hs.3321_contig1
AI804745|AI492375|AA594799|BE672611|AA814147|AA722404|AW170088|D11718|BG153444|
AI680648|AA063561|BE219054|AI590287|R55185|AI479167|AI796872|AI018324|AI701122|
BE218203|AA905336|AI681917|BI084742|AI480008|AI217994|AI401468
polyA = 2 polyA = 3 (SEQ ID NO: 12)
>Hs.306216_singlet1 AW083022 polyA = 1 polyA = 2 (SEQ ID NO: 13)
>Hs.99235_contig1 AA456140|AI167259|AA450056 polyA = 2 polyA = 3 (SEQ ID NO: 14)
>Hs.169172_mRNA_2 gi|2274961|emb|AJ000388.1|HSCANPX *Homo sapiens* mRNA for calpain-like protease CANPX polyA = 3 (SEQ ID NO: 15)
>Hs.351486_mRNA_1 gi|16549178|dbj|AK054605.1|AK054605 *Homo sapiens* cDNA FLJ30043 fis, clone 3NB692001548 polyA = 0 (SEQ ID NO: 16)

```
>Hs.153504_contig2
BE962007|AW016349|AW016358|AW139144|AA932969|AI025620|AI688744|AI865632|AA854291|
AA932970|AU156702|AI634439|AA152496|AI539557|AI123490|AI613215|AI318363|
AW105672|AA843483|AI366889|AW181938|AI813801|AI433695|AA934772|N72230|AI760632|
BE858965|AW058302|AI760087|AI682077|AA886672|AI350384|AW243848|AW300574|
BE466359|AI859529|AI921588|BF062899|BE855597|BE617708 polyA = 2 polyA = 3
(SEQ ID NO: 17)
>Hs.199354_singlet1 AI669760 polyA = 1 polyA = 2 (SEQ ID NO: 18)
>Hs.162020_contig1 AW291189|AA505872 polyA = 2 polyA = 3 (SEQ ID NO: 19)
>Hs.30743_mRNA_3 gi|18201906|ref|NM_006115.2| *Homo sapiens* preferentially
expressed antigen in melanoma (PRAME), mRNA polyA = 3 (SEQ ID NO: 20)
>Hs.271580_contig1
AI632869|AW338882|AW338875|AW613773|AI982899|AW193151|BE206353|BE208200|AI811548|
AW264021 polyA = 2 polyA = 3 (SEQ ID NO: 21)
>Hs.69360_mRNA_2 gi|14250609|gb|BC008764.1|BC008764 *Homo sapiens* clone
MGC: 1266 IMAGE: 3347571 polyA = 3 (SEQ ID NO: 22)
>Hs.30827_contig1 H07885|N39347|W85913|AA583408|W86449 polyA = 2 polyA = 3 (SEQ
ID NO: 23)
>Hs.211593_contig2
BF592799|AI570478|AA234440|R40214|BE501078|AW593784|AI184050|AI284161|W72149|
AW780437|AI247981|AW241273|H60824 polyA = 2 polyA = 3 (SEQ ID NO: 24)
>Hs.155097_mRNA_1 gi|15080385|gb|BC011949.1|BC011949 *Homo sapiens* clone
MGC: 9006 IMAGE: 3863603 polyA = 3 (SEQ ID NO: 25)
>Hs.5163_mRNA_1 gi|15990433|gb|BC015582.1|BC015582 *Homo sapiens* clone
MGC: 23280 IMAGE: 4637504 polyA = 3 (SEQ ID NO: 26)
>Hs.55150_mRNA_1 gi|17068414|gb|BC017586.1|BC017586 *Homo sapiens* clone
MGC: 26610 IMAGE: 4837506 polyA = 3 (SEQ ID NO: 27)
>Hs.170177_contig3
AI620495|AW291989|AA780896|AA976262|AI298326|BF111862|AW591523|AI922518|AI480280|
BF589437|AA600354|AI886238|AA035599|H90049|BF112011|N52601|AI570965|AI565367|
AW768847|H90073|BE504361|N45292|AI632075|AA679729|AW168052|AI978827|
AI968410|AI669255|N45300|AI651256|AI698970|AI521256|AW078614|AI802070|AI885947|
AI342534|AI653624|AW243936|T16586|R15989|AI289789|AI871636|AI718785|AW148847
polyA = 2 polyA = 3 (SEQ ID NO: 28)
>Hs.184601_mRNA_5 gi|4426639|gb|AF104032.1|AF104032 *Homo sapiens* polyA = 2
(SEQ ID NO: 29)
>Hs.351972_singlet1 AA865917 polyA = 2 polyA = 3 (SEQ ID NO: 30)
>Hs.5366_mRNA_2 gi|15277845|gb|BC012926.1|BC012926 *Homo sapiens* clone
MGC: 16817 IMAGE: 3853503 polyA = 3 (SEQ ID NO: 31)
>Hs.18140_contig1
AI685931|AA410954|T97707|AA706873|AI911572|AW614616|AA548520|AW027764|BF511251|
AI914294|AW151688 polyA = 1 polyA = 1 (SEQ ID NO: 32)
>Hs.133196_contig2
BF224381|BE467992|AW137689|AI695045|AW207361|BF445141|AA405473 polyA = 2 WARN
polyA = 3 (SEQ ID NO: 33)
>Hs.63325_mRNA_5 gi|15451939|ref|NM_019894.1| *Homo sapiens* transmembrane
protease, serine 4 (TMPRSS4), mRNA polyA = 3 (SEQ ID NO: 34)
>Hs.250692_mRNA_2 gi|184223|gb|M95585.1|HUMHLF Human hepatic leukemia
factor (HLF) mRNA, complete cds polyA = 3 (SEQ ID NO: 35)
>Hs.250726_singlet4 AW298545 polyA = 2 polyA = 3 (SEQ ID NO: 36)
>Hs.79217_mRNA_2 gi|16306657|gb|BC001504.1|BC001504 *Homo sapiens* clone
MGC: 2273 IMAGE: 3505512 polyA = 3 (SEQ ID NO: 37)
>Hs.47986_mRNA_1 gi|13279253|gb|BC004331.1|BC004331 *Homo sapiens* clone
MGC: 10940 IMAGE: 3630835 polyA = 3 (SEQ ID NO: 38)
>Hs.94367_mRNA_1 gi|10440200|dbj|AK027147.1|AK027147 *Homo sapiens* cDNA:
FLJ23494 fis, clone LNG01885 polyA = 3 (SEQ ID NO: 39)
>Hs.49215_contig1
BI493248|N66529|AA452255|BI492877|AW196683|AI963900|BF478125|AI421654|BE466675
polyA = 1 polyA = 1 (SEQ ID NO: 40)
>Hs.281587_contig2
R61469|R15891|AA007214|R61471|AI014624|N69765|AW592075|H09780|AA709038|AI335898|
AI559229|F09750|R49594|H11055|T72573|AA935558|AA988654|AA826438|AI002431|
AI299721 polyA = 1 polyA = 2 (SEQ ID NO: 41)
>Hs.79378_mRNA_1 gi|16306528|ref|NM_003914.2| *Homo sapiens* cyclin A1
(CCNA1), mRNA polyA = 3 (SEQ ID NO: 42)
>Hs.156469_contig2 AI341378|AI670817|AI701687|AI3In set
22|AW235883|AI948598|AA446356 polyA = 2 polyA = 3 (SEQ ID NO: 43)
>Hs.6631_mRNA_1 gi|7020430|dbj|AK000380.1|AK000380 *Homo sapiens* cDNA
FLJ20373 fis, clone HEP19740 polyA = 3 (SEQ ID NO: 44)
>Hs.155977_contig1 AI309080|AI313045 polyA = 1 WARN polyA = 1 (SEQ ID NO: 45)
>Hs.95197_mRNA_4 gi|5817138|emb|AL110274.1|HSM800829 *Homo sapiens* mRNA;
cDNA DKFZp564I0272 (from clone DKFZp564I0272) polyA = 3 (SEQ ID NO: 46)
>Hs.48956_contig1 N64339|AI569513|AI694073 polyA = 1 polyA = 1 (SEQ ID NO: 47)
>Hs.118825_mRNA_10 gi|1495484|emb|X96757.1|HSSAPKK3 *H. sapiens* mRNA for MAP
kinase kinase polyA = 3 (SEQ ID NO: 48)
>Hs.135118_contig3
AI683181|AI082848|AW770198|AI333188|AI873435|AW169942|AI806302|AW340718|BF196955|
AA909720 polyA = 1 polyA = 2 (SEQ ID NO: 49)
>Hs.171857_mRNA_1 gi|13161080|gb|AF332224.1|AF332224 *Homo sapiens* testis
```

-continued protein mRNA, partial cds polyA = 3 (SEQ ID NO: 50)
>Hs.18910__mRNA__3 gi|12804464|gb|BC001639.1|BC001639 Homo sapiens clone
MGC: 1944 IMAGE: 2959372 polyA = 3 (SEQ ID NO: 51)
>Hs.194774__mRNA__1 gi|16306633|gb|BC001492.1|BC001492 Homo sapiens clone
MGC: 1774 IMAGE: 3510004 polyA = 3 (SEQ ID NO: 52)
>Hs.127428__mRNA__2 gi|16306818|gb|BC006537.1|BC006537 Homo sapiens clone
MGC: 1934 IMAGE: 2987903 polyA = 3 (SEQ ID NO: 53)
>Hs.126852__contig1
AI802118|BF197404|BF2244 34|AA931964|AW236083|AI253119|AW614335|AI671372|AI793240|
AW006851|AI953604|AI640505|AI633982|AW195809|AI493069|AW058576|AW293622
polyA = 2 polyA = 3 (SEQ ID NO: 54)
>Hs.28149__mRNA__1 gi|14714936|gb|BC010626.1|BC010626 Homo sapiens clone
MGC: 17687 IMAGE: 3865868 polyA = 3 (SEQ ID NO: 55)
>Hs.35453__mRNA__3 gi|7018494|emb|AL157475.1|HSM802461 Homo sapiens mRNA;
cDNA DKFZp761G151 (from clone DKFZp761G151); partial cds polyA = 3 (SEQ ID
NO: 56)
>Hs.180570__contig1 R08175|AA707224|AA699986|R11209|W89099|T98002|AA494546
polyA = 2 polyA = 3 (SEQ ID NO: 57)
>Hs.196270__mRNA__1 gi|11545416|gb|AF283645.1|AF283645 Homo sapiens
chromosome 8 map 8q21 polyA = 3 (SEQ ID NO: 58)
>Hs.9030__mRNA__3 gi|12652600|gb|BC000045.1|BC000045 Homo sapiens clone
MGC: 2032 IMAGE: 3504527 polyA = 3 (SEQ ID NO: 59)
>Hs.1282__mRNA__3 gi|4559405|ref|NM__000065.1| Homo sapiens complement
component 6 (C6), mRNA polyA = 1 (SEQ ID NO: 60)
>Hs.268562__mRNA__2 gi|15341874|gb|BC013117.1|BC013117 Homo sapiens clone
MGC: 8711 IMAGE: 3882749 polyA = 3 (SEQ ID NO: 61)
>Hs.151301__mRNA__3 gi|16041747|gb|BC015754.1|BC015754 Homo sapiens clone
MGC: 23085 IMAGE: 4862492 polyA = 3 (SEQ ID NO: 62)
>Hs.111__contig1 AA946776|AW242338|H24274|AI078616 polyA = 1 polyA = 2 (SEQ ID
NO: 63)
>Hs.150753__contig1 AI123582|AI288234 polyA = 0 polyA = 0 (SEQ ID NO: 64)
>Hs.82109__mRNA__1 gi|14250611|gb|BC008765.1|BC008765 Homo sapiens clone
MGC: 1622 IMAGE: 3347793 polyA = 3 (SEQ ID NO: 65)
>Hs.44276__mRNA__2 gi|12654896|gb|BC001293.1|BC001293 Homo sapiens clone
MGC: 5259 IMAGE: 3458115 polyA = 3 (SEQ ID NO: 66)
>Hs.2142__mRNA__4 gi|13325274|gb|BC004453.1|BC004453 Homo sapiens clone
MGC: 4303 IMAGE: 2819400 polyA = 3 (SEQ ID NO: 67)
>Hs.180908__contig1 AA846824|AW611680|AA846182|AA846342|AA846360 polyA = 2
polyA = 3 (SEQ ID NO: 68)
>Hs.89436__mRNA__1 gi|16507959|ref|NM__004063.2| Homo sapiens cadherin 17, LI
cadherin (liver-intestine) (CDH17), mRNA polyA = 1 (SEQ ID NO: 69)
>Hs.151544__mRNA__8 gi|3153107|emb|AL023657.1|HSDSHP Homo sapiens SH2D1A
cDNA, formerly known as DSHP polyA = 3 (SEQ ID NO: 70)
>Hs.1657__contig4
AW473119|AA164586|AI540656|AI758480|AI810941|AI978964|AI675862|AI784397|AW591562|
AW514102|AI888116|AI983175|AI634735|AI669577|AI202659|AI910598|AI961352|
AI565481|AI886254|AI538838|AA291749|AW571455|AI370308|AI274727|AW473925|
AW514787|AI273871|AW470552|AI524356|AI888281|AW089672|AI952766|AW440601|AI654044|
AW438839|AI972926 polyA = 2 polyA = 3 (SEQ ID NO: 71)
>Hs.35984__mRNA__1 gi|6049161|gb|AF133587.1|AF133587 Homo sapiens chromosome
22 map 22q11.2 polyA = 3 (SEQ ID NO: 72)
>Hs.334534__mRNA__2 gi|17389403|gb|BC017742.1|BC017742 Homo sapiens, clone
IMAGE: 4391536, mRNA polyA = 3 (SEQ ID NO: 73)
>Hs.60162__mRNA__1 gi|10437644|dbj|AK025181.1|AK025181 Homo sapiens cDNA:
FLJ21528 fis, Clone COL05977 polyA = 3 (SEQ ID NO: 74)

As would be understood by the skilled person, detection of expression of any of the above identified sequences, as well as sequences of the set of 90 below, or the sequences provided in the attached Sequence Listing may be performed by the detection of expression of any appropriate portion or fragment of these sequences. Preferably, the portions are sufficiently large to contain unique sequences relative to other sequences expressed in a cell containing sample. Moreover, the skilled person would recognize that the disclosed sequences represent one strand of a double stranded molecule and that either strand may be detected as an indicator of expression of the disclosed sequences. This follows because the disclosed sequences are expressed as RNA molecules in cells which are preferably converted to cDNA molecules for ease of manipulation and detection. The resultant cDNA molecules may have the sequences of the expressed RNA as well as those of the complementary strand thereto. Thus either the RNA sequence strand or the complementary strand may be detected. Of course is it also possible to detect the expressed RNA without conversion to cDNA.

In some embodiments of the invention, the expression levels of gene sequences is measured by detection of expressed sequences in a cell containing sample as hybridizing to the following oligonucleotides, which correspond to the above sequences as indicated by the accession numbers provided.

>AF133587

(SEQ ID NO: 75)
CCCGGATCGCCATCAGTGTCATCGAGTTCAAACCCTGAGCCCTTCATT

CACCTCTGTGAG

>BC017742

(SEQ ID NO: 76)
TGCCCTTGCTCTGTGTCATCTCAGTCATTTGACTTAGAAAGTGCCCTT

CAAAAGGACCCT

>BF43793

(SEQ ID NO: 77)
GGAGGGAGGGCTAATTATATATTTTGTTGTTCCTCTATACTTTGTTCT

GTTGTCTGCGCC

>AI620495

(SEQ ID NO: 78)
CAGTTTGGATTGTATAATAACGCCAAGCCCAGTTGTAGTCGTTTGAGT

GCAGTAATGAAA

>AK000380

(SEQ ID NO: 79)
AAATCAGAGTAACCCTTTCTGTATTGAGTGCAGTGTTTTTTACTCTTT

TCTCATGCACAT

>BC009237

(SEQ ID NO: 80)
TGCCTGGCACAAAGAAGGAAGAATATAAATGATAGTTCGACTCGTCTG

TGGAAGAACTTA

>BC008765

(SEQ ID NO: 81)
AGTCTTTTGCTTTTGGCAAAACTCTACTTAATCCAATGGGTTTTTCCC

TGTACAGTAGAT

>BC001504

(SEQ ID NO: 82)
GGTTACTGTGGGTGGAATAGTGGAGGCCTTCAACTGATTAGACAAGGC

CCGCCCACATCT

>NM_019894

(SEQ ID NO: 83)
TAAAATGCACTGCCCTACTGTTGGTATGACTACCGTTACCTACTGTTG

TCATTGTTATTA

>BF224381

(SEQ ID NO: 84)
TTCTCTTTTGGGGGCAAACACTATGTCCTTTTCTTTTTCTAGATACAG

TTAATTCCTGGA

>AL157475

(SEQ ID NO: 85)
AAGACCCACACCCTGTAGCAATACCAAGTGCTATTACATAATCAATGG

ACGATTTATACT

>AY033998

(SEQ ID NO: 86)
AGTGTTGCAAGTTTCCTTTAAAAACCAACAAAGCCCACAAGTCCTGAAT

TTCCCATTCTTA

>H07885

(SEQ ID NO: 87)
GTCACTGTCATAGCAGCTGTGATTTCACAAGGAAGGGTGCTGCAGGGG

GACCTGGTTGAT

>NM_004496

(SEQ ID NO: 88)
TTTCATCCAGTGTTATGCACTTTCCACAGTTGGTGTTAGTATAGCCAG

AGGGTTTCATTA

>AA846824

(SEQ ID NO: 89)
GGGAAGTAGGGATTATTCGTTTAAATTCAATCGCGAGCACCAAGTCGG

ACTGGCCGGGGA

>BC017586

(SEQ ID NO: 90)
GGGACCAGGCCCTGGGACAGCCATGTGGCTCCAAATGACTAAATGTCA

GCTCAAAAACCA

>AA456140

(SEQ ID NO: 91)
TCCGTTTATGGAGGCAATTCCATATCCTTTCTTGAACGCACATTCAGC

TTACCCCAGAGA

>NM_002283

(SEQ ID NO: 92)
AGAGTTAAGCCACTTCCTGGGTCTCCTTCTTATGACTGTCTATGGGTG

CATTGCCTTCTG

>AL023657

(SEQ ID NO: 93)
GTGGCCTGAGTAATGCATTATGGGTGGTTTACCATTTCTTGAGGTAAA

AGCATCACATGA

>BC001639

(SEQ ID NO: 94)
ACACATGCATGTGTCTGTGTATGTGTGAATGTGAGAGAGACACAGCCC

TCCTTTCAGAAG

>BC015754

(SEQ ID NO: 95)
TCTGTAACTGCACAACCCTGGGGTTTGCTGCAGAGCTATTTCTTTCCA

TGTAAAGTAGTG

>AF332224

(SEQ ID NO: 96)
AAACACTCTTTCCGACTCCAGAGGAGAAGCTGGCAGCTCTCTGTAAGA

AATATGCTGATC

>BC001270

(SEQ ID NO: 97)
GCTTCCTCTATCGCCCAATGCAAAATCGATGAAATGGGGAGTTCTCTG

GGCCAGGCCACA

>AI147926

(SEQ ID NO: 98)
GTAGAATCCTCTGTTCATAATGAACAAGATGAACCAATGTGGATTAGA

AAGAAGTCCGAG

>AW298545

(SEQ ID NO: 99)
CTGTTTTAAAACTGAATGGCACGAAATTGTTTTCCTCAACTCGGAGAT

TCCTGTATGGAG

>AI802118

(SEQ ID NO: 100)
AATAAATAGTAGCTCTGCTGATGATGACGTTGATAACCAAACTGTTCT

GTGGTCTTAAGT

>AI683181

(SEQ ID NO: 101)
CAAACAGCCCGGTCTTGATGCAGGAGAGTCTGGAAAAGGAAGAAAATG

GTTTCAGTTTCA

-continued

```
>M95585
                                    (SEQ ID NO: 102)
AACATGGACCATCCAAATTTATGGCCGTATCAAATGGTAGCTGAAAAA

ACTATATTTGAG

>AK027147
                                    (SEQ ID NO: 103)
TTGTAATCATGCCAATTCCAGATCAATAACTGCATGTCTGTTCTTTGG

TAGAAATAGCTT

>AW291189
                                    (SEQ ID NO: 104)
AAAGATTATTAACCCAAATCACCTTTCTTGCTTACTCCAGATGCCTCA

GCCTCTGATATA

>AI632869
                                    (SEQ ID NO: 105)
GACTTCCTTTAGGATCTCAGGCTTCTGCAGTTCTCATGACTCCTACTT

TTCATCCTAGTC

>BC006537
                                    (SEQ ID NO: 106)
CTGTATATTTTGCAATAGTTACCTCAAGGCCTACTGACCAAATTGTTG

TGTTGAGATGAT

>R61469
                                    (SEQ ID NO: 107)
TGTTCAAACAGACTTTAACCTCTGCATCATACTTAACCCTGCGACATG

CGTACAGTATGC

>BC009084
                                    (SEQ ID NO: 108)
TGAGTCATATACATTTACTGACCACTGTTGCTTGTTGCTCACTGTGCT

GCTTTTCCATGA

>N64339
                                    (SEQ ID NO: 109)
CTGAAATGTGGATGTGATTGCCTCAATAAAGCTCGTCCCCATTGCTTA

AGCCTTCAAAAA

>AI200660
                                    (SEQ ID NO: 110)
ATCAAGAAAACCTAATCTTCTGACTCCCAGGCCAGGATGTTTTATTTC

TCACATCATGTC

>AK054605
                                    (SEQ ID NO: 111)
TTCATTTCCAAACATCATCTTTAAGACTCCAAGGATTTTTCCAGGCAC

AGTGGCTCATAC

>NM_006115
                                    (SEQ ID NO: 112)
AGTTAGAAATAGAATCTGAATTTCTAAAGGGAGATTCTGGCTTGGGAA

GTACATGTAGGA

>X96757
                                    (SEQ ID NO: 113)
CAATTTTCTTTTTACTCCCCCTCTTAAGGGGGCCTTGGAATCTATAGT

ATAGAATGAACT

>AI804745
                                    (SEQ ID NO: 114)
GGGTGGAGTTTCAGTGAGAATAAACGTGTCTGCCTTTGTGTGTGTGTA

TATATACAGAGA

>AJ000388
                                    (SEQ ID NO: 115)
CTCGCTCATTTTTTACCATGTTTTCCAGTCTGTTTAACTTCTGCAGTG

CCTTCACTACAC

>BC008764
                                    (SEQ ID NO: 116)
CTTTGGGCCGAGCACTGAATGTCTTGTACTTTAAAAAAATGTTTCTGA

GACCTCTTTCTA

>AI309080
                                    (SEQ ID NO: 117)
CTGGACCCTTGGAGCAGTGTTGTGTGAACTTGCCTAGAACTCTGCCTT

CTCCGTTGTCAA

>AA865917
                                    (SEQ ID NO: 118)
CCACCTCCTTCGACCTCCACTGCGCCCCACCTCCCTGCCTGTGTGTGT

TATTTCAAAGGA

>AA946776
                                    (SEQ ID NO: 119)
TCTGGCTGGTGGCCTGCGCGAGGGTGCAGTCTTACTTAAAAGACTTTC

AGTTAATTCTCA

>AF104032
                                    (SEQ ID NO: 120)
AGATGCTGTCGGCACCATGTTTATTTATTTCCAGTGGTCATGCTCAGC

CTTGCTGCTCTG

>AW194680
                                    (SEQ ID NO: 121)
TCCTTCCTCTTCGGTGAATGCAGGTTATTTAAACTTTGGGAAATGTAC

TTTTAGTCTGTC

>BC001293
                                    (SEQ ID NO: 122)
GTCCTGTCCCTGTCTGGGAGTTGTGTTATTTAAAGATATTCTGTATGT

TGTATCTTTTGC

>BE962007
                                    (SEQ ID NO: 123)
ATTATATTTCAGGTGTCCTGAACAGGTCACTAGACTCTACATTGGGCA

GCCTTTAAATAT

>BI493248
                                    (SEQ ID NO: 124)
AGGAATGGTACTACCGTTCCAGATTTTCTGTAATTGCTTCTGCAAAGT

AATAGGCTTCTT

>AF283645
                                    (SEQ ID NO: 125)
CTGTACCCAAAGGATGCCAGAATACTAGTATTTTTATTTATCGTAAAC

ATCCACGAGTGC

>AI669760
                                    (SEQ ID NO: 126)
ATTGCCCCCTAACCAATCATGCAAACTTTTCCCCCCCTGGGGTAATT

CACCAGTTAAAA

>BC001492
                                    (SEQ ID NO: 127)
CCCACAGTATTTAATGCCCTGTCAGTCCCTTCTAGTCTGACTCAATGG

TAACTTGCTGTA
```

>BC004453

(SEQ ID NO: 128)
AAAACCAACTCTCTACTACACAGGCCTGATAACTCTGTACGAGGCTTC

TCTAACCCCTAG

>BC010626

(SEQ ID NO: 129)
CTCAGACTGGGCTCCACACTCTTGGGCTTCAGTCTGCCCATCTGCTGA

ATGGAGACAGCA

>BC013117

(SEQ ID NO: 130)
CCTAATGGGGATTCCTCTGGTTGTTCACTGCCAAAACTGTGGCATTTT

CATTACAGGAGA

>BC011949

(SEQ ID NO: 131)
CACTCACAATTGTTGACTAAAATGCTGCCTTTAAAACATAGGAAAGTA

GAATGGTTGAGT

>AW083022

(SEQ ID NO: 132)
CTTTGAAGGGCTGCTGCACATTGTTGAATCCATCGACCTTTAGCTGCA

ATGGGATCTCTA

>R08175

(SEQ ID NO: 133)
TGCCTCATCGATATTATAGGGGTCCATCACAACCCAACTGTGTGGCCG

GATCCTGAGTCT

>NM_000065

(SEQ ID NO: 134)
AAAACAGACAAAAGCCTTTGCCTTCATGAAGCATACATTCATTCAGGG

GTAGACACACAA

>AK025181

(SEQ ID NO: 135)
TAACAAACAAAGGCAGTAGCTCATCACTTGGGTAGCAGGTACCCATTT

TAGGACCCTACA

>NM_003914

(SEQ ID NO: 136)
ATATCAGAAGTGCCAATAATCGTCATAGGCTTCTGCACGTTGGATCAA

CTAATGTTGTTT

>AI123582

(SEQ ID NO: 137)
ATCATAGCCCAACCATGTGAGAAGAAGGAGAAGGCCCCCCTTTCTTCA

TTAATCTGAAAA

>BC004331

(SEQ ID NO: 138)
GCAGACCATTCTATCATACCTGGCAGGGCTTCTGTTTTATTTTGTAGG

CTGGATGCTACC

>AI341378

(SEQ ID NO: 139)
ACTACAAGCCTCTTGTTTTTCACCAAAACCCTACATCTCAGGCTTACT

AATTTTTGTGAT

>NM_004063

(SEQ ID NO: 140)
GCCATGCATACATGCTGCGCATGTTTTCTTCATTCGTATGTTAGTAAA

GTTTTGGTTATT

>BC012926

(SEQ ID NO: 141)
CACCTATTTATTTTACCTCTTTCCCAAACCTGGAGCATTTATGCCTAG

GCTTGTCAAGAA

>AL110274

(SEQ ID NO: 142)
GTGGACATAGCCACTAACCAACTAGTTACCTTTGGACTGCAACAAAAA

ATGTGAAAATGA

>AW473119

(SEQ ID NO: 143)
ACTTGTAAACCTCTTTTGCACTTTGAAAAAGAATCCAGCGGGATGCTC

GAGCACCTGTAA

>AI685931

(SEQ ID NO: 144)
AATTCTCTATAAACGGTTCACCAGCAAACCACCAATACATTCCATTGT

TTGCCTAGAGAG

>BF592799

(SEQ ID NO: 145)
AATGGCCCATGCATGCTGTTTGCAGCAGTCAATTGAGTTGAATTAGAA

TTCCAACCATAC

>BC000045

(SEQ ID NO: 146)
GAGCTCAGTACTTGCCCTGTGAAAATCCCAGAAGCCCCCGCTGTCAAT

GTTCCCCATCCA

>BC015582

(SEQ ID NO: 147)
ATGAAGCGGAATTAGCCTCCCGAGCTAAGGGACTCGCCTAGGGTCTCA

CAGTGAGTAGGA

>M60502

(SEQ ID NO: 148)
AGTGGCTATATCAACATCAGGGCTAGCACATCTTTCTCTATTATCCTT

CTATTGGAATTC

The invention also provides a second group of 90 gene sequences from which 50 or more may be used in the practice of the invention. The 50 to 90 gene sequences may be used along with the determination of expression levels of additional sequences so long as the expression levels of gene sequences from the set of 90 are used in classifying. A non-limiting example of such embodiments of the invention is where the expression of the 90 gene sequences, or at least 50 (or 50 to about 90) members thereof, is measured along with the expression levels of a plurality of other sequences, such as by use of a microarray based platform used to perform the invention. Where those other expression levels are not used in classification, they may be considered the results of "excess" transcribed sequences and not critical to the practice of the invention. Alternatively, and where those other expression levels are used in classification, they are within the scope of the invention, where the use of the above described sequences does not necessarily exclude the use of expression levels of additional sequences.

38 members of the set of 90 are included in the first set of 74 described above. The accession numbers of these members in common between the two sets are AA456140, AA846824, AA946776, AF332224, AI620495, AI632869, AI802118, AI804745, AJ000388, AK025181, AK027147, AL157475, AW194680, AW291189, AW298545, AW473119, BC000045, BC001293, BC001504, BC004453, BC006537, BC008765, BC009084, BC011949, BC012926, BC013117, BC015754, BE962007, BF224381, BF437393, BI493248, M60502, NM_000065, NM_003914, NM_004063, NM_004496, NM_006115, and R61469. mRNA sequences corresponding to members of the set of 90 that are not present in the set of 74 gene sequences are also provided in the Sequence Listing and identified as SEQ ID NOS: 149-200. The listing of identifying information for these 52 unique members by accession numbers, as well as corresponding oligonucleotide sequences which may be used in the practice of the invention, is provided by the following.

>R15881
(SEQ ID NO: 201)
ACTTCTGGTGATGATAAAAATGGTTTTATCACCCAGATGTGAAAGAAG

CTGCCTGTTTAC

>AI041545
(SEQ ID NO: 202)
GTGGTTCTGTAAAAACGCAGAGGAAAAGAGCCAGAAGGTTTCTGTTTA

ATGCATCTTGCC

>NM_024434
(SEQ ID NO: 203)
TTTATAAGGAAGCAGCTGTCTAAAATGCAGTGGGGTTTGTTTTGCAAT

GTTTTAAACAGA

>AB038160
(SEQ ID NO: 204)
CTTATGAAGCTGGCCGGGCCACTCACGTTCAATGGTACATCTGGGTCT

CTATGTGGTTCT

>AK026790
(SEQ ID NO: 205)
GTGAGCCAGCATTTCCCATAGCTAACCCTATTCTCTTAGTCTTTCAAA

ATGTAGAATGGG

>BC012727
(SEQ ID NO: 206)
CTTTACACCTGATAAAATATTTTGCGAAGAGAGGTGTTCTTTTTCCTT

ACTGGTGCTGAA

>BC016451
(SEQ ID NO: 207)
GCATACATCTCATCCACAGGGGAAGATAAAGATGGTCACACAAACAGT

TTCCATAAAGAT

>H09748
(SEQ ID NO: 208)
TGAGTTCAGCATGTGTCTGTCCATTTCATTTGTACGCTTGTTCAAAAC

CAAGTTTGTTCT

>NM_006142
(SEQ ID NO: 209)
AAGACCGAGACTGAGGGAAAGCATGTCTGCTGGGTGTGACCATGTTTC

CTCTCAATAAAG

>AF191770
(SEQ ID NO: 210)
GGCATCTGGCCCCTGGTAGCCAGCTCTCCAGAATTACTTGTAGGTAAT

TCCTCTCTTCAT

>NM_006378
(SEQ ID NO: 211)
TGGATGTTTGTGCGCGTGTGTGGACAGTCTTATCTTCCAGCATGATAG

GATTTGACCATT

>BC006819
(SEQ ID NO: 212)
TCCTGGCAGAGCCATGGTCCCAGGCTTCCCAAAAGTGTTTGTGGCAAT

TATTCCCCTAGG

>X79676
(SEQ ID NO: 213)
TTTGATGATAGCAGACATTGTTACAAGGACATGGTGAGTCTATTTTTA

ATGCACCAATCT

>BC006811
(SEQ ID NO: 214)
TTCTTCCAGTTGCACTATTCTGAGGGAAAATCTGACACCTAAGAAATT

TACTGTGAAAAA

>NM_000198
(SEQ ID NO: 215)
GAACAATTGTGGTCTCTCTTAACTTGAGGTTCTCTTTTGACTAATAGA

GCTCCATTTCCC

>AF301598
(SEQ ID NO: 216)
GTTAAGTGTGGCCAAGCGCACGGCGGCAAGTTTTCAAGCACTGAGTTT

CTATTCCAAGAT

>NM_002847
(SEQ ID NO: 217)
CGGCCTACTGAGCGGACAGAATGATGCCAAAATATTGCTTATGTCTCT

ACATGGTATTGT

>NM_004062
(SEQ ID NO: 218)
CAGGGTGTTTGCCCAATAATAAAGCCCCAGAGAACTGGGCTGGGCCCT

ATGGGATTGGTA

>AW118445
(SEQ ID NO: 219)
TGTACAGTTTGGTTGTTGCTGTAAATATGGTAGCGTTTTGTTGTTGTT

GTTTTTTCATGC

>BC002551
(SEQ ID NO: 220)
TACCAAACTGGGACTCACAGCTTTATTGGGCTTTCTTTGTGTCTTGTG

TGTTTCTTTTAT

>AA765597
(SEQ ID NO: 221)
CATTGAGGTTTGGATGGTGGCAGGTAAAACAGAAAGGCAAGATGTCAT

CTGACATTAGGC

>AL137761
(SEQ ID NO: 222)
AGTTCAGCACTGTGGTTATCATTGGTGATGCCAGAAAACATTAGTAGA

CTTAGACAATTG

>X78202
(SEQ ID NO: 223)
TAAAATTTCTTGATTGTGACTATGTGGTCATATGCCCGTGTTTGTCAC

TTACAAAAATGT

>AK025615
(SEQ ID NO: 224)
AGCCATCTGGTGTGAAGAACTCTATATTTGTATGTTGAGAGGGCATGG

AATAATTGTATT

>BC001665

(SEQ ID NO: 225)
CTTATTGTCACTGGTTAAGAACTTGGCGAGATTGAAGGGCTTTTGTTA

TTGTTGTTGGAT

>AI985118

(SEQ ID NO: 226)
CTTTCTAGTGAGCTAACCGTAACAGAGAGCCTACAGGATACACGTGAG

ATAATGTCACGT

>AL039118

(SEQ ID NO: 227)
TTGTCTTAAAATTTCTTGATTGTGATACTGTGGTCATATGCCCGTGTT

TGTCACTTACAA

>AA782845

(SEQ ID NO: 228)
CCTGGGGGAAAGGGGCATTCATGACCTGAACTTTTTAGCAAATTATTA

TTCTCAGTTTCC

>BC016340

(SEQ ID NO: 229)
TTCATTAACAGTACTAAGTGGAAGGGATCTGCAGATTCCAAATTGGAA

TAAGCTCTATCA

>AA745593

(SEQ ID NO: 230)
CCAATGCAGAAGAGTATTAAGAAAGATGCTCAAGTCCCATGGCACAGA

GCAAGGCGGGCA

>NM_004967

(SEQ ID NO: 231)
CAAGGCTACGATGGCTATGATGGTCAGAATTACTACCACCACCAGTGA

AGCTCCAGCCTG

>BF510316

(SEQ ID NO: 232)
AGCTCACAGCTGGACAGGTGTTGTATATAGAGTGGAATCTCTTGGATG

CAGCTTCAAGAA

>AA993639

(SEQ ID NO: 233)
TCCAAAGTAGAAAGGGTTCTTTTAGAAAACTTGAAGAATGTGCCTCCT

CTTAGCATCTGT

>AV656862

(SEQ ID NO: 234)
GATGCATTTTTCAGTCCCTTTTCAGAGCAAATGCTTTTGCAATGGTAG

TAATGTTTAGTT

>X69699

(SEQ ID NO: 235)
CCTGTGGGCTTCTCTCCTTGATGCTTCTTTCTTTTTTTAAAGACAAC

CTGCCATTACCA

>BC013282

(SEQ ID NO: 236)
TTGCACTAAGTCATGCTGTTTCCTCAAAGAAGCTTTGTTTTTTGTTAA

CGTATTACTCAG

>AI457360

(SEQ ID NO: 237)
CTGGATCCCAGGCCCTGGCACCCCTCAGGAAATACAAGAAAAAGAATA

TTCACATCTGTT

>AW445220

(SEQ ID NO: 238)
TTAGAGGGGCCACCTATCAACTCATCAGTGTTCAAAGAATATGCTGGG

AGCATGGGTGAG

>AF038191

(SEQ ID NO: 239)
GGCCCATTTATGTCCCTCATGTCTCTAGATTTTCTCGTCACCCAGCCT

CAAAAATATATG

>X05615

(SEQ ID NO: 240)
TCCCCAAAAACCTCACCCGAGGCTGCCCACTATGGTCATCTTTTTCTC

TAAAATAGTTAC

>BC005364

(SEQ ID NO: 241)
GAAATTCCTCACACCTTGCACCTTCCCTACTTTTCTGAATTGCTATGA

CTACTCCTTGTT

>AK025701

(SEQ ID NO: 242)
TGTCTGTCCACCACGAGATGGGAGGAGGAGAAAAAGCGGTACGATGCC

TTCCTGACCTCA

>BF446419

(SEQ ID NO: 243)
GTCTTATCTCTCAGGGGGGTTTAAGTGCCGTTTGCAATAATGTCGTC

TTATTTATTTAG

>AK025470

(SEQ ID NO: 244)
CCGAGTAGTATGGGTCTCTGTGTGAGAAACCAGGAGATATTTTCATCT

TGTTCGGAAATA

>BE552004

(SEQ ID NO: 245)
TTGTGCAAAAGTCCCACAACCTTTCTGGATTGATAGTTTGTGGTGAAA

TAAACAATTTTA

>H05388

(SEQ ID NO: 246)
TCCAGTATTCTGCAGGGCCAGTCAGTTGTACAGAAGTTGGAATATTCT

GTTCCAGAATTA

>NM_033229

(SEQ ID NO: 247)
GTCTCGAACAGCGGTTGTTTTACTTTATTTATCTTAGGCCCTCAGCT

CCCTGACGTCCT

>BC010437

(SEQ ID NO: 248)
AGTGAATCTTTTCCTCTTGGTAGCATCAACACTGGGGATAAATCAGAA

CCATTCTGTGGA

>AI952953

(SEQ ID NO: 249)
TGAGAGCCCAGAACAAGAAGGAGCAGAAGGGCACTTTGACCTTCATTA

TTATGAAAATCA

>R45389

(SEQ ID NO: 250)
GGAAGAACTGATGCTTGCTGCTAACTAAAGTTTTGGATGTATCGATTT

AGAGAACCAATT

-continued

>NM_001337

(SEQ ID NO: 251)

GAATGAGAGAATAAGTCATGTTCCTTCAAGATCATGTACCCCAATTTA

CTTGCCATTACT

>AI499593

(SEQ ID NO: 252)

TACGGAAAGGAAACAGGTTATACTCTTAGATTTAAAAAGTGAAAGAAA

CTGCAGGCGCCT

In some embodiments of the invention, the expression levels of gene sequences is measured by detection of expressed sequences in a cell containing sample as hybridizing to the above oligonucleotides, which correspond to sequences in the Sequence Listing as indicated by the accession numbers provided.

In additional embodiments, the invention provides for use of any number of the gene sequences of the set of 74 or the set of 90 in the methods of the invention. Thus anywhere from 1 to all of the 50 or more gene sequences used in the invention may be from either or both of the above sets. So from one, two, three, four, five, six, seven, eight, nine, ten, or more of the 50 or more sequences may be from the set of 74 or the set of 90.

As used herein, a "tumor sample" or "tumor containing sample" or "tumor cell containing sample" or variations thereof, refer to cell containing samples of tissue or fluid isolated from an individual suspected of being afflicted with, or at risk of developing, cancer. The samples may contain tumor cells which may be isolated by known methods or other appropriate methods as deemed desirable by the skilled practitioner. These include, but are not limited to, microdissection, laser capture microdissection (LCM), or laser microdissection (LMD) before use in the instant invention. Alternatively, undissected cells within a "section" of tissue may be used. Non-limiting examples of such samples include primary isolates (in contrast to cultured cells) and may be collected by any non-invasive or minimally invasive means, including, but not limited to, ductal lavage, fine needle aspiration, needle biopsy, the devices and methods described in U.S. Pat. No. 6,328,709, or any other suitable means recognized in the art. Alternatively, the sample may be collected by an invasive method, including, but not limited to, surgical biopsy.

The detection and measurement of transcribed sequences may be accomplished by a variety of means known in the art or as deemed appropriate by the skilled practitioner. Essentially, any assay method may be used as long as the assay reflects, quantitatively or qualitatively, expression of the transcribed sequence being detected.

The ability to classify tumor samples is provided by the recognition of the relevance of the level of expression of the gene sequences (whether randomly selected or specified) and not by the form of the assay used to determine the actual level of expression. An assay of the invention may utilize any identifying feature of a individual gene sequence as disclosed herein as long as the assay reflects, quantitatively or qualitatively, expression of the gene in the "transcriptome" (the transcribed fraction of genes in a genome) or the "proteome" (the translated fraction of expressed genes in a genome). Additional assays include those based on the detection of polypeptide fragments of the relevant member or members of the proteome. Non-limiting examples of the latter include detection of proteolytic fragments found in a biological fluid, such as blood or serum. Identifying features include, but are not limited to, unique nucleic acid sequences used to encode (DNA), or express (RNA), said gene or epitopes specific to, or activities of, a protein encoded by a gene sequence.

Additional means include detection of nucleic acid amplification as indicative of increased expression levels and nucleic acid inactivation, deletion, or methylation, as indicative of decreased expression levels. Stated differently, the invention may be practiced by assaying one or more aspect of the DNA template(s) underlying the expression of each gene sequence, of the RNA used as an intermediate to express the sequence, or of the proteinaceous product expressed by the sequence, as well as proteolytic fragments of such products. As such, the detection of the presence of, amount of, stability of, or degradation (including rate) of, such DNA, RNA and proteinaceous molecules may be used in the practice of the invention.

In some embodiments, all or part of a gene sequence may be amplified and detected by methods such as the polymerase chain reaction (PCR) and variations thereof, such as, but not limited to, quantitative PCR (Q-PCR), reverse transcription PCR (RT-PCR), and real-time PCR (including as a means of measuring the initial amounts of mRNA copies for each sequence in a sample), optionally real-time RT-PCR or real-time Q-PCR. Such methods would utilize one or two primers that are complementary to portions of a gene sequence, where the primers are used to prime nucleic acid synthesis. The newly synthesized nucleic acids are optionally labeled and may be detected directly or by hybridization to a polynucleotide of the invention. The newly synthesized nucleic acids may be contacted with polynucleotides (containing gene sequences) of the invention under conditions which allow for their hybridization. Additional methods to detect the expression of expressed nucleic acids include RNAse protection assays, including liquid phase hybridizations, and in situ hybridization of cells.

Alternatively, the expression of gene sequences in FFPE samples may be detected as disclosed in U.S. applications 60/504,087, filed Sep. 19, 2003, Ser. No. 10/727,100, filed Dec. 2, 2003, and Ser. No. 10/773,761, filed Feb. 6, 2004 (all three of which are hereby incorporated by reference as if fully set forth). Briefly, the expression of all or part of an expressed gene sequence or transcript may be detected by use of hybridization mediated detection (such as, but not limited to, microarray, bead, or particle based technology) or quantitative PCR mediated detection (such as, but not limited to, real time PCR and reverse transcriptase PCR) as non-limiting examples. The expression of all or part of an expressed polypeptide may be detected by use of immunohistochemistry techniques or other antibody mediated detection (such as, but not limited to, use of labeled antibodies that bind specifically to at least part of the polypeptide relative to other polypeptides) as non-limiting examples. Additional means for analysis of gene expression are available, including detection of expression within an assay for global, or near global, gene expression in a sample (e.g. as part of a gene expression profiling analysis such as on a microarray). Non-limiting examples linear RNA amplification and those described in U.S. patent application Ser. No. 10/062,857 (filed on Oct. 25, 2001), as well as U.S. Provisional Patent Applications 60/298,847 (filed Jun. 15, 2001) and 60/257,801 (filed Dec. 22, 2000), all of which are hereby incorporated by reference in their entireties as if fully set forth.

In embodiments using a nucleic acid based assay to determine expression includes immobilization of one or more gene sequences on a solid support, including, but not limited to, a solid substrate as an array or to beads or bead based technology as known in the art. Alternatively, solution based expression assays known in the art may also be used. The immobilized gene sequence(s) may be in the form of polynucleotides that are unique or otherwise specific to the gene(s) such that the polynucleotides would be capable of hybridizing to the DNA or RNA of said gene(s). These polynucleotides may be the full length of the gene(s) or be short sequences of the genes (up to one nucleotide shorter than the full length sequence known in the art by deletion from the 5' or 3' end of the sequence) that are optionally minimally interrupted (such as by mismatches or inserted non-complementary basepairs) such that hybridization with a DNA or RNA corresponding to the genes is not affected. In some embodiments, the polynucleotides used are from the 3' end of the gene, such as within about 350, about 300, about 250, about 200, about 150, about 100, or about 50 nucleotides from the polyadenylation signal or polyadenylation site of a gene or expressed sequence. Polynucleotides containing mutations relative to the sequences of the disclosed genes may also be used so long as the presence of the mutations still allows hybridization to produce a detectable signal. Thus the practice of the present invention is unaffected by the presence of minor mismatches between the disclosed sequences and those expressed by cells of a subject's sample. A non-limiting example of the existence of such mismatches are seen in cases of sequence polymorphisms between individuals of a species, such as individual human patients within *Homo sapiens*.

As will be appreciated by those skilled in the art, some gene sequences include 3' poly A (or poly T on the complementary strand) stretches that do not contribute to the uniqueness of the disclosed sequences. The invention may thus be practiced with gene sequences lacking the 3' poly A (or poly T) stretches. The uniqueness of the disclosed sequences refers to the portions or entireties of the sequences which are found only in nucleic acids, including unique sequences found at the 3' untranslated portion thereof. Some unique sequences for the practice of the invention are those which contribute to the consensus sequences for the genes such that the unique sequences will be useful in detecting expression in a variety of individuals rather than being specific for a polymorphism present in some individuals. Alternatively, sequences unique to an individual or a subpopulation may be used. The unique sequences may be the lengths of polynucleotides of the invention as described herein.

In additional embodiments of the invention, polynucleotides having sequences present in the 3' untranslated and/or non-coding regions of gene sequences are used to detect expression levels in cell containing samples of the invention. Such polynucleotides may optionally contain sequences found in the 3' portions of the coding regions of gene sequences. Polynucleotides containing a combination of sequences from the coding and 3' non-coding regions preferably have the sequences arranged contiguously, with no intervening heterologous sequence(s).

Alternatively, the invention may be practiced with polynucleotides having sequences present in the 5' untranslated and/or non-coding regions of gene sequences to detect the level of expression in cells and samples of the invention. Such polynucleotides may optionally contain sequences found in the 5' portions of the coding regions. Polynucleotides containing a combination of sequences from the coding and 5' non-coding regions may have the sequences arranged contiguously, with no intervening heterologous sequence(s). The invention may also be practiced with sequences present in the coding regions of gene sequences.

The polynucleotides of some embodiments contain sequences from 3' or 5' untranslated and/or non-coding regions of at least about 16, at least about 18, at least about 20, at least about 22, at least about 24, at least about 26, at least about 28, at least about 30, at least about 32, at least about 34, at least about 36, at least about 38, at least about 40, at least about 42, at least about 44, or at least about 46 consecutive nucleotides. The term "about" as used in the previous sentence refers to an increase or decrease of 1 from the stated numerical value. Other embodiments use polynucleotides containing sequences of at least or about 50, at least or about 100, at least about or 150, at least or about 200, at least or about 250, at least or about 300, at least or about 350, or at least or about 400 consecutive nucleotides. The term "about" as used in the preceding sentence refers to an increase or decrease of 10% from the stated numerical value.

Sequences from the 3' or 5' end of gene coding regions as found in polynucleotides of the invention are of the same lengths as those described above, except that they would naturally be limited by the length of the coding region. The 3' end of a coding region may include sequences up to the 3' half of the coding region. Conversely, the 5' end of a coding region may include sequences up the 5' half of the coding region. Of course the above described sequences, or the coding regions and polynucleotides containing portions thereof, may be used in their entireties.

In another embodiment of the invention, polynucleotides containing deletions of nucleotides from the 5' and/or 3' end of gene sequences may be used. The deletions are preferably of 1-5, 5-10, 10-15, 15-20, 20-25, 25-30, 30-35, 35-40, 40-45, 45-50, 50-60, 60-70, 70-80, 80-90, 90-100, 100-125, 125-150, 150-175, or 175-200 nucleotides from the 5' and/or 3' end, although the extent of the deletions would naturally be limited by the length of the sequences and the need to be able to use the polynucleotides for the detection of expression levels.

Other polynucleotides of the invention from the 3' end of gene sequences include those of primers and optional probes for quantitative PCR. Preferably, the primers and probes are those which amplify a region less than about 750, less than about 700, less than about 650, less than about 6000, less than about 550, less than about 500, less than about 450, less than about 400, less than about 350, less than about 300, less than about 250, less than about 200, less than about 150, less than about 100, or less than about 50 nucleotides from the from the polyadenylation signal or polyadenylation site of a gene or expressed sequence. The size of a PCR amplicon of the invention may be of any size, including at least or about 50, at least or about 100, at least about or 150, at least or about 200, at least or about 250, at least or about 300, at least or about 350, or at least or about 400 consecutive nucleotides, all with inclusion of the portion complementary to the PCR primers used.

Other polynucleotides for use in the practice of the invention include those that have sufficient homology to gene sequences to detect their expression by use of hybridization techniques. Such polynucleotides preferably have about or 95%, about or 96%, about or 97%, about or 98%, or about or 99% identity with the gene sequences to be used. Identity is determined using the BLAST algorithm, as described above. The other polynucleotides for use in the practice of the invention may also be described on the basis of the ability to hybridize to polynucleotides of the invention under stringent conditions of about 30% v/v to about 50% formamide and from about 0.01M to about 0.15M salt for hybridization and from about 0.01M to about 0.15M salt for wash conditions at about 55 to about 65° C. or higher, or conditions equivalent thereto.

In a further embodiment of the invention, a population of single stranded nucleic acid molecules comprising one or both strands of a human gene sequence is provided as a probe such that at least a portion of said population may be hybridized to one or both strands of a nucleic acid molecule quantitatively amplified from RNA of a cell or sample of the invention. The population may be only the antisense strand of a human gene sequence such that a sense strand of a molecule from, or amplified from, a cell may be hybridized to a portion of said population. The population preferably comprises a sufficiently excess amount of said one or both strands of a human gene sequence in comparison to the amount of expressed (or amplified) nucleic acid molecules containing a complementary gene sequence.

The invention further provides a method of classifying a human tumor sample by detecting the expression levels of 50 or more transcribed sequences in a nucleic acid or cell containing sample obtained from a human subject, and classifying the sample as containing a tumor cell of a tumor type found in humans to the exclusion of one or more other human tumor types. In some embodiments, the method may be used to classify a sample as being, or having cells of, one of the 53 tumor types listed above to the exclusion of one or more of the other 52. In other embodiments, the method is used to classify a sample as being, or having cells of, one of the 34 tumor types listed above to the exclusion of one or more of the other 33 tumor types. In further embodiments, the method is used to classify a sample as being, or having cells of, one of the 39 tumor types listed above to the exclusion of one or more of the other 38 tumor types.

The invention also provides a method for classifying tumor samples as being one of a subset of the possible tumor types described herein by detecting the expression levels of 50 or more transcribed sequences in a nucleic acid containing tumor sample obtained from a human subject, and classifying the sample as being one of a number of tumor types found in humans to the exclusion of one or more other human tumor types. In some embodiments of the invention, the number of other tumor types is from 1 to about 3, more preferably from 1 to about 5, from 1 to about 7, or from 1 to about 9 or about 10. In other embodiments, the number of tumor types are all of the same tissue or organ origin such as those listed above. This aspect of the invention is related to the above discussion of FIG. 8 and of trading off specificity in favor of increased confidence, and may be advantageously applied to situations where the classification of a sample as a single tumor type is at a level of accuracy or performance that can be improved by classifying the sample as one of a subset of possible tumor types.

In additional embodiments, the invention may be practiced by analyzing gene expression from single cells or homogenous cell populations which have been dissected away from, or otherwise isolated or purified from, contaminating cells of a sample as present in a simple biopsy. One advantage provided by these embodiments is that contaminating, non-tumor cells (such as infiltrating lymphocytes or other immune system cells) may be removed as so be absent from affecting the genes identified or the subsequent analysis of gene expression levels as provided herein. Such contamination is present where a biopsy is used to generate gene expression profiles.

In further embodiments of the invention utilizing Q-PCR or reverse transcriptase Q-PCR as the assay platform, the expression levels of gene sequences of the invention may be compared to expression levels of reference genes in the same sample or a ratio of expression levels may be used. This provides a means to "normalize" the expression data for comparison of data on a plurality of known tumor types and a cell containing sample to be assayed. While a variety of reference genes may be used, the invention may also be practiced with the use of 8 particular reference gene sequences that were identified for use with the set of 39 tumor types. Moreover, the Q-PCR may be performed in whole or in part with use of a multiplex format.

mRNA sequences corresponding to the 8 reference sequences are provided in the attached Sequence Listing. A listing of the corresponding SEQ ID NOs, with corresponding identifying information, including accession numbers and other information, is provided by the following.

```
>Hs.77031_mRNA_1 gi|16741772|gb|BC016680.1|BC016680 Homo sapiens clone
MGC: 21349 IMAGE: 4338754 polyA = 3 (SEQ ID NO: 253)
>Hs.77541_mRNA_1 gi|12804364|gb|BC003043.1|BC003043 Homo sapiens clone
MGC: 4370 IMAGE: 2822973 polyA = 3 (SEQ ID NO: 254)
>Hs.7001_mRNA_1 gi|6808256|emb|AL137727.1|HSM802274 Homo sapiens mRNA; cDNA
DKFZp434M0519 (from clone DKFZp434M0519); partial cds polyA = 3 (SEQ ID
NO: 255)
>Hs.302144_mRNA_1 gi|11493400|gb|AF130047.1|AF130047 Homo sapiens clone
FLB3020 polyA = 0 (SEQ ID NO: 256)
>Hs.26510_mRNA_2 gi|11345385|gb|AF308803.1|AF308803 Homo sapiens chromosome
15 map 15q26 polyA = 3 (SEQ ID NO: 257)
>Hs.324709_mRNA_2 gi|12655026|gb|BC001361.1|BC001361 Homo sapiens clone
MGC: 2474 IMAGE: 3050694 polyA = 2 (SEQ ID NO: 258)
>Hs.65756_mRNA_3 gi|3641494|gb|AF035154.1|AF035154 Homo sapiens chromosome
16 map 16p13.3 polyA = 3 (SEQ ID NO: 259)
>Hs.165743_mRNA_2 gi|13543889|gb|BC006091.1|BC006091 Homo sapiens clone
MGC: 12673 IMAGE: 3677524 polyA = 3 (SEQ ID NO: 260)
```

Detection of expression of any of the above reference sequences may be by the same or different methodology as for the other gene sequences described above. In some embodiments of the invention, the expression levels of gene sequences is measured by detection of expressed sequences in a cell containing sample as hybridizing to the following oligonucleotides, which correspond to the above sequences as indicated by the accession numbers provided.

```
>BC006091
                                            (SEQ ID NO: 261)
TCATCTTCACCAAACCAGTCCGAGGGGTCGAAGCCAGACACGAGAGGAA

GAGGGTCCTGG
```

-continued

>BC003043
(SEQ ID NO: 262)
CTCTGCTCCTGCTCCTGCCTGCATGTTCTCTCTGTTGTTGGAGCCTGGA

GCCTTGCTCTC

>AF130047
(SEQ ID NO: 263)
TGCTCCCGGCTGTCCTCCTCTCCTCTTCCCTAGTGAGTGGTTAATGAGT

GTTAATGCCTA

>AF035154
(SEQ ID NO: 264)
CCCCATCTCTAAAACCAGTAAATCAGCCAGCGAATACCCGGAAGCAAGA

TGCACAGGCGG

>BC001361
(SEQ ID NO: 265)
CCAGAAACAAGGAAGAGGAAAGACAAAGGGAAGGGACGGGAGCCCTGGA

GAAGCCCGACC

>AF308803
(SEQ ID NO: 266)
AAGTACAACCCATGCTGCTAAGATGCGAGCAGGAAGAGGCATCCTTTGC

TAAATCCTGTT

>BC016680
(SEQ ID NO: 267)
ACCTCACCCCTGCCCGGCCCAAGCTCTACTTGTGTACAGTGTATATTGT

ATAATAGACAA

>AL137727
(SEQ ID NO: 268)
TTCCCTTAATTCCTCCTCCCGACCTTTTTTACCCCCCCAGTTGCAGTAT

TTAACTGGGCT

In an additional aspect, the methods provided by the present invention may also be automated in whole or in part. This includes the embodiment of the invention in software. Non-limiting examples include processor executable instructions on one or more computer readable storage devices wherein said instructions direct the classification of tumor samples based upon gene expression levels as described herein. Additional processor executable instructions on one or more computer readable storage devices are contemplated wherein said instructions cause representation and/or manipulation, via a computer output device, of the process or results of a classification method.

The invention includes software and hardware embodiments wherein the gene expression data of a set of gene sequences in a plurality of known tumor types is embodied as a data set. In some embodiments, the gene expression data set is used for the practice of a method of the invention. The invention also provides computer related means and systems for performing the methods disclosed herein. In some embodiments, an apparatus for classifying a cell containing sample is provided. Such an apparatus may comprise a query input configured to receive a query storage configured to store a gene expression data set, as described herein, received from a query input; and a module for accessing and using data from the storage in a classification algorithm as described herein. The apparatus may further comprise a string storage for the results of the classification algorithm, optionally with a module for accessing and using data from the string storage in an output algorithm as described herein.

The steps of a method, process, or algorithm described in connection with the embodiments disclosed herein may be embodied directly in hardware, in a software module executed by a processor, or in a combination of the two. The various steps or acts in a method or process may be performed in the order shown, or may be performed in another order. Additionally, one or more process or method steps may be omitted or one or more process or method steps may be added to the methods and processes. An additional step, block, or action may be added in the beginning, end, or intervening existing elements of the methods and processes.

A further aspect of the invention provides for the use of the present invention in relation to clinical activities. In some embodiments, the determination or measurement of gene expression as described herein is performed as part of providing medical care to a patient, including the providing of diagnostic services in support of providing medical care. Thus the invention includes a method in the medical care of a patient, the method comprising determining or measuring expression levels of gene sequences in a cell containing sample obtained from a patient as described herein. The method may further comprise the classifying of the sample, based on the determination/measurement, as including a tumor cell of a tumor type or tissue origin in a manner as described herein. The determination and/or classification may be for use in relation to any aspect or embodiment of the invention as described herein.

The determination or measurement of expression levels may be preceded by a variety of related actions. In some embodiments, the measurement is preceded by a determination or diagnosis of a human subject as in need of said measurement. The measurement may be preceded by a determination of a need for the measurement, such as that by a medical doctor, nurse or other health care provider or professional, or those working under their instruction, or personnel of a health insurance or maintenance organization in approving the performance of the measurement as a basis to request reimbursement or payment for the performance.

The measurement may also be preceded by preparatory acts necessary to the actual measuring. Non-limiting examples include the actual obtaining of a cell containing sample from a human subject; or receipt of a cell containing sample; or sectioning a cell containing sample; or isolating cells from a cell containing sample; or obtaining RNA from cells of a cell containing sample; or reverse transcribing RNA from cells of a cell containing sample. The sample may be any as described herein for the practice of the invention.

In additional embodiments, the invention provides for a method of ordering, or receiving an order for, the performance of a method in the medical care of a patient or other method of the invention. The ordering may be made by a medical doctor, a nurse, or other health care provider, or those working under their instruction, while the receiving, directly or indirectly, may be made by any person who performs the method(s). The ordering may be by any means of communication, including communication that is written, oral, electronic, digital, analog, telephonic, in person, by facsimile, by mail, or otherwise passes through a jurisdiction within the United States.

The invention further provides methods in the processing of reimbursement or payment for a test, such as the above method in the medical care of a patient or other method of the invention. A method in the processing of reimbursement or payment may comprise indicating that 1) payment has been received, or 2) payment will be made by another payer, or 3) payment remains unpaid on paper or in a database after performance of an expression level detection, determination or measurement method of the invention. The database may be in any form, with electronic forms such as a computer implemented database included within the scope of the invention. The indicating may be in the form of a code on paper or in the database. The "another payer" may be any person or entity beyond that to whom a previous request for reimbursement or payment was made.

Alternative, the method may comprise receiving reimbursement or payment for the technical or actual performance of the above method in the medical care of a patient; for the interpretation of the results from said method; or for any other method of the invention. Of course the invention also includes embodiments comprising instructing another person or party to receive the reimbursement or payment. The ordering may be by any communication means, including those described above. The receipt may be from any entity, including an insurance company, health maintenance organization, governmental health agency, or a patient as non-limiting examples. The payment may be in whole or in part. In the case of a patient, the payment may be in the form of a partial payment known as a co-pay.

In yet another embodiment, the method may comprise forwarding or having forwarded a reimbursement or payment request to an insurance company, health maintenance organization, governmental health agency, or to a patient for the performance of the above method in the medical care of a patient or other method of the invention. The request may be by any communication means, including those described above.

In a further embodiment, the method may comprise receiving indication of approval for payment, or denial of payment, for performance of the above method in the medical care of a patient or other method of the invention. Such an indication may come from any person or party to whom a request for reimbursement or payment was made. Non-limiting examples include an insurance company, health maintenance organization, or a governmental health agency, like Medicare or Medicaid as non-limiting examples. The indication may be by any communication means, including those described above.

An additional embodiment is where the method comprises sending a request for reimbursement for performance of the above method in the medical care of a patient or other method of the invention. Such a request may be made by any communication means, including those described above. The request may have been made to an insurance company, health maintenance organization, federal health agency, or the patient for whom the method was performed.

A further method comprises indicating the need for reimbursement or payment on a form or into a database for performance of the above method in the medical care of a patient or other method of the invention. Alternatively, the method may simply indicate the performance of the method. The database may be in any form, with electronic forms such as a computer implemented database included within the scope of the invention. The indicating may be in the form of a code on paper or in the database.

In the above methods in the medical care of a patient or other method of the invention, the method may comprise reporting the results of the method, optionally to a health care facility, a health care provider or professional, a doctor, a nurse, or personnel working therefor. The reporting may also be directly or indirectly to the patient. The reporting may be by any means of communication, including those described above.

The invention further provides kits for the determination or measurement of gene expression levels in a cell containing sample as described herein. A kit will typically comprise one or more reagents to detect gene expression as described herein for the practice of the present invention. Non-limiting examples include polynucleotide probes or primers for the detection of expression levels, one or more enzymes used in the methods of the invention, and one or more tubes for use in the practice of the invention. In some embodiments, the kit will include an array, or solid media capable of being assembled into an array, for the detection of gene expression as described herein. In other embodiments, the kit may comprise one or more antibodies that is immunoreactive with epitopes present on a polypeptide which indicates expression of a gene sequence. In some embodiments, the antibody will be an antibody fragment.

A kit of the invention may also include instructional materials disclosing or describing the use of the kit or a primer or probe of the present invention in a method of the invention as provided herein. A kit may also include additional components to facilitate the particular application for which the kit is designed. Thus, for example, a kit may additionally contain means of detecting the label (e.g. enzyme substrates for enzymatic labels, filter sets to detect fluorescent labels, appropriate secondary labels such as a sheep anti-mouse-HRP, or the like). A kit may additionally include buffers and other reagents recognized for use in a method of the invention.

Having now generally described the invention, the same will be more readily understood through reference to the following examples which are provided by way of illustration, and are not intended to be limiting of the present invention, unless specified.

EXAMPLES

Example 1

Materials and Methods

The following table shows the types and number of samples of known tumors used in Example 2.

| Tumor type | Number of samples |
| --- | --- |
| Adrenal | 7 |
| Brain-glial | 16 |
| Brain-Meningioma | 7 |
| Breast | 43 |
| Cervix-adeno | 8 |
| Cervix-squamous | 13 |
| Endometrium | 13 |
| GallBladder | 5 |
| Germ-cell | 22 |
| GIST | 10 |
| Kidney | 11 |
| Leiomyosarcoma | 13 |
| Liver | 14 |
| Lung-adeno | 9 |
| Lung-large | 9 |
| Lung-small | 8 |
| Lung-squamous | 10 |
| Lymphoma-B | 7 |
| Lymphoma-Hodgkins | 9 |
| Lymphoma-T | 5 |
| Mesothelioma | 10 |
| Osteosarcoma | 7 |
| Ovary-clear | 14 |
| Ovary-serous | 14 |
| Pancreas | 24 |
| Prostate | 11 |
| Skin-basal-cell | 5 |
| Skin-melanoma | 10 |
| Skin-squamous | 6 |
| Small-and-large-bowel | 42 |

| Tumor type | Number of samples |
| --- | --- |
| Soft-tissue-Liposarcoma | 5 |
| Soft-tissue-MFH | 11 |
| Soft-tissue-Sarcoma-synovial | 7 |
| Stomach-adeno | 9 |
| Testis-Seminoma | 10 |
| Thyroid-follicular-papillary | 12 |
| Thyroid-medullary | 7 |
| UrinaryBladder | 25 |
| Total | 468 |
| Bile-Duct | 1 |
| Cholangiocarcinoma | 4 |
| Esophagus | 2 |
| Esophagus-Barretts | 4 |
| Esophagus-squamous | 4 |
| HN-squamous | 3 |
| Ovary (unclassified) | 1 |
| Ovary-endometriod | 1 |
| Ovary-mucinous | 4 |
| Ovary-stromal | 1 |
| Soft-tissue-Ewings-sarcoma | 2 |
| Soft-tissue-Fibrosarcoma | 2 |
| Soft-tissue-Rhabdomyosarcoma | 3 |
| Total | 32 |

The 500 samples were fresh or frozen samples of tumor containing tissue. The 468 samples shown above were used for further experiments by taking 374 as the training set and the remaining 94 samples as the testing set. Tumor types of fewer than 5 samples were not used initially.

The samples contained both primary and metastatic tumors with a confirmed diagnosis. A single 5 µm section was stained (H+E), and the tumor visualized. Pure tumor populations were obtained by either manual dissection, or laser capture microdissection (Arcturus, Mountain View, Calif.).

RNA extraction and quality control were performed on each sample. Briefly, samples were processed using a silica spin column-based extraction method (Arcturus, Mountain View, Calif.). The total quantity of RNA extracted was assessed using quantitative PCR (Taqman, ABI), with primers specific for β-actin transcription. Only samples with greater than 10 ng of RNA were amplified.

Samples were amplified using a modified RNA polymerase 2-round amplification protocol (Arcturus, Mountain View, Calif.). Following amplification, the RNA product yield was quantitated by OD(260/280) spectroscopy, and the amplified product visualized by agarose (2%) denaturing gel electrophoresis.

The amplified product from each sample was then hybridized to a microarray to detect the level of transcript expression in the samples. Random gene selection was performed using random sampling function software. For each number of genes selected, random samples were selected 100 times and used to compute the cross-validation and predictive accuracies on both training and testing sets. Cross-validation was by dividing the training set into parts with one being used to train and another being used as a test.

Example 2

Results

The mean of the accuracies from 100 samplings and the 95% confidence interval were calculated and plotted for each step from 50 to 16948 genes. The plots showed the cross-validation and predictive accuracies from KNN (k-nearest neighbor) algorithm versus the number of genes selected by chance. Random gene selection used random sampling function in R software.

50 or more genes were capable of accurately classifying among the numerous tumor types in toto with a better than 50% accuracy. Similar results are observed with the use of the samples and KNN with known FFPE tumor specimens from which RNA was extracted and analyzed for gene expression.

It should be noted that while the accuracy stabilized with the use of additional genes, it is expected that there are particular sets of 50 or more genes that have significantly higher accuracies. Classification of additional tumor types, such as those totaling 32 samples in the table above, may be made with the inclusion of additional samples.

The accuracy level of a set of 100 randomly selected expressed gene sequences was determined to be 66% and was used as described in Example 3 to generate FIGS. 1 and 2.

Example 3

Information Capacity of Random Gene Sets

Subsets of the 100 randomly selected expressed gene sequences used to classify among 39 tumor types were tested for their ability to classify among subsets of the 39 tumor types. The expression levels of random combinations of 50, 55, 60, 65, 70, 75, 80, 85, 90, 95 and all 100 (each combination sampled 10 times) of the 100 expressed sequences were used with data from tumor types and then used to predict test random sets of tumor samples (each sampled 10 times) ranging from 2 to all 39 types. FIG. 1 shows the classification capability of various gene sets are shown relative to the number of tumor types classified. As expected, a higher number of gene sequences are needed to classify tumor types with higher accuracies. FIG. 2 shows the classification performance for various numbers of tumor types relative to the number of gene sequences used.

The GenBank accession numbers of the 100 gene sequences are AF269223, BC006286, AK025501, AJ002367, AI469140, AW013883, NM_001238, AI476350, BC006546, AI041212, BF724944, AI376951, R56211, BC006393, X13274, BC001133, N62397, BC000885, AK001588, AK057901, AF146760, AI951287, AK025604, BC007581, BC015025, R43102, AW449550, AI922539, AI684144, AI277662, BC015999, AW444656, BC011612, BC015401, BF447279, BC009956, AL050163, BC001248, BE672684, AL137353, BC001340, U45975, BE856598, BC009060, AL137728, AA713797, AL583913, AK054617, AI028262, AI753041, BG939593, AL080179, AA814915, AF131798, AI961568, BC009849, AK021603, BC012561, AI570494, BC006973, AW294857, BC004952, AK026535, AI923614, AW082090, AI005513, AF339768, AK023167, AF169693, AF076249, BC007662, BC015520, AI814187, AI565381, AW271626, AK024120, AF139065, BC014075, AI887245, AF257081, AI767898, AF070634, AF155132, X69804, U65579, NM_004933, AI655104, AW131780, AI650407, AF131774, AA814057, AJ311123, BC009702, AF264036, AL161961, AJ010857, AF106912, AK023542, AF073518, and D83032. They were indexed from 1 to 100, and representative, and non-limiting, random sets used in the invention are as follows:

For 50-genes, set 1, genes 9, 52, 55, 24, 44, 58, 20, 79, 81, 86, 22, 84, 27, 32, 73, 70, 18, 41, 54, 38, 46, 78, 87, 49, 15, 95, 12, 23, 30, 13, 36, 98, 28, 56, 21, 19, 35, 51, 25, 43, 99, 34, 64, 66, 82, 72, 11, 92, 59, and 71 were used. In set 2, genes 72, 92, 27, 8, 14, 87, 42, 83, 65, 85, 40, 21, 74, 66, 6, 28, 13, 98, 91, 78, 49, 52, 33, 30, 97, 84, 2, 95, 88, 64, 93, 11, 1, 45, 61, 39, 12, 67, 53, 89, 43, 17, 54, 7, 55, 38, 3, 15, 70, and 31 were used. In set 3, genes 9, 35, 87, 52, 73, 74, 88, 22, 41, 28, 93, 15, 67, 20, 68, 17, 46, 43, 51, 24, 84, 79, 19, 100, 76, 6, 49, 97, 16, 59, 89, 66, 45, 63, 2, 27, 13, 98, 69, 60, 26, 86, 83, 58, 71, 54, 82, 32, 42, and 77 were used. In set 4, genes 34, 67, 48, 53, 24, 61, 6, 64, 89, 76, 35, 21, 86, 83, 68, 7, 25, 65, 58, 28, 97, 90, 31, 57, 3, 50, 2, 96, 84, 29, 42, 46, 82, 62, 19, 95, 44, 52, 33, 36, 15, 37, 70, 11, 43, 13, 8, 49, 16, and 99 were used. In set 5, genes 11, 22, 87, 25, 5, 38, 35, 68, 94, 51, 60, 53, 20, 42, 95, 92, 33, 15, 14, 24, 85, 37, 69, 17, 19, 93, 8, 97, 46, 83, 26, 86, 66, 89, 63, 16, 74, 28, 52, 2, 96, 99, 71, 10, 65, 90, 29, 34, 77, and 45 were used. In set 6, genes 62, 6, 69, 12, 19, 50, 51, 5, 1, 32, 41, 84, 27, 10, 93, 28, 79, 21, 88, 47, 58, 64, 74, 39, 33, 46, 17, 86, 87, 4, 60, 98, 97, 45, 26, 72, 40, 63, 30, 54, 52, 11, 15, 96, 14, 24, 73, 67, 59, and 38 were used. In set 7, genes 67, 21, 62, 15, 59, 6, 23, 30, 89, 94, 82, 74, 96, 17, 41, 38, 48, 100, 5, 71, 20, 55, 79, 28, 44, 64, 92, 65, 51, 37, 32, 22, 72, 98, 12, 54, 78, 50, 60, 76, 88, 3, 40, 80, 77, 16, 24, 42, 8, and 14 were used. In set 8, genes 43, 68, 8, 38, 82, 73, 12, 23, 77, 63, 56, 33, 66, 14, 47, 17, 53, 62, 42, 57, 30, 89, 44, 58, 34, 24, 81, 40, 45, 1, 99, 52, 37, 80, 96, 10, 71, 50, 20, 51, 18, 54, 31, 70, 84, 3, 83, 76, 59, and 91 were used. In set 9, genes 36, 90, 34, 79, 29, 24, 44, 51, 27, 58, 52, 37, 68, 49, 89, 80, 57, 8, 22, 77, 54, 65, 26, 91, 21, 64, 59, 61, 13, 74, 87, 50, 63, 20, 78, 23, 96, 67, 30, 55, 81, 35, 72, 56, 95, 82, 39, 42, 88, and 92 were used. In set 10, genes 59, 94, 91, 88, 3, 45, 13, 96, 66, 58, 60, 69, 21, 95, 4, 7, 67, 83, 44, 2, 37, 24, 8, 12, 53, 47, 34, 9, 31, 46, 11, 68, 1, 6, 29, 14, 33, 54, 43, 80, 39, 18, 100, 10, 84, 65, 5, 76, 26, and 22 were used.

For 55 genes, set 1, genes 20, 76, 33, 73, 15, 83, 47, 2, 95, 67, 26, 49, 97, 25, 46, 13, 51, 42, 14, 11, 39, 94, 37, 100, 56, 63, 6, 66, 45, 75, 3, 78, 55, 7, 72, 44, 35, 48, 65, 38, 60, 90, 30, 36, 77, 23, 16, 32, 80, 89, 8, 91, 43, 50, and 28 were used. In set 2, genes 11, 63, 93, 79, 21, 57, 66, 10, 42, 83, 75, 94, 3, 38, 49, 91, 53, 90, 50, 52, 39, 99, 85, 48, 31, 18, 89, 25, 87, 56, 40, 5, 19, 88, 27, 92, 20, 100, 59, 43, 95, 80, 86, 44, 55, 68, 54, 33, 96, 45, 2, 9, 81, 73, and 37 were used. In set 3, genes 20, 73, 76, 29, 44, 33, 84, 98, 15, 69, 32, 14, 50, 70, 63, 41, 87, 74, 99, 34, 23, 36, 37, 68, 89, 43, 91, 18, 26, 45, 9, 90, 28, 92, 7, 30, 22, 54, 96, 72, 16, 38, 58, 52, 56, 79, 57, 47, 83, 17, 49, 2, 80, 51, and 46 were used. In set 4, genes 90, 63, 60, 82, 81, 50, 25, 24, 56, 9, 8, 89, 70, 55, 15, 4, 35, 75, 77, 46, 87, 6, 49, 85, 98, 58, 28, 27, 64, 47, 99, 51, 86, 21, 54, 80, 41, 74, 88, 14, 36, 2, 23, 32, 19, 30, 52, 84, 62, 37, 43, 53, 72, 39, and 92 were used. In set 5, genes 27, 43, 33, 84, 89, 31, 60, 97, 15, 45, 42, 73, 4, 6, 90, 61, 72, 56, 2, 38, 96, 74, 94, 14, 25, 77, 58, 86, 21, 32, 82, 3, 50, 17, 28, 48, 44, 7, 70, 20, 59, 83, 1, 71, 52, 95, 69, 54, 39, 46, 63, 51, 57, 34, and 22 were used. In set 6, genes 96, 12, 94, 27, 11, 33, 25, 22, 26, 50, 60, 70, 68, 30, 82, 34, 17, 32, 29, 19, 87, 76, 81, 7, 55, 35, 45, 56, 31, 99, 5, 24, 54, 97, 21, 92, 98, 36, 88, 23, 58, 77, 14, 95, 9, 73, 84, 61, 2, 38, 83, 65, 42, 74, and 48 were used. In set 7, genes 52, 11, 79, 27, 23, 64, 96, 33, 75, 12, 34, 94, 26, 78, 67, 51, 57, 70, 28, 89, 9, 98, 62, 91, 41, 65, 73, 74, 8, 16, 90, 37, 1, 10, 59, 81, 63, 30, 80, 18, 15, 48, 36, 19, 84, 14, 45, 38, 97, 99, 3, 82, 54, 22, and 5 were used. In set 8, genes 83, 57, 6, 37, 44, 76, 5, 59, 74, 62, 72, 23, 93, 75, 32, 100, 98, 29, 30, 65, 21, 17, 78, 46, 13, 82, 14, 50, 66, 63, 90, 49, 54, 68, 60, 10, 87, 94, 58, 91, 33, 31, 36, 8, 11, 92, 51, 38, 43, 52, 7, 86, 89, 84, and 70 were used. In set 9, genes 29, 100, 79, 21, 63, 12, 51, 2, 18, 77, 81, 33, 68, 69, 13, 23, 37, 39, 14, 3, 93, 36, 5, 35, 30, 40, 28, 61, 49, 71, 27, 99, 75, 96, 83, 97, 78, 54, 19, 89, 62, 38, 8, 53, 26, 43, 52, 25, 58, 9, 31, 86, 65, 6, and 60 were used. In set 10, genes 7, 37, 22, 39, 41, 89, 57, 75, 6, 23, 47, 51, 55, 93, 49, 5, 15, 79, 20, 11, 42, 87, 78, 33, 68, 76, 94, 77, 62, 16, 31, 54, 28, 99, 90, 61, 25, 21, 59, 73, 83, 95, 30, 91, 65, 24, 4, 17, 10, 72, 63, 98, 34, 69, and 1 were used.

For 60 genes, set 1, genes 67, 60, 53, 20, 3, 9, 87, 16, 1, 14, 96, 82, 79, 94, 35, 32, 44, 22, 17, 46, 59, 29, 40, 57, 68, 52, 48, 31, 34, 23, 91, 38, 92, 49, 51, 86, 88, 55, 50, 39, 83, 65, 11, 42, 4, 63, 47, 73, 84, 75, 77, 18, 74, 100, 26, 5, 72, 10, 90, and 76 were used. In set 2, genes 62, 67, 70, 82, 8, 10, 26, 45, 98, 38, 76, 14, 72, 36, 89, 95, 86, 96, 18, 91, 75, 74, 7, 46, 16, 83, 65, 33, 29, 57, 32, 42, 34, 37, 80, 100, 99, 9, 2, 22, 64, 11, 87, 35, 23, 55, 60, 61, 81, 49, 5, 58, 3, 40, 71, 54, 85, 94, 66, and 20 were used. In set 3, genes 49, 10, 76, 94, 83, 90, 42, 57, 38, 85, 29, 1, 60, 71, 65, 30, 64, 23, 72, 27, 70, 13, 100, 43, 20, 44, 4, 88, 79, 24, 84, 91, 87, 41, 21, 48, 54, 68, 16, 35, 6, 89, 2, 34, 96, 22, 99, 52, 28, 3, 15, 47, 7, 61, 63, 75, 19, 97, 56, and 39 were used. In set 4, genes 99, 94, 58, 51, 46, 87, 77, 23, 9, 74, 52, 4, 47, 42, 5, 62, 48, 14, 35, 32, 75, 98, 95, 18, 67, 76, 50, 8, 1, 19, 22, 72, 11, 83, 82, 89, 12, 24, 90, 80, 92, 85, 26, 66, 38, 78, 79, 60, 49, 59, 25, 84, 36, 29, 45, 55, 27, 70, 39, and 57 were used. In set 5, genes 39, 21, 70, 81, 88, 30, 2, 57, 45, 5, 47, 93, 1, 34, 51, 49, 3, 6, 65, 97, 41, 67, 95, 85, 98, 29, 82, 38, 17, 84, 72, 52, 20, 33, 53, 66, 7, 54, 25, 23, 80, 61, 76, 9, 14, 48, 26, 12, 32, 4, 64, 73, 56, 87, 59, 35, 31, 62, 13, and 15 were used. In set 6, genes 99, 80, 35, 87, 17, 27, 53, 43, 38, 45, 61, 34, 81, 3, 16, 42, 24, 37, 19, 39, 59, 6, 28, 74, 32, 92, 18, 31, 25, 66, 79, 41, 51, 97, 58, 7, 49, 70, 71, 33, 78, 85, 63, 72, 89, 15, 40, 29, 46, 1, 73, 68, 56, 54, 47, 5, 65, 100, 44, and 22 were used. In set 7, genes 15, 51, 66, 47, 4, 82, 78, 71, 72, 75, 61, 10, 34, 18, 12, 55, 32, 80, 45, 14, 3, 62, 20, 74, 96, 48, 94, 88, 69, 64, 86, 9, 24, 41, 8, 28, 81, 13, 37, 87, 53, 44, 57, 43, 30, 38, 67, 5, 100, 91, 50, 2, 42, 77, 7, 83, 73, 99, 68, and 6 were used. In set 8, genes 41, 21, 20, 62, 50, 86, 13, 23, 94, 45, 80, 51, 42, 52, 47, 76, 18, 72, 25, 8, 35, 58, 37, 32, 46, 71, 99, 33, 48, 77, 38, 19, 44, 66, 7, 53, 12, 10, 74, 96, 84, 28, 30, 15, 2, 81, 7, 26, 79, 88, 24, 49, 65, 17, 95, 63, 75, 11, 55, and 36 were used. In set 9, genes 14, 40, 30, 48, 37, 3, 28, 57, 58, 22, 70, 74, 91, 98, 46, 76, 81, 65, 54, 23, 11, 34, 17, 53, 26, 67, 80, 42, 86, 73, 25, 24, 9, 88, 38, 45, 13, 56, 83, 87, 31, 36, 43, 100, 35, 41, 16, 33, 61, 6, 49, 63, 71, 64, 96, 8, 19, 39, 68, and 84 were used. In set 10, genes 97, 39, 83, 8, 35, 74, 13, 96, 20, 19, 69, 10, 81, 57, 65, 17, 12, 48, 86, 4, 94, 25, 92, 22, 55, 43, 34, 45, 73, 18, 31, 15, 2, 61, 51, 91, 89, 82, 68, 46, 24, 77, 27, 88, 72, 16, 37, 70, 29, 60, 80, 14, 23, 44, 49, 66, 62, 32, 28, and 98 were used.

For 65 genes, set 1, genes 68, 57, 82, 75, 62, 43, 41, 76, 59, 34, 78, 95, 32, 79, 88, 46, 4, 89, 96, 84, 66, 10, 31, 23, 52, 16, 85, 98, 28, 25, 74, 69, 39, 63, 64, 58, 65, 30, 13, 19, 40, 50, 48, 6, 93, 2, 11, 51, 100, 26, 27, 24, 1, 87, 91, 38, 5, 21, 56, 35, 61, 17, 90, 94, and 83 were used. In set 2, genes 62, 33, 59, 65, 12, 97, 20, 99, 13, 64, 29, 23, 49, 35, 66, 74, 77, 46, 14, 11, 81, 32, 42, 34, 70, 17, 54, 44, 24, 53, 3, 8, 71, 47, 96, 80, 86, 40, 15, 37, 90, 67, 73, 50, 25, 51, 36, 75, 72, 92, 93, 4, 84, 18, 76, 21, 38, 88, 68, 9, 60, 52, 45, 7, and 41 were used. In set 3, genes 12, 80, 56, 70, 50, 95, 15, 85, 93, 53, 45, 47, 10, 99, 32, 76, 67, 89, 83, 35, 91, 62, 6, 84, 23, 52, 65, 9, 37, 4, 51, 42, 48, 49, 100, 21, 5, 43, 75, 92, 98, 36, 16, 27, 19, 22, 82, 73, 58, 63, 34, 74, 3, 71, 87, 72, 81, 1, 68, 46, 55, 88, 64, 11, and 33 were used. In set 4, genes 16, 41, 15, 40, 19, 47, 77, 96, 5, 21, 38, 84, 22, 27, 81, 46, 74, 36, 8, 52, 98, 87, 91, 54, 86, 80, 25, 39, 75, 42, 10, 83, 51, 90, 62, 78, 17, 9, 53, 68, 12, 100, 24, 89, 20, 58, 59, 11, 92, 32, 30, 95, 49, 55, 73, 82, 99, 70, 97, 13, 6, 93, 67, 29, and 45 were used. In set 5, genes 94, 3, 31, 85, 51, 80, 8, 55, 22, 93, 97, 49, 14, 81, 67, 76, 77, 75, 19, 59, 5, 72, 34, 62, 58, 43, 7, 44, 35, 98, 24, 74, 41, 73, 63, 13, 87, 56, 15, 42, 12, 91, 50, 37, 29, 40, 53, 83, 2, 99, 100, 1, 10, 33, 16, 26, 9, 71, 39, 11, 46, 57, 66, 92, and 82 were used. In set 6, genes 86, 55, 15, 9, 13, 94, 33, 16, 14, 11, 32, 59, 88, 64, 90, 50, 45, 82, 7, 44, 48, 98, 21, 51, 62, 99, 75, 25, 19, 41, 24, 26, 17, 23, 6, 71, 72, 47, 42, 2, 85, 22, 56, 81, 78, 79, 43, 18, 100, 36, 34, 70, 39, 80, 66, 97, 58, 31, 30, 57, 35, 96, 12, 29, and 10 were used. In set 7, genes 16, 50, 4, 18, 60, 65, 37, 94, 1, 88, 76, 71, 31, 2, 53, 59, 19, 26, 28, 89, 87, 77, 63, 57, 92, 55, 20, 93, 72, 38, 46, 62, 45, 11, 52, 95, 54, 14, 36, 42, 39, 64, 7, 99, 86, 78, 27, 43, 66, 58, 25, 81, 79, 41, 90, 13, 73, 67, 32, 44, 23, 34, 29, 6, and 35 were used. In set 8, genes 8, 53, 3, 33, 84, 61, 74, 98, 31, 9, 55, 62, 4, 88, 27, 50, 85, 34, 69, 83, 99, 17, 25, 19, 40, 90, 45, 30, 28, 92, 93, 75, 95, 37, 6, 24, 79, 96, 70, 60, 91, 52, 89, 49, 10, 100, 39, 77, 41, 23, 29, 20, 22, 5, 16, 59, 21, 46, 80, 32, 73, 72, 2, 26, and 48 were used. In set 9, genes 98, 82, 24, 35, 25, 93, 5, 56, 76, 96, 2, 78, 40, 13, 83, 86, 92, 77, 81, 29, 58, 99, 97, 80, 18, 27, 1, 65, 14, 16, 59, 20, 26, 67, 32, 22, 90, 37, 85, 7, 41, 34, 4, 68, 45, 12, 79, 62, 17, 75, 84, 91, 54, 72, 57, 10, 95, 44, 52, 9, 28, 89, 100, 33, and 21 were used. In set 10, genes 96, 40, 22, 50, 75, 38, 98, 89, 55, 60, 86, 18, 87, 85, 49, 2, 57, 73, 33, 29, 59, 42, 63, 68, 62, 92, 74, 53, 8, 7, 51, 71, 11, 30, 83, 56, 77, 81, 79, 16, 37, 69, 61, 64, 27, 67, 25, 100, 31, 3, 13, 4, 12, 21, 65, 99, 36, 66, 6, 94, 44, 35, 72, 95, and 90 were used.

For 70 genes, set 1, genes 36, 6, 100, 39, 37, 3, 27, 45, 93, 19, 89, 43, 68, 9, 60, 46, 51, 80, 32, 52, 62, 35, 58, 14, 10, 33, 85, 12, 64, 67, 75, 86, 17, 44, 83, 24, 87, 84, 23, 96, 79, 20, 13, 8, 11, 76, 88, 56, 38, 98, 29, 16, 99, 2, 66, 30, 48, 26, 5, 25, 78, 42, 47, 94, 15, 4, 55, 65, 97, and 71 were used. In set 2, genes 96, 98, 38, 32, 52, 25, 31, 14, 91, 53, 8, 94, 49, 27, 69, 20, 44, 4, 92, 56, 61, 97, 18, 65, 66, 54, 21, 3, 29, 79, 80, 70, 77, 50, 39, 99, 58, 23, 85, 51, 15, 72, 33, 19, 24, 68, 7, 41, 81, 64, 57, 73, 84, 46, 22, 74, 11, 45, 55, 82, 6, 47, 59, 42, 88, 9, 16, 34, 83, and 30 were used. In set 3, genes 27, 46, 30, 54, 47, 94, 26, 38, 73, 31, 43, 8, 50, 48, 6, 56, 59, 25, 89, 52, 78, 68, 49, 29, 83, 92, 97, 98, 4, 3, 95, 87, 23, 1, 51, 44, 34, 35, 85, 61, 22, 84, 42, 13, 75, 93, 45, 88, 19, 80, 39, 24, 77, 2, 55, 62, 11, 90, 18, 81, 57, 20, 96, 28, 7, 70, 86, 5, 63, and 69 were used. In set 4, genes 65, 29, 88, 19, 42, 30, 15, 16, 74, 53, 25, 8, 95, 5, 69, 99, 59, 67, 84, 14, 80, 12, 37, 13, 71, 39, 43, 100, 60, 79, 51, 11, 45, 82, 83, 61, 62, 90, 6, 20, 2, 18, 97, 1, 48, 81, 35, 87, 56, 36, 93, 41, 54, 46, 10, 27, 47, 33, 55, 64, 26, 57, 85, 89, 9, 96, 72, 68, 23, and 32 were used. In set 5, genes 25, 41, 56, 91, 19, 22, 63, 39, 59, 83, 7, 74, 20, 86, 84, 2, 43, 73, 69, 58, 35, 26, 23, 42, 29, 10, 13, 77, 16, 72, 71, 81, 40, 66, 80, 50, 12, 48, 64, 100, 24, 94, 97, 57, 98, 68, 78, 92, 53, 31, 45, 38, 61, 75, 5, 1, 44, 99, 3, 36, 88, 34, 21, 17, 15, 89, 37, 51, 85, and 79 were used. In set 6, genes 59, 78, 34, 83, 5, 11, 60, 97, 3, 9, 20, 90, 33, 8, 31, 10, 80, 7, 92, 15, 23, 72, 14, 86, 82, 18, 42, 88, 94, 48, 79, 73, 77, 52, 95, 16, 87, 28, 98, 71, 74, 21, 67, 6, 66, 35, 99, 29, 32, 75, 26, 39, 47, 45, 50, 41, 54, 1, 84, 85, 91, 100, 61, 12, 37, 4, 25, 55, 46, and 13 were used. In set 7, genes 63, 14, 66, 75, 12, 2, 90, 81, 27, 72, 70, 89, 59, 46, 6, 53, 22, 80, 30, 79, 82, 71, 92, 19, 73, 83, 38, 40, 1, 68, 20, 8, 50, 74, 94, 26, 35, 28, 43, 34, 77, 18, 96, 16, 95, 85, 15, 9, 11, 84, 39, 10, 54, 65, 57, 25, 60, 51, 55, 33, 17, 44, 29, 58, 93, 62, 21, 4, 7, and 78 were used. In set 8, genes 60, 76, 17, 29, 68, 24, 54, 87, 16, 66, 15, 8, 85, 92, 67, 100, 82, 74, 41, 33, 3, 35, 94, 78, 58, 75, 98, 63, 95, 12, 47, 81, 91, 9, 7, 83, 77, 22, 89, 56, 49, 31, 96, 2, 70, 23, 46, 6, 39, 90, 59, 71, 44, 10, 36, 52, 42, 86, 5, 64, 55, 69, 84, 28, 93, 53, 38, 27, 13, and 26 were used. In set 9, genes 21, 24, 41, 29, 92, 30, 51, 31, 83, 71, 37, 23, 11, 53, 14, 93, 45, 69, 52, 56, 70, 68, 3, 79, 26, 58, 66, 15, 50, 95, 16, 2, 4, 5, 28, 42, 34, 9, 82, 6, 63, 44, 87, 32, 59, 80, 55, 96, 54, 89, 22, 94, 36, 46, 40, 86, 98, 38, 67, 85, 35, 60, 25, 1, 78, 61, 17, 64, 7, and 91 were used. In set 10, genes 93, 44, 77, 3, 31, 64, 39, 89, 23, 51, 78, 85, 35, 81, 22, 74, 97, 14, 27, 13, 16, 88, 28, 61, 57, 79, 99, 37, 30, 36, 24, 11, 45, 34, 54, 50, 41, 1, 7, 48, 56, 63, 58, 49, 17, 26, 15, 69, 2, 53, 43, 62, 55, 100, 95, 52, 83, 29, 19, 38, 59, 76, 20, 87, 66, 25, 72, 70, 4, and 73 were used.

For 75 genes, set 1, genes 73, 40, 56, 32, 59, 42, 70, 12, 100, 6, 28, 11, 43, 55, 5, 64, 80, 99, 23, 57, 18, 82, 60, 61, 31, 81, 14, 3, 91, 76, 86, 19, 26, 83, 38, 29, 8, 36, 69, 85, 96, 27, 47, 10, 35, 39, 94, 24, 62, 34, 54, 65, 25, 90, 51, 67, 41, 46, 33, 1, 37, 49, 9, 71, 13, 21, 44, 2, 98, 52, 84, 20, 74, 93, and 88 were used. In set 2, genes 26, 21, 43, 56, 15, 55, 9, 34, 58, 12, 85, 44, 20, 99, 74, 35, 39, 88, 53, 8, 92, 67, 6, 48, 69, 28, 23, 87, 71, 5, 72, 89, 38, 100, 25, 1, 13, 3, 14, 29, 96, 62, 64, 90, 78, 63, 68, 66, 11, 41, 77, 42, 4, 60, 24, 98, 18, 17, 52, 46, 30, 32, 70, 33, 31, 83, 45, 36, 84, 95, 82, 80, 22, 50, and 73 were used. In set 3, genes 96, 11, 58, 14, 77, 32, 6, 28, 55, 12, 40, 72, 83, 7, 89, 67, 51, 63, 95, 15, 74, 99, 88, 81, 84, 38, 36, 13, 87, 5, 69, 62, 19, 86, 90, 76, 66, 33, 52, 4, 20, 78, 59, 27, 17, 2, 43, 75, 64, 79, 53, 26, 3, 42, 100, 48, 71, 85, 41, 25, 61, 57, 49, 70, 37, 80, 24, 94, 30, 54, 9, 35, 21, 16, and 22 were used. In set 4, genes 48, 31, 73, 90, 10, 100, 32, 56, 83, 38, 93, 7, 53, 8, 79, 15, 63, 5, 92, 76, 58, 59, 35, 67, 2, 98, 23, 37, 24, 94, 25, 9, 46, 36, 82, 40, 89, 27, 34, 71, 84, 97, 86, 6, 21, 54, 22, 72, 17, 44, 26, 57, 64, 11, 91, 75, 80, 95, 62, 88, 51, 39, 99, 69, 43, 68, 42, 52, 16, 4, 30, 77, 81, 60, and 50 were used. In set 5, genes 86, 46, 90, 79, 40, 99, 53, 67, 97, 82, 7, 15, 49, 71, 94, 48, 68, 80, 20, 51, 19, 96, 100, 38, 91, 83, 50, 33, 76, 66, 93, 22, 74, 85, 45, 31, 10, 62, 84, 25, 88, 77, 43, 78, 69, 24, 61, 57, 41, 56, 63, 32, 16, 59, 12, 4, 14, 28, 87, 44, 65, 55, 98, 35, 9, 64, 75, 47, 89, 18, 52, 36, 29, 54, and 81 were used. In set 6, genes 70, 47, 96, 46, 43, 2, 66, 39, 54, 40, 31, 84, 92, 30, 5, 75, 21, 9, 4, 24, 59, 90, 42, 44, 45, 97, 55, 69, 74, 79, 87, 86, 91, 56, 13, 98, 12, 64, 34, 99, 67, 83, 27, 68, 16, 10, 81, 61, 80, 7, 94, 82, 49, 71, 53, 15, 76, 36, 11, 19, 41, 65, 8, 28, 14, 95, 62, 51, 63, 88, 3, 60, 18, 58, and 52 were used. In set 7, genes 90, 80, 39, 46, 51, 91, 25, 16, 3, 36, 20, 30, 17, 99, 95, 44, 27, 89, 61, 9, 65, 19, 86, 13, 84, 14, 5, 10, 82, 67, 85, 45, 59, 81, 35, 41, 4, 71, 32, 24, 22, 6, 53, 98, 54, 66, 42, 18, 97, 94, 87, 49, 79, 56, 72, 57, 76, 69, 28, 43, 23, 11, 52, 92, 7, 93, 96, 75, 73, 8, 58, 83, 50, 29, and 68 were used. In set 8, genes 95, 93, 14, 43, 31, 32, 100, 6, 92, 28, 68, 99, 35, 60, 90, 70, 22, 49, 54, 94, 56, 4, 97, 85, 2, 46, 11, 50, 63, 30, 38, 76, 39, 58, 64, 67, 83, 33, 88, 79, 87, 40, 57, 27, 55, 18, 3, 29, 82, 53, 98, 91, 61, 80, 26, 84, 20, 77, 86, 51, 1, 74, 23, 19, 10, 21, 47, 69, 24, 66, 81, 96, 15, 36, and 41 were used. In set 9, genes 33, 41, 48, 68, 53, 45, 30, 79, 23, 70, 86, 13, 71, 92, 58, 1, 77, 26, 61, 81, 69, 14, 73, 88, 44, 87, 74, 9, 4, 12, 20, 75, 60, 57, 55, 82, 22, 94, 46, 65, 16, 19, 52, 40, 59, 66, 64, 28, 96, 91, 93, 39, 72, 5, 98, 6, 3, 62, 24, 36, 49, 31, 47, 90, 35, 89, 84, 99, 32, 11, 56, 17, 83, 51, and 97 were used. In set 10, genes 40, 10, 67, 9, 43, 13, 52, 73, 50, 41, 54, 56, 98, 100, 83, 85, 28, 32, 47, 66, 74, 65, 79, 81, 94, 36, 90, 69, 31, 64, 88, 99, 44, 18, 33, 75, 95, 42, 58, 92, 15, 53, 97, 34, 63, 30, 24, 3, 45, 29, 82, 48, 17, 14, 26, 49, 93, 27, 87, 6, 57, 39, 68, 12, 70, 4, 25, 91, 11, 89, 21, 23, 96, 84, and 46 were used.

For 80 genes, set 1, genes 75, 2, 91, 94, 19, 31, 43, 50, 96, 49, 29, 14, 93, 58, 69, 82, 28, 6, 65, 26, 66, 40, 64, 34, 33, 53, 13, 4, 37, 80, 57, 59, 1, 87, 11, 16, 83, 21, 35, 52, 25, 99, 45, 46, 36, 89, 88, 7, 39, 55, 90, 72, 17, 9, 85, 44, 22, 56, 8, 23, 18, 77, 12, 10, 48, 97, 61, 74, 92, 81, 95, 68, 47, 71, 62, 24, 70, 20, 79, and 32 were used. In set 2, genes 1, 34, 89, 27, 22, 77, 28, 35, 11, 7, 39, 21, 46, 49, 74, 43, 13, 75, 14, 65, 73, 92, 19, 66, 29, 81, 88, 78, 40, 32, 12, 71, 9, 44, 23, 70, 45, 10, 98, 48, 68, 55, 82, 5, 56, 59, 15, 95, 33, 99, 87, 85, 18, 97, 100, 83, 53, 63, 6, 2, 37, 17, 67, 62, 50, 42, 25, 94, 31, 69, 90, 84, 64, 16, 57, 51, 54, 80, 86, and 38 were used. In set 3, genes 63, 28, 35, 67, 96, 9, 12, 31, 1, 59, 22, 44, 11, 82, 6, 64, 87, 47, 21, 94, 42, 2, 72, 19, 20, 27, 89, 13, 77, 3, 16, 79, 38, 10, 80, 52, 50, 33, 25, 4, 30, 40, 32, 36, 8, 43, 26, 51, 18, 66, 61, 68, 56, 74, 53, 7, 73, 88, 49, 23, 46, 76, 92, 93, 83, 70, 24, 98, 97, 58, 65, 29, 55, 91, 95, 90, 5, 69, 86, and 78 were used. In set 4, genes 79, 72, 68, 31, 42, 95, 78, 36, 10, 34, 59, 91, 46, 40, 82, 1, 44, 4, 69, 3, 17, 43, 35, 63, 18, 13, 77, 81, 67, 26, 60, 86, 25, 61, 89, 76, 55, 27, 22, 29, 20, 11, 7, 30, 54, 39, 62, 8, 74, 28, 71, 12, 38, 65, 66, 64, 21, 9, 56, 16, 88, 99, 96, 32, 94, 51, 90, 37, 87, 92, 97, 70, 41, 57, 50, 45, 83, 24, 48, and 58 were used. In set 5, genes 100, 69, 33, 24, 83, 84, 97, 22, 40, 45, 17, 3, 43, 52, 50, 30, 8, 99, 9, 46, 7, 14, 35, 61, 15, 16, 64, 6, 23, 41, 60, 63, 96, 98, 38, 36, 49, 13, 76, 85, 87, 71, 66, 56, 80, 20, 34, 29, 57, 91, 81, 78, 27, 88, 37, 94, 51, 5, 1, 74, 44, 70, 58, 25, 19, 89, 39, 47, 65, 62, 68, 95, 18, 75, 79, 59, 2, 10, 73, and 53 were used. In set 6, genes 69, 100, 3, 35, 58, 56, 96, 43, 39, 50, 61, 36, 71, 95, 30, 18, 90, 63, 21, 31, 94, 46, 44, 23, 7, 10, 88, 49, 9, 53, 25, 54, 2, 97, 82, 75, 68, 48, 26, 91, 70, 65, 51, 19, 84, 29, 47, 12, 99, 85, 20, 16, 5, 22, 73, 93, 92, 89, 62, 81, 77, 41, 83, 1, 72, 27, 15, 79, 67, 37, 11, 64, 87, 86, 80, 74, 55, 8, 13, and 60 were used. In set 7, genes 67, 73, 85, 95, 92, 60, 29, 28, 24, 90, 72, 71, 37, 76, 27, 78, 53, 34, 98, 70, 87, 33, 5, 41, 42, 68, 62, 82, 100, 96, 69, 65, 6, 91, 21, 38, 3, 80, 25, 75, 31, 52, 79, 20, 84, 83, 19, 86, 57, 9, 77, 58, 64, 97, 14, 8, 50, 2, 51, 94, 56, 46, 35, 93, 7, 39, 1, 88, 59, 17, 48, 74, 32, 81, 99, 16, 11, 49, 13, and 30 were used. In set 8, genes 80, 52, 14, 42, 21, 76, 32, 69, 30, 60, 86, 61, 48, 24, 67, 92, 16, 75, 93, 2, 6, 99, 20, 73, 9, 97, 98, 56, 47, 12, 35, 26, 36, 41, 96, 55, 11, 84, 7, 87, 4, 70, 79, 88, 44, 17, 50, 27, 89, 28, 29, 43, 77, 39, 8, 15, 91, 65, 22, 71, 53, 37, 34, 95, 83, 45, 68, 1, 18, 13, 31, 85, 3, 90, 51, 49, 19, 66, 63, and 54 were used. In set 9, genes 91, 22, 68, 85, 53, 89, 10, 77, 97, 4, 7, 33, 46, 51, 14, 76, 82, 62, 17, 3, 65, 70, 84, 75, 31, 50, 73, 63, 19, 52, 42, 26, 23, 47, 96, 2, 64, 56, 9, 54, 38, 93, 13, 90, 86, 8, 59, 57, 79, 28, 21, 88, 5, 66, 1, 94, 55, 35, 15, 87, 74, 32, 27, 92, 72, 18, 69, 80, 37, 67, 71, 34, 95, 99, 40, 83, 30, 81, 48, and 39 were used. In set 10, genes 92, 76, 86, 5, 20, 1, 48, 42, 62, 29, 12, 7, 37, 46, 47, 82, 32, 66, 97, 77, 56, 91, 30, 80, 36, 72, 17, 31, 2, 81, 23, 28, 51, 55, 98, 40, 95, 13, 10, 58, 33, 21, 14, 74, 85, 88, 22, 75, 94, 27, 43, 3, 100, 61, 67, 4, 25, 6, 44, 60, 24, 93, 63, 89, 70, 41, 15, 11, 53, 87, 16, 65, 52, 68, 57, 99, 50, 45, 71, and 38 were used.

For 85 genes, set 1, genes 38, 35, 85, 59, 17, 7, 31, 58, 96, 97, 16, 70, 82, 42, 21, 54, 88, 34, 63, 4, 27, 29, 3, 19, 69, 36, 9, 99, 74, 86, 76, 24, 15, 81, 73, 93, 40, 52, 26, 57, 37, 87, 55, 90, 41, 79, 45, 77, 91, 71, 61, 11, 94, 83, 25, 48, 1, 5, 8, 22, 33, 46, 60, 56, 20, 44, 89, 18, 10, 23, 78, 65, 50, 72, 75, 47, 98, 28, 66, 68, 32, 12, 51, 13, and 100 were used. In set 2, genes 32, 90, 94, 21, 77, 63, 17, 27, 62, 41, 35, 81, 100, 14, 45, 69, 3, 75, 34, 76, 65, 15, 95, 86, 39, 92, 89, 24, 57, 4, 54, 50, 58, 88, 5, 56, 22, 59, 6, 52, 28, 1, 9, 40, 98, 99, 91, 19, 8, 23, 96, 2, 73, 67, 7, 25, 53, 12, 44, 18, 13, 87, 60, 49, 93, 55, 20, 72, 42, 66, 30, 80, 33, 26, 64, 46, 84, 31, 70, 61, 71, 83, 38, 36, and 29 were used. In set 3, genes 88, 20, 1, 58, 53, 32, 65, 34, 50, 75, 71, 36, 59, 39, 30, 61, 8, 62, 14, 3, 94, 66, 35, 37, 17, 47, 77, 60, 4, 80, 74, 28, 97, 87, 93, 33, 64, 48, 29, 18, 49, 21, 56, 69, 22, 25, 43, 54, 91, 7, 81, 79, 12, 85, 96, 40, 63, 52, 82, 86, 41, 24, 44, 84, 70, 6, 15, 38, 57, 16, 55, 90, 76, 42, 51, 23, 11, 67, 45, 98, 19, 10, 27, 2, and 31 were used. In set 4, genes 64, 86, 54, 83, 47, 21, 67, 57, 73, 23, 71, 76, 56, 9, 44, 75, 82, 11, 8, 99, 72, 13, 79, 28, 92, 5, 27, 90, 24, 91, 33, 68, 51, 60, 94, 58, 78, 48, 18, 42, 53, 98, 70, 32, 41, 49, 45, 6, 30, 63, 95, 80, 36, 87, 97, 65, 77, 3, 26, 35, 59, 40, 84, 37, 61, 81, 39, 46, 22, 1, 2, 50, 25, 69, 4, 43, 15, 29, 20, 17, 88, 10, 38, 100, and 19 were used. In set 5, genes 11, 92, 15, 42, 33, 19, 6, 57, 23, 87, 31, 5, 30, 21, 54, 51, 14, 68, 97, 34, 59, 24, 20, 50, 29, 65, 13, 80, 16, 73, 8, 25, 47, 55, 27, 45, 100, 96, 85, 38, 37, 81, 44, 4, 9, 70, 98, 77, 48, 35, 28, 79, 41, 71, 86, 61, 2, 49, 60, 67, 66, 69, 72, 3, 83, 26, 1, 89, 17, 39, 52, 10, 32, 75, 82, 99, 40, 95, 90, 53, 22, 91, 62, 78, and 56 were used. In set 6, genes 87, 32, 4, 63, 15, 81, 92, 10, 74, 44, 7, 23, 89, 93, 28, 59, 50, 72, 30, 60, 54, 71, 39, 12, 21, 85, 40, 37, 68, 64, 97, 66, 52, 67, 98, 91, 1, 83, 61, 6, 24, 38, 86, 77, 26, 88, 43, 100, 48, 20, 14, 31, 82, 9, 13, 62, 55, 45, 57, 11, 27, 90, 25, 80, 17, 5, 94, 42, 53, 49, 29, 99, 78, 2, 84, 73, 58, 75, 18, 19, 65, 3, 47, 41, and 36 were used. In set 7, genes 56, 38, 23, 74, 34, 99, 93, 4, 13, 18, 61, 49, 20, 5, 76, 88, 91, 31, 78, 32, 1, 89, 12, 16, 51, 54, 81, 70, 86, 97, 66, 19, 59, 39, 8, 80, 73, 35, 71, 77, 24, 53, 68, 33, 62, 69, 43, 41, 15, 94, 44, 52, 29, 100, 55, 36, 27, 25, 67, 21, 96, 30, 42, 92, 11, 3, 45, 63, 72, 57, 47, 46, 75, 90, 2, 48, 14, 6, 9, 87, 22, 98, 95, 84, and 65 were used. In set 8, genes 79, 64, 71, 18, 37, 40, 54, 34, 26, 65, 39, 67, 14, 62, 95, 11, 49, 92, 59, 48, 6, 12, 57, 9, 20, 81, 16, 50, 38, 33, 100, 47, 63, 3, 84, 87, 35, 98, 56, 93, 66, 23, 2, 29, 90, 78, 85, 60, 19, 72, 97, 36, 13, 94, 25, 45, 41, 27, 69, 52, 8, 68, 46, 30, 1, 96, 7, 83, 80, 4, 99, 15, 76, 10, 58, 89, 88, 51, 55, 82, 53, 28, 44, 73, and 77 were used. In set 9, genes 35, 85, 81, 4, 20, 88, 66, 74, 13, 36, 6, 24, 95, 97, 2, 21, 90, 57, 89, 42, 73, 79, 64, 59, 46, 68, 92, 67, 82, 28, 56, 14, 65, 99, 39, 38, 8, 62, 61, 78, 11, 48, 93, 91, 29, 33, 76, 16, 69, 47, 84, 94, 7, 54, 30, 32, 23, 70, 52, 43, 51, 41, 60, 100, 27, 63, 75, 77, 80, 5, 3, 44, 10, 87, 40, 71, 37, 72, 1, 53, 22, 83, 49, 17, and 34 were used. In set 10, genes 23, 39, 86, 48, 65, 73, 24, 27, 61, 37, 99, 64, 58, 74, 3, 22, 57, 60, 13, 93, 44, 100, 66, 69, 38, 83, 6, 81, 59, 36, 68, 95, 71, 70, 84, 62, 96, 26, 30, 32, 20, 54, 80, 19, 97, 16, 4, 77, 12, 5, 35, 29, 18, 52, 53, 87, 98, 90, 10, 75, 72, 55, 50, 88, 28, 34, 41, 94, 11, 76, 7, 45, 31, 46, 49, 9, 82, 17, 79, 1, 25, 40, 67, 47, and 85 were used.

For 90 genes, set 1, genes 79, 5, 27, 100, 96, 11, 32, 63, 42, 68, 13, 65, 88, 75, 17, 64, 82, 72, 37, 45, 98, 2, 90, 94, 1, 87, 73, 86, 69, 92, 3, 25, 29, 84, 60, 50, 39, 4, 95, 47, 12, 10, 33, 22, 77, 71, 57, 97, 38, 89, 91, 53, 51, 9, 67, 44, 7, 78, 34, 85, 15, 41, 54, 49, 62, 76, 83, 46, 59, 23, 24, 8, 14, 26, 30, 52, 18, 6, 66, 31, 20, 93, 36, 16, 61, 28, 74, 43, 56, and 48 were used. In set 2, genes 95, 28, 46, 62, 91, 99, 53, 65, 66, 60, 22, 29, 50, 2, 93, 33, 54, 57, 92, 24, 9, 4, 69, 5, 8, 58, 88, 43, 6, 100, 51, 18, 16, 45, 81, 44, 68, 14, 59, 82, 63, 73, 30, 86, 98, 13, 84, 94, 1, 55, 38, 83, 3, 37, 11, 89, 77, 85, 26, 97, 12, 21, 40, 96, 56, 41, 10, 42, 64, 17, 76, 27, 49, 20, 87, 34, 75, 15, 74, 35, 19, 31, 39, 48, 23, 67, 78, 32, 7, and 80 were used. In set 3, genes 88, 89, 6, 94, 17, 60, 8, 76, 45, 90, 47, 80, 15, 85, 51, 5, 46, 36, 65, 4, 25, 67, 78, 77, 97, 23, 11, 40, 61, 53, 39, 12, 38, 21, 59, 55, 32, 34, 71, 69, 20, 50, 93, 3, 30, 29, 75, 73, 49, 98, 58, 43, 18, 95, 42, 82, 66, 16, 33, 37, 92, 52, 56, 41, 87, 99, 74, 24, 86, 48, 81, 57, 83, 26, 79, 68, 13, 63, 72, 9, 70, 14, 54, 100, 64, 19, 96, 7, 31, and 2 were used. In set 4, genes 19, 33, 41, 40, 70, 51, 14, 48, 42, 12, 90, 4, 32, 60, 89, 64, 45, 86, 73, 16, 50, 5, 9, 72, 81, 3, 27, 87, 76, 58, 29, 31, 13, 21, 55, 18, 6, 62, 56, 96, 47, 63, 37, 98, 28, 91, 36, 82, 39, 100, 68, 25, 88, 11, 93, 35, 66, 24, 43, 59, 8, 65, 74, 30, 10, 22, 17, 99, 49, 44, 26, 54, 2, 80, 94, 57, 71, 38, 67, 79, 75, 77, 23, 85, 61, 52, 83, 7, 78, and 53 were used. In set 5, genes 49, 55, 13, 97, 59, 83, 61, 34, 80, 19, 12, 65, 86, 72, 89, 25, 39, 77, 82, 47, 22, 48, 20, 11, 23, 84, 31, 4, 54, 91, 8, 87, 33, 14, 32, 45, 68, 27, 51, 28, 96, 1, 100, 92, 37, 29, 64, 15, 7, 98, 60, 53, 17, 69, 24, 75, 81, 74, 5, 18, 26, 78, 62, 94, 88, 46, 73, 44, 63, 52, 9, 93, 76, 6, 95, 99, 42, 50, 66, 38, 90, 70, 35, 57, 85, 58, 16, 43, 30, and 10 were used. In set 6, genes 81, 52, 60, 16, 18, 40, 67, 47, 58, 51, 26, 5, 53, 34, 24, 68, 14, 43, 49, 69, 99, 73, 29, 96, 37, 62, 66, 38, 88, 48, 11, 50, 79, 74, 15, 39, 83, 57, 94, 95, 100, 12, 84, 10, 33, 3, 93, 91, 17, 46, 59, 86, 7, 9, 71, 19, 22, 80, 27, 97, 4, 75, 89, 21, 78, 85, 63, 61, 77, 31, 32, 56, 6, 72, 92, 55, 76, 90, 36, 35, 98, 1, 82, 25, 23, 44, 65, 64, 28, and 42 were used. In set 7, genes 51, 1, 54, 94, 93, 56, 22, 29, 53, 67, 88, 82, 16, 44, 65, 21, 14, 35, 48, 91, 12, 97, 31, 74, 6, 99, 86, 26, 28, 19, 72, 58, 24, 34, 5, 38, 81, 11, 49, 39, 3, 89, 75, 64, 96, 52, 59, 69, 42, 78, 33, 100, 2, 25, 66, 77, 90, 40, 71, 9, 4, 57, 13, 36, 10, 50, 17, 87, 15, 47, 60, 46, 63, 68, 70, 23, 80, 37, 30, 92, 7, 32, 27, 43, 98, 84, 8, 61, 73, and 41 were used. In set 8, genes 53, 63, 17, 43, 6, 44, 95, 58, 78, 13, 3, 15, 28, 41, 12, 93, 2, 92, 23, 42, 62, 57, 33, 8, 65, 49, 80, 81, 50, 71, 74, 39, 4, 70, 77, 51, 84, 21, 30, 36, 46, 75, 47, 94, 16, 67, 55, 1, 26, 52, 60, 19, 59, 90, 96, 14, 87, 37, 40, 66, 88, 73, 29, 10, 5, 56, 100, 45, 31, 34, 22, 64, 91, 54, 48, 25, 98, 61, 18, 72, 69, 27, 68, 99, 83, 35, 24, 82, 85, and 38 were used. In set 9, genes 62, 91, 49, 28, 69, 38, 19, 35, 89, 3, 24, 79, 32, 12, 47, 40, 39, 50, 86, 6, 44, 65, 33, 70, 16, 41, 21, 53, 72, 74, 87, 14, 51, 7, 60, 67, 100, 42, 93, 36, 2, 57, 76, 20, 25, 27, 95, 18, 73, 97, 54, 99, 63, 66, 96, 22, 77, 56, 90, 81, 61, 17, 48, 23, 15, 4, 30, 45, 59, 8, 71, 52, 85, 92, 46, 98, 64, 94, 75, 83, 13, 26, 43, 84, 5, 1, 29, 68, 82, and 31 were used. In set 10, genes 45, 10, 63, 9, 18, 7, 70, 50, 22, 52, 91, 88, 5, 38, 17, 80, 54, 92, 20, 19, 24, 8, 13, 40, 15, 21, 87, 72, 12, 14, 2, 53, 46, 93, 4, 44, 99, 76, 47, 32, 60, 27, 23, 81, 78, 68, 36, 71, 64, 30, 95, 82, 90, 26, 74, 86, 100, 89, 62, 37, 66, 35, 83, 94, 31, 43, 65, 84, 11, 67, 25, 33, 61, 79, 97, 16, 75, 73, 98, 57, 28, 59, 1, 96, 51, 41, 69, 3, 56, and 55 were used.

For 95 genes, set 1, genes 35, 64, 32, 25, 20, 69, 88, 42, 97, 6, 23, 86, 98, 93, 16, 44, 53, 51, 91, 21, 70, 73, 31, 81, 74, 14, 29, 66, 4, 87, 11, 94, 52, 95, 56, 63, 18, 8, 78, 100, 62, 99, 39, 89, 17, 50, 71, 10, 90, 65, 84, 83, 60, 48, 22, 5, 92, 13, 15, 24, 27, 37, 57, 33, 38, 82, 3, 9, 30, 1, 34, 7, 40, 68, 67, 58, 28, 47, 46, 19, 12, 43, 41, 61, 76, 96, 72, 36, 75, 54, 45, 80, 49, 79, an d55 were used. In set 2, genes 58, 44, 39, 62, 1, 19, 61, 33, 84, 36, 91, 21, 53, 30, 63, 35, 92, 45, 11, 87, 10, 82, 96, 64, 8, 32, 42, 78, 69, 59, 24, 72, 48, 66, 15, 27, 49, 75, 40, 47, 57, 52, 31, 95, 97, 94, 26, 5, 93, 34, 60, 81, 88, 29, 23, 67, 76, 6, 98, 37, 74, 43, 100, 20, 18, 12, 13, 51, 41, 54, 14, 2, 68, 99, 3, 38, 70, 77, 50, 4, 17, 22, 9, 83, 71, 85, 25, 79, 46, 86, 7, 73, 16, 65, and 28 were used. In set 3, genes 15, 4, 25, 94, 92, 77, 78, 70, 17, 52, 36, 23, 44, 98, 39, 99, 59, 50, 75, 16, 82, 48, 18, 90, 10, 72, 8, 34, 9, 19, 1, 57, 93, 46, 54, 69, 32, 21, 81, 91, 28, 38, 68, 3, 41, 47, 87, 63, 24, 13, 84, 5, 65, 67, 74, 62, 85, 12, 53, 30, 73, 51, 2, 80, 29, 26, 83, 43, 55, 86, 88, 89, 35, 66, 31, 96, 100, 58, 60, 14, 6, 61, 49, 22, 20, 27, 7, 64, 37, 45, 97, 95, 40, 71, and 11 were used. In set 4, genes 21, 78, 42, 23, 84, 10, 64, 36, 48, 26, 79, 71, 72, 39, 49, 56, 44, 20, 47, 82, 63, 1, 91, 2, 8, 40, 96, 18, 68, 9, 57, 28, 100, 89, 60, 75, 70, 73, 25, 15, 46, 85, 86, 97, 32, 94, 65, 90, 74, 98, 16, 45, 3, 6, 31, 77, 41, 11, 12, 35, 95, 93, 53, 50, 30, 61, 81, 92, 80, 54, 13, 38, 58, 14, 52, 22, 76, 83, 5, 17, 37, 69, 66, 87, 19, 88, 51, 34, 59, 99, 24, 33, 27, 4, and 62 were used. In set 5, genes 29, 34, 28, 58, 89, 1, 73, 30, 92, 76, 68, 33, 38, 8, 49, 3, 42, 9, 40, 36, 43, 81, 97, 59, 7, 79, 54, 15, 11, 61, 18, 82, 100, 41, 52, 23, 31, 13, 57, 66, 65, 27, 72, 44, 16, 69, 39, 26, 2, 55, 71, 80, 86, 77, 12, 25, 14, 50, 88, 22, 93, 51, 75, 64, 47, 62, 96, 10, 35, 5, 67, 60, 32, 84, 94, 48, 56, 90, 95, 83, 21, 6, 37, 91, 46, 70, 24, 87, 85, 17, 98, 99, 45, 19, and 63 were used. In set 6, genes 36, 34, 46, 2, 5, 77, 91, 59, 61, 29, 9, 85, 52, 16, 17, 60, 51, 95, 69, 58, 57, 23, 82, 33, 18, 45, 43, 49, 90, 1, 94, 93, 47, 37, 35, 63, 27, 96, 32, 15, 25, 86, 55, 24, 26, 71, 48, 7, 28, 79, 11, 44, 76, 3, 68, 88, 62, 73, 54, 39, 22, 13, 75, 19, 66, 98, 70, 10, 83, 100, 42, 31, 38, 4, 92, 78, 99, 97, 56, 21, 20, 6, 72, 40, 65, 67, 53, 30, 8, 14, 84, 50, 12, 80, and 81 were used. In set 7, genes 26, 7, 14, 64, 91, 50, 8, 48, 23, 29, 34, 28, 9, 20, 74, 97, 27, 63, 25, 66, 60, 43, 92, 61, 58, 46, 68, 49, 21, 98, 2, 41, 52, 1, 51, 77, 53, 69, 36, 93, 62, 55, 17, 38, 31, 40, 76, 54, 71, 5, 99, 83, 82, 78, 42, 15, 24, 70, 84, 100, 73, 10, 59, 33, 96, 4, 56, 3, 94, 75, 90, 13, 32, 65, 89, 79, 19, 30, 11, 87, 37, 95, 12, 6, 88, 80, 18, 47, 81, 72, 44, 16, 86, 85, and 67 were used. In set 8, genes 24, 84, 92, 71, 56, 68, 93, 67, 59, 75, 85, 35, 72, 86, 39, 46, 65, 51, 23, 100, 8, 37, 70, 69, 57, 27, 17, 87, 44, 1, 2, 50, 9, 91, 63, 29, 95, 3, 5, 40, 96, 47, 54, 64, 66, 18, 28, 13, 14, 36, 80, 21, 12, 61, 48, 26, 88, 83, 7, 43, 42, 97, 99, 41, 10, 16, 94, 53, 45, 98, 15, 73, 89, 55, 74, 81, 20, 90, 79, 34, 38, 82, 76, 4, 60, 33, 31, 78, 58, 62, 22, 6, 52, 49, and 19 were used. In set 9, genes 99, 77, 10, 92, 24, 43, 41, 15, 46, 78, 38, 19, 2, 5, 3, 81, 82, 22, 56, 63, 47, 90, 33, 34, 75, 100, 62, 65, 13, 30, 95, 98, 94, 25, 67, 11, 6, 66, 14, 48, 93, 4, 21, 89, 35, 68, 97, 45, 27, 59, 76, 85, 42, 49, 23, 40, 37, 74, 26, 52, 8, 91, 53, 57, 58, 86, 31, 20, 9, 16, 84, 69, 96, 44, 32, 54, 60, 7, 51, 83, 72, 28, 29, 61, 80, 55, 64, 17, 18, 70, 50, 1, 12, 73, and 39 were used. In set 10, genes 76, 1, 12, 25, 77, 24, 100, 17, 66, 65, 26, 29, 60, 91, 63, 52, 6, 30, 8, 72, 82, 68, 15, 16, 54, 43, 59, 34, 89, 20, 44, 87, 70, 56, 3, 28, 74, 86, 7, 2, 33, 35, 46, 67, 58, 22, 49, 21, 75, 14, 27, 64, 90, 42, 73, 36, 97, 40, 11, 37, 51, 19, 83, 45, 47, 50, 55, 23, 80, 61, 95, 71, 78, 32, 81, 93, 98, 62, 92, 99, 9, 4, 53, 84, 18, 13, 41, 57, 88, 5, 79, 38, 39, 31, and 94 were used.

Classification of subsets of the 39 tumor types was performed with use of random selections of tumor types from the group of 39. The expression levels of gene sequence sets as described herein were used to classify random combinations of tumor types. Different random sets of tumor types were used with each of the sets of 100, 74, and 90 gene sequences as described in these examples. Representative, and non-limiting, examples of random sets of from 2 to 20 tumor types used are as follows, where the set of 39 tumor types were indexed from 1 to 39.

For 2 tumor types, set 1 used types 26 and 16. Set 2 used types 8 and 5. Set 3 used types 39 and 8. Set 4 used types 27 and 23. Set 5 used types 8 and 19. Set 6 used 12 and 21. Set 7 used types 30 and 15. Set 8 used types 30 and 5. Set 9 used types 18 and 22. Set 10 used types 27 and 26.

For 4 tumor types, set 1 used types 20, 35, 15 and 7. Set 2 used types 36, 1, 28 and 19. Set 3 used types 13, 4, 12 and 21. Set 4 used types 12, 33, 14 and 28. Set 5 used types 6, 28, 5 and 37. Set 6 used types 5, 25, 36 and 15. Set 7 used types 12, 26, 21 and 19. Set 8 used types 19, 3, 20 and 17. Set 9 used types 18, 10, 8 and 9. Set 10 used types 28, 20, 2 and 22.

For 6 tumor types, set 1 used types 27, 3, 10, 39, 11 and 20. Set 2 used types 33, 10, 20, 32, 13 and 19. Set 3 used types 31, 27, 18, 39, 8 and 16. Set 4 used types 25, 28, 10, 12, 7 and 39. Set 5 used types 14, 13, 28, 24, 30 and 36. Set 6 used types 9, 24, 8, 17, 36 and 26. Set 7 used types 20, 1, 34, 26, 6 and 19. Set 8 used types 12, 13, 3, 17, 34 and 22. Set 9 used types 7, 1, 17, 13, 20 and 34. Set 10 used types 5, 11, 25, 29, 28 and 35.

For 8 tumor types, set 1 used types 34, 33, 28, 3, 23, 25, 9 and 29. Set 2 used types 27, 8, 38, 28, 20, 14, 12 and 9. Set 3 used types 29, 21, 19, 1, 13, 26, 11 and 31. Set 4 used types 25, 17, 7, 20, 34, 8, 28 and 10. Set 5 used types 36, 28, 35, 26, 2, 8, 29 and 7. Set 6 used types 10, 23, 2, 27, 33, 21, 25 and 35. Set 7 used types 10, 18, 38, 2, 6, 7, 19 and 32. Set 8 used types 11, 37, 6, 28, 3, 9, 2 and 16. Set 9 used types 22, 2, 10, 8, 17, 19 and 33. Set 10 used types 35, 39, 8, 10, 37, 4, 36 and 6.

For 10 tumor types, set 1 used types 25, 10, 26, 2, 32, 31, 39, 23, 22 and 18. Set 2 used types 12, 35, 6, 16, 20, 3, 39, 36, 11 and 2. Set 3 used types 34, 1, 15, 29, 5, 39, 2, 12, 25 and 18. Set 4 used types 10, 8, 14, 18, 31, 19, 23, 20, 32 and 33. Set 5 used types 10, 18, 37, 15, 4, 35, 33, 24, 39 and 20. Set 6 used types 22, 16, 4, 3, 18, 21, 1, 25, 37 and 13. Set 7 used types 14, 6, 28, 18, 11, 13, 2, 32, 33 and 19. Set 8 used types 39, 2, 38, 4, 34, 8, 25, 6, 32 and 35. Set 9 used types 3, 10, 11, 16, 6, 15, 18, 14, 12 and 26. Set 10 used types 24, 25, 21, 9, 36, 29, 20, 39, 10 and 37.

For 12 tumor types, set 1 used types 26, 20, 4, 12, 2, 31, 38, 18, 16, 39, 3 and 33. Set 2 used types 25, 16, 4, 9, 29, 27, 14, 24, 21, 7, 23 and 2. Set 3 used types 31, 18, 23, 13, 25, 1, 29, 21, 35, 10, 32 and 39. Set 4 used types 8, 34, 23, 9, 35, 14, 25, 21, 2, 33, 18 and 28. Set 5 used types 6, 11, 21, 8, 5, 7, 19, 32, 3, 13, 36 and 9. Set 6 used types 12, 33, 14, 26, 27, 15, 2, 21, 36, 35, 9 and 39. Set 7 used types 26, 29, 32, 17, 31, 19, 6, 5, 20, 34, 2 and 24. Set 8 used types 17, 12, 8, 22, 28, 9, 27, 29, 14, 35, 4 and 32. Set 9 used types 29, 9, 36, 23, 33, 18, 21, 35, 3, 6, 2 and 1. Set 10 used types 1, 3, 35, 29, 22, 27, 8, 23, 2, 36, 14 and 19.

For 14 tumor types, set 1 used types 9, 26, 38, 25, 31, 3, 15, 14, 17, 33, 12, 35, 39 and 16. Set 2 used types 1, 26, 16, 25, 20, 12, 14, 37, 38, 24, 23, 33, 27 and 35. Set 3 used types 11, 21, 35, 38, 32, 34, 27, 39, 16, 15, 4, 5, 13 and 18. Set 4 used types 27, 5, 13, 28, 18, 17, 15, 20, 29, 37, 21, 36, 25 and 14. Set 5 used types 5, 12, 17, 9, 25, 21, 33, 37, 8, 15, 24, 3, 34 and 28. Set 6 used types 11, 19, 34, 26, 9, 6, 32, 14, 27, 29, 30, 16, 24 and 17. Set 7 used types 31, 26, 11, 18, 19, 20, 9, 8, 5, 36, 12, 6, 27 and 38. Set 8 used types 20, 17, 11, 5, 15, 9, 2, 39, 34, 24, 27, 26, 35 and 10. Set 9 used types 1, 14, 39, 30, 17, 6, 10, 35, 31, 33, 15, 29, 32 and 7. Set 10 used types 1, 19, 24, 28, 34, 12, 13, 18, 32, 11, 14, 21, 22 and 25.

For 16 tumor types, set 1 used types 27, 15, 8, 12, 6, 20, 26, 19, 25, 2, 37, 38, 7, 39, 4 and 33. Set 2 used types 17, 18, 28, 5, 6, 31, 25, 13, 8, 20, 37, 36, 35, 9, 23 and 27. Set 3 used types 23, 37, 34, 14, 16, 27, 32, 33, 21, 38, 4, 30, 24, 22, 17 and 25. Set 4 used types 7, 37, 38, 21, 34, 31, 32, 25, 10, 36, 19, 11, 6, 26, 18 and 35. Set 5 used types 9, 32, 12, 24, 20, 13, 38, 21, 39, 23, 36, 18, 37, 22, 5 and 3. Set 6 used types 14, 21, 5, 17, 6, 20, 18, 35, 22, 10, 3, 23, 13, 2, 34 and 26. Set 7 used types 1, 8, 19, 6, 9, 39, 28, 18, 13, 31, 14, 16, 37, 12, 3 and 25. Set 8 used types 32, 36, 28, 38, 9, 33, 2, 5, 4, 11, 19, 18, 13, 8, 12 and 3. Set 9 used types 9, 14, 10, 5, 28, 32, 23, 6, 39, 3, 17, 8, 19, 1, 31 and 12. Set 10 used types 4, 34, 11, 6, 38, 19, 7, 20, 23, 3, 25, 37, 26, 1, 15 and 12.

For 18 tumor types, set 1 used types 15, 24, 39, 35, 7, 30, 16, 13, 20, 3, 26, 4, 12, 10, 34, 25, 21 and 28. Set 2 used types 21, 23, 29, 11, 10, 19, 13, 28, 4, 20, 17, 24, 30, 12, 39, 34, 31 and 9. Set 3 used types 7, 17, 27, 6, 30, 8, 22, 2, 32, 26, 21, 14, 4, 38, 1, 35, 16 and 28. Set 4 used types 17, 13, 20, 33, 10, 3, 16, 22, 1, 38, 2, 9, 28, 5, 6, 19, 12 and 11. Set 5 used types 4, 35, 21, 25, 18, 17, 8, 14, 31, 30, 9, 1, 2, 23, 36, 29, 32 and 37. Set 6 used types 17, 34, 2, 18, 19, 15, 16, 13, 4, 24, 5, 35, 6, 22, 28, 37, 38 and 1. Set 7 used types 34, 26, 12, 25, 27, 3, 17, 7, 2, 32, 9, 36, 21, 19, 22, 8, 20 and 29. Set 8 used types 12, 34, 38, 25, 17, 22, 14, 39, 10, 7, 31, 2, 3, 11, 29, 30, 16 and 24. Set 9 used types 13, 26, 27, 14, 5, 10, 8, 7, 16, 30, 37, 4, 6, 35, 28, 1, 36 and 20. Set 10 used types 15, 2, 17, 23, 26, 28, 36, 38, 12, 6, 19, 37, 20, 14, 9, 39, 11 and 21.

For 20 tumor types, set 1 used types 25, 13, 21, 15, 37, 20, 12, 28, 9, 10, 26, 22, 14, 24, 16, 7, 39, 34, 33 and 4. Set 2 used types 20, 17, 10, 27, 19, 28, 5, 1, 23, 21, 38, 7, 13, 22, 32, 31, 9, 4, 3 and 24. Set 3 used types 17, 13, 7, 20, 11, 38, 34, 3, 15, 12, 5, 39, 9, 10, 4, 35, 27, 6, 21 and 33. Set 4 used types 6, 13, 17, 26, 1, 7, 33, 5, 10, 32, 3, 23, 35, 4, 14, 28, 12, 38, 8 and 27. Set 5 used types 10, 23, 9, 38, 5, 29, 12, 27, 25, 6, 7, 26, 37, 31, 24, 36, 19, 15, 16 and 11. Set 6 used types 30, 24, 21, 11, 23, 25, 8, 9, 7, 31, 27, 5, 14, 29, 1, 19, 16, 12, 22 and 17. Set 7 used types 26, 13, 23, 19, 22, 11, 25, 21, 33, 20, 6, 17, 2, 10, 31, 34, 27, 37, 7 and 9. Set 8 used types 30, 1, 38, 7, 31, 37, 11, 25, 6, 19, 28, 33, 17, 29, 10, 27, 16, 3, 14 and 15. Set 9 used types 15, 19, 26, 24, 5, 33, 11, 2, 13, 18, 31, 22, 32, 20, 23, 6, 10, 25, 36 and 3. Set 10 used types 24, 25, 21, 29, 14, 18, 31, 2, 20, 39, 23, 9, 38, 12, 6, 32, 22, 26, 33 and 7.

Example 4

Specified Gene Sets

Figure 3:
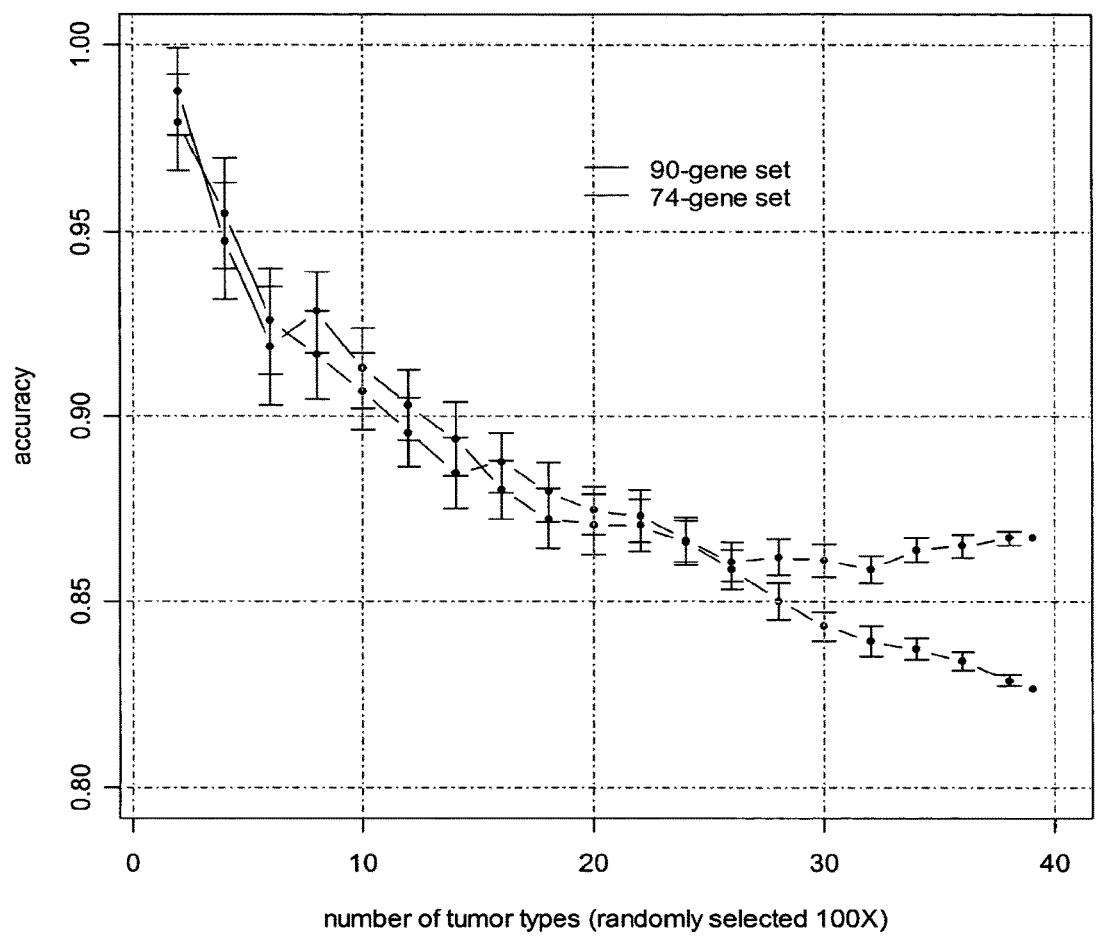
FIG. 3 shows the performance of using all genes from a first set of 74 gene sequences and a second set of 90 gene sequences to classify various numbers of tumor types. Generally, the accuracy of the two sets are very similar, with the set of 74 displaying a more noticeable higher accuracy with about 28 or more (up to 39) tumor types.

A first set of 74 genes and a second set of 90 genes, where the two sets have 38 members in common, were used in the practice of the invention. The performance of the two sets versus varying numbers of tumor types is shown in FIG. 3.

Figure 4:
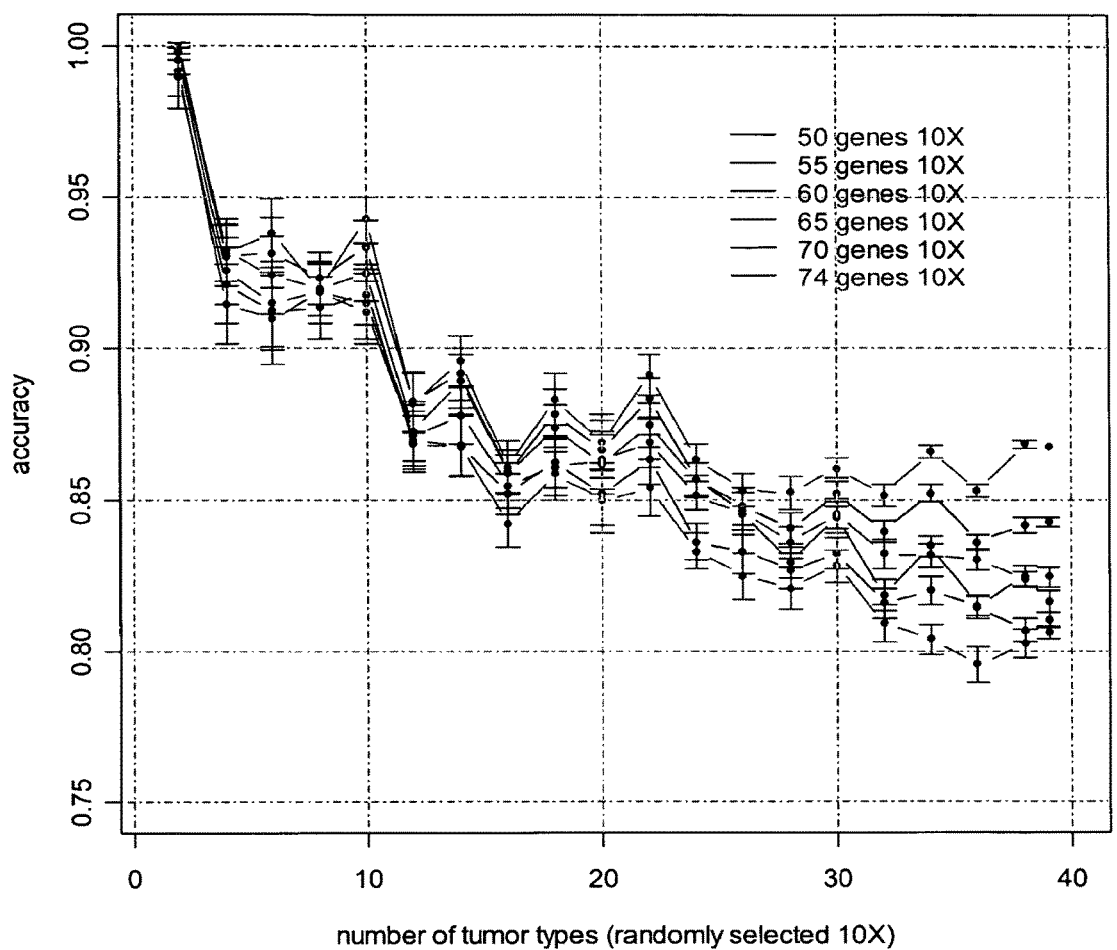
FIG. 4 shows a capacity plot for the ability to use the expression levels of all or portions of a first set of 74 expressed gene sequences to classify among 39 tumor types and subsets thereof. Expression levels of random combinations of 50, 55, 60, 65, and 70 (each sampled 10 times) as well as all 74 of the sequences were used with data from tumor types and then used to predict test random sets of tumor samples (each sampled 10 times) ranging from 2 to 39 types. A plot of numbers of tumor types versus prediction accuracies for results using from 50 to 74 genes are shown as non-limiting examples. Generally, accuracy improves with higher numbers of gene sequences, with the use of 74 genes being more noticeable as providing the highest accuracies, and 50 gene sequences producing the lowest accuracies, when used with about 20 or more tumor types.
Figure 5:
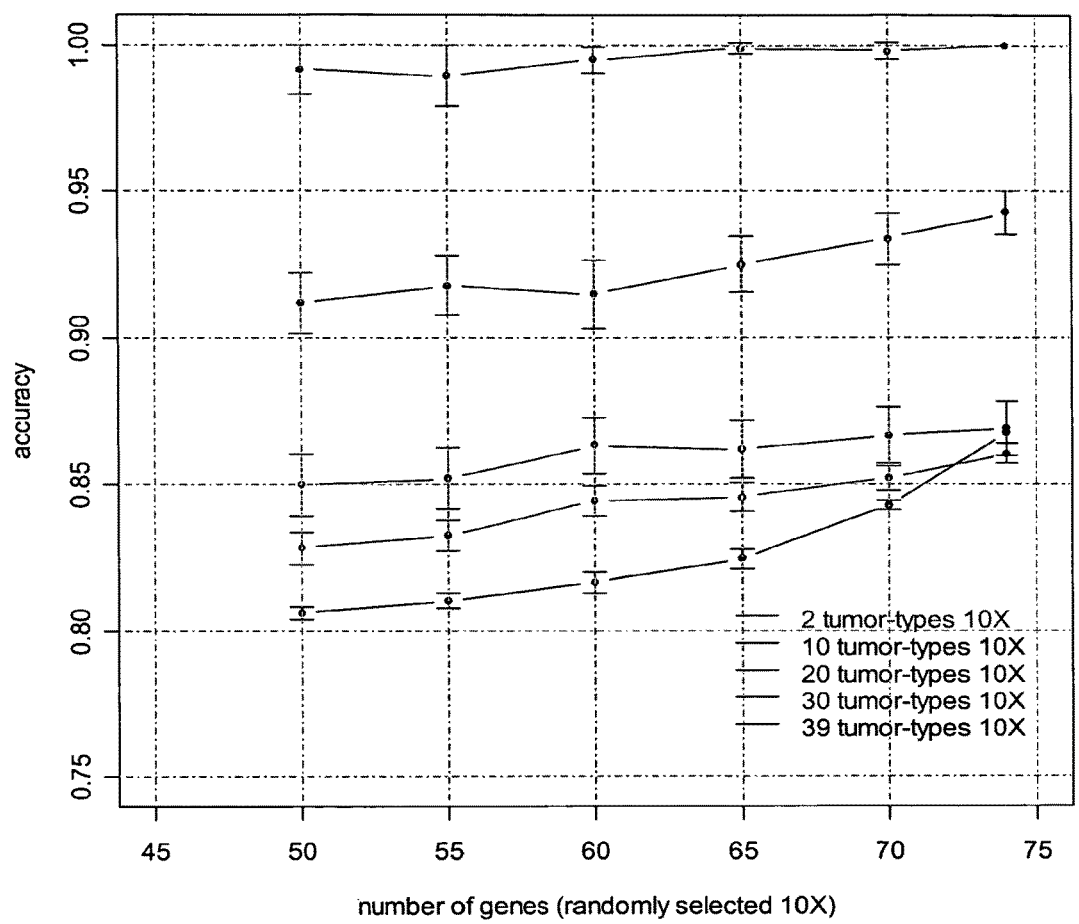
FIG. 5 shows an alternative presentation of the data used with respect to FIG. 4. A plot of numbers of gene sequences used, ranging from 50-74, versus prediction accuracies for various representative numbers of tumor types is shown. The plotted lines, from top to bottom, are of the results from 2, 10, 20, 30, and 39 tumor types, respectively.

Random subsets of 50 to all members of the set of 74 expressed gene sequences were evaluated in a manner analogous to that described in Example 3. Again, the expression levels of random combinations of 50, 55, 60, 65, 70, and all 74 (each combination sampled 10 times) of the 74 expressed sequences were used with data from tumor types and then used to predict test random sets of tumor samples (each sampled 10 times) ranging from 2 to all 39 types. The resulting data are shown in FIGS. 4 and 5.

The members of the 74 gene sequences were indexed from 1 to 74, and representative random sets used in the invention are as follows:

For 50-genes, set 1, genes 69, 64, 74, 29, 4, 57, 30, 72, 36, 59, 42, 47, 11, 33, 60, 35, 39, 10, 50, 49, 41, 12, 34, 51, 32, 66, 71, 37, 13, 14, 8, 25, 53, 21, 68, 7, 67, 55, 27, 22, 1, 44, 46, 28, 48, 19, 73, 23, 16, and 3 were used. In set 2, genes 60, 61, 23, 17, 10, 31, 16, 8, 72, 73, 18, 49, 71, 46, 29, 21, 66, 39, 22, 27, 43, 30, 51, 3, 38, 19, 37, 35, 70, 54, 40, 2, 55, 28, 45, 33, 25, 14, 48, 20, 36, 47, 62, 9, 69, 68, 53, 58, 15, and 7 were used. In set 3, genes 53, 68, 31, 2, 62, 17, 49, 71, 6, 56, 3, 66, 23, 21, 33, 30, 45, 73, 74, 11, 58, 27, 64, 18, 72, 42, 7, 28, 34, 43, 38, 65, 12, 47, 16, 40, 41, 36, 54, 61, 19, 63, 25, 46, 59, 9, 39, 55, 22, and 48 were used. In set 4, genes 23, 70, 48, 1, 11, 25, 60, 26, 5, 58, 46, 39, 28, 71, 35, 34, 2, 59, 69, 55, 49, 40, 15, 14, 68, 57, 10, 31, 67, 74, 62, 44, 16, 12, 64, 63, 61, 13, 52, 45, 19, 50, 36, 33, 9, 24, 32, 29, 56, and 72 were used. In set 5, genes 30, 26, 10, 34, 67, 73, 15, 59, 3, 64, 14, 70, 23, 47, 72, 71, 44, 49, 31, 48, 5, 61, 53, 20, 33, 58, 37, 50, 43, 18, 21, 38, 29, 16, 12, 63, 39, 4, 45, 60, 69, 25, 24, 65, 55, 13, 36, 11, 17, and 22 were used. In set 6, genes 43, 34, 61, 19, 35, 56, 24, 3, 23, 15, 13, 69, 1, 67, 42, 41, 64, 25, 63, 28, 8, 53, 38, 71, 6, 36, 68, 14, 18, 65, 51, 33, 4, 60, 5, 22, 40, 30, 50, 37, 29, 17, 27, 11, 9, 66, 62, 57, 59, and 10 were used. In set 7, genes 51, 55, 46, 31, 21, 72, 8, 67, 56, 1, 64, 6, 63, 32, 20, 16, 25, 61, 2, 45, 35, 22, 66, 38, 36, 3, 34, 27, 74, 47, 54, 30, 14, 13, 37, 23, 19, 12, 59, 18, 52, 5, 17, 33, 7, 39, 43, 58, 41, and 10 were used. In set 8, genes 28, 68, 71, 46, 48, 47, 5, 23, 22, 35, 60, 3, 40, 33, 41, 72, 12, 24, 15, 37, 1, 20, 45, 53, 61, 65, 74, 4, 10, 51, 26, 30, 38, 44, 55, 73, 66, 6, 39, 52, 36, 2, 59, 67, 27, 43, 50, 18, 8, and 69 were used. In set 9, genes 73, 51, 67, 63, 24, 55, 42, 61, 13, 29, 23, 64, 49, 53, 19, 2, 43, 11, 15, 31, 58, 40, 38, 46, 44, 4, 27, 41, 28, 69, 8, 26, 5, 68, 37, 70, 25, 62, 22, 52, 1, 57, 54, 34, 16, 71, 9, 65, 14, and 30 were used. In set 10, genes 9, 13, 46, 2, 62, 47, 50, 36, 58, 23, 55, 31, 6, 40, 32, 27, 35, 33, 39, 1, 22, 19, 65, 16, 52, 72, 30, 3, 12, 7, 74, 21, 54, 20, 41, 10, 28, 37, 24, 53, 69, 11, 14, 67, 25, 71, 15, 42, 18, and 73 were used.

For 55 genes, set 1, genes 19, 3, 26, 44, 16, 59, 11, 39, 46, 54, 22, 7, 60, 30, 72, 6, 74, 53, 57, 14, 43, 47, 27, 45, 37, 24, 33, 64, 21, 36, 20, 50, 68, 62, 63, 17, 61, 10, 70, 18, 25, 71, 29, 65, 51, 56, 58, 69, 5, 55, 12, 1, 40, 49, and 13 were used. In set 2, genes 35, 15, 11, 33, 5, 29, 73, 69, 31, 70, 10, 45, 41, 72, 74, 26, 32, 12, 30, 34, 16, 64, 13, 50, 46, 38, 18, 48, 37, 68, 40, 61, 62, 6, 63, 47, 36, 65, 17, 67, 71, 39, 4, 59, 22, 24, 8, 9, 58, 3, 52, 20, 14, 25, and 7 were used. In set 3, genes 7, 19, 50, 62, 47, 74, 22, 26, 37, 8, 41, 53, 52, 67, 16, 40, 54, 34, 30, 46, 25, 55, 31, 3, 69, 38, 29, 65, 45, 43, 51, 68, 18, 57, 21, 5, 32, 20, 27, 73, 66, 10, 49, 24, 12, 13, 11, 71, 60, 23, 63, 35, 48, 39, and 70 were used. In set 4, genes 58, 70, 43, 68, 39, 57, 71, 27, 21, 53, 16, 23, 25, 60, 40, 36, 2, 63, 33, 49, 5, 54, 32, 66, 50, 59, 14, 52, 15, 48, 45, 44, 19, 72, 26, 10, 6, 41, 34, 61, 42, 67, 17, 24, 8, 11, 29, 74, 3, 51, 47, 65, 69, 28, and 1 were used. In set 5, genes 60, 53, 21, 63, 7, 19, 69, 3, 9, 22, 10, 50, 59, 71, 20, 11, 70, 6, 4, 17, 58, 16, 40, 68, 73, 38, 18, 15, 57, 26, 34, 67, 41, 27, 49, 28, 46, 54, 1, 13, 31, 48, 32, 61, 42, 66, 29, 5, 55, 72, 25, 30, 39, 44, and 56 were used. In set 6, genes 4, 36, 17, 47, 16, 6, 14, 51, 65, 42, 31, 38, 26, 15, 70, 28, 41, 72, 30, 3, 29, 55, 34, 32, 54, 24, 48, 39, 22, 57, 37, 23, 71, 61, 50, 21, 27, 53, 25, 40, 20, 69, 58, 66, 46, 1, 43, 12, 33, 63, 18, 68, 10, 56, and 45 were used. In set 7, genes 71, 7, 38, 61, 22, 33, 51, 25, 68, 6, 1, 49, 9, 58, 18, 55, 5, 50, 65, 52, 26, 59, 35, 11, 15, 70, 54, 27, 60, 28, 19, 63, 21, 10, 32, 42, 73, 36, 45, 66, 47, 2, 56, 23, 64, 44, 34, 29, 48, 69, 37, 16, 74, 53, and 43 were used. In set 8, genes 25, 42, 70, 28, 6, 48, 43, 20, 60, 18, 56, 74, 27, 9, 55, 67, 58, 68, 39, 38, 29, 1, 21, 45, 44, 66, 53, 34, 47, 64, 41, 57, 10, 3, 31, 65, 54, 46, 50, 59, 23, 73, 24, 51, 36, 26, 16, 49, 37, 62, 7, 32, 19, 22, and 14 were used. In set 9, genes 49, 65, 20, 59, 21, 45, 54, 29, 51, 50, 17, 37, 55, 47, 57, 9, 8, 18, 11, 10, 25, 1, 30, 68, 5, 6, 74, 70, 60, 53, 48, 39, 4, 23, 27, 73, 35, 40, 41, 44, 24, 3, 58, 19, 14, 13, 33, 63, 62, 46, 2, 12, 72, 36, and 7 were used. In set 10, genes 73, 53, 26, 24, 58, 25, 59, 71, 34, 65, 46, 2, 57, 48, 68, 21, 44, 22, 16, 70, 60, 8, 66, 45, 14, 27, 43, 37, 20, 36, 72, 18, 56, 4, 7, 6, 23, 15, 74, 1, 9, 50, 5, 35, 40, 32, 12, 38, 69, 33, 61, 62, 10, 47, and 39 were used.

For 60 genes, set 1, genes 49, 60, 66, 26, 22, 53, 33, 56, 10, 44, 17, 36, 41, 6, 21, 57, 39, 65, 24, 30, 31, 15, 43, 68, 64, 59, 28, 73, 13, 18, 51, 34, 63, 40, 71, 58, 48, 11, 37, 42, 70, 45, 72, 3, 67, 35, 52, 46, 32, 55, 27, 38, 19, 25, 5, 69, 62, 14, 23, and 4 were used. In set 2, genes 57, 5, 31, 15, 20, 54, 21, 42, 71, 50, 17, 68, 61, 53, 9, 35, 67, 12, 14, 52, 41, 38, 22, 45, 32, 39, 70, 18, 6, 26, 59, 40, 25, 28, 56, 10, 3, 47, 34, 8, 60, 2, 9, 62, 66, 19, 11, 37, 27, 36, 69, 7, 65, 4, 33, 24, 51, 55, 48, and 44 were used. In set 3, genes 37, 54, 44, 66, 36, 1, 61, 62, 47, 69, 4, 30, 31, 11, 8, 63, 38, 16, 65, 25, 74, 21, 34, 60, 20, 71, 12, 19, 43, 15, 27, 57, 6, 55, 64, 22, 14, 39, 53, 23, 17, 28, 51, 56, 40, 29, 58, 48, 42, 59, 68, 5, 35, 50, 72, 10, 45, 32, 33, and 73 were used. In set 4, genes 24, 2, 49, 57, 35, 45, 40, 51, 42, 7, 47, 5, 8, 17, 61, 74, 64, 72, 50, 60, 70, 26, 9, 56, 32, 4, 16, 44, 27, 43, 53, 33, 46, 55, 41, 68, 48, 11, 10, 39, 19, 6, 3, 14, 65, 69, 30, 34, 29, 36, 58, 28, 1, 23, 73, 15, 25, 13, 54, and 18 were used. In set 5, genes 18, 28, 1, 22, 71, 37, 62, 46, 31, 25, 70, 64, 66, 35, 5, 60, 10, 26, 9, 43, 67, 20, 59, 51, 33, 42, 3, 24, 49, 13, 27, 38, 61, 14, 52, 63, 11, 74, 7, 16, 23, 72, 39, 73, 15, 6, 17, 30, 57, 8, 50, 48, 34, 53, 2, 69, 29, 56, 44, and 47 were used. In set 6, genes 33, 74, 12, 7, 49, 25, 38, 1, 8, 4, 48, 26, 58, 54, 21, 50, 72, 45, 62, 66, 36, 13, 42, 5, 39, 17, 28, 23, 67, 41, 29, 73, 19, 56, 51, 69, 10, 16, 55, 14, 24, 64, 22, 59, 52, 35, 2, 31, 3, 9, 27, 71, 30, 32, 53, 11, 40, 61, 15, and 70 were used. In set 7, genes 30, 65, 26, 48, 47, 20, 17, 56, 35, 32, 10, 11, 1, 59, 50, 53, 45, 13, 63, 49, 41, 74, 16, 57, 15, 64, 12, 54, 5, 8, 67, 69, 31, 14, 61, 60, 37, 66, 43, 71, 23, 36, 51, 44, 34, 2, 42, 19, 58, 25, 27, 68, 18, 52, 21, 7, 70, 22, 28, and 62 were used. In set 8, genes 12, 58, 11, 5, 72, 70, 63, 66, 49, 44, 14, 48, 26, 73, 51, 47, 13, 65, 1, 39, 61, 17, 40, 8, 24, 54, 42, 34, 64, 21, 53, 59, 46, 4, 20, 29, 57, 74, 31, 67, 6, 69, 7, 68, 41, 3, 18, 62, 19, 32, 10, 43, 36, 71, 28, 60, 30, 15, 23, and 52 were used. In set 9, genes 7, 20, 69, 12, 58, 40, 70, 57, 3, 37, 6, 16, 61, 11, 13, 31, 55, 17, 49, 22, 36, 47, 44, 18, 45, 68, 25, 72, 19, 14, 39, 46, 30, 59, 56, 5, 66, 2, 41, 51, 9, 54, 35, 15, 26, 27, 23, 65, 4, 63, 1, 60, 21, 74, 24, 43, 38, 64, 50, and 67 were used. In set 10, genes 5, 43, 54, 22, 49, 48, 25, 24, 52, 35, 14, 70, 26, 72, 59, 71, 9, 41, 74, 36, 17, 47, 29, 34, 20, 27, 65, 68, 3, 73, 45, 62, 57, 56, 53, 44, 6, 7, 31, 55, 30, 23, 15, 33, 38, 42, 10, 60, 66, 8, 1, 64, 19, 16, 12, 61, 63, 51, 18, and 2 were used.

For 65 genes, set 1, genes 11, 10, 1, 69, 43, 33, 54, 24, 39, 27, 42, 18, 9, 46, 12, 20, 61, 44, 51, 64, 35, 8, 36, 38, 21, 7, 57, 59, 23, 49, 17, 15, 22, 55, 29, 16, 37, 72, 30, 31, 45, 63, 40, 28, 41, 32, 66, 65, 5, 47, 53, 60, 25, 50, 74, 52, 14, 68, 48, 13, 2, 4, 3, 6, and 67 were used. In set 2, genes 37, 8, 31, 4, 23, 57, 69, 40, 3, 9, 5, 32, 42, 44, 56, 21, 10, 34, 74, 61, 39, 38, 13, 70, 41, 19, 48, 47, 29, 52, 26, 72, 49, 45, 7, 63, 16, 25, 24, 14, 18, 60, 59, 11, 35, 2, 30, 68, 58, 67, 27, 33, 66, 12, 71, 51, 55, 6, 20, 54, 1, 46, 64, 62, and 53 were used. In set 3, genes 24, 19, 35, 57, 27, 8, 23, 30, 65, 32, 59, 29, 4, 47, 17, 53, 34, 54, 73, 14, 20, 63, 43, 3, 38, 61, 31, 49, 25, 42, 41, 51, 18, 7, 40, 39, 33, 50, 70, 28, 13, 74, 36, 45, 64, 5, 16, 58, 1, 66, 62, 46, 15, 12, 72, 21, 2, 68, 71, 9, 44, 26, 37, 6, and 55 were used. In set 4, genes 62, 29, 5, 41, 18, 4, 21, 63, 65, 8, 55, 61, 66, 34, 23, 28, 14, 49, 68, 15, 1, 11, 19, 73, 13, 57, 20, 27, 50, 2, 72, 22, 6, 7, 40, 67, 51, 45, 10, 36, 53, 64, 54, 24, 25, 37, 74, 12, 52, 26, 38, 32, 3, 30, 33, 39, 48, 58, 17, 42, 71, 43, 69, 56, and 9 were used. In set 5, genes 49, 58, 74, 65, 67, 44, 57, 28, 56, 18, 59, 31, 10, 17, 41, 39, 63, 7, 21, 55, 38, 2, 51, 42, 5, 53, 20, 34, 16, 43, 19, 15, 50, 4, 6, 11, 52, 37, 8, 64, 69, 12, 48, 60, 1, 66, 27, 36, 45, 30, 14, 72, 68, 73, 35, 47, 71, 22, 70, 33, 32, 46, 25, 13, and 54 were used. In set 6, genes 7, 44, 23, 68, 46, 30, 10, 4, 3, 53, 22, 38, 50, 26, 55, 49, 20, 11, 73, 12, 62, 63, 43, 69, 6, 61, 52, 25, 65, 16, 47, 34, 33, 28, 42, 58, 29, 39, 31, 1, 36, 13, 5, 60, 35, 19, 40, 18, 59, 64, 41, 70, 72, 57, 67, 9, 74, 8, 14, 71, 45, 56, 32, 51, and 2 were used. In set 7, genes 57, 61, 9, 48, 31, 4, 40, 35, 1, 16, 44, 67, 68, 34, 6, 64, 7, 54, 53, 10, 18, 39, 23, 14, 33, 74, 51, 38, 24, 19, 72, 63, 36, 65, 32, 2, 27, 45, 3, 43, 21, 49, 30, 60, 50, 70, 41, 20, 11, 37, 13, 15, 5, 12, 46, 26, 22, 71, 8, 62, 29, 28, 25, 17, and 52 were used. In set 8, genes 11, 21, 3, 6, 74, 58, 52, 40, 17, 23, 41, 63, 22, 56, 55, 8, 60, 54, 51, 57, 66, 68, 29, 24, 69, 39, 16, 49, 72, 59, 48, 61, 2, 7, 44, 37, 43, 45, 35, 25, 1, 4, 20, 14, 36, 42, 65, 62, 71, 32, 19, 70, 28, 27, 9, 46, 33, 18, 67, 15, 30, 26, 12, 47, and 53 were used. In set 9, genes 48, 27, 64, 55, 30, 2, 33, 16, 31, 21, 57, 50, 63, 17, 44, 29, 4, 6, 60, 65, 23, 19, 58, 68, 25, 59, 14, 7, 42, 12, 69, 45, 53, 73, 56, 34, 41, 3, 18, 5, 72, 70, 40, 37, 62, 43, 51, 24, 52, 20, 39, 8, 13, 26, 10, 66, 54, 22, 49, 61, 11, 46, 32, 67, and 36 were used. In set 10, genes 31, 39, 50, 60, 17, 33, 73, 30, 3, 27, 10, 62, 29, 12, 59, 1, 34, 69, 51, 72, 65, 52, 16, 36, 28, 23, 42, 40, 66, 58, 48, 46, 38, 74, 20, 55, 21, 49, 63, 2, 70, 7, 26, 53, 41, 45, 25, 44, 71, 32, 24, 13, 14, 6, 57, 11, 68, 35, 54, 22, 64, 8, 9, 56, and 37 were used.

For 70 genes, set 1, genes 72, 74, 31, 73, 52, 16, 32, 24, 14, 66, 59, 28, 54, 1, 11, 12, 34, 57, 5, 67, 25, 42, 62, 71, 68, 69, 48, 7, 18, 20, 47, 19, 53, 2, 4, 15, 26, 63, 37, 17, 10, 60, 65, 8, 22, 70, 36, 30, 41, 9, 21, 35, 49, 38, 33, 56, 46, 27, 45, 44, 39, 43, 29, 50, 61, 40, 23, 64, 55, and 3 were used. In set 2, genes 45, 32, 60, 2, 42, 56, 8, 46, 30, 27, 17, 62, 26, 24, 65, 49, 16, 70, 3, 47, 50, 4, 40, 28, 1, 36, 22, 59, 48, 9, 57, 5, 72, 23, 13, 44, 67, 14, 12, 34, 21, 41, 71, 39, 66, 25, 69, 19, 15, 6, 68, 29, 52, 43, 64, 58, 54, 11, 37, 38, 55, 7, 20, 61, 53, 63, 10, 74, 51, and 35 were used. In set 3, genes 66, 71, 40, 62, 60, 51, 61, 5, 19, 15, 34, 13, 18, 8, 28, 59, 35, 54, 2, 55, 29, 22, 41, 37, 45, 64, 48, 7, 73, 27, 30, 69, 63, 23, 25, 42, 1, 24, 14, 38, 4, 70, 53, 3, 36, 12, 74, 68, 26, 57, 33, 17, 67, 72, 52, 58, 46, 39, 43, 56, 65, 10, 44, 11, 20, 47, 50, 9, 21, and 49 were used. In set 4, genes 73, 26, 33, 40, 71, 50, 62, 59, 10, 39, 64, 68, 3, 1, 44, 9, 72, 57, 43, 37, 24, 65, 48, 6, 11, 23, 36, 19, 7, 31, 67, 69, 38, 29, 16, 35, 63, 21, 46, 15, 47, 28, 2, 5, 52, 70, 14, 22, 56, 45, 17, 4, 25, 66, 13, 55, 20, 30, 32, 54, 51, 49, 58, 74, 42, 53, 61, 34, 12, and 60 were used. In set 5, genes 7, 1, 24, 70, 26, 35, 68, 71, 74, 33, 5, 20, 49, 27, 65, 10, 72, 21, 66, 12, 4, 43, 9, 55, 23, 56, 47, 31, 42, 59, 61, 45, 67, 13, 63, 58, 17, 54, 28, 3, 64, 53, 39, 36, 30, 40, 37, 16, 41, 11, 52, 14, 62, 8, 46, 25, 44, 69, 29, 48, 51, 22, 73, 57, 18, 15, 19, 38, 6, and 50 were used. In set 6, genes 41, 36, 1, 27, 9, 51, 4, 38, 8, 25, 73, 5, 7, 22, 68, 30, 6, 33, 65, 70, 21, 26, 60, 62, 63, 54, 57, 74, 58, 44, 11, 31, 53, 34, 10, 48, 23, 3, 42, 35, 49, 13, 71, 17, 50, 28, 19, 20, 40, 64, 56, 43, 69, 59, 39, 66, 72, 46, 32, 2, 14, 47, 52, 45, 15, 37, 12, 16, 24, and 67 were used. In set 7, genes 39, 70, 16, 5, 43, 6, 36, 30, 9, 53, 2, 34, 72, 42, 64, 73, 56, 63, 38, 13, 19, 27, 29, 60, 37, 52, 1, 3, 21, 22, 68, 69, 26, 55, 61, 11, 18, 12, 45, 8, 51, 65, 32, 33, 67, 48, 50, 10, 20, 28, 58, 7, 49, 35, 57, 71, 23, 17, 24, 62, 59, 54, 15, 40, 14, 41, 47, 46, 44, and 4 were used. In set 8, genes 3, 5, 50, 35, 53, 57, 14, 49, 55, 8, 25, 22, 71, 60, 13, 19, 12, 32, 26, 44, 15, 39, 17, 31, 61, 23, 66, 68, 4, 6, 7, 41, 24, 40, 58, 67, 46, 70, 45, 64, 51, 69, 18, 62, 47, 52, 11, 30, 73, 28, 33, 2, 36, 1, 72, 42, 20, 27, 10, 16, 63, 38, 59, 74, 43, 9, 56, 34, 21, and 65 were used. In set 9, genes 18, 49, 70, 46, 29, 9, 52, 53, 64, 28, 37, 27, 7, 57, 44, 19, 72, 61, 67, 30, 62, 47, 2, 39, 8, 65, 26, 14, 63, 4, 20, 59, 45, 15, 10, 3, 16, 58, 25, 38, 60, 71, 66, 32, 23, 55, 69, 12, 33, 6, 42, 36, 22, 48, 24, 68, 41, 17, 54, 13, 21, 51, 73, 74, 40, 43, 1, 11, 56, and 35 were used. In set 10, genes 14, 12, 65, 74, 58, 6, 36, 5, 34, 11, 18, 33, 32, 7, 22, 37, 64, 59, 9, 52, 41, 26, 3, 19, 48, 35, 56, 62, 42, 60, 1, 8, 43, 50, 25, 61, 54, 49, 20, 70, 44, 30, 15, 46, 72, 38, 4, 29, 68, 21, 39, 17, 16, 53, 45, 73, 63, 31, 55, 47, 24, 69, 2, 71, 13, 28, 66, 23, 57, and 40 were used.

Figure 6:
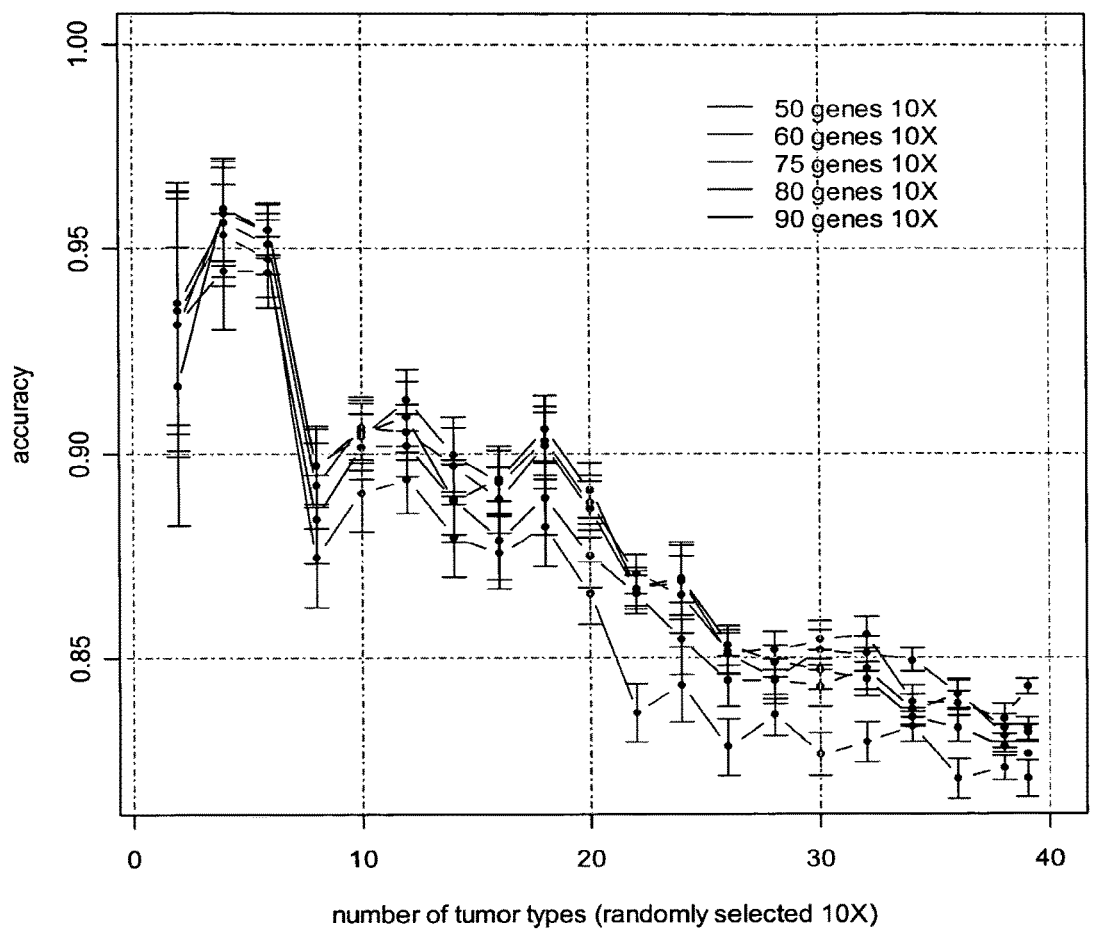
FIG. 6 shows a capacity plot for the ability to use the expression levels of subsets of a set of 90 expressed gene sequences to classify among 39 tumor types and subsets thereof. Expression levels of random combinations of 50, 55, 60, 65, 70, 75, 80, and 85 (each sampled 10 times) as well as all 90 of the sequences were used with data from tumor types and then used to predict test random sets of tumor samples (each sampled 10 times) ranging from 2 to 39 types. A plot of numbers of tumor types versus prediction accuracies for results using from 50 to 90 genes are shown as non-limiting examples. Generally, accuracy improves with higher numbers of gene sequences, where 50 gene sequences results in noticeably reduced accuracy when used with about 20 or more tumor types.
Figure 7:
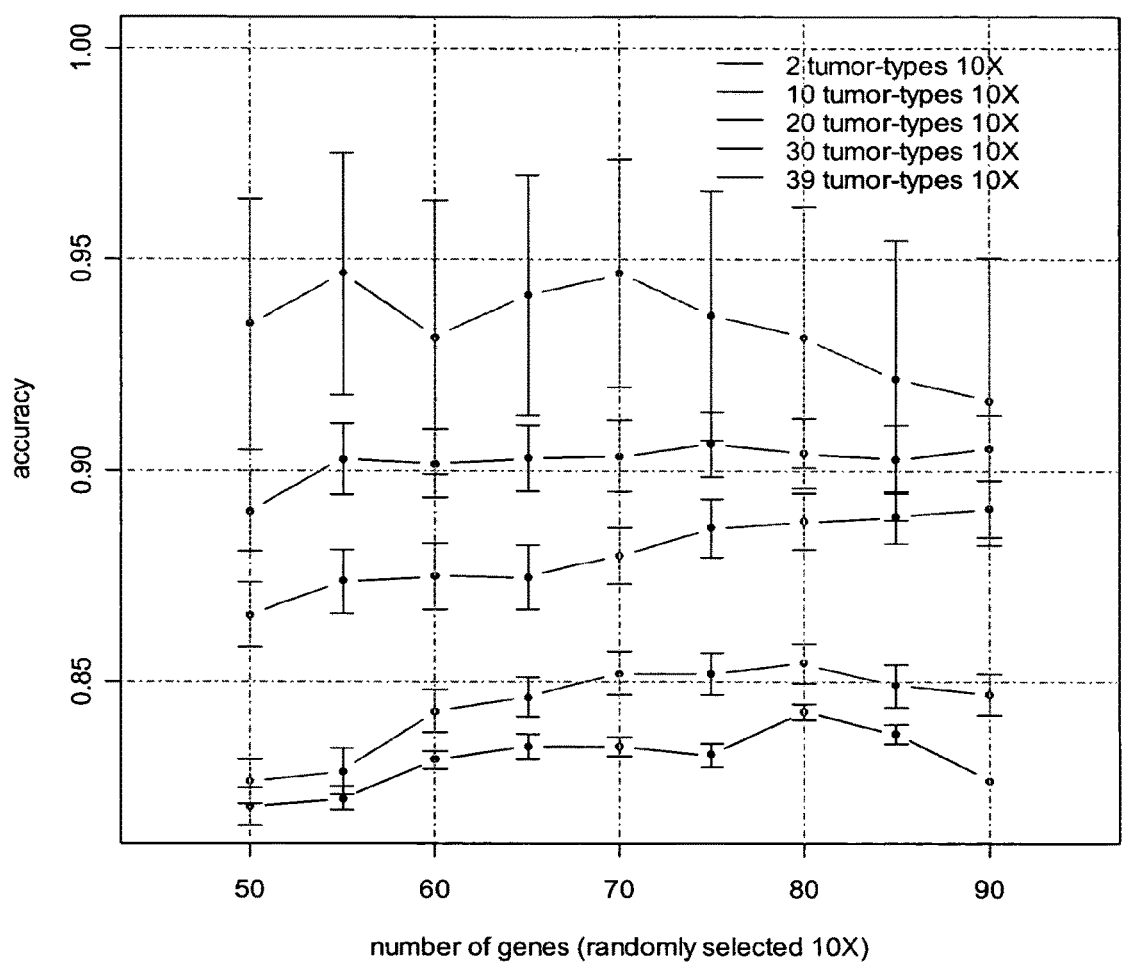
FIG. 7 shows an alternative presentation of the data used with respect to FIG. 6. A plot of numbers of gene sequences used, ranging from 50-90, versus prediction accuracies for various representative numbers of tumor types is shown. The plotted lines, from top to bottom, are of the results from 2, 10, 20, 30, and 39 tumor types, respectively.
Figure 8A:
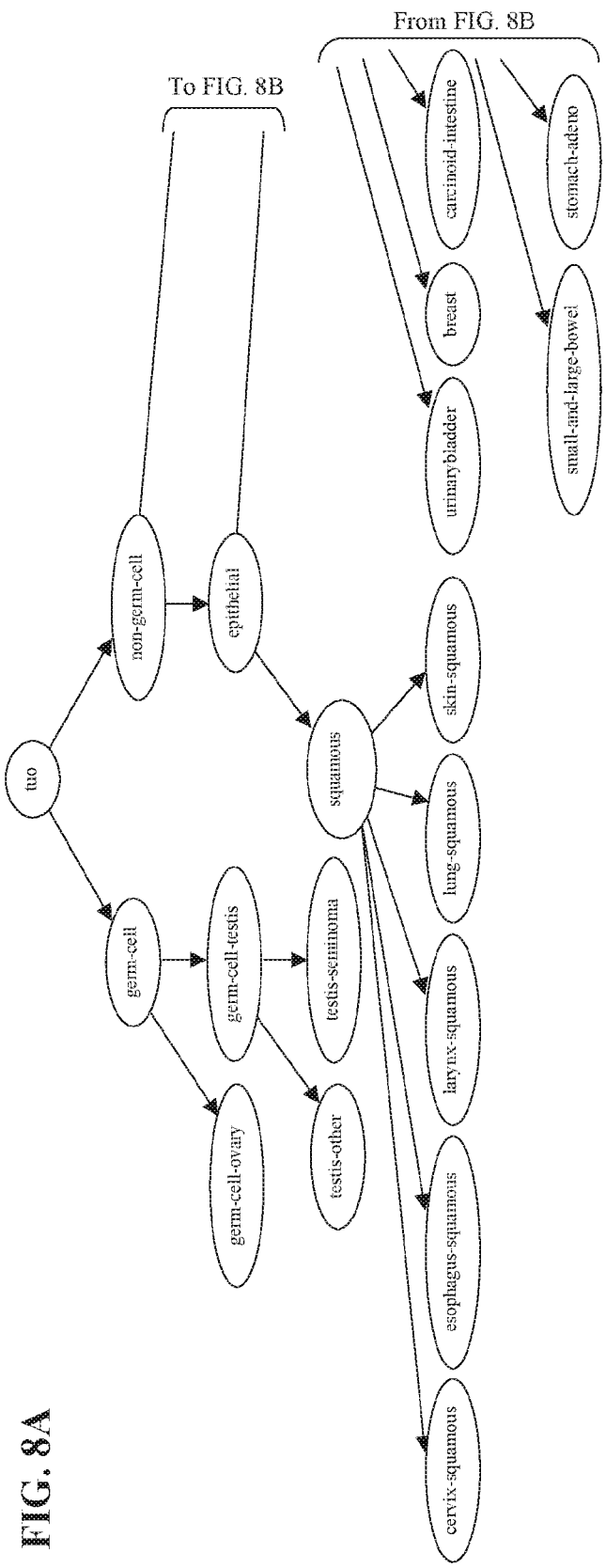
FIGS. 8A-8D show a "tree" that classifies tumor types covered herein as well as additional known tumor types. It was constructed mainly according to "Cancer, Principles and Practice of Oncology, (DeVito, Hellman and Rosenberg), 6$^{th}$ edition". Thus beginning with a "tumor of unknown origin" (or "tuo"), the first possibilities are that it is either of a germ cell or non-germ cell origin. If it is the former, then it may be of ovary or testes origin. Within those of testes origin, the tumor may be of seminoma origin or an "other" origin.
Figure 8B:
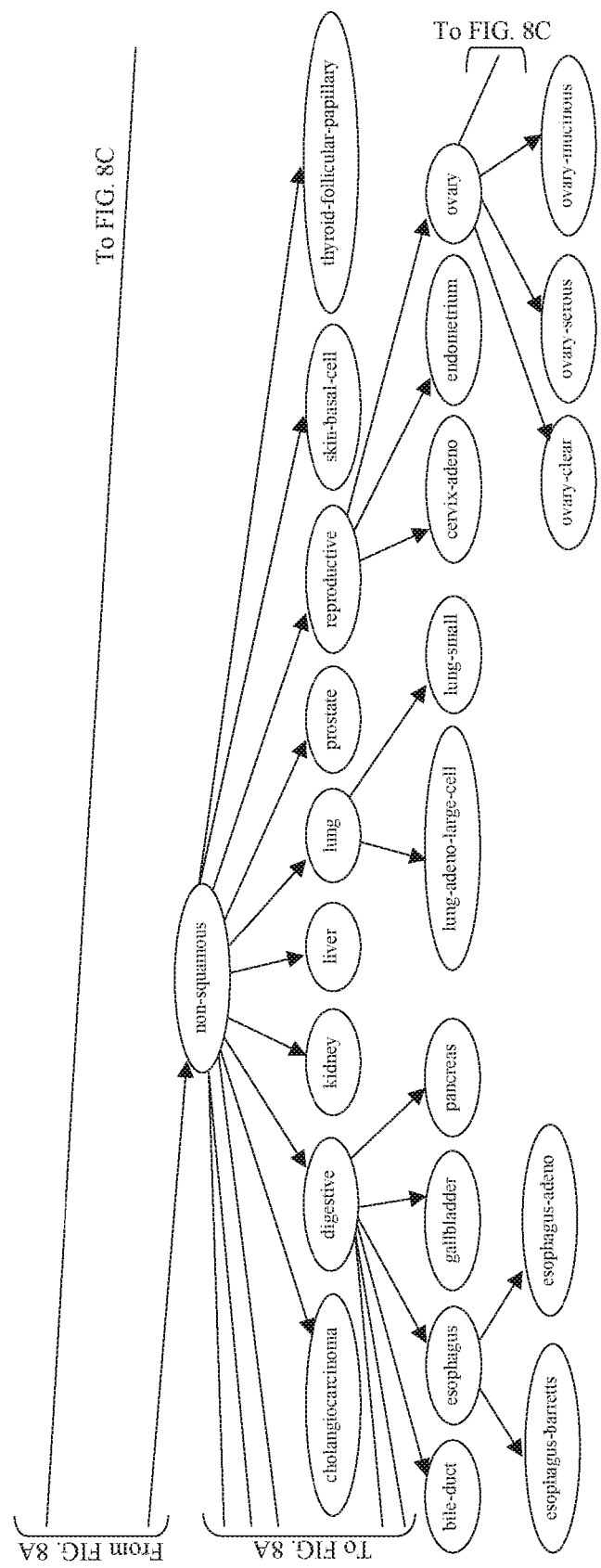
Figure 8C:
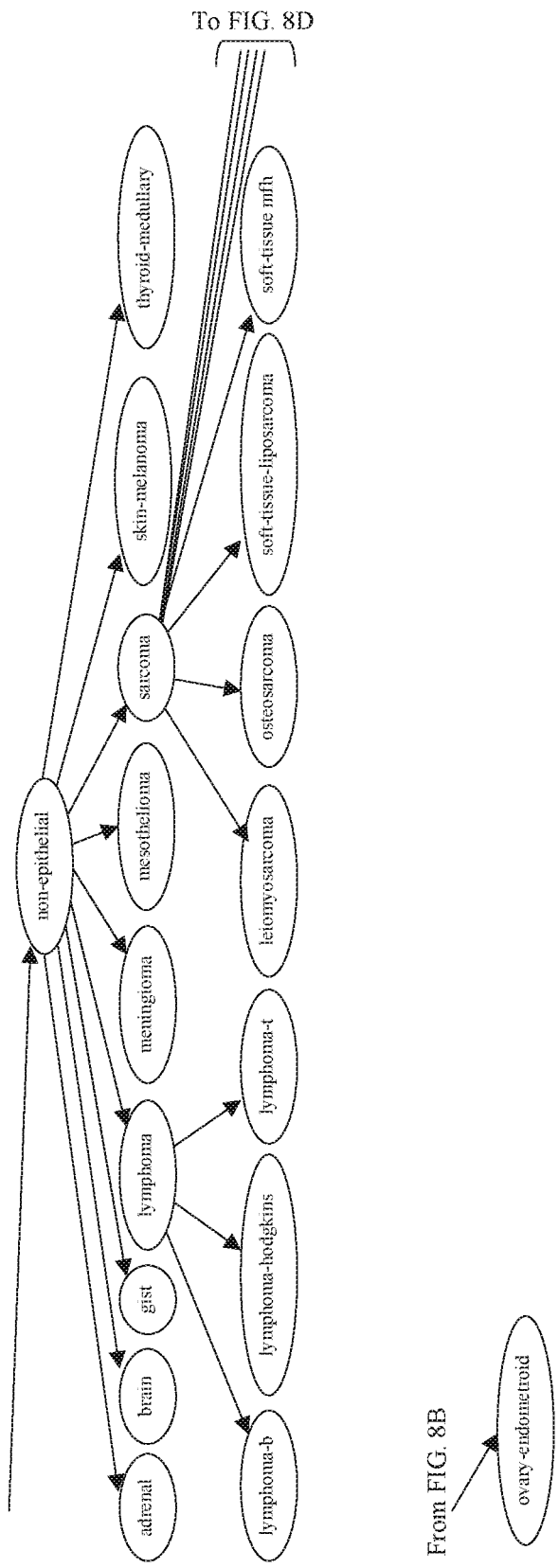
Figure 8D:
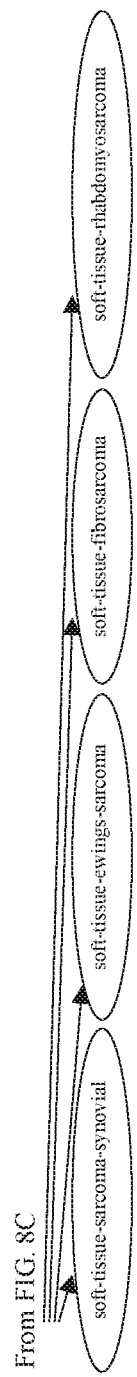

A similar experiment was performed with random subsets of 50 to all members of the set of 90 expressed gene sequences. Again, the expression levels of random combinations of 50, 55, 60, 65, 70, and all 90 (each combination sampled 10 times) of the 90 expressed sequences were used with data from tumor types and then used to predict test random sets of tumor samples (each sampled 10 times) ranging from 2 to all 39 types. The resulting data are shown in FIGS. 6 and 7.

The members of the 90 gene sequences were indexed from 1 to 90, and representative random sets used in the invention are as follows:

For 50-genes, set 1, genes 89, 30, 62, 23, 31, 20, 53, 25, 15, 38, 11, 22, 68, 44, 58, 7, 14, 61, 67, 32, 18, 71, 9, 54, 46, 3, 57, 50, 59, 79, 48, 90, 82, 64, 39, 21, 60, 37, 47, 10, 52, 77, 33, 45, 35, 83, 16, 69, 74, and 27 were used. In set 2, genes 25, 17, 64, 82, 23, 5, 77, 48, 72, 63, 34, 60, 61, 35, 58, 19, 56, 83, 8, 13, 38, 89, 59, 62, 88, 71, 11, 29, 31, 68, 65, 67, 78, 44, 27, 81, 24, 1, 18, 55, 85, 46, 41, 14, 84, 26, 16, 21, 12, and 69 were used. In set 3, genes 24, 39, 35, 15, 49, 44, 28, 58, 20, 3, 88, 23, 54, 31, 33, 37, 62, 25, 87, 75, 17, 41, 21, 19, 38, 85, 86, 74, 8, 12, 77, 30, 27, 43, 76, 73, 9, 14, 6, 63, 64, 81, 26, 66, 2, 56, 34, 60, 57, and 61 were used. In set 4, genes 40, 71, 55, 63, 2, 13, 38, 58, 26, 18, 76, 74, 17, 67, 69, 4, 9, 20, 21, 10, 35, 70, 49, 37, 12, 77, 61, 60, 15, 7, 36, 89, 33, 59, 78, 39, 82, 16, 64, 28, 6, 66, 52, 5, 44, 73, 34, 75, 31, and 29 were used. In set 5, genes 16, 37, 57, 18, 29, 66, 54, 6, 44, 70, 20, 65, 5, 61, 72, 83, 85, 58, 87, 73, 23, 76, 25, 68, 49, 24, 79, 89, 55, 75, 47, 19, 33, 39, 21, 63, 84, 32, 77, 40, 12, 11, 42, 50, 1, 9, 78, 3, 74, and 7 were used. In set 6, genes 42, 29, 74, 68, 27, 54, 15, 63, 30, 51, 78, 56, 82, 66, 80, 79, 90, 64, 22, 44, 71, 2, 89, 39, 46, 52, 36, 32, 84, 6, 59, 9, 38, 4, 55, 19, 7, 60, 49, 23, 73, 5, 11, 50, 70, 34, 61, 81, 67, and 28 were used. In set 7, genes 31, 27, 24, 75, 7, 46, 40, 60, 51, 37, 87, 28, 67, 62, 50, 66, 61, 63, 49, 1, 39, 74, 81, 4, 52, 22, 79, 45, 12, 41, 15, 90, 26, 33, 78, 48, 83, 10, 53, 73, 6, 19, 71, 59, 68, 56, 64, 13, 32, and 30 were used. In set 8, genes 88, 57, 5, 4, 1, 43, 12, 32, 66, 81, 90, 19, 51, 18, 55, 9, 29, 75, 11, 73, 23, 61, 6, 79, 69, 60, 13, 62, 8, 71, 2, 52, 67, 59, 87, 33, 80, 21, 14, 89, 39, 65, 56, 38, 47, 31, 84, 25, 45, and 41 were used. In set 9, genes 60, 45, 51, 32, 49, 2, 44, 66, 83, 50, 87, 1, 90, 28, 42, 85, 13, 40, 70, 82, 79, 89, 64, 63, 27, 52, 10, 86, 77, 15, 56, 8, 33, 53, 38, 46, 67, 19, 68, 29, 48, 21, 34, 61, 18, 55, 25, 35, 39, and 80 were used. In set 10, genes 80, 39, 23, 76, 87, 33, 30, 88, 85, 89, 24, 47, 44, 43, 48, 55, 14, 73, 22, 19, 67, 1, 42, 51, 60, 12, 9, 6, 75, 17, 40, 25, 28, 74, 38, 66, 5, 50, 8, 37, 15, 29, 21, 11, 35, 31, 13, 36, 52, and 18 were used.

For 55 genes, set 1, genes 86, 47, 80, 15, 74, 20, 79, 35, 14, 49, 41, 2, 48, 30, 81, 65, 5, 24, 51, 10, 31, 68, 7, 21, 28, 37, 38, 4, 18, 23, 44, 77, 42, 19, 61, 27, 75, 67, 36, 22, 26, 50, 32, 58, 71, 57, 76, 1, 66, 72, 33, 6, 34, 59, and 13 were used. In set 2, genes 73, 88, 39, 52, 87, 78, 84, 1, 42, 69, 62, 58, 10, 51, 38, 14, 77, 49, 36, 35, 34, 15, 65, 60, 20, 17, 61, 2, 59, 22, 81, 11, 19, 41, 5, 29, 12, 43, 7, 4, 64, 40, 74, 48, 72, 54, 68, 86, 66, 6, 67, 89, 21, 16, and 9 were used. In set 3, genes 28, 89, 35, 86, 49, 56, 69, 18, 15, 27, 13, 6, 51, 77, 8, 80, 16, 78, 43, 29, 37, 20, 9, 31, 32, 67, 48, 65, 82, 62, 76, 25, 54, 41, 90, 47, 2, 71, 87, 84, 57, 74, 61, 59, 85, 75, 10, 66, 46, 73, 24, 44, 14, 4, and 7 were used. In set 4, genes 48, 76, 17, 62, 65, 87, 19, 24, 83, 29, 55, 12, 68, 82, 73, 18, 20, 10, 81, 53, 33, 56, 34, 5, 60, 46, 16, 25, 2, 42, 6, 49, 4, 45, 88, 32, 77, 8, 1, 71, 3, 27, 72, 59, 79, 64, 11, 80, 57, 61, 75, 39, 23, 52, and 37 were used. In set 5, genes 54, 77, 74, 76, 81, 17, 25, 57, 29, 36, 55, 75, 66, 15, 2, 41, 37, 59, 12, 45, 4, 9, 69, 18, 49, 22, 42, 62, 10, 52, 48, 31, 44, 19, 79, 50, 40, 32, 89, 87, 11, 5, 73, 20, 80, 35, 70, 53, 83, 72, 88, 47, 84, 39, and 65 were used. In set 6, genes 86, 43, 75, 90, 32, 85, 38, 54, 87, 42, 73, 55, 27, 34, 11, 14, 65, 82, 77, 21, 26, 46, 83, 10, 15, 22, 66, 20, 67, 72, 35, 68, 3, 53, 44, 50, 70, 40, 30, 31, 84, 81, 62, 51, 80, 79, 59, 57, 88, 69, 2, 64, 23, 28, and 16 were used. In set 7, genes 76, 15, 53, 8, 89, 52, 20, 3, 47, 83, 45, 31, 80, 82, 4, 57, 65, 41, 29, 77, 46, 60, 24, 33, 70, 37, 12, 66, 42, 61, 63, 86, 30, 11, 40, 27, 39, 56, 9, 49, 35, 22, 10, 48, 18, 68, 58, 62, 34, 85, 84, 26, 43, 81, and 38 were used. In set 8, genes 3, 46, 11, 89, 63, 61, 26, 69, 47, 82, 27, 39, 52, 2, 70, 6, 41, 14, 36, 30, 65, 74, 28, 34, 42, 79, 59, 4, 72, 37, 66, 50, 45, 23, 73, 71, 10, 19, 78, 62, 20, 5, 56, 25, 75, 38, 13, 86, 88, 22, 32, 58, 60, 1, and 51 were used. In set 9, genes 16, 61, 85, 3, 42, 24, 55, 4, 9, 22, 28, 31, 53, 74, 25, 52, 10, 49, 2, 21, 30, 78, 54, 26, 38, 87, 35, 37, 45, 84, 83, 57, 64, 65, 68, 50, 1, 34, 75, 67, 60, 5, 7, 58, 59, 76, 27, 77, 44, 32, 6, 11, 48, 56, and 15 were used. In set 10, genes 72, 86, 46, 5, 3, 29, 54, 66, 20, 44, 41, 47, 14, 65, 83, 56, 43, 26, 49, 48, 69, 24, 45, 27, 73, 11, 40, 22, 78, 2, 39, 15, 31, 35, 77, 61, 9, 52, 37, 1, 89, 79, 60, 18, 50, 17, 88, 80, 57, 71, 12, 53, 36, 58, and 42 were used.

For 60 genes, set 1, genes 75, 54, 79, 78, 4, 48, 36, 29, 28, 32, 82, 38, 21, 8, 80, 46, 47, 57, 76, 50, 18, 68, 85, 13, 61, 65, 71, 56, 45, 58, 84, 25, 72, 43, 7, 77, 74, 69, 86, 31, 19, 63, 35, 83, 70, 3, 62, 90, 52, 87, 44, 41, 66, 12, 23, 59, 1, 10, 49, and 67 were used. In set 2, genes 6, 50, 10, 38, 29, 59, 60, 12, 74, 14, 65, 61, 54, 2, 89, 68, 9, 62, 20, 81, 70, 67, 66, 52, 45, 58, 43, 31, 86, 79, 82, 1, 42, 88, 85, 22, 87, 84, 24, 21, 5, 39, 25, 51, 40, 63, 49, 7, 35, 36, 71, 90, 47, 15, 56, 23, 83, 34, 76, and 19 were used. In set 3, genes 17, 68, 41, 53, 15, 58, 90, 21, 10, 61, 72, 44, 22, 8, 32, 47, 55, 48, 45, 3, 5, 7, 1, 4, 24, 49, 75, 54, 39, 57, 19, 70, 79, 66, 6, 60, 51, 56, 46, 14, 85, 80, 36, 31, 37, 86, 42, 84, 87, 23, 2, 81, 11, 50, 40, 52, 13, 65, 62, and 76 were used. In set 4, genes 54, 24, 50, 11, 77, 63, 84, 71, 16, 51, 78, 83, 10, 28, 31, 29, 43, 14, 30, 61, 81, 58, 4, 48, 64, 37, 18, 39, 1, 67, 45, 40, 80, 79, 8, 55, 36, 2, 32, 25, 21, 46, 73, 38, 34, 52, 49, 65, 13, 66, 6, 76, 20, 85, 15, 44, 60, 69, 86, and 88 were used. In set 5, genes 89, 22, 12, 82, 28, 14, 87, 8, 79, 48, 69, 84, 66, 43, 88, 13, 9, 50, 75, 71, 20, 36, 5, 54, 80, 62, 4, 23, 24, 60, 19, 10, 63, 81, 68, 30, 32, 52, 56, 37, 15, 83, 16, 90, 26, 44, 78, 39, 61, 59, 45, 74, 58, 86, 35, 33, 47, 57, 18, and 42 were used. In set 6, genes 41, 38, 76, 54, 12, 29, 66, 35, 68, 80, 64, 57, 46, 25, 27, 49, 86, 36, 20, 5, 16, 19, 69, 59, 48, 4, 10, 70, 17, 60, 50, 63, 18, 33, 65, 39, 23, 82, 51, 55, 8, 28, 53, 84, 67, 22, 71, 77, 13, 9, 42, 21, 62, 31, 78, 11, 89, 45, 52, and 74 were used. In set 7, genes 84, 12, 17, 10, 33, 56, 50, 61, 74, 21, 78, 11, 37, 36, 3, 5, 30, 43, 47, 54, 27, 32, 77, 51, 42, 4, 76, 71, 83, 46, 57, 73, 87, 24, 90, 8, 72, 29, 35, 66, 28, 70, 22, 39, 65, 85, 1, 82, 40, 89, 80, 58, 52, 38, 59, 86, 69, 13, 16, and 14 were used. In set 8, genes 71, 3, 44, 6, 16, 69, 34, 20, 56, 72, 5, 68, 9, 52, 49, 58, 79, 76, 2, 59, 7, 73, 51, 74, 19, 88, 60, 30, 61, 13, 89, 50, 31, 40, 81, 10, 21, 54, 45, 77, 67, 36, 46, 1, 43, 83, 55, 12, 80, 28, 41, 86, 47, 39, 53, 17, 78, 63, 87, and 48 were used. In set 9, genes 47, 30, 10, 11, 39, 23, 41, 29, 21, 36, 45, 49, 69, 1, 24, 66, 57, 12, 56, 22, 71, 9, 89, 52, 83, 28, 80, 37, 72, 67, 76, 87, 82, 5, 88, 4, 3, 68, 58, 64, 62, 46, 74, 7, 20, 15, 48, 53, 54, 63, 19, 13, 43, 32, 51, 31, 33, 27, 35, and 40 were used. In set 10, genes 75, 29, 27, 66, 15, 47, 14, 3, 12, 80, 31, 32, 41, 17, 74, 7, 57, 59, 64, 25, 13, 77, 33, 43, 81, 55, 48, 68, 30, 54, 69, 88, 62, 86, 67, 37, 20, 8, 42, 19, 70, 24, 49, 73, 23, 10, 1, 85, 89, 44, 58, 2, 11, 63, 76, 5, 53, 83, 50, and 9 were used.

For 65 genes, set 1, genes 55, 36, 14, 26, 67, 60, 28, 31, 46, 85, 16, 10, 17, 45, 73, 87, 7, 72, 90, 4, 84, 34, 78, 19, 71, 54, 29, 43, 76, 12, 35, 61, 49, 57, 89, 20, 50, 47, 86, 88, 59, 75, 15, 8, 5, 3, 32, 81, 74, 23, 41, 13, 33, 63, 77, 22, 9, 38, 64, 69, 80, 25, 1, 18, and 30 were used. In set 2, genes 32, 81, 5, 65, 79, 12, 52, 83, 2, 39, 19, 37, 44, 66, 63, 72, 56, 60, 3, 22, 70, 64, 9, 67, 15, 8, 50, 48, 71, 82, 76, 14, 28, 18, 25, 11, 29, 58, 35, 31, 10, 69, 38, 90, 80, 74, 53, 75, 4, 77, 89, 55, 57, 59, 51, 42, 41, 68, 23, 84, 45, 40, 20, 85, and 61 were used. In set 3, genes 33, 52, 22, 67, 7, 36, 40, 6, 56, 29, 48, 41, 28, 68, 83, 90, 51, 70, 60, 24, 87, 88, 18, 58, 73, 1, 17, 8, 26, 89, 38, 4, 10, 47, 75, 72, 50, 13, 23, 66, 20, 30, 12, 43, 46, 15, 16, 5, 55, 31, 63, 32, 53, 69, 39, 71, 42, 62, 57, 34, 44, 14, 25, 64, and 80 were used. In set 4, genes 30, 45, 74, 3, 13, 63, 76, 27, 46, 11, 51, 2, 20, 78, 66, 65, 43, 7, 69, 40, 28, 19, 25, 52, 26, 34, 49, 44, 60, 59, 38, 48, 85, 87, 18, 82, 15, 42, 24, 67, 61, 71, 70, 35, 68, 79, 47, 83, 80, 84, 31, 32, 9, 77, 72, 62, 8, 55, 54, 1, 58, 16, 53, 89, and 90 were used. In set 5, genes 14, 55, 53, 45, 32, 63, 49, 15, 10, 11, 47, 52, 3, 13, 71, 68, 85, 34, 66, 64, 83, 78, 28, 21, 30, 54, 29, 88, 59, 73, 26, 84, 50, 77, 65, 82, 20, 86, 19, 57, 62, 25, 43, 27, 8, 6, 87, 38, 51, 61, 56, 2, 18, 46, 44, 80, 9, 31, 36, 76, 1, 7, 33, 48, and 58 were used. In set 6, genes 66, 44, 18, 85, 54, 28, 80, 65, 25, 1, 88, 72, 74, 46, 76, 71, 24, 51, 47, 31, 21, 60, 83, 32, 3, 63, 64, 69, 52, 27, 2, 38, 34, 10, 12, 35, 77, 33, 29, 56, 67, 40, 30, 22, 49, 5, 7, 43, 17, 13, 81, 20, 79, 14, 48, 73, 53, 90, 70, 59, 19, 16, 8, 36, and 23 were used. In set 7, genes 89, 37, 48, 32, 75, 46, 90, 2, 66, 44, 55, 17, 9, 59, 68, 83, 24, 53, 19, 67, 74, 35, 72, 4, 13, 76, 15, 62, 63, 28, 51, 26, 39, 20, 18, 45, 36, 78, 41, 84, 87, 11, 80, 12, 81, 3, 50, 86, 6, 61, 73, 31, 27, 88, 42, 71, 33, 43, 60, 30, 69, 34, 21, 49, and 70 were used. In set 8, genes 84, 73, 14, 23, 36, 47, 31, 61, 57, 50, 78, 53, 90, 68, 37, 39, 75, 4, 10, 80, 35, 32, 85, 18, 81, 29, 66, 76, 54, 41, 62, 30, 58, 49, 33, 64, 45, 87, 25, 79, 20, 69, 42, 17, 88, 24, 2, 34, 16, 28, 86, 15, 7, 82, 1, 60, 11, 48, 89, 22, 77, 74, 72, 6, and 43 were used. In set 9, genes 1, 74, 39, 48, 44, 47, 3, 8, 80, 54, 16, 41, 76, 9, 85, 86, 49, 70, 52, 89, 19, 66, 43, 17, 15, 63, 29, 53, 42, 32, 30, 4, 36, 7, 77, 2, 84, 87, 28, 67, 20, 56, 65, 31, 12, 25, 40, 10, 73, 6, 83, 64, 50, 13, 22, 58, 45, 21, 57, 60, 72, 82, 26, 33, and 35 were used. In set 10, genes 18, 31, 52, 70, 48, 76, 57, 66, 10, 14, 60, 30, 67, 45, 35, 51, 1, 79, 46, 71, 3, 42, 33, 85, 4, 61, 2, 63, 87, 50, 36, 37, 90, 80, 24, 6, 77, 28, 21, 88, 17, 82, 83, 49, 75, 54, 25, 5, 7, 73, 59, 29, 69, 47, 65, 19, 15, 56, 9, 55, 58, 40, 20, 89, and 74 were used.

For 70 genes, set 1, genes 79, 50, 38, 63, 74, 71, 66, 4, 33, 1, 69, 88, 85, 18, 27, 77, 70, 65, 14, 40, 64, 29, 59, 6, 3, 9, 84, 22, 62, 60, 30, 7, 11, 13, 45, 57, 35, 72, 15, 75, 39, 36, 10, 53, 67, 80, 83, 31, 5, 25, 90, 89, 58, 23, 56, 2, 16, 41, 76, 47, 26, 43, 17, 55, 82, 87, 24, 12, 48, and 81 were used. In set 2, genes 6, 66, 68, 83, 77, 81, 21, 88, 18, 60, 50, 17, 13, 61, 14, 25, 39, 76, 75, 78, 89, 37, 87, 59, 55, 90, 9, 5, 12, 10, 43, 29, 51, 31, 46, 58, 49, 24, 52, 28, 64, 42, 8, 11, 67, 84, 70, 19, 41, 45, 71, 16, 33, 23, 34, 30, 86, 69, 4, 57, 47, 80, 20, 82, 2, 1, 56, 65, 62, and 48 were used. In set 3, genes 72, 87, 89, 53, 56, 17, 84, 60, 45, 61, 62, 76, 13, 37, 20, 21, 2, 23, 3, 57, 83, 90, 82, 49, 24, 59, 9, 48, 32, 33, 47, 42, 78, 88, 65, 52, 79, 41, 34, 19, 74, 66, 43, 27, 36, 63, 81, 44, 40, 80, 31, 86, 12, 29, 77, 67, 14, 71, 68, 1, 35, 16, 10, 30, 6, 22, 75, 55, 85, and 4 were used. In set 4, genes 70, 81, 71, 17, 8, 59, 6, 15, 52, 74, 23, 9, 19, 14, 82, 86, 27, 73, 66, 38, 22, 41, 88, 76, 47, 58, 56, 11, 55, 64, 44, 84, 62, 21, 35, 80, 36, 28, 12, 13, 4, 1, 75, 60, 5, 87, 89, 2, 50, 46, 25, 85, 37, 90, 78, 34, 24, 18, 45, 79, 77, 30, 32, 51, 57, 67, 83, 68, 54, and 29 were used. In set 5, genes 70, 23, 22, 30, 85, 48, 21, 32, 86, 84, 78, 87, 64, 40, 4, 34, 67, 19, 25, 7, 55, 42, 65, 53, 49, 83, 50, 80, 62, 16, 37, 77, 71, 54, 28, 27, 29, 18, 13, 57, 79, 56, 15, 36, 5, 24, 3, 1, 75, 90, 73, 47, 51, 88, 38, 58, 66, 81, 35, 76, 43, 46, 82, 68, 10, 14, 8, 41, 39, and 59 were used. In set 6, genes 88, 3, 40, 60, 24, 43, 62, 85, 58, 53, 39, 56, 59, 81, 71, 63, 25, 16, 22, 14, 10, 72, 89, 90, 84, 5, 33, 12, 45, 57, 70, 38, 32, 19, 44, 46, 2, 64, 8, 49, 42, 27, 37, 29, 13, 6, 28, 7, 77, 41, 17, 50, 31, 69, 26, 83, 23, 73, 80, 51, 61, 76, 82, 18, 15, 78, 67, 54, 36, and 65 were used. In set 7, genes 35, 52, 48, 42, 65, 38, 61, 79, 23, 20, 12, 8, 53, 57, 22, 54, 69, 9, 56, 43, 5, 66, 86, 49, 81, 19, 40, 45, 85, 60, 10, 50, 55, 11, 15, 73, 13, 2, 29, 59, 78, 67, 18, 80, 84, 39, 87, 90, 58, 46, 17, 32, 7, 62, 14, 34, 27, 6, 83, 70, 51, 26, 68, 21, 82, 77, 44, 47, 24, and 37 were used. In set 8, genes 40, 55, 22, 47, 86, 19, 62, 51, 25, 59, 8, 65, 48, 79, 1, 66, 17, 70, 32, 49, 23, 61, 85, 28, 36, 54, 20, 39, 83, 73, 50, 4, 81, 27, 41, 63, 15, 80, 87, 7, 46, 33, 9, 68, 56, 77, 14, 75, 82, 74, 12, 37, 16, 84, 72, 30, 2, 38, 13, 57, 76, 5, 64, 45, 89, 58, 29, 10, 78, and 90 were used. In set 9, genes 84, 16, 21, 81, 89, 60, 79, 30, 47, 69, 83, 85, 75, 52, 49, 72, 86, 3, 9, 59, 18, 55, 17, 82, 14, 23, 38, 24, 87, 65, 77, 80, 66, 19, 41, 53, 1, 34, 27, 56, 40, 67, 32, 20, 37, 70, 36, 15, 22, 8, 29, 48, 58, 45, 25, 71, 7, 4, 73, 10, 12, 2, 42, 90, 63, 43, 51, 6, 54, and 78 were used. In set 10, genes 19, 51, 29, 22, 66, 13, 32, 89, 62, 45, 65, 35, 24, 73, 55, 47, 67, 76, 69, 26, 37, 64, 53, 10, 15, 34, 79, 2, 56, 30, 3, 20, 78, 31, 75, 46, 27, 52, 6, 86, 16, 9, 54, 87, 58, 33, 61, 11, 43, 40, 74, 60, 50, 25, 80, 72, 83, 57, 38, 1, 70, 5, 7, 77, 85, 59, 88, 63, 14, and 84 were used.

For 75 genes, set 1, genes 87, 17, 52, 44, 57, 53, 78, 37, 2, 71, 9, 68, 6, 63, 50, 58, 13, 26, 16, 60, 67, 3, 32, 21, 79, 12, 77, 73, 24, 35, 80, 47, 29, 40, 30, 84, 39, 90, 11, 81, 75, 76, 89, 66, 86, 42, 34, 64, 54, 7, 41, 56, 62, 55, 46, 28, 5, 25, 27, 83, 19, 20, 49, 69, 85, 33, 18, 23, 74, 1, 10, 43, 22, 8, and 45 were used. In set 2, genes 75, 33, 52, 86, 24, 50, 70, 10, 17, 90, 28, 46, 48, 77, 47, 61, 12, 4, 83, 27, 45, 88, 35, 36, 22, 68, 73, 31, 57, 69, 65, 64, 15, 9, 54, 39, 14, 20, 67, 79, 44, 38, 78, 23, 84, 37, 66, 5, 11, 18, 41, 13, 21, 49, 16, 76, 1, 29, 53, 40, 42, 63, 25, 56, 6, 82, 71, 85, 89, 80, 34, 51, 60, 30, and 58 were used. In set 3, genes 39, 82, 36, 31, 52, 84, 30, 83, 49, 1, 44, 10, 87, 78, 77, 18, 79, 9, 73, 69, 75, 45, 14, 16, 56, 40, 58, 15, 32, 34, 42, 60, 19, 63, 47, 41, 68, 13, 61, 90, 89, 5, 46, 57, 8, 37, 66, 43, 21, 17, 11, 72, 74, 4, 33, 53, 12, 65, 50, 2, 81, 24, 62, 6, 23, 25, 88, 51, 67, 64, 7, 80, 54, 22, and 3 were used. In set 4, genes 63, 2, 5, 52, 10, 62, 75, 4, 6, 51, 29, 54, 49, 55, 36, 37, 77, 46, 44, 79, 11, 59, 38, 14, 65, 43, 48, 35, 86, 78, 73, 72, 57, 8, 16, 58, 56, 82, 60, 42, 80, 13, 9, 90, 53, 66, 21, 67, 88, 89, 45, 22, 71, 31, 84, 74, 15, 23, 26, 3, 68, 1, 39, 7, 50, 41, 40, 81, 87, 34, 18, 12, 70, 47, and 25 were used. In set 5, genes 62, 82, 46, 89, 81, 43, 57, 69, 9, 19, 18, 16, 80, 63, 72, 2, 54, 86, 44, 53, 31, 5, 1, 61, 20, 37, 58, 32, 28, 47, 34, 6, 41, 68, 15, 90, 85, 13, 23, 10, 4, 70, 76, 33, 11, 51, 35, 88, 67, 84, 8, 24, 66, 65, 26, 59, 40, 79, 64, 42, 45, 22, 17, 87, 30, 12, 27, 14, 39, 56, 38, 71, 52, 36, and 60 were used. In set 6, genes 16, 85, 19, 39, 64, 76, 44, 15, 50, 73, 27, 36, 6, 62, 54, 46, 58, 68, 28, 13, 14, 21, 86, 47, 71, 87, 18, 5, 67, 1, 65, 78, 12, 66, 43, 82, 38, 23, 75, 24, 49, 57, 17, 10, 29, 72, 22, 89, 90, 26, 42, 45, 2, 33, 41, 9, 8, 7, 69, 31, 30, 79, 80, 84, 55, 35, 20, 70, 83, 48, 88, 60, 25, 74, and 63 were used. In set 7, genes 24, 66, 86, 48, 63, 51, 74, 37, 2, 82, 77, 22, 72, 21, 11, 90, 80, 55, 76, 68, 34, 42, 29, 62, 46, 39, 56, 31, 47, 28, 16, 38, 44, 52, 1, 43, 14, 20, 64, 83, 78, 58, 12, 18, 84, 67, 75, 85, 36, 25, 50, 49, 40, 33, 23, 45, 41, 73, 88, 59, 17, 32, 70, 13, 60, 57, 3, 7, 54, 4, 8, 53, 26, 15, and 69 were used. In set 8, genes 80, 38, 59, 41, 85, 44, 12, 22, 39, 17, 52, 24, 32, 62, 18, 8, 78, 74, 9, 66, 76, 14, 3, 16, 40, 28, 48, 58, 54, 29, 43, 5, 81, 77, 86, 23, 75, 82, 34, 7, 51, 64, 4, 6, 72, 61, 37, 84, 45, 33, 71, 19, 67, 88, 1, 35, 47, 83, 25, 49, 11, 42, 50, 70, 2, 46, 15, 26, 27, 68, 57, 65, 13, 53, and 90 were used. In set 9, genes 4, 66, 28, 44, 20, 34, 12, 85, 6, 17, 88, 8, 39, 65, 22, 19, 10, 48, 63, 23, 33, 13, 47, 81, 79, 89, 64, 53, 87, 11, 46, 74, 14, 70, 37, 62, 30, 7, 71, 76, 50, 59, 77, 51, 15, 68, 55, 72, 83, 82, 78, 54, 25, 21, 27, 41, 69, 9, 58, 3, 31, 75, 84, 26, 86, 49, 18, 42, 61, 45, 16, 2, 24, 80, and 73 were used. In set 10, genes 78, 47, 32, 30, 46, 6, 2, 64, 11, 27, 85, 22, 79, 63, 80, 39, 90, 65, 71, 72, 21, 26, 58, 15, 16, 23, 81, 1, 44, 43, 40, 55, 13, 19, 25, 83, 41, 18, 53, 68, 37, 20, 49, 69, 33, 61, 38, 28, 60, 45, 17, 82, 24, 4, 86, 89, 36, 51, 84, 31, 14, 88, 59, 76, 48, 5, 35, 75, 74, 7, 67, 62, 52, 56, and 54 were used.

For 80 genes, set 1, genes 29, 80, 5, 50, 63, 3, 1, 55, 38, 48, 58, 30, 86, 82, 83, 6, 23, 2, 41, 60, 54, 69, 15, 34, 64, 10, 27, 70, 28, 44, 8, 68, 56, 14, 36, 17, 73, 13, 88, 42, 72, 59, 67, 71, 26, 53, 37, 24, 79, 62, 52, 74, 4, 40, 47, 19, 78, 11, 76, 31, 90, 12, 87, 89, 75, 66, 81, 16, 49, 65, 57, 84, 46, 20, and 21 were used. In set 2, genes 15, 21, 70, 5, 79, 85, 84, 53, 69, 33, 28, 14, 75, 76, 58, 48, 13, 45, 51, 88, 25, 74, 39, 71, 64, 9, 60, 44, 78, 7, 8, 3, 32, 89, 73, 1, 4, 29, 41, 17, 46, 57, 72, 20, 86, 47, 49, 87, 55, 19, 37, 27, 80, 62, 54, 18, 52, 67, 63, 77, 65, 24, 31, 26, 83, 2, 22, 90, 50, 12, 16, 35, 11, 10, and 56 were used. In set 3, genes 41, 4, 59, 73, 29, 22, 60, 45, 70, 10, 64, 21, 81, 36, 52, 67, 54, 38, 65, 90, 27, 87, 28, 7, 74, 43, 56, 75, 9, 35, 42, 20, 72, 47, 14, 63, 18, 68, 23, 69, 8, 50, 89, 3, 11, 82, 39, 80, 46, 16, 53, 58, 25, 79, 49, 76, 37, 30, 78, 83, 2, 84, 57, 88, 6, 32, 12, 71, 15, 55, 48, 34, 62, 61, and 13 were used. In set 4, genes 23, 31, 53, 90, 3, 40, 34, 6, 1, 83, 9, 60, 56, 50, 44, 85, 51, 35, 43, 80, 65, 46, 38, 88, 17, 54, 87, 10, 45, 42, 75, 68, 63, 58, 36, 64, 67, 77, 21, 47, 30, 59, 14, 49, 70, 66, 72, 74, 27, 61, 19, 81, 20, 25, 33, 57, 62, 76, 55, 78, 84, 16, 69, 37, 79, 29, 39, 32, 15, 5, 2, 12, 71, 11, and 73 were used. In set 5, genes 29, 71, 21, 60, 43, 78, 55, 61, 51, 90, 10, 37, 35, 53, 28, 62, 15, 1, 31, 67, 48, 36, 75, 27, 63, 87, 24, 32, 54, 79, 16, 70, 64, 40, 47, 41, 17, 38, 3, 45, 81, 68, 72, 56, 77, 8, 13, 34, 57, 26, 73, 14, 6, 82, 4, 58, 89, 30, 7, 74, 69, 88, 20, 5, 46, 2, 11, 49, 50, 23, 33, 42, 83, 52, and 86 were used. In set 6, genes 39, 54, 30, 24, 80, 10, 21, 7, 14, 69, 38, 83, 52, 65, 46, 42, 66, 36, 61, 16, 50, 33, 2, 73, 13, 81, 48, 8, 6, 41, 12, 25, 43, 79, 35, 26, 89, 75, 60, 67, 82, 45, 20, 90, 68, 77, 58, 34, 18, 47, 22, 84, 4, 57, 32, 5, 19, 59, 86, 74, 1, 31, 62, 85, 29, 53, 88, 28, 40, 37, 63, 15, 64, 49, and 55 were used. In set 7, genes 21, 68, 81, 50, 36, 6, 80, 76, 90, 74, 12, 79, 34, 53, 1, 4, 5, 41, 56, 47, 15, 63, 11, 14, 7, 78, 57, 65, 73, 20, 8, 64, 84, 30, 3, 13, 52, 49, 27, 86, 60, 72, 62, 29, 75, 40, 32, 2, 82, 33, 10, 24, 51, 17, 46, 38, 19, 37, 28, 69, 61, 85, 88, 22, 48, 89, 18, 25, 71, 58, 31, 35, 26, 55, and 44 were used. In set 8, genes 30, 64, 67, 79, 52, 71, 13, 3, 22, 8, 75, 41, 65, 21, 60, 36, 49, 84, 33, 29, 57, 86, 15, 12, 85, 63, 6, 20, 66, 53, 51, 90, 87, 55, 11, 32, 31, 61, 78, 58, 42, 48, 5, 1, 17, 50, 70, 76, 25, 45, 2, 73, 28, 14, 89, 56, 39, 44, 7, 74, 16, 72, 35, 19, 47, 27, 43, 83, 68, 26, 18, 37, 69, 54, and 23 were used. In set 9, genes 79, 85, 48, 29, 23, 31, 62, 37, 5, 33, 3, 19, 53, 9, 36, 18, 58, 17, 81, 46, 8, 35, 66, 87, 14, 30, 74, 77, 21, 40, 75, 43, 42, 15, 39, 70, 60, 13, 10, 2, 72, 44, 45, 38, 4, 25, 84, 68, 50, 24, 7, 27, 82, 55, 80, 32, 89, 57, 6, 69, 83, 28, 56, 22, 16, 1, 41, 63, 26, 78, 12, 59, 64, 61, and 11 were used. In set 10, genes 45, 9, 24, 85, 68, 80, 73, 17, 56, 7, 8, 5, 69, 58, 37, 44, 21, 29, 50, 15, 53, 25, 40, 88, 36, 32, 59, 75, 49, 35, 43, 67, 83, 31, 51, 28, 60, 77, 30, 74, 22, 41, 42, 64, 61, 23, 90, 13, 33, 11, 16, 20, 46, 66, 6, 87, 39, 47, 65, 3, 82, 10, 72, 34, 18, 1, 38, 57, 79, 71, 26, 27, 19, 48, and 76 were used.

For 85 genes, set 1, genes 62, 19, 38, 77, 64, 49, 14, 16, 47, 73, 28, 3, 54, 78, 70, 12, 75, 35, 15, 40, 21, 60, 58, 86, 83, 33, 66, 59, 44, 45, 56, 9, 5, 81, 72, 68, 27, 37, 71, 52, 48, 36, 79, 6, 41, 74, 22, 46, 2, 20, 34, 13, 55, 53, 10, 88, 57, 61, 4, 39, 24, 85, 76, 87, 65, 25, 23, 90, 32, 26, 80, 63, 89, 82, and 7 were used. In set 2, genes 72, 30, 36, 64, 47, 57, 67, 20, 58, 1, 6, 61, 71, 32, 42, 53, 87, 65, 25, 17, 9, 60, 83, 12, 51, 8, 37, 75, 59, 89, 85, 22, 44, 19, 63, 7, 62, 13, 81, 41, 79, 43, 49, 4, 34, 68, 88, 74, 28, 31, 10, 39, 11, 55, 15, 5, 69, 50, 66, 18, 77, 46, 76, 33, 3, 35, 38, 14, 40, 86, 54, 23, 24, 48, and 78 were used. In set 3, genes 5, 67, 57, 18, 12, 42, 43, 71, 50, 19, 26, 51, 52, 32, 74, 88, 46, 2, 9, 77, 30, 58, 69, 81, 35, 87, 90, 34, 22, 15, 84, 44, 8, 3, 47, 60, 55, 66, 33, 20, 86, 39, 16, 37, 85, 73, 4, 13, 56, 27, 65, 76, 49, 54, 75, 31, 68, 82, 23, 62, 7, 53, 78, 36, 64, 40, 45, 6, 70, 17, 79, 10, 21, 48, and 89 were used. In set 4, genes 67, 47, 68, 38, 50, 82, 54, 56, 64, 49, 63, 14, 22, 7, 25, 12, 57, 85, 88, 5, 28, 23, 77, 44, 80, 89, 83, 20, 81, 73, 11, 17, 76, 75, 32, 34, 55, 62, 21, 6, 30, 10, 71, 39, 36, 74, 42, 60, 43, 8, 59, 58, 65, 3, 61, 72, 70, 79, 16, 13, 18, 19, 45, 4, 84, 1, 87, 26, 46, 40, 37, 78, 15, 69, and 41 were used. In set 5, genes 82, 42, 35, 86, 14, 37, 39, 30, 41, 60, 44, 9, 12, 34, 50, 68, 5, 29, 46, 19, 11, 28, 48, 3, 20, 77, 67, 57, 88, 55, 32, 78, 51, 71, 47, 63, 6, 10, 45, 70, 8, 81, 18, 43, 69, 79, 21, 13, 66, 59, 33, 1, 31, 74, 36, 2, 24, 54, 23, 85, 72, 73, 80, 64, 84, 7, 38, 87, 58, 75, 22, 65, 15, 53, and 52 were used. In set 6, genes 55, 2, 11, 72, 4, 85, 43, 18, 46, 27, 80, 69, 9, 31, 39, 5, 81, 22, 32, 3, 36, 17, 83, 37, 90, 38, 87, 44, 56, 66, 13, 6, 28, 77, 54, 79, 41, 78, 47, 29, 8, 21, 63, 64, 73, 48, 14, 34, 82, 70, 30, 58, 84, 24, 26, 68, 1, 65, 60, 42, 33, 20, 7, 75, 12, 57, 59, 16, 74, 88, 23, 49, 50, 40, and 71 were used. In set 7, genes 18, 40, 66, 35, 20, 85, 12, 19, 86, 26, 36, 89, 84, 88, 74, 15, 33, 75, 50, 16, 49, 32, 38, 31, 2, 27, 87, 68, 69, 53, 60, 79, 7, 21, 63, 17, 90, 30, 29, 11, 56, 25, 58, 62, 48, 8, 45, 9, 72, 64, 28, 76, 3, 78, 46, 1, 10, 34, 43, 83, 5, 52, 14, 65, 51, 41, 22, 44, 61, 24, 70, 54, 59, 77, and 13 were used. In set 8, genes 35, 40, 80, 57, 23, 28, 9, 83, 13, 47, 82, 36, 86, 44, 90, 55, 30, 22, 12, 42, 38, 49, 45, 8, 87, 17, 52, 3, 33, 15, 32, 21, 76, 58, 7, 53, 20, 67, 19, 29, 85, 68, 71, 39, 24, 25, 84, 4, 6, 75, 63, 73, 5, 18, 31, 48, 65, 41, 60, 37, 88, 72, 1, 46, 79, 16, 78, 10, 77, 34, 66, 56, 61, 70, and 2 were used. In set 9, genes 51, 59, 73, 9, 79, 21, 39, 67, 71, 68, 28, 65, 85, 30, 41, 61, 29, 8, 16, 78, 34, 1, 77, 90, 45, 33, 60, 89, 49, 56, 43, 62, 83, 6, 11, 18, 50, 66, 47, 19, 4, 22, 13, 27, 86, 26, 20, 17, 52, 10, 70, 54, 42, 53, 24, 76, 81, 75, 38, 64, 74, 36, 48, 32, 82, 44, 37, 57, 72, 35, 7, 14, 15, 3, and 23 were used. In set 10, genes 18, 85, 61, 1, 52, 87, 42, 13, 88, 66, 46, 57, 50, 36, 75, 39, 14, 27, 54, 20, 53, 10, 4, 30, 37, 43, 79, 80, 40, 84, 76, 45, 60, 74, 12, 31, 15, 44, 48, 3, 56, 11, 68, 19, 86, 72, 6, 9, 21, 70, 34, 83, 89, 5, 69, 64, 22, 24, 63, 65, 55, 8, 41, 28, 2, 16, 35, 77, 26, 47, 90, 49, 59, 23, and 17 were used.

Example 5

PCR Based Detection

As noted above, the determination or measurement of gene expression may be performed by PCR, such as the use of quantitative PCR. Detecting expression of 50 or more expressed sequences in the human genome may be used in such embodiments of the invention. Additionally, expression levels of 50 or more gene sequences in the set of 74, the set of 90, or a combination set of the two (with a total of 126 gene sequences given the presence of 38 gene sequences in common between the two sets) may also be used. The invention contemplates the use of quantitative PCR to measure expression levels, as described above, of 87 gene sequences (or 50 or more sequences thereof), all of which are present in either the set of 74 or the set of 90. Of the 87 gene sequences, 60 are present in the set of 74, and 63 are present in the set of 90. The identifiers/accession numbers of the 87 gene sequences are AA456140, AA745593, AA765597, AA782845, AA865917, AA946776, AA993639, AB038160, AF104032, AF133587, AF301598, AF332224, AI041545, AI147926, AI309080, AI341378, AI457360, AI620495, AI632869, AI683181, AI685931, AI802118, AI804745, AI952953, AI985118, AJ000388, AK025181, AK027147, AK054605, AL023657, AL039118, AL110274, AL157475, AW118445, AW194680, AW291189, AW298545, AW445220, AW473119, AY033998, BC000045, BC001293, BC001504, BC001639, BC002551, BC004331, BC004453, BC005364, BC006537, BC006811, BC006819, BC008764, BC008765, BC009084, BC009237, BC010626, BC011949, BC012926, BC013117, BC015754, BC017586, BE552004, BE962007, BF224381, BF437393, BF446419, BF592799, BI493248, H05388, H07885, H09748, M95585, N64339, NM_000065, NM_001337, NM_003914, NM_004062, NM_004063, NM_004496, NM_006115, NM_019894, NM_033229, R15881, R45389, R61469, X69699, and X96757.

The use of from 50 to all of these sequences in the practice of the invention may include the use of expression levels measured for reference gene sequences as described herein. In some embodiments, the reference gene sequences are one or more of the 8 disclosed herein. The invention contemplates the use of one or more of the reference sequences identified by AF308803, AL137727, BC003043, BC006091, and BC016680 in PCR or QPCR based embodiments of the invention. Of course all 5 of these reference sequences may also be used.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method of classifying a cell-containing sample obtained from a subject as containing tumor cells of a type of tissue, said method comprising selecting randomly 50 or more transcribed sequences of the subject;

producing cDNA copies of the 50 or more randomly selected transcribed sequences from cells in the cell-containing sample;

amplifying the cDNA copies to produce amplified molecules;

determining expression levels of the 50 or more transcribed sequences;

comparing the determined expression levels to expression levels of the same 50 or more transcribed sequences in a plurality of known tumor types comprising one or more tumor types selected from the group consisting of testicular germ cell, sarcoma, adrenal gland, brain, breast, carcinoid-intestine, cervix-adenocarcinoma, cervix-squamous, endometrium, gall bladder, germ cell-ovary, GIST (gastrointestinal stromal tumor), kidney, liver, lung-adenocarcinoma-large cell, lung-small cell, lung-squamous, lymphoma-B cell, lymphoma-Hodgkin's, lymphoma-T cell, meningioma, mesothelioma, ovary-clear cell, ovary-serous, pancreas, prostate, skin-basal cell, skin-melanoma, skin-squamous, small and large bowel, soft tissue-MFH (malignant fibrous histiocytoma), stomach-adenocarcinoma, thyroid-follicular-papillary, thyroid-medullary, and urinary bladder, and classifying the sample as containing or not containing tumor cells of a tumor type or tissue in the plurality of known tumor types.

2. The method of claim 1 wherein said expression levels are determined by use of a microarray.

3. The method of claim 1 wherein said classifying is with an accuracy of 60% or higher.

4. The method of claim 1 wherein said determining comprises measurement in comparison to one or more reference transcribed sequences.

5. The method of claim 1 wherein said determining comprises measuring the expression of all or part of each one of the 50 or more transcribed sequences.

6. The method of claim 1 wherein said determining comprises amplification of all or part of each one of the 50 or more transcribed sequences, or reverse transcription and labeling RNA obtained from said transcribed sequences.

7. The method of claim 6 wherein said amplification comprises linear RNA amplification or quantitative PCR.

8. The method of claim 6 wherein said amplification is of sequences present within 600 nucleotides of the polyadenylation sites of the transcribed sequences.

9. The method of claim 6 wherein said amplification is quantitative PCR amplification of at least 50 nucleotides of the transcribed sequences.

10. A microarray comprising oligonucleotide probes to detect products of the amplification of claim 6.

11. The method of claim 1 wherein said transcribed sequences are selected to be non-redundant.

12. The method of claim 11, further comprising determining the expression levels of an excess number of transcribed sequences which are redundant to those used for said classifying.

13. The method of claim 1, wherein said sample is a clinical sample from a human patient.

14. The method of claim 13, wherein said sample is a formalin fixed, paraffin embedded (FFPE) sample.

15. The method of claim 1, wherein the 50 or more transcribed sequences are 50 to 350 transcribed sequences.

16. The method of claim 1, wherein at least one of the 50 or more transcribed sequences is not associated with tumor cells of the plurality of known tumor types.

17. The method of claim 1, wherein the 50 or more transcribed sequences are not selected based upon a ranking of significance of correlation of the expression level of the transcribed sequence with any one of the known tumor types.

18. The method of claim 1, wherein the 50 or more transcribed sequences are selected randomly from nucleotide sequences of
(a) SEQ ID NOs: 1 to 74, or
(b) SEQ ID NO: 1, SEQ ID NO: 3, SEQ ID NO: 9, SEQ ID NO: 10, SEQ ID NO: 11, SEQ ID NO: 12, SEQ ID NO: 14, SEQ ID NO: 15, SEQ ID NO: 17, SEQ ID NO: 19, SEQ ID NO: 20, SEQ ID NO: 21, SEQ ID NO: 25, SEQ ID NO: 28, SEQ ID NO: 31, SEQ ID NO: 33, SEQ ID NO: 36, SEQ ID NO: 37, SEQ ID NO: 39, SEQ ID NO: 40, SEQ ID NO: 41, SEQ ID NO: 42, SEQ ID NO: 50, SEQ ID NO: 53, SEQ ID NO: 54, SEQ ID NO: 56, SEQ ID NO: 59, SEQ ID NO: 60, SEQ ID NO: 61, SEQ ID NO: 62, SEQ ID NO: 63, SEQ ID NO: 65, SEQ ID NO: 66, SEQ ID NO: 67, SEQ ID NO: 68, SEQ ID NO: 69, SEQ ID NO: 71, SEQ ID NO: 74, and SEQ ID NOs: 149-200.

19. The method of claim 1, wherein the step of selecting is performed by randomly selecting more than 50 transcribed sequences of the subject and reducing the number of selected transcribed sequences to 50 or more transcribed sequences by removing one or more transcribed sequence whose expression level correlates with at least one other transcribed sequence.

20. The method of claim 19, wherein the expression level of more than 10% of the 50 or more transcribed sequences are not correlated with another transcribed sequence of the 50 or more transcribed sequences.

* * * * *